(12) United States Patent
Fodor et al.

(10) Patent No.: US 9,290,809 B2
(45) Date of Patent: Mar. 22, 2016

(54) DIGITAL COUNTING OF INDIVIDUAL MOLECULES BY STOCHASTIC ATTACHMENT OF DIVERSE LABELS

(71) Applicant: Cellular Research, Inc., Palo Alto, CA (US)

(72) Inventors: Stephen P. A. Fodor, Palo Alto, CA (US); Glenn K. Fu, Dublin, CA (US)

(73) Assignee: Cellular Research, Inc., Menlo Park, CA (US)

( * ) Notice: Subject to any disclaimer, the term of this patent is extended or adjusted under 35 U.S.C. 154(b) by 0 days.

(21) Appl. No.: 14/540,018

(22) Filed: Nov. 12, 2014

(65) Prior Publication Data

US 2015/0141292 A1   May 21, 2015

Related U.S. Application Data

(63) Continuation of application No. 14/281,706, filed on May 19, 2014, which is a continuation of application No. 12/969,581, filed on Dec. 15, 2010, now Pat. No. 8,835,358, which is a continuation of application No. 13/327,526, filed on Dec. 15, 2011, which is a continuation-in-part of application No. 12/969,581.

(60) Provisional application No. 61/286,768, filed on Dec. 15, 2009.

(51) Int. Cl.
| | |
|---|---|
| *C12Q 1/68* | (2006.01) |
| *C40B 30/04* | (2006.01) |
| *C12N 15/10* | (2006.01) |
| *G06F 19/20* | (2011.01) |

(52) U.S. Cl.
CPC .......... *C12Q 1/6876* (2013.01); *C12N 15/1065* (2013.01); *C12Q 1/686* (2013.01); *C12Q 1/6809* (2013.01); *C12Q 1/6837* (2013.01); *C12Q 1/6869* (2013.01); *C12Q 1/6874* (2013.01); *G06F 19/20* (2013.01)

(58) Field of Classification Search
CPC ........... C12Q 1/6806; C12Q 2563/149; C12Q 2537/143; C12Q 1/6841; C12Q 2563/155; C12Q 1/6874; C12Q 1/6876; C12Q 2563/179; C12Q 2563/185; C12N 15/1006; C12N 15/1065; C12N 15/1037
See application file for complete search history.

(56) References Cited

U.S. PATENT DOCUMENTS

| | | |
|---|---|---|
| 4,725,536 A | 2/1988 | Fritsch et al. |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,968,740 A | 10/1999 | Fodor et al. |
| 5,981,176 A | 11/1999 | Wallace |
| 5,981,179 A | 11/1999 | Lorinez et al. |

(Continued)

FOREIGN PATENT DOCUMENTS

| | | |
|---|---|---|
| EP | 0799897 A1 | 10/1997 |
| EP | 1647600 A2 | 4/2006 |

(Continued)

OTHER PUBLICATIONS

Alkan, et al. Personalized copy number and segmental duplication maps using next-generation sequencing. Nat Genet. Oct. 2009;41(10):1061-7. doi: 10.1038/ng.437. Epub Aug. 30, 2009.

(Continued)

*Primary Examiner* — Anne Gussow
*Assistant Examiner* — Channing S Mahatan
(74) *Attorney, Agent, or Firm* — Wilson Sonsini Goodrich & Rosati

(57) ABSTRACT

Compositions, methods and kits are disclosed for high-sensitivity single molecule digital counting by the stochastic labeling of a collection of identical molecules by attachment of a diverse set of labels. Each copy of a molecule randomly chooses from a non-depleting reservoir of diverse labels. Detection may be by a variety of methods including hybridization based or sequencing. Molecules that would otherwise be identical in information content can be labeled to create a separately detectable product that is unique or approximately unique in a collection. This stochastic transformation relaxes the problem of counting molecules from one of locating and identifying identical molecules to a series of binary digital questions detecting whether preprogrammed labels are present. The methods may be used, for example, to estimate the number of separate molecules of a given type or types within a sample.

18 Claims, 31 Drawing Sheets

(56) References Cited

U.S. PATENT DOCUMENTS

| | | | |
|---|---|---|---|
| 6,013,445 A | 1/2000 | Albrecht et al. |
| 6,040,138 A | 3/2000 | Lockhart et al. |
| 6,046,005 A | 4/2000 | Ju et al. |
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,268,152 B1 | 7/2001 | Fodor et al. |
| 6,284,460 B1 | 9/2001 | Fodor et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Bernhart et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,404 B2 | 2/2005 | Park et al. |
| 6,852,488 B2 | 2/2005 | Fodor et al. |
| 6,858,412 B2 | 2/2005 | Willis et al. |
| 7,424,368 B2 | 9/2008 | Huang et al. |
| 7,537,897 B2 | 5/2009 | Brenner et al. |
| 7,544,473 B2 | 6/2009 | Brenner |
| 7,635,566 B2 | 12/2009 | Brenner |
| 7,822,555 B2 | 10/2010 | Huang et al. |
| 7,824,889 B2 | 11/2010 | Vogelstein et al. |
| 7,915,015 B2 | 3/2011 | Vogelstein et al. |
| 8,148,068 B2 | 4/2012 | Brenner |
| 8,168,385 B2 | 5/2012 | Brenner |
| 8,241,850 B2 | 8/2012 | Brenner |
| 8,298,767 B2 | 10/2012 | Brenner et al. |
| 8,318,433 B2 | 11/2012 | Brenner |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,835,358 B2 | 9/2014 | Fodor et al. |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0259118 A1 | 12/2004 | Macevicz |
| 2005/0019776 A1 | 1/2005 | Callow et al. |
| 2005/0250147 A1 | 11/2005 | Macevicz |
| 2006/0035258 A1 | 2/2006 | Tadakamalla et al. |
| 2006/0073506 A1 | 4/2006 | Christians et al. |
| 2006/0211030 A1 | 9/2006 | Brenner |
| 2007/0020640 A1 | 1/2007 | McCloskey et al. |
| 2007/0065823 A1 | 3/2007 | Dressman et al. |
| 2008/0299609 A1 | 12/2008 | Kwon et al. |
| 2009/0105959 A1 | 4/2009 | Braverman et al. |
| 2009/0137407 A1 | 5/2009 | Church et al. |
| 2009/0226891 A2 | 9/2009 | Nova et al. |
| 2009/0298709 A1 | 12/2009 | Ma |
| 2010/0069250 A1 | 3/2010 | White et al. |
| 2010/0105886 A1 | 4/2010 | Woudenberg et al. |
| 2010/0291666 A1 | 11/2010 | Collier et al. |
| 2010/0323348 A1 | 12/2010 | Hamady et al. |
| 2011/0059436 A1 | 3/2011 | Hardin et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0294689 A1 | 12/2011 | Namsaraev |
| 2012/0010091 A1* | 1/2012 | Linnarson .......... C12N 15/1096 506/7 |
| 2012/0316074 A1 | 12/2012 | Saxonov |
| 2013/0005585 A1 | 1/2013 | Anderson et al. |
| 2013/0022977 A1 | 1/2013 | Lapidus et al. |
| 2013/0116130 A1 | 5/2013 | Fu et al. |
| 2013/0210643 A1 | 8/2013 | Casbon et al. |
| 2013/0224743 A1 | 8/2013 | Casbon et al. |
| 2013/0237458 A1 | 9/2013 | Casbon et al. |
| 2013/0267424 A1 | 10/2013 | Casbon et al. |
| 2014/0155295 A1 | 6/2014 | Hindson et al. |
| 2014/0227684 A1 | 8/2014 | Hindson et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1 | 1/2015 | Hindson et al. |
| 2015/0066385 A1 | 3/2015 | Schnall-Levin et al. |

FOREIGN PATENT DOCUMENTS

| | | |
|---|---|---|
| WO | WO 97/10365 A1 | 3/1997 |
| WO | WO 99/28505 A1 | 6/1999 |
| WO | WO 00/58516 A2 | 10/2000 |
| WO | WO 02/056014 A2 | 7/2002 |
| WO | WO 2005/080604 A2 | 9/2005 |
| WO | WO 2005/111242 A2 | 11/2005 |
| WO | WO 2006/071776 A2 | 7/2006 |
| WO | WO 2006/102264 A1 | 9/2006 |
| WO | WO 2009/152928 A2 | 12/2009 |
| WO | WO 2009/152928 A3 | 2/2010 |
| WO | WO 2010/117620 A2 | 10/2010 |
| WO | WO 2011/143659 A2 | 11/2011 |
| WO | WO 2012/042374 A2 | 4/2012 |
| WO | WO 2012/048341 A1 | 4/2012 |
| WO | WO 2012/083225 A2 | 6/2012 |
| WO | WO 2012/129363 A2 | 9/2012 |
| WO | WO 2012/142213 A2 | 10/2012 |
| WO | WO 2012/148477 A1 | 11/2012 |
| WO | WO 2013/019075 A2 | 2/2013 |
| WO | WO 2013/130674 A1 | 9/2013 |
| WO | WO 2014/018460 A1 | 1/2014 |
| WO | WO 2014/028537 A1 | 2/2014 |
| WO | WO 2014/093676 A1 | 6/2014 |
| WO | WO 2014/124336 A2 | 8/2014 |
| WO | WO 2014/124338 A1 | 8/2014 |
| WO | WO 2014/210353 A2 | 12/2014 |
| WO | WO 2015/031691 A1 | 3/2015 |

OTHER PUBLICATIONS

Ansorge. Next-generation DNA sequencing techniques. New Biotechnology, 25(4): 195-203 (2009).

Atanur, et al. The genome sequence of the spontaneously hypertensive rat: Analysis and functional significance. Genome Res.

(56) References Cited

OTHER PUBLICATIONS

Jun. 2010;20(6):791-803. doi: 10.1101/gr.103499.109. Epub Apr. 29, 2010.
Audic, et al. The Significance of Digital Gene Expression Profiles. Genome Research, 7: 986-995 (1997).
Bendall, et al. Single-cell mass cytometry of differential immune and drug responses across a human hematopoietic continuum. Science. May 6, 2011;332(6030):687-96, doi: 10.1126/science.1198704.
Bonaldo, et al. Normalization and subtraction: two approaches to facilitate gene discovery. Genome Res. Sep. 1996;6(9):791-806.
Braha, et al. Simultaneous stochastic sensing of divalent metal ions. Nature Biotechnology, 18: 1005-1007 (2000).
Bratke, et al. Differential expression of human granzymes A, B, and K in natural killer cells and during CD8+ T cell differentiation in peripheral blood. Eur J Immunol. Sep. 2005;35(9):2608-16.
Brenner, et al. Gene expression analysis by massively parallel signature sequencing (MPSS) on microbead arrays. Nature Biotechnology, 18: 630-634 (2000).
Brenner, et al. In vitro cloning of complex mixtures of DNA on microbeads physical separation of differentially expressed cDNAs. Proc Natl Acad Sci U S A. Feb. 15, 2000;97(4);1665-70.
Carr, et al. Inferring relative proportions of DNA variants from sequencing electropherograms. Bioinfomiatics, Dec. 15, 2009;25(24):3244-50. doi: 10.1093/bioinformatics/btp583. Epub Oct. 9, 2009.
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.
Castle, et al. DNA copy number, including telomeres and mitochondria, assayed using next-generation sequencing. BMC Genomics. Apr. 16, 2010;11:244. doi: 10.1186/1471-2164-11-244.
Chang, et al. Detection of allelic imbalance in ascitic supernatant by digital single nucleotide polymorphism analysis. Olin Cancer Res. Aug. 2002;8(8):2580-5.
Chee, et al. Accessing genetic information with high-density DNA arrays. Science, 274: 610-614 (1996).
Chee. Enzymatic multiplex DNA sequencing. Nucleic Acids Research, 19(12): 3301-3305 (1991).
Church, et al. Multiplex DNA sequencing. Science, 240: 185-188 (1988).
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.
Cox. Bar coding objects with DNA. Analyst. May 2001;126(5):545-7.
Daines, et al. High-throughput multiplex sequencing to discover copy number variants in Drosophila. Genetics. Aug. 2009;182(4):935-41. doi: 10.1534/genetics.109.103218. Epub Jun. 15, 2009.
Daser, et al. Interrogation of genomes by molecular copy-number counting (MCC). Nature Methods, 3(6): 447-453 (2006).
De Saizieu, et al. Bacterial transcript imaging by hybridization of total RNA to oligonucleotide arrays. Nature Biotechnology, 16: 45-48 (1998).
Fan, et al. Microfluidic digital PCR enables rapid prenatal diagnosis of fetal aneuploidy. Am Obstet Gynecol. 2009; 200:543.e1-543.e7.
Fan, et al. Non-invasive prenatal measurement of the fetal genome. Nature. Jul. 19, 2012;487(7407):320-4. doi: 10.1038/nature11251.
Fan, et al. Parallel Genotyping of Human SNPs Using Generic High-density Oligonucleotide Tag Arrays. Genome Research, 10: 853-860 (2000).
Fu, et al. Counting individual DNA molecules by the stochastic attachment of diverse labels. Proc Natl Acad Sci U S A. May 31, 2011;108(22)9026-31. Epub May 11, 2011.
Fu, et al. Digital encoding of cellular mRNAs enabling precise and absolute gene expression measurement by single-molecule counting. Anal Chem. Mar. 18, 2014;86(6):2867-70. doi: 10.1021/ac500459p. Epub Mar. 4, 2014.

Gerry, et al. Universal DNA microarray method for multiplex detection of low abundance point mutations. Journal of Molecular Biology, 292(2): 251-262 (1999).
Gillespie. .Exact stochastic simulation of coupled chemical reactions. The Journal of Physical Chemistry, 81(25): 2340-2361 (1977).
Grant, et al. SNP genotyping on a genome-wide amplified DOP-PCR template. Nucleic Acids Res. Nov. 15, 2002;30(22);e125.
Gundry, et al. Direct mutation analysis by high-throughput sequencing: from germline to low-abundant, somatic variants. Mutat Res. Jan. 3, 2012;729(1-2):1-15. doi: 10.1016/mrfmmm.2011.10.001. Epub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hamady, et al. Error-correcting barcoded primers for pyrosequencing hundreds of samples in multiplex, Nat Methods. Mar. 2008;5(3);235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al, Parallel, tag-directed assembly of locally derived short sequence reads. Nat Methods. Feb. 2010;7(2);119-22. doi: 10.1038/nmeth.1416. Epub Jan. 17, 2010.
Hiatt, et al. Single molecule molecular inversion probes for targeted, high-accuracy detection of low-frequency variation. Genome Res. May 2013;23(5);843-54. doi: 10.1101/gr.147686.112. Epub Feb. 4, 2013.
Hollas, et al. A stochastic approach to count RNA molecules using DNA sequencing methods. Lecture Notes in Computer Science, 2812: 55-62 (2003).
Ingolia, et al. Genome-wide analysis in vivo of translation with nucleotide resolution using ribosome profiling. Science. Apr. 10, 2009;324(5924):218-23. Epub Feb. 12, 2009.
International search report and written opinion dated Jun. 6, 2012 for PCT/US2011/065291.
International search report and written opinion dated Aug. 16, 2013 for PCT/US2013/027891.
International search report and written opnion dated May 7, 2012 for PCT/IB2011/003160.
Islam, et al. Characterization of the single-cell transcriptional landscape by highly multiplex RNA-seq. Genome Res. Jul. 2011;21(7):1160-7. doi: 10.1101/gr.110882.110. Epub May 4, 2011.
Jabara, et al. Accurate sampling and deep sequencing of the HIV-1 protease gene using a Primer ID, Dec. 3, 2011, PNAS, vol. 108, No. 50, p. 20166-20171.
Kanagawa. Bias and artifacts in multitemplate polymerase chain reactions (PCR), 2003, Journal of Bioscience and Bioengineeting, vol. 96, No. 4, p. 317-323.
Kinde, et al. Detection and quantification of rare mutations with massively parallel sequencing, Jun. 7, 2011, PNAS, vol. 108, No. 23, p. 9530-9535.
Kivioja, et al. Counting absolute numbers of molecules using unique molecular identifiers. Nat Methods. Nov. 20, 2011;9(1):72-4. doi: 10.1038/nmeth.1778.
Koboldt, et al. VarScan: variant detection in massively parallel sequencing of individual and pooled samples. Bioinformatics. Sep. 1, 2009;25(17):2283-5. doi: 10.1093/bioinformatics/btp373. Epub Jun. 19, 2009.
Konig, et al. iCLIP reveals the function of hnRNAP particles in splicing at individual nucleotide resolution, Jul. 2010, Nature Structural & Molecular Biology, 17(7):909-916.
Lizardi, et al. Mutation detection and single-molecule counting using isothermal rolling-circle amplification. Nat Genet. Jul. 1998;19(3):225-32,
Lockhart, et al. Expression monitoring by hybridization to high-density oligonucleotide arrays. Nature Biotechnology, 14: 1675-1680 (1996).
Lucito, et al. Representational Oligonucleotide Microarray Analysis: A High-Resolution Method to Detect Genome Copy Number Variation. Genome Research, 13: 2291-2305.

(56) References Cited

OTHER PUBLICATIONS

Maamar, et al. Noise in Gene Expression Determines Cell Fate in *Bacillus subtilis*. Science, 317: 526-529 (2007).

Makrigiorgos, et al. A PCR-based amplification method retaining the quantitative difference between two complex genomes. Nat Biotechnol. Sep. 2002;20(9):936-9. Epub Aug 5, 2002.

McCloskey, et al. Encoding PCR products with batch-stamps and barcodes. Biochem Genet. Dec. 2007;45(11-12):761-7. Epub Oct. 23, 2007.

Medvedev, et al. Detecting copy number variation with mated short reads. Genome Res. Nov. 2010;20(11):1613-22. doi: 10.1101/gr.106344.110. Epub Aug. 30, 2010.

Mei, et al. Identification of recurrent regions of Copy-Number Variants multiple individuals. BMC Bioinformatics, Mar. 22, 2010;11:147. doi: 10.1186/1471-2105-11-147.

Mortazavi, et al. Mapping and quantifying mammalian transcriptomes by RNA-Seq. Nat. Methods. 2008; 5, 621-628.

Newell, et al. Cytometry by time-of-flight shows combinatorial cytokine expression and virus-specific cell niches within a continuum of CD8+ T cell phenotypes. Immunity. Jan. 27, 2012;36(1):142-52. doi: 10.1016/j.immuni.2012.01.002.

Ogino, et al. Quantification of PCR bias caused by a single nucleotide polymorphism in SMN gene dosage analysis. J Mol Diagn. Nov. 2002;4(4):185-90.

Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.

Pihlak, et al. Rapid genome sequencing with short universal tiling probes. Nature Biotechnology, 26: 676-684 (2008).

Pinkel, et al. Comparative Genomic Hybridization. Annual Review of Genomics and Human Genetics, 6: 331-354 (2005).

Pleasance, et al. A small-cell lung cancer genome with complex signatures of tobacco exposure. Nature. Jan. 14, 2010;463(7278):184-90. doi: 10.1038/nature08629. Epub Dec. 16, 2009.

Qiu, et al. DNA sequence-based "bar codes" for tracking the origins of expressed sequence tags from a maize cDNA library constructed using multiple mRNA sources. Plant Physiol. Oct. 2003;133(2):475-81.

Schmitt, et al. Detection of ultra-rare mutations by next-generation sequencing. Proc Nati Acad Sci U S A. Sep. 4, 2012;109(36):14508-13. doi: 10.1073/pnas.1208715109. Epub Aug. 1, 2012.

Sebat, et al. Large-Scale Copy Number Polymorphism in the Human Genome. Science, 305: 525-528 (2004).

Shalek, et al. Single-cell transcriptomics reveals bimodality in expression and splicing in immune cells. Nature. Jun. 13, 2013;498(7453):236-40. doi: 10.1038/nature12172. Epub May 19, 2013.

Shiroguchi, et al. Digital RNA sequencing minimizes sequence-dependent bias and amplification noise with optimized single-molecule barcodes, PNAS, Jan. 24, 2012;109(4):1347-52.

Shoemaker, et al. Quantitative phenotypic analysis of yeast deletion mutants using a highly parallel molecular bar-coding strategy. Nature Genetics, 14: 450-456 (1996).

Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.

Smith, et al. Highly-multiplexed barcode sequencing: an efficient method for parallel analysis of pooled samples. Nucleic Acids Research, 38(13): e142 (2010).

Tan, et al. Genome-wide comparison of DNA hydroxymethylation in mouse embryonic stem cells and neural progenitor cells by a new comparative hMeDIP-seq method. Nucleic Acids Res. Apr. 2013;41(7);e84. doi: 10.1093/nar/gkt091. Epub Feb. 13, 2013.

Taudien, et al. Haplotyping and copy No. estimation of the highly polymorphic human beta-defensin locus on 8p23 by 454 amplicon sequencing. BMC Genomics. Apr. 19, 2010;11:252. doi: 10.1186/1471-2164-11-252.

Tomaz, et al. Differential methylation as a cause of allele dropout at the imprinted GNAS locus. Genet Test Mol Biomarkers. Aug. 2010;14(4):455-60. doi: 10.1089/gtmb.2010.0029.

Treutlein, et al. Reconstructing lineage hierarchies of the distal lung epithelium using single-cell RNA-seq. Nature. May 15, 2014;509(7500):371-5. doi: 10.1038/nature13173. Epub Apr. 13, 2014.

Velculescu, et al. Characterization of the Yeast Transcriptome. Cell, 88: 243-251 (1997).

Velculescu, et al. Serial Analysis of Gene Expression. Science, 270: 484-487 (1995).

Walker, et al. Isothermal in vitro amplification of DNA by a restriction enzyme/DNA polymerase system. Proc Natl Acad Sci U S A. Jan. 1, 1992;89(1);392-6.

Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.

Wang, et al. iCLIP predicts the dual splicing effects of TIA-RNA interactions, Oct. 2010, PLoS Biol, 8(10):e1000530.

Wang, et al. RNA-Seq: a revolutionary tool for transcriptomics. Nature Reviews Genetics, 10: 57-63 (2009).

Weber, et al. A real-time polymerase chain reaction assay for quantification of allele ratios and correction of amplification bias. Anal Biochem. Sep. 15, 2003;320(2):252-8.

Wittes, et al. Searching for Evidence of Altered Gene Expression: a Comment on Statistical Analysis of Microarray Data. Journal of the National Cancer Institute, 91(5): 400-401 (1999).

Wodicka, et al. Genome-wide expression monitoring in Saccharomyces cerevistae. Nature Biotechnology, 15: 1359-1367 (1997).

Wojdacs, et al. Primer design versus PCR bias in methylation independent PCR amplifications. Epigenetics. May 16, 2009;4(4):231-4. Epub May 14, 2009.

Wood, et al. Using next-generation sequencing for high resolution multiplex analysis of copy number variation from nanogram quantities of DNA from formalin-fixed paraffin-embedded specimens. Nucleic Acids Res. Aug. 2010;38(14):e151. doi: 10.1093/nar/gkq510. Epub Jun. 4, 2010.

Wu, et al. Quantitative assessment of single-cell RNA-sequencing methods. Nat Methods. Jan.11, 2014(1)41-6. doi: 10.1038/nmeth.2694. Epub Oct. 20, 2013.

Yandell, et al. A probabilistic disease-gene finder for personal genomes. Genome Res. Sep. 2011;21(9):1529-42. dot: 10.110/gr.123158.111. Epub Jun. 23, 2011.

Ye, et al. Fluorescent microsphere-based readout technology for multiplexed human single nucleotide polymorphism analysis and bacterial identification. Human Mutation, 17(4): 305-316 (2001).

Yoon, et al. Sensitive and accurate detection of copy number variants using read depth of coverage. Genome Res. Sep. 2009;19(9):1586-92. doi: 10.1101/gr.092981.109. Epub Aug. 5, 2009.

Zhang, et al. The impact of next-generation sequencing on genomics. J Genet Genomics. Mar. 20, 2011;38(3):95-109. doi: 10.1016/j.jgg.2011.02.003. Epub Mar. 15, 2011.

Zhao, et al. Homozygous Deletions and Chromosome Amplifications in Human Lung Carcinomas Revealed by Single Nucleotide Polymorphism Array Analysis. Cancer Research, 65: 5561-5570 (2005).

Zhou, et al. Counting alleles reveals a connection between chromosome 18q loss and vascular invasion. Nature Biotechnology, 19: 78-81 (2001).

Craig, et al. Identification of genetic variants using bar-coded multiplexed sequencing. Nat Methods. Oct. 5, 2008(10):887-93. doi: 10.1038/nmeth.1251. Epub Sep. 14, 2008.

U.S. Appl. No. 61/432,119, filed Jan. 12, 2011, Casbon et al.

Casbon, et al. A method for counting PCR template molecules with application next-generation sequencing. Nucleic Acids Res. Jul. 2011;39(12):e81. doi: 10.1093/nar/gkr217. Epub Apr. 13, 2011.

D'Antoni, et al. Rapid quantitative analysis using a single molecule counting approach. Anal Biochem. May 1, 2006;352(1):97-109. Epub Feb. 10, 2006.

(56) References Cited

OTHER PUBLICATIONS

Fan, et al. Expression profiling. Combinatorial labeling of single cells for gene expression cytometry. Science. Feb. 6, 2015;347(6222):1258367. doi: 10.1126/science.1258367.

Fu, et al. Counting individual DNA molecules by the stochastic attachment of diverse labels. Proc Natl Acad Sci U S A. May 31, 2011;108(22):9026-31. Epub May 11, 2011.

Gunderson, et al. Decoding Randomly Ordered DNA Arrays. Genome Research pp. 871-878.

Hug, et al. Measurement of the number of molecules of a single mRNA species in a complex mRNA preparation. J Theor Biol. Apr. 21, 2003;221(4):615-24.

International search report and written opinion dated Feb. 3, 2015 for PCT Application No. US2014/053301. 18 pages.

International search report and written opinion dated Jun. 6, 2012 for PCT/US2011/065291. 4 pages.

International search report dated Aug. 6, 2014 for PCT Application No. GB1408829.8. 7 pages.

Larson, et al. A single molecule view of of gene expression. Trends Cell Biol. Nov. 2009;19(11):630-7. Epub Oct. 8, 2009.

Lee, et al. Highly Multiplexed Subcellular RNA Sequencing in Situ. Sciencexpress, Feb. 27, 2014, p. 1-6.

Lovatt, et al. Trancriptome in vivo analysis (TIVA) of spatially defined single cells in live tissue. Nature Methods, vol. 11, No. 2, Feb. 2014, pp. 190-195.

Notice of allowance dated Mar. 21, 2014 for U.S. Appl. No. 12/969,581. 8 pages.

Notice of allowance dated Jun. 19, 2014 for U.S. Appl. No. 12/969,581. 7 pages.

Notice of allowance dated Aug. 22, 2014 for U.S. Appl. No. 12/969,581. 8 pages.

Office action dated Feb. 18, 2015 for U.S. Appl. No. 14/540,007. 16 pages.

Office action dated Feb. 26, 2015 for U.S. Appl. No. 14/540,029. 24 pages.

Office action dated Oct. 3, 2013 for U.S. Appl. No. 12/969,581. 18 pages.

Response with alllowed claims dated Mar. 4, 2014 for U.S. Appl. No. 12/969,581. 12 pages.

Vogelstein, et al. Digital PCR. Proc. Natl. Acad. Sci., 96(16): 9236-9241 (1999).

\* cited by examiner

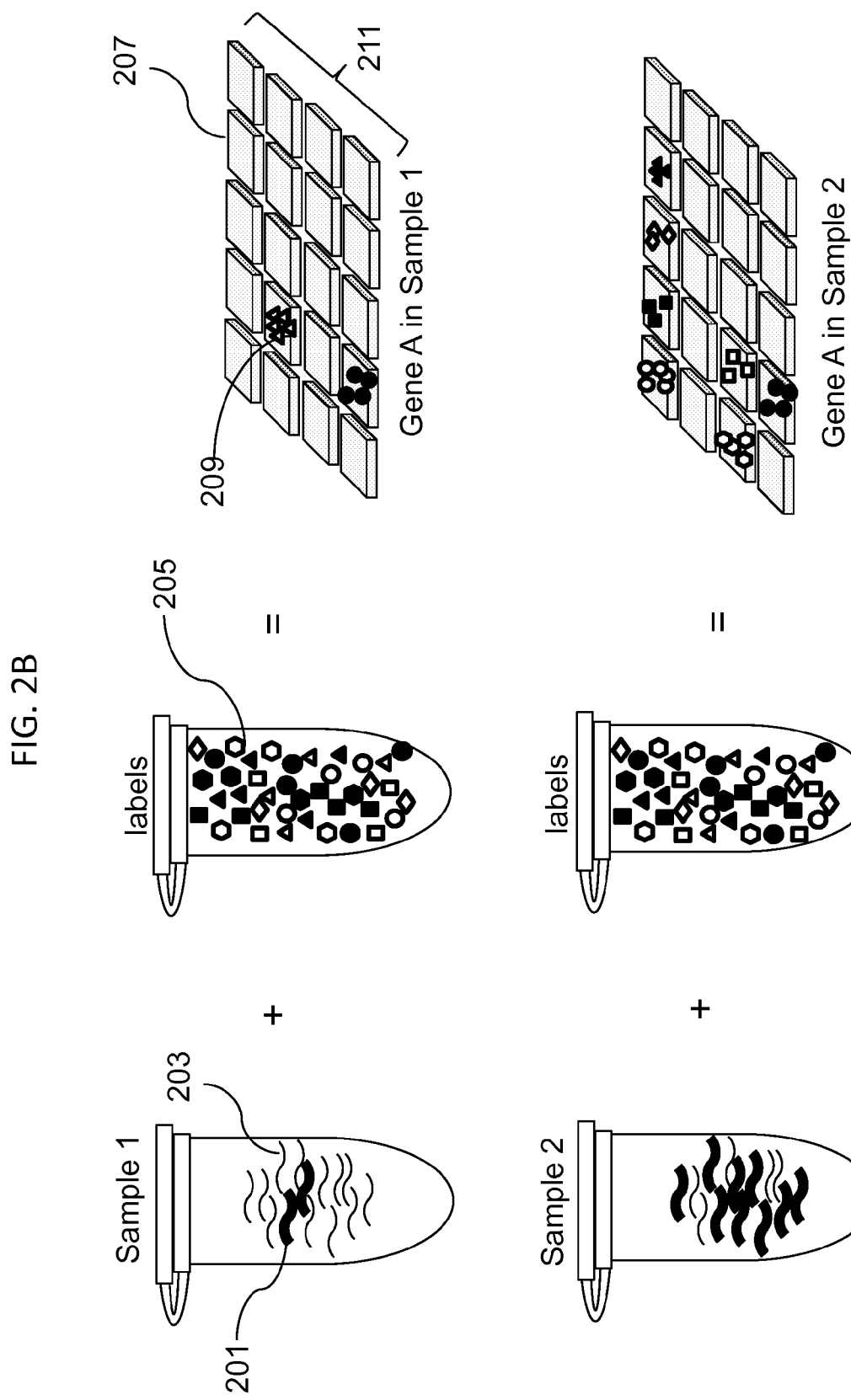

DIGITAL COUNTING OF INDIVIDUAL MOLECULES BY STOCHASTIC ATTACHMENT OF DIVERSE LABELS

RELATED APPLICATIONS

This application claims priority to U.S. Provisional application No. 61/286,768 filed Dec. 15, 2009, the entire disclosure of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 23, 2014, is named 41977-701-301-Seqlist.txt and is 393 Kilobytes in size.

FIELD OF THE INVENTION

Methods, compositions and products for counting individual molecules by stochastic attachment of diverse labels from a set of labels, followed by amplification and detection are disclosed.

BACKGROUND OF THE INVENTION

Many processes are characterized or regulated by the absolute or relative amounts of a plurality of items. For example, in biology, the level of expression of particular genes or groups of genes or the number of copies of chromosomal regions can be used to characterize the status of a cell or tissue. Analog methods such as microarray hybridization methods and real-time PCR are alternatives, but digital readout methods such as those disclosed herein have advantages over analog methods. Methods for estimating the abundance or relative abundance of genetic material having increased accuracy of counting would be beneficial.

The availability of convenient and efficient methods for the accurate identification of genetic variation and expression patterns among large sets of genes may be applied to understanding the relationship between an organism's genetic make-up and the state of its health or disease, Collins et al, Science, 282: 682-689 (1998). In this regard, techniques have been developed for the analysis of large populations of polynucleotides based either on specific hybridization of probes to microarrays, e.g. Lockhart et al. Hacia et al, *Nature Genetics*, 21: 4247 (1999), or on the counting of tags or signatures of DNA fragments, e.g. Velculescu et al, *Science*, 270: 484487 (1995); Brenner et al, *Nature Biotechnology*, 18: 630-634 (2000). These techniques have been used in discovery research to identify subsets of genes that have coordinated patterns of expression under a variety of circumstances or that are correlated with, and predictive of events, of interest, such as toxicity, drug responsiveness, risk of relapse, and the like, e.g. Golub et al, *Science*, 286: 531-537 (1999); Alizadeh et al, *Nature*, 403: 503-511 (2000); Perou et al, *Nature*, 406: 747-752 (2000); Shipp et al, *Nature Medicine*, 8: 68-74 (2002); Hakak et al, *Proc. Natl. Acad. Sci.*, 98: 47454751 (2001); Thomas et al, *Mol. Pharmacol.*, 60: 1189-1194 (2001); De Primo et al, BMC Cancer 2003, 3:3; and the like. Not infrequently the subset of genes found to be relevant has a size in the range of from ten or under to a few hundred.

In addition to gene expression, techniques have also been developed to measure genome-wide variation in gene copy number. For example, in the field of oncology, there is interest in measuring genome-wide copy number variation of local regions that characterize many cancers and that may have diagnostic or prognostic implications. For a review see Zhang et al. *Annu. Rev. Genomics Hum. Genet.* 2009. 10:451-81.

While such hybridization-based techniques offer the advantages of scale and the capability of detecting a wide range of gene expression or copy number levels, such measurements may be subject to variability relating to probe hybridization differences and cross-reactivity, element-to-element differences within microarrays, and microarray-to-microarray differences, Audic and Clayerie, *Genomic Res.*, 7: 986-995 (1997); Wittes and Friedman, *J. Natl. Cancer Inst.* 91: 400-401 (1999).

On the other hand, techniques that provide digital representations of abundance, such as SAGE (Velculescu et al, cited above) or MPSS (Brenner et al, cited above), are statistically more robust; they do not require repetition or standardization of counting experiments as counting statistics are well-modeled by the Poisson distribution, and the precision and accuracy of relative abundance measurements may be increased by increasing the size of the sample of tags or signatures counted, e.g. Audic and Clayerie (cited above).

Both digital and non-digital hybridization-based assays have been implemented using oligonucleotide tags that are hybridized to their complements, typically as part of a detection or signal generation schemes that may include solid phase supports, such as microarrays, microbeads, or the like, e.g. Brenner et al, Proc. Natl. Acad. Sci., 97: 1665-1670 (2000); Church et al, Science, 240: 185-188 (1988); Chee, *Nucleic Acids Research*, 19: 3301-3305 (1991); Shoemaker et al., *Nature Genetics*, 14: 450456 (1996); Wallace, U.S. Pat. No. 5,981,179; Gerry et al, *J. Mol. Biol.*, 292: 251-262 (1999); Fan et al., *Genome Research*, 10: 853-860 (2000); Ye et al., *Human Mutation*, 17: 305-316 (2001); and the like. Bacterial transcript imaging by hybridization of total RNA to nucleic acid arrays may be conducted as described in Saizieu et al., *Nature Biotechnology*, 16:45-48 (1998). Accessing genetic information using high density DNA arrays is further described in Chee et al., *Science* 274:610-614 (1996). Tagging approaches have also been used in combination with next-generation sequencing methods, see for example, Smith et al. NAR (May 11, 2010), 1-7.

A common feature among all of these approaches is a one-to-one correspondence between probe sequences and oligonucleotide tag sequences. That is, the oligonucleotide tags have been employed as probe surrogates for their favorable hybridizations properties, particularly under multiplex assay conditions.

Determining small numbers of biological molecules and their changes is essential when unraveling mechanisms of cellular response, differentiation or signal transduction, and in performing a wide variety of clinical measurements. Although many analytical methods have been developed to measure the relative abundance of different molecules through sampling (e.g., microarrays and sequencing), few techniques are available to determine the absolute number of molecules in a sample. This can be an important goal, for example in single cell measurements of copy number or stochastic gene expression, and is especially challenging when the number of molecules of interest is low in a background of many other species. As an example, measuring the relative copy number or expression level of a gene across a wide number of genes can currently be performed using PCR, hybridization to a microarray or by direct sequence counting. PCR and microarray analysis rely on the specificity of hybridization to identify the target of interest for amplification or capture respectively, then yield an analog signal proportional to the original number of molecules. A major advantage of these approaches is in the use of hybridization to isolate the specific molecules of interest within the background of many other molecules, generating specificity for the readout or detection step. The disadvantage is that the readout signal to noise is proportional to all molecules (specific and non-specific) specified by selective amplification or hybridization. The situation is reversed for sequence counting. No intended sequence specificity is imposed in the sequence capture step, and all molecules are sequenced. The major advantage is that the detection step simply yields a digital list of those sequences found, and since there is no specificity in the isolation step, all sequences must be analyzed at a sufficient statistical depth in order to learn about a specific sequence. Although very major technical advances in sequencing speed and throughput have occurred, the statistical requirements imposed to accurately measure small changes in concentration of a specific gene within the background of many other sequences requires measuring many sequences that don't matter to find the ones that do matter. Each of these techniques, PCR, array hybridization and sequence counting is a comparative technique in that they primarily measure relative abundance, and do not typically yield an absolute number of molecules in a solution. A method of absolute counting of nucleic acids is digital PCR (B. Vogelstein, K. W. Kinzler, Proc Natl Acad Sci USA 96, 9236 (Aug. 3, 1999)), where solutions are progressively diluted into individual compartments until there is an average probability of one molecule per two wells, then detected by PCR. Although digital PCR can be used as a measure of absolute abundance, the dilutions must be customized for each type of molecule, and thus in practice is generally limited to the analysis of a small number of different molecules.

SUMMARY OF THE INVENTION

High-sensitivity single molecule digital counting by the stochastic labeling of a collection of identical molecules is disclosed. Each copy of a molecule randomly chooses from a non-depleting reservoir of diverse labels. The uniqueness of each labeled molecule is determined by the statistics of random choice, and depends on the number of copies of identical molecules in the collection compared to the diversity of labels. The size of the resulting set of labeled molecules is determined by the stochastic nature of the labeling process, and analysis reveals the original number of molecules. When the number of copies of a molecule to the diversity of labels is low, the labeled molecules are highly unique, and the digital counting efficiency is high. This stochastic transformation relaxes the problem of counting molecules from one of locating and identifying identical molecules to a series of yes/no digital questions detecting whether preprogrammed labels are present. The conceptual framework for stochastic mapping of a variety of molecule types is developed and the utility of the methods are demonstrated by stochastically labeling 360,000 different fragments of the human genome. The labeled fragments for a target molecule of choice are detected with high specificity using a microarray readout system, and with DNA sequencing. The results are consistent with a stochastic process, and yield highly precise relative and absolute counting statistics of selected molecules within a vast background of other molecules.

Methods are disclosed herein for digital counting of individual molecules of one or more targets. In preferred embodiments the targets are nucleic acids, but may be a variety of biological or non-biological elements. Targets are labeled so that individual occurrences of the same target are marked by attachment of a different label to difference occurrences. The attachment of the label confers a separate, determinable identity to each occurrence of targets that may otherwise be indistinguishable. Preferably the labels are different sequences that tag or mark each target occurrence uniquely. The resulting modified target comprises the target sequence and the unique identifier (which may be referred to herein as tag, counter, label, or marker). The junction of the target and identifier forms a uniquely detectable mechanism for counting the occurrence of that copy of the target. The attachment of the identifier to each occurrence of the target is a random sampling event. Each occurrence of target could choose any of the labels. Each identifier is present in multiple copies so selection of one copy does not remove that identifier sequence from the pool of identifiers so it is possible that the same identifier will be selected twice. The probability of that depends on the number of target occurrences relative to the number of different identifier sequences.

Each stochastic attachment event, where a target occurrence is attached to a unique identifier, results in the creation of a novel sequence formed at the junction of the identifier and the target. For a given target, all resulting products will contain the same target portion, but each will contain a different identifier sequence (T1L1, T1L2, ... T1LN where N is the number of different occurrences of target1, "T1" and L is the identifier, L1, L2 ... LN). In preferred aspects the occurrences are detected by hybridization. In some aspects the methods and systems include a probe array comprising features, wherein each feature has a different combination of target sequence with identifiers, 1 to N wherein N is the number of unique identifiers in the pool of identifiers. The array has N features for each target, so if there are 8 targets to be analyzed there are 8 times N features on the array to interrogate the 8 targets.

BRIEF DESCRIPTION OF THE DRAWINGS

FIG. 2B shows a schematic of detection of labeled targets on an array having features that are label specific and target specific.

DETAILED DESCRIPTION OF THE INVENTION

Figure 1:
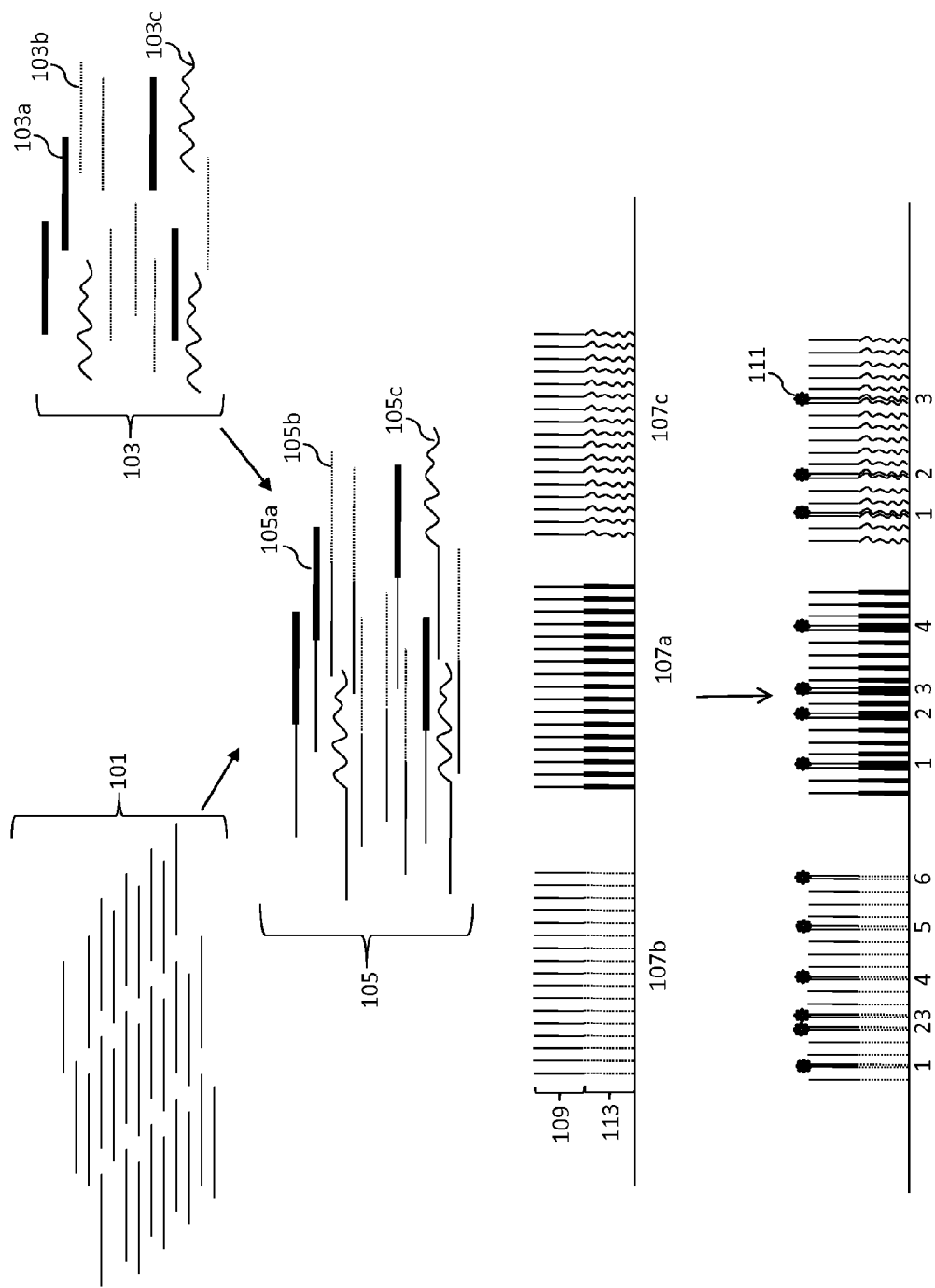
FIG. 1 is a schematic of a method of stochastic labeling and counting by hybridization to an array of support bound probes.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention has many preferred embodiments and relies on many patents, applications and other references for details known to those of the art. Therefore, when a patent, application, or other reference, such as a printed publication, is cited or repeated below, it should be understood that it is incorporated by reference in its entirety for all purposes and particularly for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV)*, *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Gait, "*Oligonucleotide Synthesis: A Practical Approach*" 1984, IRL Press, London, Nelson and Cox (2000), Lehninger et al., (2008) *Principles of Biochemistry* 5th Ed., W.H. Freeman Pub., New York, N.Y. and Berg et al. (2006) *Biochemistry, 6th* Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques may be applied to polypeptide arrays.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Patent Publication Nos. 20030036069 and 20070065816 and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain embodiments. Prior to or concurrent with analysis, the sample may be amplified by a variety of mechanisms. In some aspects nucleic acid amplification methods such as PCR may be combined with the disclosed methods and systems. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. Enzymes and related methods of use in molecular biology that may be used in combination with the disclosed methods and systems are reviewed, for example, in Rittie and Perbal, *J. Cell Commun. Signal.* (2008) 2:25-45. The sample may be amplified on the array. See, for example, U.S. Pat. No. 6,300,070 and which is incorporated herein by reference in its entirety for all purposes.

Many of the methods and systems disclosed herein utilize enzyme activities. A variety of enzymes are well known, have been characterized and many are commercially available from one or more supplier. For a review of enzyme activities commonly used in molecular biology see, for example, Rittie and Perbal, *J. Cell Commun. Signal.* (2008) 2:25-45, incorporated herein by reference in its entirety. Exemplary enzymes include DNA dependent DNA polymerases (such as those shown in Table 1 of Rittie and Perbal), RNA dependent DNA polymerase (see Table 2 of Rittie and Perbal), RNA polymerases, ligases (see Table 3 of Rittie and Perbal), enzymes for phosphate transfer and removal (see Table 4 of Rittie and Perbal), nucleases (see Table 5 of Rittie and Perbal), and methylases.

Other methods of genome analysis and complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 and U.S. Patent Publication Nos. 20030039069, 20050079536, 20030096235, 20030082543, 20040072217, 20050142577, 20050233354, 20050227244, 20050208555, 20050074799, 20050042654 and 20040067493, which are each incorporated herein by reference in their entireties.

The design and use of allele-specific probes for analyzing polymorphisms is described by e.g., Saiki et al., *Nature* 324, 163-166 (1986); Dattagupta, EP 235,726, and WO 89/11548. Allele-specific probes can be designed that hybridize to a segment of target DNA from one individual but do not hybridize to the corresponding segment from another individual due to the presence of different polymorphic forms in the respective segments from the two individuals.

The term "WGSA (Whole Genome Sampling Assay) Genotyping Technology" refers to a technology that allows the genotyping of thousands of SNPs simultaneously in complex DNA without the use of locus-specific primers. WGSA reduces the complexity of a nucleic acid sample by amplifying a subset of the fragments in the sample. In this technique, a nucleic acid sample is fragmented with one or more restriction enzymes of interest and adaptors are ligated to the digested fragments. A single primer that is complementary of the adaptor sequence is used to amplify fragments of a desired size, for example, 400-800, 400-2000 bps, using PCR. Fragments that are outside the selected size range are not efficiently amplified. WGSA is disclosed in, for example, U.S. Patent Publication Nos. 20040185475, 20040157243 (also PCT Application published as W004/044225), 20040146890, 20030186279, 20030186280, 20030232353, 20040067493, 20030025075, 20020142314, 20070065816 and U.S. patent application Ser. No. 10/646,674, each of which is hereby incorporated by reference in its entirety for all purposes. In U.S. Patent Publication Nos. 20040185475, US20030186279, and US20030186280, the accuracy of genotype calls was determined in two ways: through the use of genotypes obtained by independent genotyping methods, and by dideoxynucleotide sequencing of discordant genotype calls. U.S. Patent Publication No. 20020142314, arrays are designed to detect specific SNPS or simply to detect the presence of a region known to frequently contain SNPS. In the latter case, other techniques such as sequencing could be employed to identify the SNP. In U.S. Patent Publication No. 20070065816, methods that may be used to determine the identity of an allele include, but are not limited to, detecting hybridization of a molecular beacon probe, electrical pore analysis, electrical conductance analysis, atomic force microscopy analysis, pyrosequencing, MALDI-TOF mass spectrometry, Surface Enhanced Raman Scattering, current amplitude analysis, use of an eSensor system, and use of electrochemical DNA biosensors.

Sample preparation methods are also contemplated in many embodiments. Prior to or concurrent with analysis, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. See also U.S. Pat. No. 6,300,070 which is incorporated herein by reference. Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Patent Pub. Nos. 20030096235, 20030082543 and 20030036069.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245), rolling circle amplification (RCA) (for example, Fire and Xu, PNAS 92:4641 (1995) and Liu et al., J. Am. Chem. Soc. 118:1587 (1996)) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 6,582,938, 5,242,794, 5,494,810, 4,988,617, and US Pub. No. 20030143599 each of which is incorporated herein by reference.

Molecular inversion probes may also be used for amplification of selected targets. MIPs may be generated so that the ends of the pre-circle probe are complementary to regions that flank the region to be amplified. The gap can be closed by extension of the end of the probe so that the complement of the target is incorporated into the MIP prior to ligation of the ends to form a closed circle. The closed circle can be amplified as previously disclosed in Hardenbol et al., *Genome Res.* 15:269-275 (2005) and in U.S. Pat. No. 6,858,412.

In some embodiments, amplification may include the use of a strand displacing polymerase that may be primed by selected primers or by a mixture of primers, for example, random hexamers. See for example Lasken and Egholm, Trends Biotechnol. 2003 21(12):531-5; Barker et al. Genome Res. 2004 May; 14(5):901-7; Dean et al. Proc Natl Acad Sci USA 2002; 99(8):5261-6; and Paez, J. G., et al. Nucleic Acids Res. 2004; 32(9):e71. Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. DNA may also be amplified by multiplex locus-specific PCR or using adaptor-ligation and single primer PCR. Other available methods of amplification, such as balanced PCR (Makrigiorgos, et al. (2002), Nat Biotechnol, Vol. 20, pp. 936-9), may also be used. Balanced PCR operates by digesting the two genomes to be compared (target A and control B) with a restriction enzyme (SAU3A1, a four-base cutter) and then ligating composite linkers LN1 and LN2 to each of the two DNA populations. Each linker contains a sequence (P1) found in both linkers and a sequence tag unique to each DNA sample. These unique tags are included in the 3' end of the sequences P2a and P2b. Therefore, primer extension by P2a or P2b can occur only when DNA ligated to LN1 or LN2, respectively, is encountered. The ligated genomes are mixed and amplified in a single PCR reaction with the P1 common primer until the desired amount of final product is obtained. Subsequently, the mixed genomes can be distinguished by two methods: differential fluorescent labeling of one or the other DNA population in the mixture using the unique sequences P2a or P2b in a single primer-extension reaction, or reseparation of the two genomes by a low-cycle PCR reaction.

Methods of ligation will be known to those of skill in the art and are described, for example in Sambrook et at. (2001) and the New England BioLabs catalog both of which are incorporated herein by reference for all purposes. Methods include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; *E. coli* DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3'→5' phosphodiester bond, substrates include single-stranded RNA and DNA as well as dinucleoside pyrophosphates; or any other methods described in the art. Fragmented DNA may be treated with one or more enzymes, for example, an endonuclease, prior to ligation of adaptors to one or both ends to facilitate ligation by generating ends that are compatible with ligation.

Fixed content mapping arrays are available from Affymetrix, for example, the SNP 6.0 array. Methods for using mapping arrays see, for example, Kennedy et al., *Nat. Biotech.* 21:1233-1237 (2003), Matsuzaki et al., *Genome Res.* 14:414-425 (2004), Matsuzaki et al., *Nat. Meth.* 1:109-111 (2004) and U.S. Patent Pub. Nos. 20040146890 and 20050042654, each incorporated herein by reference. Applications of microarrays for SNP genotyping have been described in e.g., U.S. Pat. Nos. 6,300,063, 6,361,947, 6,368,799 and US Patent Publication Nos. 20040067493, 20030232353, 20030186279, 20050260628, 20070065816 and 20030186280, all incorporated herein by reference in their entireties for all purposes.

Fixed content mapping arrays are available from Affymetrix, for example, the SNP 6.0 array. Methods for using mapping arrays see, for example, Kennedy et al., Nat. Biotech. 21:1233-1237 (2003), Matsuzaki et al., Genome Res. 14:414-425 (2004), Matsuzaki et al., Nat. Meth. 1:109-111 (2004) and U.S. Patent Pub. Nos. 20040146890 and 20050042654, each incorporated herein by reference. Applications of microarrays for SNP genotyping have been described in e.g., U.S. Pat. Nos. 6,300,063, 6,361,947, 6,368,799 and US Patent Publication Nos. 20040067493, 20030232353, 20030186279, 20050260628, 20070065816 and 20030186280, all incorporated herein by reference in their entireties for all purposes. In U.S. Pat. No. 6,300,063, a wide variety of methods can be used to identify specific polymorphisms. For example, repeated sequencing of genomic material from large numbers of individuals, although extremely time consuming, can be used to identify such polymorphisms. In U.S. Pat. No. 6,361,947, arrays are designed to detect specific SNPS or simply to detect the presence of a region known to frequently contain SNPS. In the latter case, other techniques such as sequencing could be employed to identify the SNP.

Computer implemented methods for determining genotype using data from mapping arrays are disclosed, for example, in Liu, et al., *Bioinformatics* 19:2397-2403 (2003), Rabbee and Speed, *Bioinformatics,* 22:7-12 (2006), and Di et al., *Bioinformatics* 21:1958-63 (2005). Computer implemented methods for linkage analysis using mapping array data are disclosed, for example, in Ruschendorf and Nurnberg, *Bioinformatics* 21:2123-5 (2005) and Leykin et al., *BMC Genet.* 6:7, (2005). Computer methods for analysis of genotyping data are also disclosed in U.S. Patent Pub. Nos. 20060229823, 20050009069, 20040138821, 20060024715, 20050250151 and 20030009292.

Methods for analyzing chromosomal copy number using mapping arrays are disclosed, for example, in Bignell et al., *Genome Res.* 14:287-95 (2004), Lieberfarb, et al., *Cancer Res.* 63:4781-4785 (2003), Zhao et al., *Cancer Res.* 64:3060-71 (2004), Huang et al., *Hum Genomics* 1:287-299 (2004), Nannya et al., *Cancer Res.* 65:6071-6079 (2005), Slater et al., *Am. J. Hum. Genet.* 77:709-726 (2005) and Ishikawa et al., *Biochem. and Biophys. Res. Comm.,* 333:1309-1314 (2005). Computer implemented methods for estimation of copy number based on hybridization intensity are disclosed in U.S. Patent Pub. Nos. 20040157243, 20050064476, 20050130217, 20060035258, 20060134674 and 20060194243.

Additional methods of sample preparation and techniques for reducing the complexity of a nucleic sample are described in Dong et al., *Genome Research* 11, 1418 (2001), in U.S. Pat. Nos. 6,361,947, 6,391,592 and 6,872,529 and U.S. Patent Publication Nos. 20030036069, 20030096235 and 20030082543. Additional methods of using a genotyping array are disclosed, for example, in U.S. Patent Publication Nos. 20040146883, 20030186280, 20030186279, 20040067493, 20030232353, 20060292597, 20050233354, 20050074799, 20070065816 and 20040185475.

Methods for conducting polynucleotide hybridization assays have been well developed in the art. Hybridization assay procedures and conditions will vary depending on the application and are selected in accordance with known general binding methods, including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davis, *P.N.A.S.,* 80: 1194 (1983). Methods and apparatus for carrying out repeated and controlled hybridization reactions have been described in U.S. Pat. Nos. 5,871, 928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Patent Pub. No. 20040012676 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Patent Pub. Nos. 20040012676 and 20050059062 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Additionally, the present disclosure may have preferred embodiments that include methods for providing genetic information over networks such as the Internet as shown in U.S. Patent Pub. Nos. 20030097222, 20020183936, 20030100995, 20030120432, 20040002818, 20040126840, and 20040049354.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Single nucleotide polymorphisms (SNPs) are positions at which two alternative bases occur at appreciable frequency (>1%) in a given population. SNPs are a common type of human genetic variation and are useful in the performance of genome wide association studies (GWAS). GWAS may be used, for example for the analysis of biological pathways, see Wang and Hakonarson, Nat. Rev. Genet. 2010, 11:843-854. Other common variation includes single base deletions or insertions of a nucleotide relative to a reference allele. Copy number variants (CNVs), transversions and other rearrangements are also forms of genetic variation.

Single nucleotide polymorphisms (SNPs) are positions at which two alternative bases occur at appreciable frequency (>1%) in a given population. SNPs are the most common type of human genetic variation. A polymorphic site is frequently preceded by and followed by highly conserved sequences (e.g., sequences that vary in less than 1/100 or 1/1000 members of the populations).

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, microparticles, nanoparticles or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. See, M. Kanehisa Nucleic Acids Res. 12:203 (1984), incorporated herein by reference.

The term "copy number variation" or "CNV" refers to differences in the copy number of genetic information. In many aspects it refers to differences in the per genome copy number of a genomic region. For example, in a diploid organism the expected copy number for autosomal genomic regions is 2 copies per genome. Such genomic regions should be present at 2 copies per cell. For a recent review see Zhang et al. *Annu. Rev. Genomics Hum. Genet.* 2009. 10:451-81. CNV is a source of genetic diversity in humans and can be associated with complex disorders and disease, for example, by altering gene dosage, gene disruption, or gene fusion. They can also represent benign polymorphic variants. CNVs can be large, for example, larger than 1 Mb, but many are smaller, for example between 100 bp and 1 Mb. More than 38,000 CNVs greater than 100 bp (and less than 3 Mb) have been reported in humans. Along with SNPs these CNVs account for a significant amount of phenotypic variation between individuals. In addition to having deleterious impacts, e.g. causing disease, they may also result in advantageous variation.

Digital PCR is a technique where a limiting dilution of the sample is made across a large number of separate PCR reactions so that most of the reactions have no template molecules and give a negative amplification result. Those reactions that are positive at the reaction endpoint are counted as individual template molecules present in the original sample in a 1 to 1 relationship. See Kalina et al. NAR 25:1999-2004 (1997) and Vogelstein and Kinzler, PNAS 96:9236-9241 (1999). This method is an absolute counting method where solutions are partitioned into containers until there is an average probability of one molecule per two containers or when, $P_0=(1-e^{-n/c})=\frac{1}{2}$; where n is the number of molecules and c is the number of containers, or n/c is 0.693. Quantitative partitioning is assumed, and the dynamic range is governed by the number of containers available for stochastic separation. The molecules are then detected by PCR and the number of positive containers is counted. Each successful amplification is counted as one molecule, independent of the actual amount of product. PCR-based techniques have the additional advantage of only counting molecules that can be amplified, e.g. that are relevant to the massively parallel PCR step in the sequencing workflow. Because digital PCR has single molecule sensitivity, only a few hundred library molecules are required for accurate quantification. Elimination of the quantification bottleneck reduces the sample input requirement from micrograms to nanograms or less, opening the way for minute and/or precious samples onto the next-generation sequencing platforms without the distorting effects of pre-amplification. Digital PCR has been used to quantify sequencing libraries to eliminate uncertainty associated with the construction and application of standard curves to PCR-based quantification and enable direct sequencing without titration runs. See White et al. *BMC Genomics* 10: 116 (2009).

To vary dynamic range, micro-fabrication can be used to substantially increase the number of containers. See, Fan et al. *Am J Obstet Gynecol* 200, 543 e1 (May, 2009).

Similarly, in stochastic labeling as disclosed herein, the same statistical conditions are met when $P_0=(1-e^{-n/m})=\frac{1}{2}$; where m is the number of labels, and one half of the labels will be used at least once when n/m=0.693. The dynamic range is governed by the number of labels used, and the number of labels can be easily increased to extend the dynamic range. The number of containers in digital PCR plays the same role as the number of labels in stochastic labeling and by substituting containers for labels identical statistical equations may be applied. Using the principles of physical separation, digital PCR stochastically expands identical molecules into physical space, whereas the principle governing stochastic labeling is identity based and expands identical molecules into identity space.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations may be performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" $2^{nd}$ Ed. Cold Spring Harbor Press (1989) which is hereby incorporated by reference in its entirety for all purposes above. In some aspects salt concentrations for hybridization are preferably between about 200 mM and about 1M or between about 200 mM and about 500 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

The term "mixed population" or sometimes refer by "complex population" as used herein refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA)

The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "polymorphism" as used herein refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Single nucleotide polymorphisms (SNPs) are included in polymorphisms.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 and US Patent Pub. Nos. 20090149340 and 20080038559 for exemplary substrates.

A stochastic process is the counterpart to a deterministic process. Instead of dealing with only one possible "reality" of how the process might evolve under time, in a stochastic or random process there is some indeterminacy in its future evolution described by probability distributions. This means that even if the initial condition (or starting point) is known, there are many possibilities the process might go to, but some paths are more probable and others less.

In the simplest possible case, a stochastic process amounts to a sequence of random variables known as a time series (for example, see Markov chain). Another basic type of a stochastic process is a random field, whose domain is a region of space, in other words, a random function whose arguments are drawn from a range of continuously changing values. One approach to stochastic processes treats them as functions of one or several deterministic arguments ("inputs", in most cases regarded as "time") whose values ("outputs") are random variables: non-deterministic (single) quantities which have certain probability distributions. Random variables corresponding to various times (or points, in the case of random fields) may be completely different. The main requirement is that these different random quantities all have the same "type". Although the random values of a stochastic process at different times may be independent random variables, in most commonly considered situations they exhibit complicated statistical correlations.

Familiar examples of processes modeled as stochastic time series include stock market and exchange rate fluctuations, signals such as speech, audio and video, medical data such as a patient's EKG, EEG, blood pressure or temperature, and random movement such as Brownian motion or random walks. Examples of random fields include static images, random terrain (landscapes), or composition variations of an heterogeneous material.

The stochastic labeling process can be generalized as follows. Consider n copies of a given target molecule T, where $T=\{t_i, i=1, 2, \ldots, n\}$, and a non-depleting reservoir of m diverse labels L, where $L=\{l_j, j=1, 2, \ldots, m\}$. T reacts with L stochastically, such that each $t_i$ will choose exactly one $l_{j(i)}$, $1 \leq j(i) \leq m$ to take on a new identity $t_i l_{j(i)}$, and may be identified by its label subscript. Therefore, the new collection of molecules T* may be denoted as $T^*=\{tl_{j(i)}, i=1, 2, \ldots, n, 1 \leq j(i) \leq m\}$.

When different copies of the target molecules react with the same label, j(i) for those molecules will assume the same value, therefore, the number of uniquely labeled target molecules k cannot be greater than m. The stochastic mapping of the set of labels on a target may be described by a stochastic operator S with m members, acting upon a target population of n, such that $S(m)T(n)=T^*(m, n)$ generating the set $T^*=\{tl_{j(i)}, i=1, 2, \ldots, n, 1 \leq j(i) \leq m\}$. For simplicity, we may write $T^*=\{tl_k\}$. Furthermore, since S operates on all molecules randomly, it will independently act on many different target sequences and the method can be expanded to count copies of multiple target sequences, w, simultaneously: $ST^w=ST_1+ST_2+ \ldots +ST_w=T_1^*+T_2^*+ \ldots T_w^*=\{tl_k\}_1+\{tl_k\}_2+ \ldots +\{tl_k\}_w$, where each $T_i^*$, $i=1, 2, \ldots, w$ consists of a set $\{tl_k\}_i$. The net result of S operating on a specific target population is to map the number of molecules, n, of that target, to the number of labels captured, k, which is a random variable.

Since target molecules randomly react with a label with probability $$\frac{1}{m},$$

the probability of a label being captured by exactly x out of n copies of a target molecule can be modeled as a Binomial distribution, $$P(x) = \frac{n!}{x!(n-x)!}\left(\frac{1}{m}\right)^x\left(1-\frac{1}{m}\right)^{n-x},$$

where x! denotes the factorial of x. The probability that a label will not be captured by any copy of the target molecule is $P(0)=(1-1/m)_n$, and the probability that a label will be captured at least once is $1-P(0)$. When $n \to \infty$ and $1/m \to 0$ in the way that $n/m \to \lambda$, $P(x)$ converges to the Poisson distribution with mean $\lambda$, i.e., $$P(x) = \frac{\lambda^x}{x!}e^{-\lambda}.$$

To compute the number of unique counters captured by n copies of a target molecule, we introduce an index random variable, $X_i$, which is 1 if a counter has been captured at least once, and 0 otherwise. The number of unique counters captured is thus $$k = \sum_{i=1}^{m} X_i$$

The mean and variance of k can be derived, $$E[k] = m\left[1 - \left(1 - \frac{1}{m}\right)^n\right] \quad (1)$$

$$\text{Var}[k] = m\left[1 - \left(1 - \frac{1}{m}\right)^n\right]\left(1 - \frac{1}{m}\right)^n + m(m-1)\left[\left(1 - \frac{2}{m}\right)^n - \left(1 - \frac{1}{m}\right)^{2n}\right] \quad (2)$$

To compute the number of unique labels captured by n copies of a target molecule, we introduce an index random variable, $X_i$, which is 1 if a label has been captured at least once, and 0 otherwise. The number of unique labels captured is thus $$k = \sum_{i=1}^{m} X_i.$$

The mean and variance of k can be derived, $$E[k] = m\left[1 - \left(1 - \frac{1}{m}\right)^n\right] \quad (1)$$

$$\text{Var}[k] = m\left[1 - \left(1 - \frac{1}{m}\right)^n\right]\left(1 - \frac{1}{m}\right)^n + m(m-1)\left[\left(1 - \frac{2}{m}\right)^n - \left(1 - \frac{1}{m}\right)^{2n}\right] \quad (2)$$

Similarly, to compute the number of labels captured by exactly x copies of a target molecule, we introduce another index random variable, $Y_i$, which is 1 if a label has been captured exactly x times, and 0 otherwise. The number of labels captured x times is thus $$t = \sum_{i=1}^{m} Y_i.$$

The mean and variance of t are, $$E[t] = \frac{m \cdot n!}{x!(n-x)!}\left(\frac{1}{m}\right)^x\left(1 - \frac{1}{m}\right)^{n-x} \quad (3)$$

$$\text{Var}[t] = A(1-A) + (m-1)m \cdot \binom{n}{2x} \cdot \left(\frac{2}{m}\right)^{2x}\left(1 - \frac{2}{m}\right)^{n-2x}\binom{2x}{x}\left(\frac{1}{2}\right)^{2x} \quad (4)$$

where $$A = m \cdot \binom{n}{x}\left(\frac{1}{m}\right)^x\left(1 - \frac{1}{m}\right)^{n-x},$$

and the combination $$\binom{n}{x} = \frac{n!}{x!(n-x)!}.$$

The equations were experimentally validated by performing numerical simulations with 5000 independent runs for each simulated case. Complete agreement with the analytical solutions was observed.

Stochastic Labeling of Individual Molecules

Methods are disclosed herein that may be applied to determining small numbers of biological molecules and their changes in response to, for example, cellular response, differentiation or signal transduction. The methods may also be used in performing a wide variety of clinical measurements. Although many analytical methods have been developed to measure the relative abundance of different molecules through sampling (e.g., microarrays and sequencing), the methods disclosed herein are able to determine the absolute number of molecules in a sample.

Figure 2A:
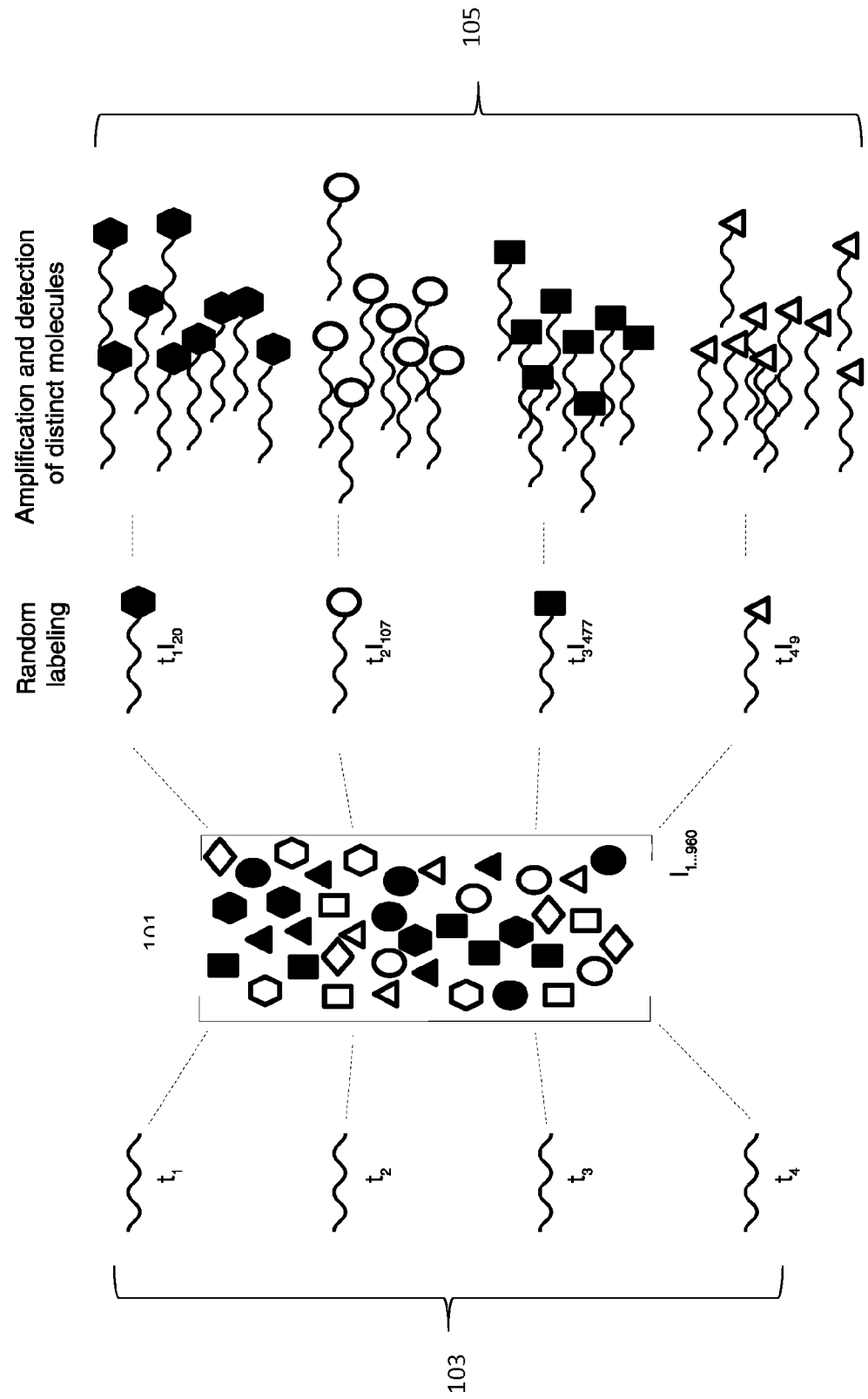
FIG. 2A shows a schematic of labeling target molecules with a pool of labels.

Methods for performing single molecule digital counting by the stochastic labeling of a collection of identical molecules are disclosed. As illustrated in FIGS. 1, 2A and 2B, each copy of a molecule (from a collection of identical target molecules 103) randomly captures a label by choosing from a large, non-depleting reservoir of diverse labels 101. The uniqueness of each labeled molecule is governed by the statistics of random choice, and depends on the number of copies of identical molecules in the collection compared to the diversity of labels. Once the molecules are labeled each has been given a unique identity and can now be separately detected. In some aspects, it is preferable to first amplify the labeled targets prior to detection so that simple present/absent threshold detection methods can be used. Counting the number of labels is used to determine the original number of molecules in solution. In some aspects, the molecules to be counted are each members of a class that shares some common feature, for example, they may each be a single copy of a particular gene sequence or nucleic acid sequence. Counting may be applied, for example, to mRNA targets, splice products, alternatively spliced products, structural RNAs, tRNA, miRNA, siRNA, microRNA and the like. Similarly, counting may be applied to DNA, for example, gene copy number, chromosome number, mitochondrial DNA, bacterial genomes, pathogen nucleic acid, viral nucleic acids and the like. Counting may be applied in research of disease in humans or other mammals or agricultural organisms, e.g. cattle, chicken, wheat, rice, fish, etc. Counting may also be applied to counting aspects of microbes, such as environmental measurements, e.g. water quality testing. The methods may be particularly useful where small numbers of items are to be counted and an accurate count is desirable rather than a relative estimate.

One embodiment is illustrated schematically in FIG. 1. The library of different label-tag sequences 101 is combined with a sample that includes an unknown number of targets of interest 103. Three different species of target are shown, 103a, 103b and 103c, present at 4, 6 and 3 copies respectively. The individual label-tag oligonucleotides from library 101 are covalently attached to the different targets to form target-label-tag molecules 105. Each target has a collection of different label-tag molecules 105a, 105b and 105c and within each target-specific collection the members differ in the label-tag oligo that is attached. On the array 107, each target is tiled in combination with all possible label-tag combinations represented with each different combination being present at a different known or determinable location on the array. In the figure each different possible combination of target and label-tag is represented by a single probe for illustration purposes, but on the array each different probe is preferably present in a feature having multiple copies of the same probe sequence. The array is divided into subarrays 107a, 107b and 107c for illustrative purposes. The upper portion 109 of the probes varies at each feature according to the different label-tag. The lower portion 113 is the same for all features of each subarray and is complementary to the target. After hybridization individual features of the array are labeled through hybridization of the complementary target-label-tag molecule to the feature. The figure shows a detectable label 111 may be used to detect features where a target-label-tag is hybridized.

FIG. 2A illustrates the attachment of different labels from the pool 101 to each of 4 different copies of the same target "t". Label 20 is attached to t1, label 107 to t2, label 477 to t3 and label 9 to t4. The labeled targets are then amplified to generate four unique populations, each population representing a single occurrence of the target in the starting sample.

FIG. 2B illustrates the method for a comparison of two samples, sample 1 and 2. The target 201 Gene A is present in 2 copies in sample 1 and 9 copies in sample 2. Both samples have non-target molecules 203. The labels 205 are combined with the samples and target molecules are attached to individual label-tag molecules in a stochastic manner. The targets with attached label-tags are hybridized to an array 211 having many features, there is a feature for each possible target-label-tag combination. Some of the features are labeled, for example, 209 and others are not, for example, 207. The labeled features indicate the presence of a specific target-label-tag combination and each corresponds to a count. As shown for gene A in sample 1 there are two labeled features so the count is 2. For Gene A in sample 2 there are 9 labeled features so the count is 9.

The stochastic labeling process can be generalized as follows for illustrative purposes. Consider a given target sequence defined as $T=\{t_1, t_2 \ldots t_n\}$; where n is the number of copies of T. A set of labels is defined as $L=\{l_1, l_2 \ldots l_m\}$, where m is the number of different labels. T reacts stochastically with L, such that each t becomes attached to one l. If the l's are in non-depleting excess, each t will choose one l randomly, and will take on a new identity $l_i t_j$; where $l_i$ is chosen from L and j is the $j^{th}$ copy from the set of n molecules. We identify each new molecule $l_i t_j$ by its label subscript and drop the subscript for the copies of T, because they are identical. The new collection of molecules becomes $T^*=l_1 t+l_2 t+ \ldots l_i t$; where $l_i$, is the $i^{th}$ choice from the set of m labels. It is important to emphasize that the subscripts of l at this point refer only to the $i^{th}$ choice and provide no information about the identity of each l. In fact, $l_1$ and $l_2$ will have some probability of being identical, depending upon the diversity m of the set of labels. Overall, T* will contain a set of k unique labels resulting from n targets choosing from the non-depleting reservoir of m labels. Or, $T^*(m,n)=\{tl_k\}$; where k represents the number of unique labels that have been captured. In all cases, k will be smaller than m, approaching m only when n becomes very large. We can define the stochastic attachment of the set of labels on a target using a stochastic operator S with m members, acting upon a target population of n, such that $S(m)T(n)=T^*(m,n)$ generating the set $\{tl_k\}$. Furthermore, since S operates on all molecules randomly, it can independently act on many different target sequences. Hence, the method can simultaneously count copies of multiple target sequences. The distribution of outcomes generated by the number of trials n, from a diversity of m, can be approximated by the Poisson equation, $P_x=^x/x! \, e^{-(n/m)}$. $P_0$ is the probability that a label will not be chosen in n trials, and therefore, $1-P_0$ is the probability that a label will occur at least once. It follows that the number of unique labels captured is given by: $k=m(1-P_0)=m(1-e^{-(n/m)})$.

Figure 2C:
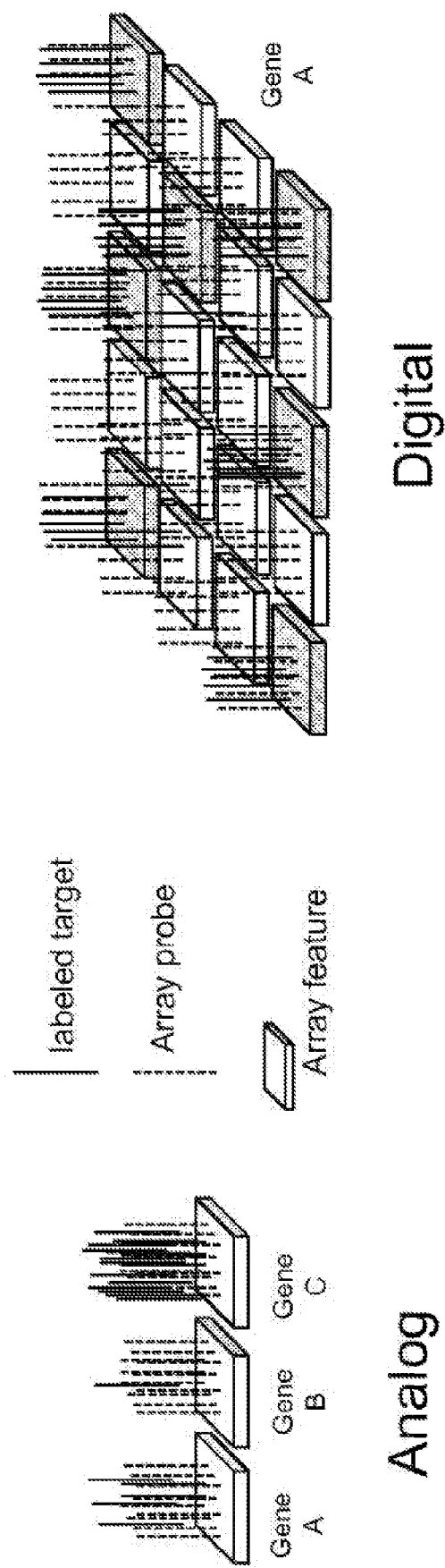
FIG. 2C shows a schematic illustration of the difference between an analog array and a digital array.

FIG. 2C illustrates a comparison of traditional analog methods where the quantity of a target is inferred from the signal strength or hybridization intensity at a single feature or a collection of target specific features and the digital counting method. The labeled target on the left is labeled generically, i.e. all targets have the same label and specificity is through target specific hybridization to the array. For digital counting on the right each target-label-tag combination is detected by a different feature, with positive features being shaded grey in the illustration. Quantity is determined by counting features with signal above background. There are 7 features that are positive for hybridization so the counting method indicates 7 copies of the target in the starting sample. These illustrations show counting for a single target, but multiple targets can be counted as well. For each different target to be counted a collection of target-label-tag features is included on the array. T1:L1, T1:L2 . . . T1:LN; T2:L1, T2:L2 . . . T2:LN etc.

Given k, we can calculate n. In addition to using the Poisson approximation, the relationship for k, n and m can be described analytically using the binomial distribution, or simulated using a random number generator, each yielding similar results (see SOM).

Figure 11:
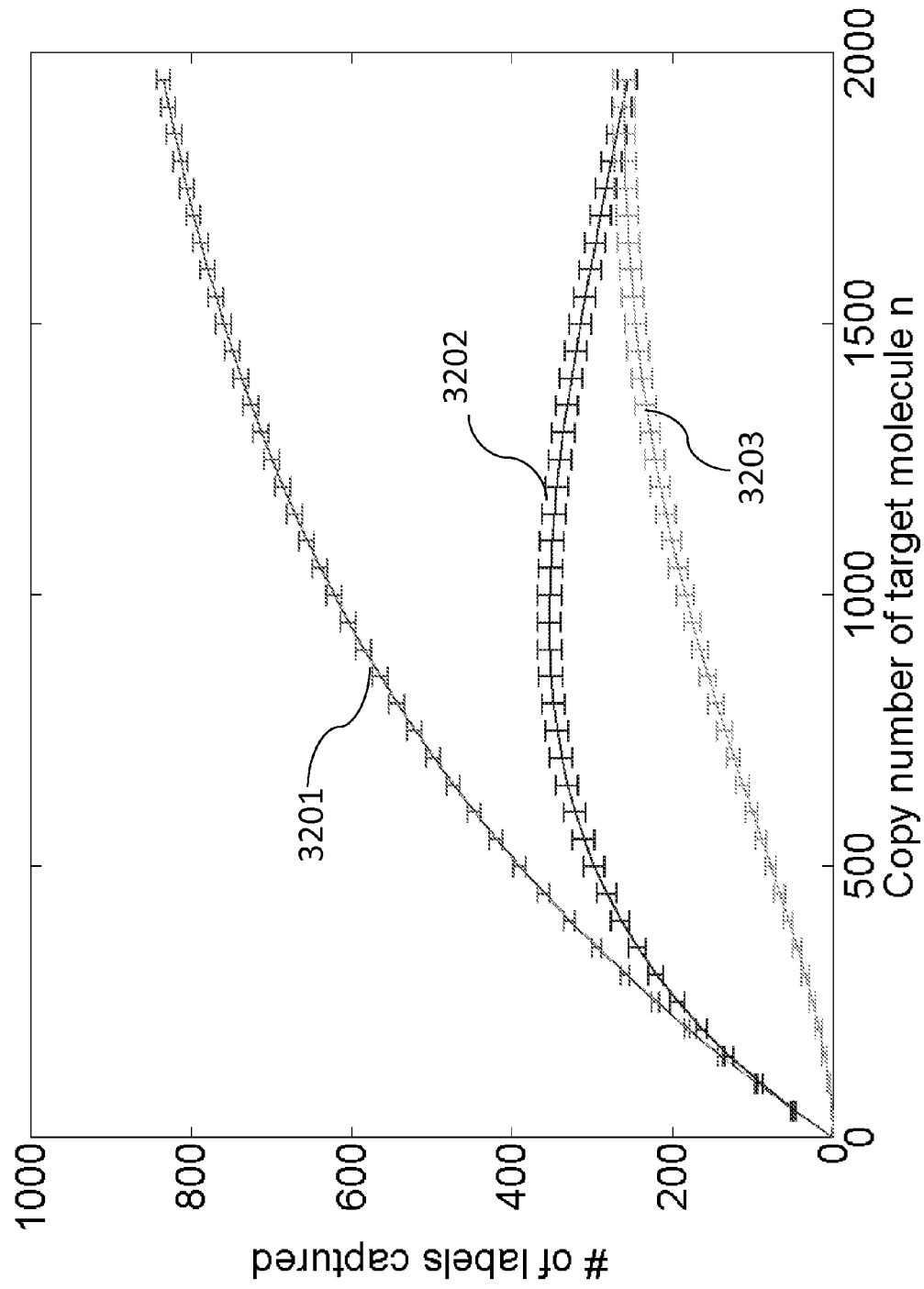
FIG. 11 is a plot of the number of labels from a non-depleting reservoir of 960 labels that are predicted to be captures at least once, exactly once or exactly twice.
Figure 15:
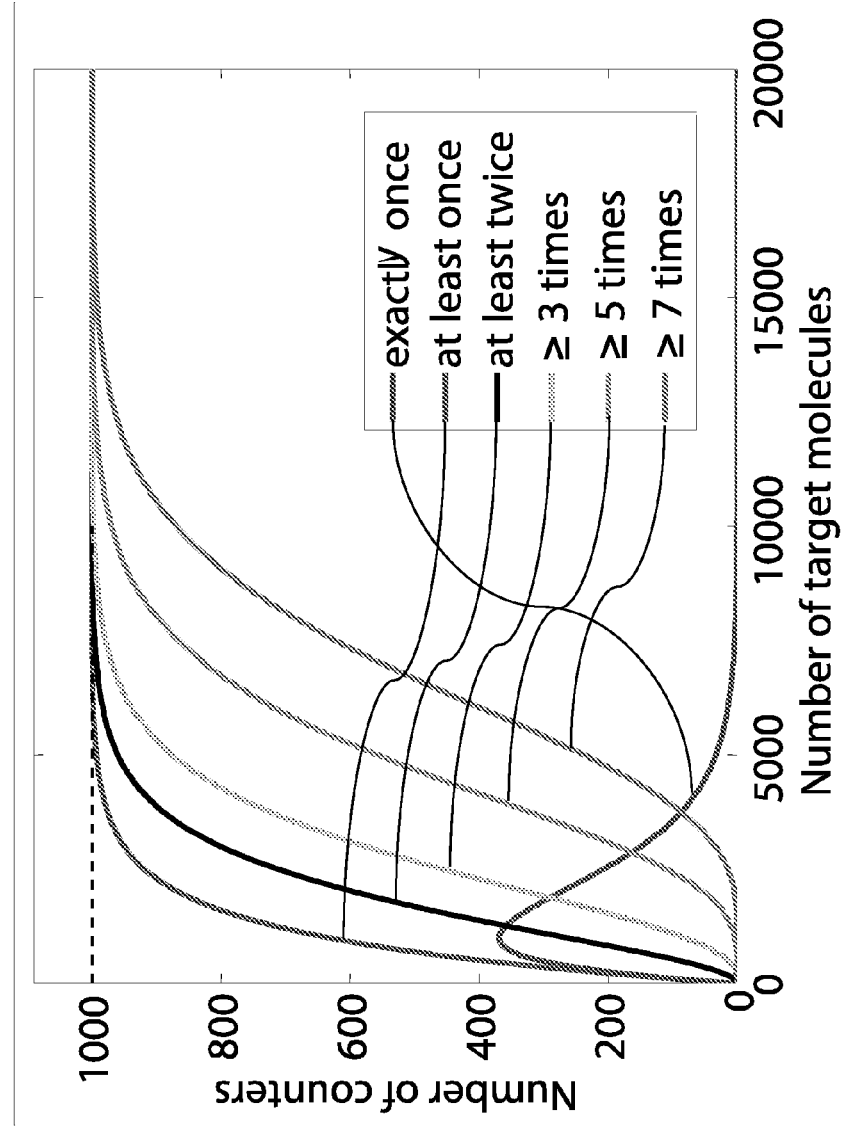
FIG. 15 shows a plot of the expected label usage (y-axis) when ligating to a given number of target molecules (x-axis).

The outcome of stochastic labeling is illustrated by examining the graph of k verses n (curve 3201 in FIG. 11) calculated using a label diversity (m) of 960. As expected, the number of unique labels captured depends on the ratio of molecules to labels, n/m. When n is much smaller than m, each molecule almost always captures a unique label, and counting k is equivalent to counting n. As n increases, k increases more slowly as given by eq. 1, and yet remains a very precise estimate of n. For example, when n/m is ~0.01, the ratio of unique labels to molecules k/n ~0.99, and we expect an increase of 10 molecules will generate 10+/−X new labels. As n/m approaches 0.5 (i.e., ~480 molecules reacted with 960 labels), k/n ~0.79 and ~6+/−X new labels are expected with an increase of 10 molecules. At high n/m, k increases more slowly as labels in the library are more likely to be captured more than once. Curve 3202 in FIG. 11 shows the number of labels chosen exactly once, and curve 3203 shows the number of labels chosen exactly twice as n increases. Curve 3201 shows the number of labels captured at least once. A more complete description of the number of times a label is chosen as a function of n is shown in FIG. 15.

The methods and examples below demonstrate that a population of indistinguishable molecules can be stochastically expanded to a population of uniquely identifiable and countable molecules. High-sensitivity threshold detection of single molecules is demonstrated, and the process can be used to count both the absolute and relative number of molecules in a sample. The method should be well suited for determining the absolute number of multiple target molecules in a specified container, for example in high-sensitivity clinical assays, or for determining the number of transcripts in single cells. The approach should also be compatible with other molecular assay systems. For example, antibodies could be stochastically labeled with DNA fragments and those that bind antigen harvested. After amplification, the number of labels detected will reflect the original number of antigens in solutions. In the examples shown here, DNA is used because of the great diversity of sequences available, and because it is easily detectable. In principle, any molecular label could be used, for example fluorescent groups or mass spectroscopy tags, as long as they are easily detected and they have sufficient diversity for the desired application. Although many of the examples refer to populations It is instructive to contrast the attributes of stochastic labeling with other quantitative methods. Microarray and sequencing technologies are commonly used to obtain relative abundance of multiple targets in a sample. In the case of microarray analysis, intensity values reflect the relative amount of hybridization bound target and can be used to compare to the intensity of other targets in the sample. In the case of sequencing, the relative number of times a sequence is found is compared to the number of times other sequences are found. Although the techniques differ by using intensity in one case and a digital count in the other, they both provide relative comparisons of the number of molecules in solution. In order to obtain absolute numbers, quantitative capture of all sequences would need to be assured; however in practice the efficiency of capture with microarray and sequencing technologies is unknown.

Digital PCR is an absolute counting method where solutions are stochastically partitioned into multi-well containers until there is an average probability of one molecule per two containers, then detected by PCR(4). This condition is satisfied when, $P_0=(1-e^{-n/c})=\frac{1}{2}$; where n is the number of molecules and c is the number of containers, or n/c is 0.693. Quantitative partitioning is assumed, and the dynamic range is governed by the number of containers available for stochastic separation. Once the molecules are partitioned, high efficiency PCR detection gives the yes/no answer and absolute counting enabled. To vary dynamic range, micro-fabrication can be used to substantially increase the number of containers (5). Similarly, in stochastic labeling, the same statistical conditions are met when $P_0=(1-e^{-n/m})=\frac{1}{2}$; where m is the number of labels, and one half of the labels will be used at least once when n/m=0.693. The dynamic range is governed by the number of labels used, and the number of labels can be easily increased to extend the dynamic range. The number of containers in digital PCR plays the same role as the number of labels in stochastic labeling and by substituting containers for labels we can write identical statistical equations. Using the principles of physical separation, digital PCR stochastically expands identical molecules into physical space, whereas the principle governing stochastic labeling is identity based and expands identical molecules into identity space.

New methods and compositions for single molecule counting employing the use of stochastic labeling are disclosed herein. In preferred aspects, a diverse set of labels is randomly attached to a population of identical molecules is converted into a population of distinct molecules suitable for threshold detection. Random attachment as used herein refers to a process whereby any label can be attached to a given molecule with the same probability. To demonstrate stochastic labeling methods experimentally the absolute and relative number of selected genes were determined after stochastically labeling 360,000 different fragments of the human genome. The approach does not require the physical separation of molecules and may take advantage of highly parallel methods such as microarray and sequencing technologies to simultaneously count absolute numbers of multiple targets. In some embodiments, stochastic labeling may be used for determining the absolute number of RNA or DNA molecules within single cells.

The methods disclosed herein may be used to take quantitative measurements of copies of identical molecules in a solution by transformation of the information to a digital process for detecting the presence of different labels. The stochastic properties of the method have been measured, and the relative and absolute digital counting of nucleic acid molecules is demonstrated. The method is extremely sensitive, quantitative, and can be multiplexed to high levels. In some aspects a microarray-based detection method is used, but the method is extendable to many other detection formats.

In some aspects, the methods are based on probability theory, where the outcome of chemical reactions occurring between a set of labeling molecules and a set of target molecules is modeled and tested. When all of the molecules in a uniform mixture of fixed volume collide and react randomly, the chemical events follow a stochastic process governed in part by the molecule concentration of each species (D. T. Gillespie, *The Journal of Physical Chemistry* 81, 2340 (1977)).

Methods for analyzing genomic information often utilize a correlation between a measurement of the amount of material associated with a location. The location can be, for example, a feature of an array that contains a specific sequence that is known or can be determined or any type of solid support such as a bead, particle, membrane, etc. A common aspect to these methods is often hybridization of a target to be measured to a complementary probe attached to the solid support. The probe may be, for example, an oligonucleotide of known or determinable sequence, but may also be BACs, PACs, or PCR amplicons.

Because of the density of different features that can be obtained using synthesis methods such as photolithography, microarrays can be applied to high density applications. For example, at feature sizes of 1 micron square an array can have about $10^8$ features per $cm^2$. Within a feature, depending on the chemistry used for synthesis, the probes are spaced typically at about 10 nm spacing resulting in about $10^4$ molecules in a $micron^2$. At approximately full saturation about 10% of those probes are hybridized with target. There are then about 640 functional molecules in an array having 1 $micron^2$ spacing between features (~800 $nm^2$ functional area). This relatively small number of functional molecules in a feature limits the dynamic range for estimating relative concentration from hybridization signal intensity.

Methods are disclosed herein to overcome the dynamic range limitations observed with small feature sizes and small numbers of molecules on the array surface, by using a counting or digital readout as a substitute for the typical analog signal resulting from array hybridization.

Methods that use signal intensity to estimate relative concentrations of targets typically label the targets with a detectable label, often after an amplification step, and through hybridization of the labeled target to the probe, the probe and thus the feature is also labeled. The amount of label is detected and correlated with a measurement of the amount of target in the sample. The estimate of amount of a given target in a sample is typically relative to other targets in the sample or to previously obtained measurements and may be based on comparison to targets present in the sample at known or expected levels or to controls within the sample. This type of analysis can and has been used successfully, for example, to estimate genomic copy number to detect copy number variation in individuals or in cell populations (see, for example, Pinkel & Albertson, *Annu. Rev. Genomics Hum. Genet.* 6, 331-354 (2005), Lucito et al. *Genome Res.* 13, 229102305 (2004), Sebat et al. *Science* 305, 525-528 (2004), Zhou et al., *Nat. Biotechnol.* 19, 78-81 (2001) and Zhao et al. *Cancer Res.* 65, 5561-5570 (2005) and US Patent Pub. Nos. 20040157243 and 20060035258) or to estimate gene expression levels (see, for example, Lockhart et al., *Nat. Biotechnol.* 14:1675-1680 (1996), and Wodicka et al., *Nat. Biotechnol.* 15:1359-1367 (1997)).

Correlating intensity of hybridization signal or signal intensity with concentration of target molecules has limitations and can typically provide only an estimate of the absolute amount of a target, and may not be an accurate count of the actual amount of target present. The estimate may be an under or over estimate, particularly when comparing different targets or different samples. This is the result of many different factors, including but not limited to, differences between probes, feature specific effects, sample specific effects, feature size (as it decreases the ability to correlate accurately decreases) and experimental variation. Much of this variation can be addressed by data analysis methods, but the methods do not provide counting of individual molecules or events and are therefore subject to estimation errors.

In preferred aspects methods are disclosed for attaching a different label-tag sequence to each molecule of a particular target sequence or more preferably a collection of target sequences of interest. For example, a sample having 100 molecules of target type 1 is mixed with an excess, for example, 1000 different label-tag sequences, forming a library of label-tag sequences under ligation conditions. Multiple copies of the library of label-tag sequences are added so there are preferably many copies of each label-tag. Different label-tag sequences from the library are appended to each of the 100 target molecules so that each of the 100 molecules of the first target sequence has a unique label-tag sequence appended thereto. This results in 100 different target-label-tag combinations. The target-label-tag molecules may then be amplified to enrich the target-label-tag products relative to other non-targets. Amplification after labeling alters the absolute amount of the target, but because each occurrence in the original sample has been uniquely labeled this will not alter the count. The amplified target-label-tag products, whether amplified or not, can then be labeled with a detectable label, and hybridized to an array of probes. The features of the array that have target-label-tag hybridized thereto can be detected, for example, by labeling the hybridization complex with a fluorescent label and detecting the presence of signal at the features. In this example, because there are 1000 different labels possible and a single target being analyzed, there are 1000 different possible label-target sequences that might be generated so an array having a different feature for each of the 1000 different possibilities can be used. Assuming each target is labeled and no label is used twice, 100 of the 1000 different features should be detectable, indicating the corresponding label has been used.

Consider 1 copy of a target molecule in solution identified as $t_1$. React this target against a set of 10 labels, $L_m=\{l_1, l_2, \ldots l_{10}\}$. Each label has a 0.1 probability of being chosen. Next consider multiple copies of the target, $t_n$, reacted against the set of $L_m$ (assume non-depleting reservoir of labels). For simplicity, consider 3 copies of t: $t_1$, $t_2$ and $t_3$. Target $t_1$ will choose a label, $t_2$ has a 0.9 probability of choosing a different label, $t_3$ has a predictable probability of choosing the same label as $t_1$ or $t_2$. For n copies choosing from m labels, outcomes can be modeled by the binomial distribution as discussed above. For 3 targets and 10 labels, the probability of a label not being chosen, $P_0$ is $(1-(1/10))^3=0.729$. The probability $P_1$ of being chosen exactly once is $(3/10)(1-(1/10))^2=0.243$. The probability of being chosen twice, $P_2$ is 0.027 and the probability $P_3$ of being chosen 3 times is 0.001. Since $P_0$ is the probability of not being chosen, $1-P_0$ is the probability of being chosen at least once. We define $k=m(1-P_0)$ as the number of labels we expect to see in an experiment. Conversely, if we know m, and observe k we can solve for the number of molecules. In the previous example where n=3 and m=10 we expect to see $10(1-P_0)$ or 2.71 labels as our most probable outcome. Increasing m dramatically increases our counting efficiency, accuracy and dynamic range, e.g. for m=1,000, k (number of labels expected for n=10, k=9.96, for n=20, k=19.8.

Once the target molecules are labeled with the counter they can be amplified freely without impacting the counting since the readout is either yes, indicating detection or no indication not detected. In one aspect, a simple detector having m elements for each target sequence can be constructed. The detector may be an array. An array having $10^8$ features or elements could assay $10^5$ different targets using $10^3$ different labels, for example. Other detection methods do not require individual elements for each counter, for example, sequencing.

In preferred aspects the "counter library" or "label-tag library" has approximately the same number of copies of each label-tag in the library. The label-tag sequences are not target specific, but are like the tags that have been used for other tagging applications, for example, the Affymetrix GENFLEX tag array. Preferably all label-tags in a set of label-tags will have similar hybridization characteristics so that the label-tags of the set can be detected under similar conditions.

For each target there are a series of features on the array, preferably one feature for each label-tag. In each of these features the portion of the probe that hybridizes to the target (or target complement) is the same but the label-tag complement is different in each feature. For example, to detect a first target RNA, "RNA1", there would be a series of features each having a different probe (RNA1-tag1, RNA1-tag2, ... RNA1-tagN). For each target to be detected there is a similar set of features, e.g. RNA2-tag1, RNA2-tag2, ... RNA2-tagN. The set of label-tags is N tags and it is the unique combination of the label-tag with the target sequence that creates a novel sequence to be detected, for example, by hybridization.

Label-tag attachment to individual targets is a stochastic process whereby the probability of any given label-tag being attached to any target is stochastic. There is a random selection of label-tags by attaching the label-tags to the end of a known target sequence in a sequence independent manner. The label-tag is attached without requirement for it to hybridize to any portion of the target so there is no or minimal bias as to which label-tag sequence is attached. Individual molecules all look the same for the purpose of attachment of the label-tag.

The label-tag may be attached to the target by any method available. In one embodiment, the label-tag is attached by ligation of the label-tag to one of the ends of the target. In preferred aspects the probes of the array are complementary to a predicted junction between target and label so it is preferable that the labels are attached to all occurrences of a target at the same position. This is facilitated if the termini of each occurrence of a selected target are the same and are known. In one aspect, target occurrences are fragmented with a restriction enzyme so that defined ends of known sequence are formed.

After label-tag attachment in some embodiments the target-label-tag segment is amplified. Attachment of universal primers to either end followed by PCR amplification is one method for amplifying. The universal primers may be added along with the label or at a subsequent ligation step.

For RNA targets an RNA ligase, such as T4 RNA ligase may be used. T4 RNA ligase 1 catalyses the ligation of a 5' phosphryl-terminated nucleic acid donor to a 3' hydroxyl-terminated nucleic acid acceptor. Substrates include single-stranded RNA and DNA. See, for example, Romaniuk, P. and Uhlenbeck, O. (1983) R. Wu, L. Grossman and K. Moldave (Eds.), *Methods Enzymol.,* 100, pp. 52-56. New York: Academic Press and Moore, M. J. and Sharp, P. A. (1992) *Science,* 256, 992-997. RNA targets may also be circularized and used as template for rolling circle amplification using an enzyme having reverse transcriptase activity. T4 RNA ligase 1 may be used for circularization of RNA by ligating the ends of the molecule together. T4 RNA ligase 1 can also be used to ligated RNA to DNA.

Full-length mRNA can be selected by treating total or poly(A) RNA with calf intestinal phosphatase (CIP) to remove the 5' phosphate from all molecules which contain free 5' phosphates (e.g. ribosomal RNA, fragmented mRNA, tRNA and genomic DNA). Full-length mRNAs are not affected. The RNA can them be treated with tobacco acid pyrophosphatase (TAP) to remove the cap structure from the full-length mRNA leaving a 5'-monophosphate. A synthetic RNA adapter can be ligated to the RNA population. Only molecules containing a 5'-phosphate, (i.e. the uncapped, full-length mRNAs) will ligate to the adapters. Preferably the adapter has a variable label sequence, and may also have a constant sequence for priming. Preferably, the constant sequence is 5' of the variable sequence. In some aspects, the adapter ligated mRNA may then be copied to form a first strand cDNA by, for example, random priming or priming using oligo dT. The cDNA may subsequently be amplified by, for example, PCR.

T4 RNA ligase may also be used for ligation of a DNA oligo to single stranded DNA. See, for example, Troutt et al., (1992) *Proc. Natl, Acad. Sci. USA,* 89, 9823-9825.

In other aspects, the ligated target-label-tag molecule may be enriched in the sample relative to other nucleic acids or other molecules. This enrichment may be, for example, by preferentially amplifying the target-label-tag methods, using for example, a DNA or RNA polymerase, or by degrading non target-label-tag molecules preferentially.

In one aspect, the target-label-tag molecule may be nuclease resistant while the unligated target and unligated label molecules may be nuclease sensitive. A nuclease can be added to the sample after ligation so that ligated target-label-tag molecules are not digested but non-ligated molecules are digested. For example, the targets may be resistant to a 5' exonuclease (but not a 3' exonuclease) while the labels are resistant to a 3' exonuclease but not a 5' exonuclease. Ligating target to label generates a molecule that is resistant to 5' and 3' exonuclease activity. After ligation the sample may be treated with a 5' exonuclease activity, a 3' exonuclease activity or both 5' and 3' exonuclease activities. For examples of nucleases see Rittie and Perbal, *J. Cell Commun. Signal.* (2008) 2:25-45, which is incorporated by reference (in particular see Table 5). Exo VII, for example degrades single stranded DNA from both the 5' and 3' ends so the sample could be treated with Exo VII after ligation to degrade molecules that are not ligation products.

In another aspect amplification may include a rolling circle amplification (RCA) step. See for example, Baner et al. (1998) NAR 26:5073, Lizardi et al. (1998) Nat. Genet. 19:225, Fire and Xu, (1995) PNAS 92:4641-5, Zhao et al. Angew Chem Int Ed Engl. 2008; 47:6330-6337 and Nilsson et al. (2008), Trends in Biotechnology, 24:83-88. The targets may be ligated so that they have a label and a universal priming (UP) sequence attached to the 5' end of the targets. The UP-label-target is then ligated to form a circle. A primer complementary to the UP is then hybridized to the circles and extended using a strand displacing polymerase. The resulting amplification product contains multiple copies of the complement of the circle, UP-target-L.

In another aspect, targets may be labeled in a copying step. For example, a primer having a 3' target specific region and a 5' variable label region may be hybridized to the targets, either RNA or DNA, and extended to create a single complimentary copy of the target. Each extension product will have a different label and the junction between the label and the target specific region is known. The extension may be performed in the presence of nuclease resistant nucleotides so that the extension product is resistant to nuclease but the unextended primers are not. After extension the reaction is treated with a 3'-5' exonuclease activity to digest unextended primer. Exonuclease I, for example, removes nucleotides from single stranded DNA in the 3' to 5' direction and Exo III removes nucleotides from the 3' termini of duplex DNA. Exonuclease T (or RNase T) is a single-stranded RNA or DNA specific nuclease that requires a free 3' terminus and removes nucleotides in the 3' to 5' direction. The extension products are then detected by hybridization to probes that are complementary to the primers and include the unique label portion and the constant target specific portion. If the target is RNA it can be digested with RNase H after extension. The extension product may also be amplified before hybridization.

In some aspects the probability that any two targets are labeled with the same label may be decreased by using two or more labeling steps. For example, a first labeling step where each target has a label selected from a set of labels followed by a second labeling set using the same set of labels. The first labeling event will be independent of the second so the probability that the first and second labeling events will both be the same in two independent targets is the product of the probability of two targets having the same label in either step. If there are N possible labels, and the first target is labeled first with label N1 and then with label N4, the probability that a second target will be labeled also with N1 and then N4 is $1/N^2$. So if there are 100 different labels, the probability that two targets will be labeled with the same label in the first round and the same label in the second round is 1/10,000.

In another aspect a first round of labeling may be done with 16 probes (for example, all possible 2 base combinations) and then a second round of labeling is done using the same 16 probes. The chance of any one probe attaching to a given target occurrence in the first round is 1 out of 16, the chance that the same probe will attach to the second target is 1/16 and the chance that the same two probes will attach is $1/16 \times 1/16$ or 1/256.

In another aspect reversible terminators are used to add a sequence to the end of each target being counted. For example, a 6 base sequence may be added and the chance of two being the same is 1 in $4^6$ or 1 in 4096. See, for example, WO 93/06121 and U.S. Pat. No. 6,140,493 which disclose stochastic methods for synthesizing random oligomers.

There is a finite set of labels, $L_{1-x}$ and each target to be detected is present in the sample at a certain integer occurrence ($T1_{1-t}^1, T2_{1-t}^2, \ldots TN_{1-t}^n$). In a preferred aspect, the method is used to count the number of each of the different targets, (e.g. how many occurrences of T1, how many of T2, . . . how many of TN) in the sample. The targets are independently labeled with the label molecules. Labeling is stochastic, so that any given target occurrence can be labeled with any one of the labels. For example, T1-1/L689, T1-2/L3, T1-3/L4,567 and so on. For Target 2, any given occurrence can also be labeled with any of the label molecules. This might generate, for example, (T2-1, L5), (T2-2, L198), (T2-3, L34) and so on. There are multiple copies of each label so T2-1 might be labeled with L5 and T1-500 may also be labeled with L5.

The methods disclosed herein may be used to measure random cell-to-cell variations in gene expression within an isogenic population of cells. Such variation can lead to transitions between alternative states for individual cells. For example, cell-to-cell variation in the expression of comK in *B. subtilis* has been shown to select cells for transition to the competent state in which genes encoding for DNA uptake proteins are expressed. See, Maamar et al. *Science* 317:526-529 (2007) which is incorporated herein by reference.

Figure 6:
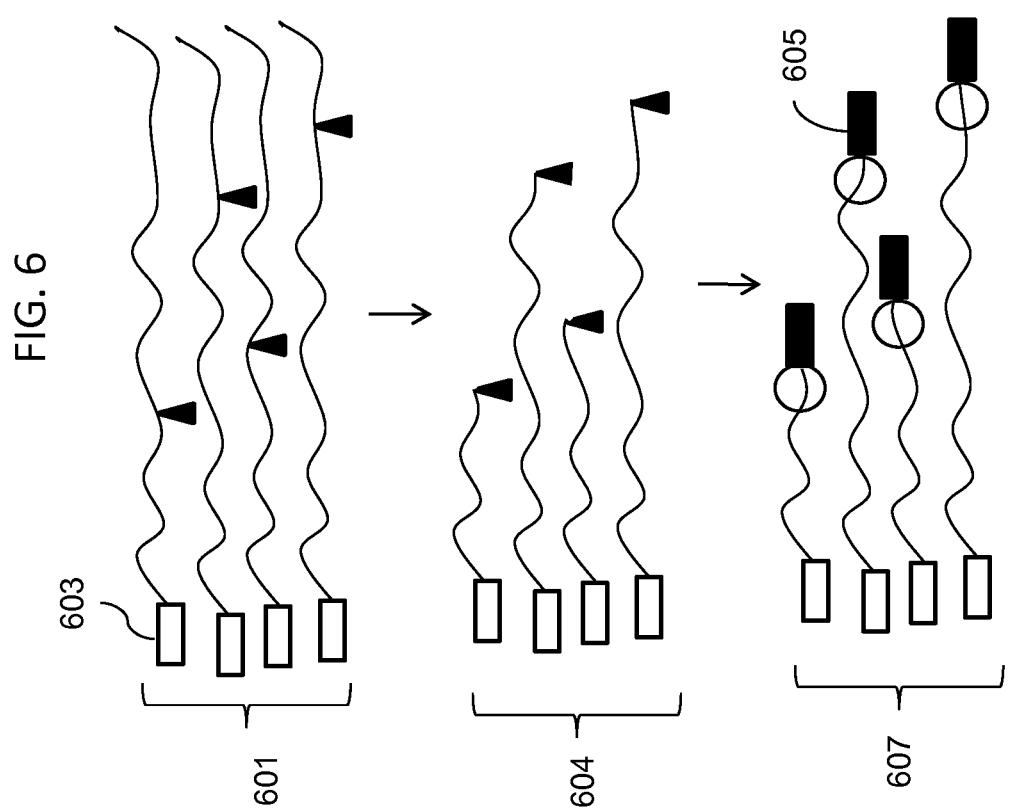
FIG. 6 shows a method for stochastic counting by fragmentation where the unique end of the fragment is the label used for counting.

In some aspects the labels are generated within the target to be counted. For example, the label may be a unique cleavage site in a target fragment as shown in FIG. 6. Each of the copies of the target to be counted 601 have a common sequence at one end identified in the figure as 603. This may be a common sequence that has been added to the targets through ligation or primer extension or it may be a naturally occurring sequence in the target. The targets are fragmented randomly, for example by shearing or sonnication resulting in cleavage at the points indicated by the arrows to generate cleavage products 604. Cleavage is at a different and unique site in each of the fragments and results in a unique sequence in the target immediately to the left of the point of cleavage in the illustration (indicated by circles in fragments 607). This unique sequence can function as a label for the disclosed methods. A second common sequence 605 may be attached to each of the targets immediately downstream of the cleavage point, through for example ligation of an adaptor sequence. The resulting targets 607 can be analyzed directly to determine how many unique sequences are present and using this number as an indication of the number of targets in the starting sample. This is illustrated for nucleic acids, but could similarly be applied to proteins or other contiguous strings of monomers or units that are assembled in a non repeating pattern.

Figure 7:
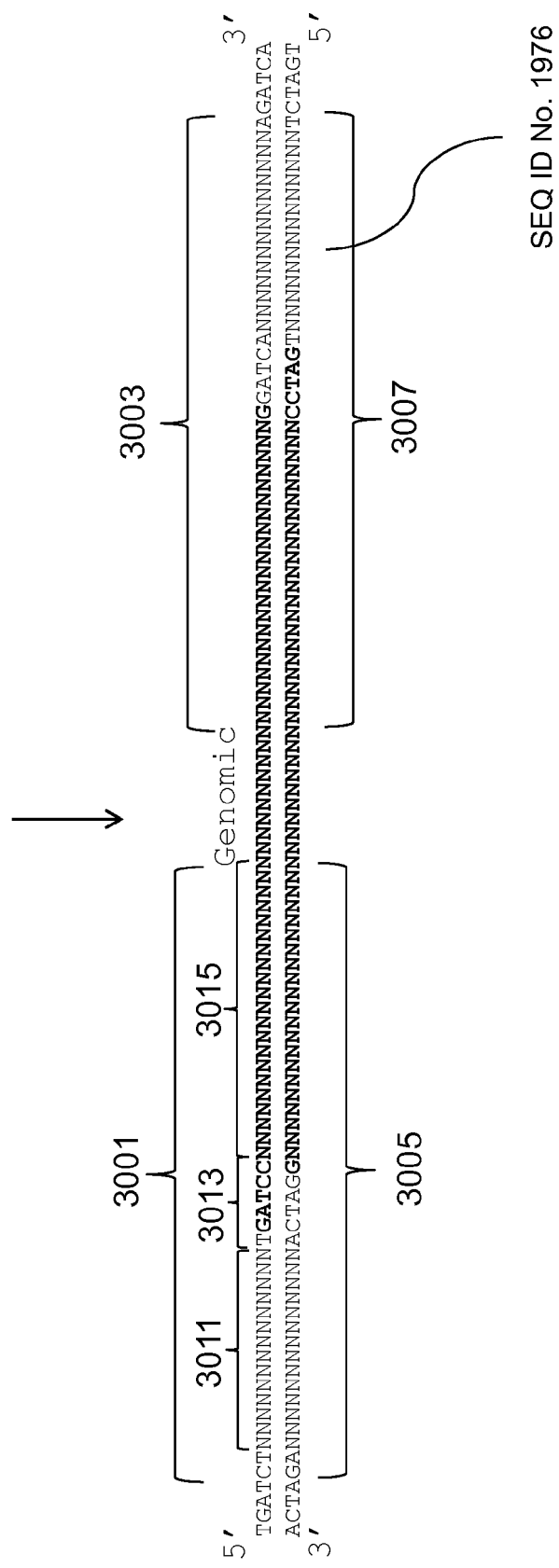
FIG. 7 provides an example of a genomic target ligated at either end to a label adaptor.

FIG. 7 shows a strategy for selecting probes for target fragments. For a double stranded fragment there are 4 possible junctions that can be targeted with array probes 3001, 3003, 3005 and 3007. Each of these junction regions as shown has a counter region 3011 denoted by N's, a fixed sequence 3013 that is defined by the restriction enzyme used for fragmentation and a target specific region 3015. The region 3015 is shown as N's but in preferred aspects it is a known and predictable sequence of the target that is adjacent to the selected restriction site. In a preferred aspect, the array probes are complementary to at least a portion of 3011, a portion of 3015 and all of 3013. For each target sequence-counter combination there are 4 different probes that could be included on the array. For example, if the targets are 10 loci from each of 4 chromosomes and 4 probes per fragment are included for 1200 different labels (1000 specific plus 200 nonspecific) the array would have 192,000 total probes (4×10×4×1200).

In some aspects methods for selecting a collection of labels optimized for use in the disclosed methods is contemplated. For example, a list of all possible 14 mers may be used as a starting pool ($4^{14}$ is ~268 million different sequences). Different label lengths can be used resulting in different numbers of starting sequences. Eliminate all labels that are not at least 50% GC content. Eliminate all labels that do not use each of the 4 possible nucleotides at least twice. Eliminate all labels that have more than two Gs or Cs in tandem, e.g. a probe with GGG or CCC would be eliminated, or with more than three As or Ts in tandem, e.g. AAAA or TTTT would be removed. Remove labels that contain a selected restriction site. Remove labels having a Tm that is outside of the range (38.5 to 39.5° C.). In other embodiments the range may be about 38 to 40, 38-39, or 39-40. Remove probes that have self complementarity beyond a selected threshold. Perform a hierarchical clustering to maximize sequence differences between labels to minimize cross hybridization, same label to same probe. Minimize self-complementarity within the collection to reduce tendency of two labels binding to each other.

Figure 8:
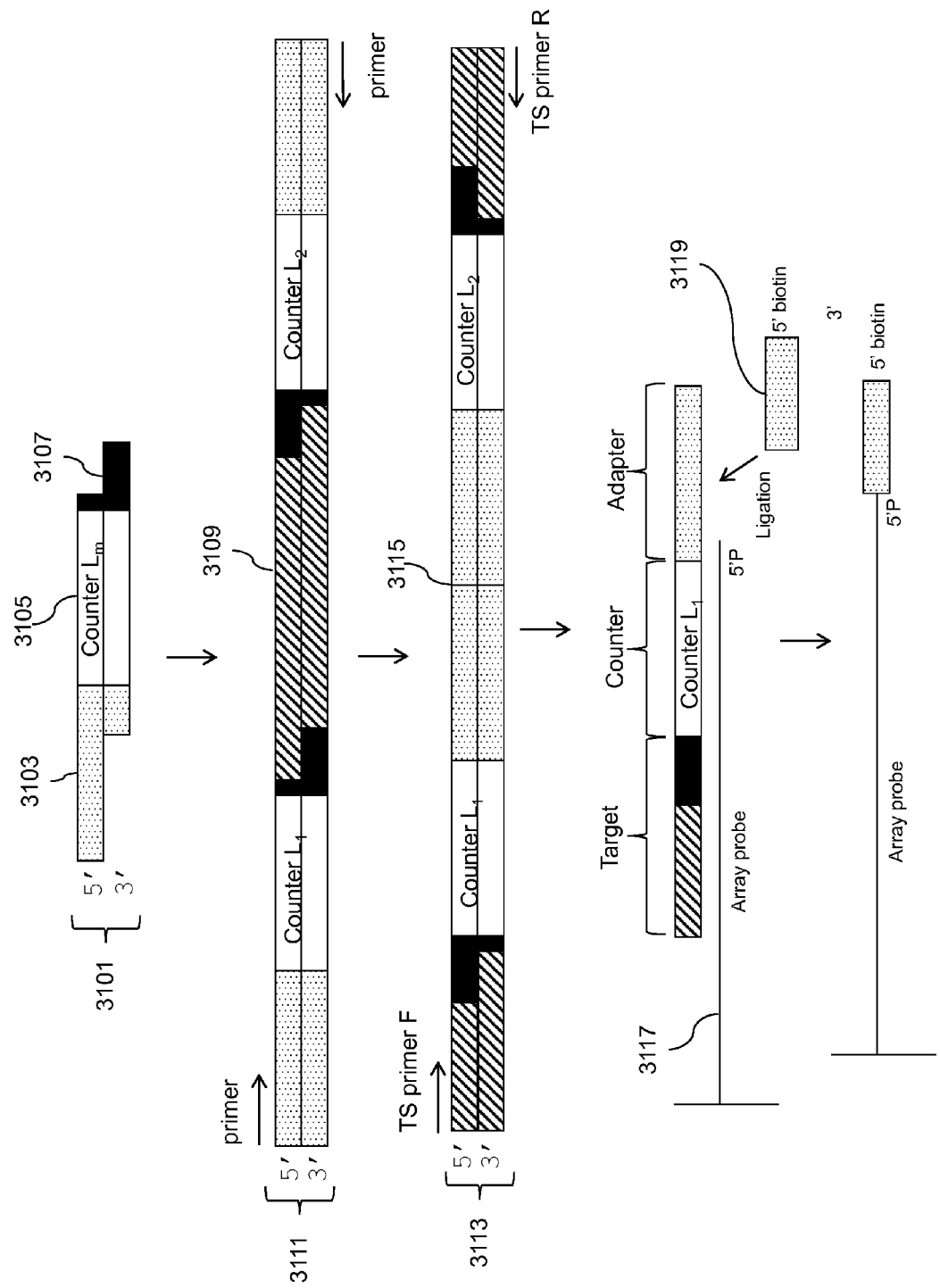
FIG. 8 shows a schematic of the arrangement and position of the adaptors, PCR primers, and the biotinylated array-ligation probe in one exemplary sample prep method.

FIG. 8 shows a counter adaptor 3101 that includes a counter region 3103, a constant region for priming 3105 and a sticky end 3107 for ligation to an overhang created by restriction digestion, for example with BamHI. After ligation of the adaptors 3101 to the target fragment 3109 there are two adaptors ligated to the target fragment, one at either end. It is probable that the counters on the two ends will be different although there is a predictable probability of having the same counter ligated to both ends of the same fragment. After adaptor ligation the fragment 3111 can be amplified by PCR using a common primer to the 3103 region of the adaptor. The adaptor may first be filled in to make it double stranded. The PCR amplification may be used to preferentially amplify fragments of a selected size range, for example, 300 to 2 kb. Smaller fragments are not amplified as efficiently because of self complementarity between the ends of the individual strands (capable of forming a panhandle structure that inhibits amplification) and longer fragments (longer than about 3 kb) also don't amplify well.

After circularization, the uncircularized fragments can be digested using an exonuclease, for example. The circularized fragments can be amplified using target specific primers to generate amplification product 3113. In the figure the target specific primers are identified as TS primer F and TS primer R. Whereas the primers used to amplify 3111 are common to all adaptor ligated fragments and will amplify all fragments that are in the size range to be amplified using PCR, the TS primers are specific for selected targets to be analyzed. The amplification product 3113 has in the 5' to 3' direction, target specific sequence, overhang sequence, a first counter, first adaptor sequence, circularization junction 3115, second adaptor sequence, second counter, second overhang sequence and a second target specific sequence. The first and second counter are different (although they may be the same at a low probability) and the first and second target sequence are different. The product 3113 or preferably fragments thereof can be detected by a variety of methods, for example, an array of probes as exemplified by probe 3117 can be used. The array probe 3117 is complementary to a region of the target, the overhang region and the counter. When hybridized the target will have an overhanging single stranded region that corresponds to the adaptor sequence. A labeled probe 3119 that is complementary to one strand of the adaptor can be hybridized and the ligated to the array probe as shown, and as described below.

Figure 9:
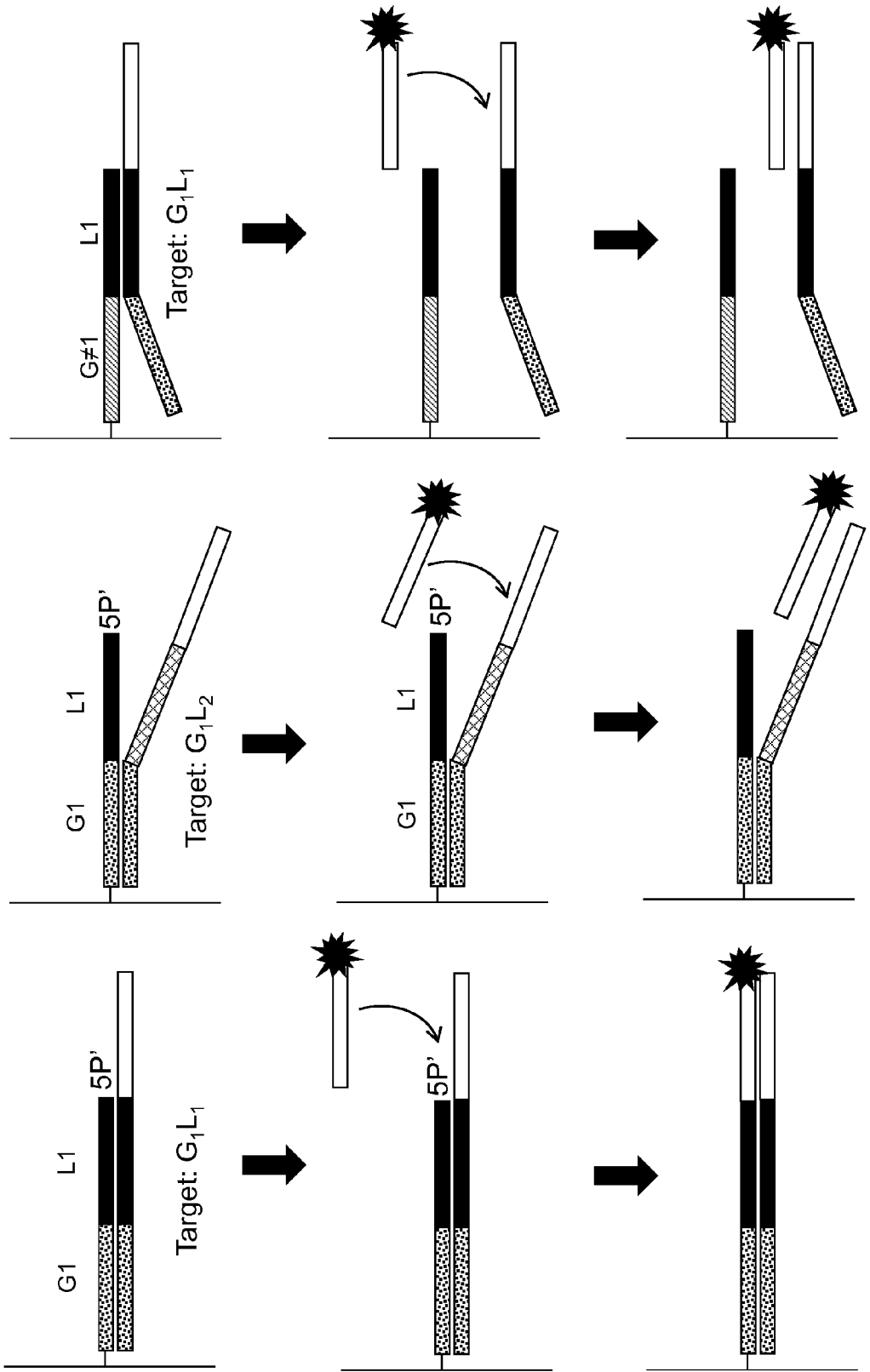
FIG. 9 is a schematic of a method for using ligation based read out on arrays to detect labeled targets and minimize partial target hybridization.

FIG. 9 shows a method for reading out the labeled targets on arrays. On the left, the target with $G_1$ ligated to $L_1$, "$G_1L_1$", is shown hybridizing to the complementary array probe over the entire length of the probe. On the right target $G_1$ ligated to label $L_2$ is shown partially hybridized to the $G_1L_1$ probe on the array. On the left the biotin labeled constant segment can hybridize to the $G_1L_1$ target and ligate to the 5' end of the $G_1L_1$ array probe. The constant segment can hybridize to the $L_2$ segment but will not ligate to $L_1$. This allows for labeling of properly hybridized target-label pairs with both hybridization and ligation discrimination. The lower panel shows an example where the target or G portion is not matching with the probe on the array. This will not ligate efficiently because it hybridizes less stably.

The left panel shows the results when target $G_1$ ligated to label $L_1$ to form $G_1L_1$ hybridizes to the complementary $G_1L_1$ probe on the array. The constant region (in white) can hybridize to its labeled complement so that the 3' end of the labeled complement is juxtaposed with the 5' end of the $L_1$ region of the probe on the array and the ends can be ligated. In the center panel the target hybridizing to the $G_1L_1$ probe is non-cognate, the label region is $L_2$ and not $L_1$ so it does not hybridize to the $L_1$ region of the probe. The labeled oligo can hybridize to the partially hybridized target but it is not juxtaposed with the 5' end of the $L_1$ region of the probe so it should not ligate to the probe. In the right panel the target shown hybridized has the $L_1$ region and is complementary to the array probe at that region, but the array probe has a G region that is not $G_1$ so the $G_1L_1$ target does not hybridize. The labeled oligo can hybridize to the target but because the L1:L1 region is short the duplex is not stable and the labeled oligo does not ligate to the end of the array probe.

If you have N targets T ($T_1, T_2, \ldots T_N$) and each is present at a number of copies C($C_1, C_2, \ldots C_x$) where X varies from target to target ($X_{T1}, X_{T2}, \ldots X_{TN}$) and you ligate to a set of Y different labels ($L_1, L_2, \ldots L_Y$) then you generate, for example, $T_1C_1L_1, T_1C_2L_2, \ldots T_NC_xL_{xT1}$, where X<<<Y). So, for example, if T1 is gene A and T2 is gene B and gene A is present in the sample at 500 copies and gene B is present at 100 copies, each copy of gene A, 1 to 500, will be attached to a different label (so there will be ~500 different labels attached to the gene A copies), and each copy of gene B, 1 to 100, will be attached to a different label.

A method for counting the number of occurrences of each of a plurality of same targets in a mixture of targets comprising multiple occurrences of each type of a plurality of different targets. In preferred aspects, the mixture of targets is a nucleic acid sample that contains different amounts of multiple target sequences. For example, there may be target sequences 1, 2, 3, 4 and 5 that are expression products from 5 different genes, occur in the sample as follows: 1000 copies of target 1, 100 copies of target 2, 500 copies of target 3, 10 copies of target 4 and 50 copies of target 5. The targets are preferably of known sequence and are treated so that they may be ligated to a label-tag sequence.

FIG. 1 shows one embodiment of the method. Labels or counters 101 are combined with assay targets 103 so that each target is combined with one label to form label-targets 105. The process of combining an individual target with individual label molecules is a stochastic process. The number of labels each target type combines with is directly proportional to the number of individual targets of that target type or the copy number of the target. The number of labels is counted by hybridization to arrays where individual label-targets are detected at different features.

The targets are mixed with a collection of label-tag sequences, each label-tag being a different sequence and the collection having a number that is preferably 10 times the number of copies of the most abundant target to be counted. In a preferred aspect, the label-tags are a collection of known sequences such as a collection of all possible timers ($N_6$). Each of the label-tag sequences is present in multiple copies in the mixture, but all are present at approximately equal amounts. The label-tag sequences are ligated to the targets. Ligation is random so that any given label-tag has about the same probability of ligating to any one target occurrence. So if there are 1000 different targets each could be ligated to a different label-tag sequence and the probability that any two target occurrences will have the same label-tag ligated is low. Because the ligation is a random stochastic process there is a known probability that if there are C copies of a given target and N different label-tags that any two copies of a target T will have the same label.

T1, T2, . . . TN. C1, C2, . . . CX, L1, L2, . . . LY where T are the different targets and there are N different targets, C are the different copies of a target and there are X copies of that target and L are the different label label-tags and there are Y label tags. X varies for each target and determining X is one of the objects of the present invention. The relationship between X and Y determines the probability that two C's will have the same L. In preferred aspects Y is greater than X for each target to be counted. This reduces the probability of undercounting due to double labeling. If C1 and C2 of T1 are both labeled with L3 both copies will be counted as a single occurrence, resulting in under counting. Undercounting can also be adjusted for by estimating the number of copies that are likely to be multiply labeled and adjusting the final count upwards to take those into account. For example, if there is a likelihood that 5 of 1000 copies will be labeled with the same label tag then the final number should be adjusted up by 0.5%.

In preferred aspects, the detection is by hybridization to an array of probes. The array has a collection of features for each target that includes a different feature for each label tag. For example, if there are X label tags there are X features for each target, T1L1, T1L2, . . . T1LX and the same for target 2, T2L1, T2L2, . . . T2LX, out to TNL1, TNL2, . . . TNLX. The number of features of the array is on the order of X times N. Each probe has a target complementary sequence and a label tag complementary sequence. Within a set of probes for a given target the target segment of the probe would remain constant and the label tag portion varies from feature to feature so that each label tag sequence is represented by at least one feature for each target.

In one aspect, the methods may be used to count the number of copies of each of a plurality of targets in a sample. The amount of target containing sample mixed with the label tags may be diluted so that the number of copies of each target to be counted is less than the number of label tags. For example, if the targets to be counted are present at about 1,000 copies per cell and there are 10,000 label tags you want to have the amount of sample in the mixture to be about the equivalent of one cell's worth of RNA. You can mix that with multiple copies of each label-tag, but you want to keep the absolute number of copies of target below the number of types of label tag sequences. Dilution of the sample and use of an appropriately small amount of starting material may be used. If a target sequence is present at low copy number per cell it is possible to use the nucleic acid from a larger number of cells. For example, to measure the DNA copy number of a chromosomal region relative to other chromosomal regions the expected copy number is low (e.g. 2 for normal) so if there are 10,000 different label tags, the number of genomes that can be added to the sample for attachment of label tags can be high, e.g. 500 to 1000.

In one aspect, the methods are used to identify regions of genomic amplification and chromosomal abnormalities. For example, the methods may be used to detect trisomy. Most of the chromosomal regions will be present in 2 copies per cell and the region of trisomy will be present in 3 copies per cell. You would expect to observe a 3:2 ratio in your count. For example, if you have 500 genomes you would have 1000 copies of most regions and 1500 copies of the trisomy regions. Small errors in the counting, resulting from undercounting, would have little or no effect on the counting.

In some aspects, controls of known copy number may be spiked in to a sample to determine accuracy.

Stochastic labeling of $t_{1,N}$ (collection of essential identical molecules of copy 1, 2 . . . N of target 1) by $L_{1,m}$ (effectively an infinite reservoir of diversity m when m is much greater than N). This allows for complete or near complete resolution of members of $t_{1,N}$, by imparting separate identities to the members of the collection of $t_{1,N}$ (provided that M is sufficiently smaller than N in the labeling). This provides for a stochastic or random projection of $t_{1,N}$ onto $L_{1,m}$. In some aspects $L_{1,m}$ is a library and the members of the library that are associated with $t_{1,N}$ can be counted to determine the number of copies of the target. In some aspects the methods can be described as indexing the members of the target. This provides a method to follow individual molecules that are members of a type of molecule that would not otherwise be distinguishable one from another.

Because stochastic labeling can impart identifiability to otherwise non-identifiable molecules it can impart identifiability to any two targets that may be very similar, but different. Examples of targets that may be highly similar but could be separately counted using the disclosed methods, include, for example, alternative splice forms of a gene, and sequences that have one or more variations, including a variation in a single base (e.g. SNP or indels (insertion or deletions of short regions, e.g. 1-5 bases). In some aspects the methods impart a clonal labeling, that allows a single copy to be separately detected and separately isolated from the solution.

Some nucleic acid sequencing reactions use methods that stochastically attach targets to a solid support followed by amplification of the attached target and analysis. The target attaches in an unknown location and the location can be determined by sequencing the amplified target at specific locations. In contrast, the disclosed methods provide for clonal amplification of known targets in a known location. The stochastic nature of the formation of the target-label-tag molecule provides a mechanism for isolating single occurrences of selected targets that can be subsequently amplified and analyzed. In some aspects the label can be used as a handle for isolating clonal populations of targets. The labeling step generates an indexed library that has a variety of applications. For example, the indexed library could be used for sequencing applications. The method adds distinguishability to any set of molecules, even molecules that are not distinguishable by other mechanisms because they may share common regions or even been identical. The indexed library can be stored and used multiple times to generate samples for analysis. Some applications include, for example, genotyping polymorphisms, studying RNA processing, and selecting clonal representatives to do sequencing.

In some aspects the methods are used to stochastically label a polyclonal antibody population. This may be used to identify different polyclonal populations.

The methods may be used to convert an analog readout of hybridization signal intensities on arrays into a measurable process that can be scored digitally on the arrays. The method leverages a random process where the tagging of assayed molecules is governed by stochastic behavior. In a random process, the more copies of a given target, the greater the probability of being tagged with multiple labels. A count of the number of incorporated labels for each target can approximate the abundance level of a given target of interest. The ability to count labels on microarrays would be a clear cost-advantage over the other existing techniques.

Serial analysis of gene expression (SAGE) is another method for analysis of gene expression patterns. SAGE relies on short sequence tags (10-14 bp) within transcripts as an indicator of the presence of a given transcript. The tags are separated from the rest of the RNA and collected. The tags can be linked together to form long serial molecules that can be cloned and sequenced. Quantitation of the number of times a particular tag is observed provides an estimate of the relative expression level of the corresponding transcript, relative to other tagged transcripts. See, for example, Velculescu et al. Science 270, 484-487 (1995) and Velculescu et al. Cell 88 (1997). Again this method provides a relative estimate of the abundance of a transcript and not an actual count of the number of times that transcript appears. Other methods based on counting and estimating relative abundance have also been described. See, for example, Wang et al. *Nat. Rev. Genet.* 10, 57-63 (2009). Additional methods for digital profiling are disclosed, for example, in U.S. Patent Pub. 20050250147 and U.S. Pat. No. 7,537,897.

A stochastic counting assay system as described herein can also be a sub-system within a much larger bio-analysis system. The bio-analysis system could include all the aspects of sample preparation prior to, for example, optical detection, the post processing of data collected in the optical detection phase and finally decision making based on these results. Sample preparation may include steps such as: extraction of the sample from the tested subject (human, animal, plant environment etc.); separation of different parts of the sample to achieve higher concentration and purity of the molecules under investigation; sample amplification (e.g. through PCR); attachment of fluorescence tags or markers to different parts of the sample; and transfer of the sample or a portion of the sample into a reaction vessel or site on a substrate. The post processing of the collected data may include: normalization; background and noise reduction; and statistical analysis such as averaging over repeated tests or correlation between different tests. The decision making may include: testing against a predefined set of rules and comparison to information stored in external data-bases.

The applications and uses of the stochastic labeling and counting methods and systems described herein can produce one or more result useful to diagnose a disease state of an individual, for example, a patient. In one embodiment, a method of diagnosing a disease comprises reviewing or analyzing data relating to the presence and/or the concentration level of a target in a sample. A conclusion based review or analysis of the data can be provided to a patient, a health care provider or a health care manager. In one embodiment the conclusion is based on the review or analysis of data regarding a disease diagnosis. It is envisioned that in another embodiment that providing a conclusion to a patient, a health care provider or a health care manager includes transmission of the data over a network.

Accordingly, business methods relating to the stochastic labeling and counting methods and methods related to use thereof as described herein are provided. One aspect of the invention is a business method comprising screening patient test samples for the amount of a biologically active analyte present in the sample to produce data regarding the analyte, collecting the analyte data, providing the analyte data to a patient, a health care provider or a health care manager for making a conclusion based on review or analysis of the data regarding a disease diagnosis or prognosis or to determine a treatment regimen. In one embodiment the conclusion is provided to a patient, a health care provider or a health care manager includes transmission of the data over a network.

Applications for the disclosed methods include diagnosing a cancerous condition or diagnosing viral, bacterial, and other pathological or nonpathological infections, as described in U.S. Pat. No. 5,800,992. Additional applications of the disclosed methods and systems include, pathogens detection and classification; chemical/biological warfare real-time detection; chemical concentration control; dangerous substance (e.g., gas, liquid) detection and alarm; sugar and insulin levels detection in diabetic patients; pregnancy testing; detection of viral and bacterial infectious diseases (e.g. AIDS, Bird Flu, SARS, West Nile virus); environmental pollution monitoring (e.g., water, air); and quality control in food processing.

Any available mechanism for detection of the labels may be used. While many of the embodiments discussed above use an array readout form, it will be obvious to one of skill in the art that other methods for readout may be used. For example, sequencing may be preferred in some embodiments.

In some aspects the readout is on an array. The array may be a solid support having immobilized nucleic acid probes attached to the surface in an ordered arrangement. The probes may be, for example, synthesized in situ on the support in known locations using photolithography or the probes may be spotted onto the support in an array format. As discussed above, in some embodiments the array includes a probe feature for each possible label-target combination. A feature preferably includes many copies of a single probe sequence. The feature may also have some probes that are not full length, resulting from truncation of synthesis. The photo activation process may not be 100% efficient so some probes are terminated at each step without having subsequent bases added. These truncated probes have the sequence of a portion of the full length probe.

Sequencing readout. After attachment of the labels to the targets in a stochastic manner, the targets may be amplified according to any of the methods disclosed herein and the amplification product may be subjected to any available sequencing method.

A number of alternative sequencing techniques have been developed and many are available commercially. For a review see, for example, Ansorge New Biotechnology 25(4):195-203 (2009), which is incorporated herein by reference. These include the use of microarrays of genetic material that can be manipulated so as to permit parallel detection of the ordering of nucleotides in a multitude of fragments of genetic material. The arrays typically include many sites formed or disposed on a substrate. Additional materials, typically single nucleotides or strands of nucleotides (oligonucleotides) are introduced and permitted or encouraged to bind to the template of genetic material to be sequenced, thereby selectively marking the template in a sequence dependent manner. Sequence information may then be gathered by imaging the sites. In certain current techniques, for example, each nucleotide type is tagged with a fluorescent tag or dye that permits analysis of the nucleotide attached at a particular site to be determined by analysis of image data.

In another aspect, mass spec analysis may be used to detect the labels and count the targets. The labels can be distinguishable based on size or other property that can be detected. Many of the examples provided herein identify the label based on unique nucleic acid sequence but any distinguishable label may be used, for example, the pool of labels may be labels that are differentially detectable based on fluorescence emission at a unique wavelength.

FIG. 9 shows a method for reading out the labeled targets on arrays. On the left, the target with $G_1$ ligated to $L_1$, "$G_1L_1$", is shown hybridizing to the complementary array probe over the entire length of the probe. On the right target $G_1$ ligated to label $L_2$ is shown partially hybridized to the $G_1L_1$ probe on the array. On the left the biotin labeled constant segment can hybridize to the $G_1L_1$ target and ligate to the 5' end of the $G_1L_1$ array probe. The constant segment can hybridize to the $L_2$ segment but will not ligate to $L_1$. This allows for labeling of properly hybridized target-label pairs with both hybridization and ligation discrimination. The lower panel shows an example where the target or G portion is not matching with the probe on the array. This will not ligate efficiently because it hybridizes less stably.

The left panel shows the results when target $G_1$ ligated to label $L_1$ to form $G_1L_1$ hybridizes to the complementary $G_1L_1$ probe on the array. The constant region (in white) can hybridize to its labeled complement so that the 3' end of the labeled complement is juxtaposed with the 5' end of the $L_1$ region of the probe on the array and the ends can be ligated. In the center panel the target hybridizing to the $G_1L_1$ probe is non-cognate, the label region is $L_2$ and not $L_1$ so it does not hybridize to the $L_1$ region of the probe. The labeled oligo can hybridize to the partially hybridized target but it is not juxtaposed with the 5' end of the $L_1$ region of the probe so it should not ligate to the probe. In the right panel the target shown hybridized has the $L_1$ region and is complementary to the array probe at that region, but the array probe has a G region that is not $G_1$ so the $G_1L_1$ target does not hybridize. The labeled oligo can hybridize to the target but because the L1:L1 region is short the duplex is not stable and the labeled oligo does not ligate to the end of the array probe.

The methods are broadly applicable to counting a population of molecules by performing a stochastic operation on the population to generate a stochastic population of identifiable molecules. The targets need not be identical. For example, the methods may be used to count the absolute number of members of a group. In one aspect, a sample having an unknown number of copies of a selected nucleic acid target is fragmented randomly so that on average each copy of the target has a different end resulting from a distinct fragmentation event. A common adaptor sequence can be ligated to the end of each fragment and used for amplification of the fragments. Each ligation event generates a new molecule having a junction formed by the end of the random fragment and the adaptor sequence. The new junction can be detected by, for example, sequencing using a primer complementary to the adaptor or a region of the adaptor. Because the fragmentation was a stochastic process the number of different ends detected is a count of the number of different starting target molecules, assuming one fragment per starting target molecule.

The examples provided herein demonstrate the concept of using a stochastic labeling strategy in the high sensitivity detection and counting of individual DNA molecules. The difficult task of quantifying single nucleic acid molecules is converted into a simple qualitative assay that leverages the statistics of random probability; and at the same time, the requirement of single molecule detection sensitivity is achieved with PCR for the robust amplification of single DNA molecules. In some aspects improved methods for amplification will be used. For example, linear amplification methods may be used to mitigate the representation distortions created by exponential cycling in PCR. Given the lack of available techniques for single molecule counting, and the increasing need for its use, the new concept of stochastic labeling is likely to find numerous applications in the near future.

EXAMPLES

To demonstrate stochastic labeling, we performed an experiment to count small numbers of nucleic acid molecules in solution. Genomic DNA from a male individual with Trisomy 21 was used to determine the absolute and relative number of DNA copies of chromosomes X, 4 and 21, representing 1, 2 and 3 target copies of each chromosome, respectively. Genomic DNA isolated from cultured B-Lymphocytes of a male caucasion with Trisomy 21 was purchased from The Coriell Institute for Medical Research (Catalog #GM01921). The DNA quantity was determined by PICOGREEN dye (Invitrogen) measurements using the lambda phage DNA provided in the kit as reference standard. DNA quality was assessed by agarose gel electrophoresis.

The DNA concentration in the stock solution was measured by quantitative staining with picogreen fluorescent dye, and dilutions containing 3.62 ng, 1.45 ng, 0.36 ng and 0.036 ng were prepared. In each dilution, the number of copies of target molecules in the sample was calculated from a total DNA mass of 3.5 pg per haploid nucleus (see, T. R. Gregory et al., *Nucleic Acids Res* 35, D332 (2007), and represent approximately 500, 200, 50 and 5 haploid genomes. The absolute quantity of DNA in the sample was determined by optical density measurements and quantitative staining with PICOGREEN fluorescent dye (Invitrogen) prior to making dilutions.

Figure 3:
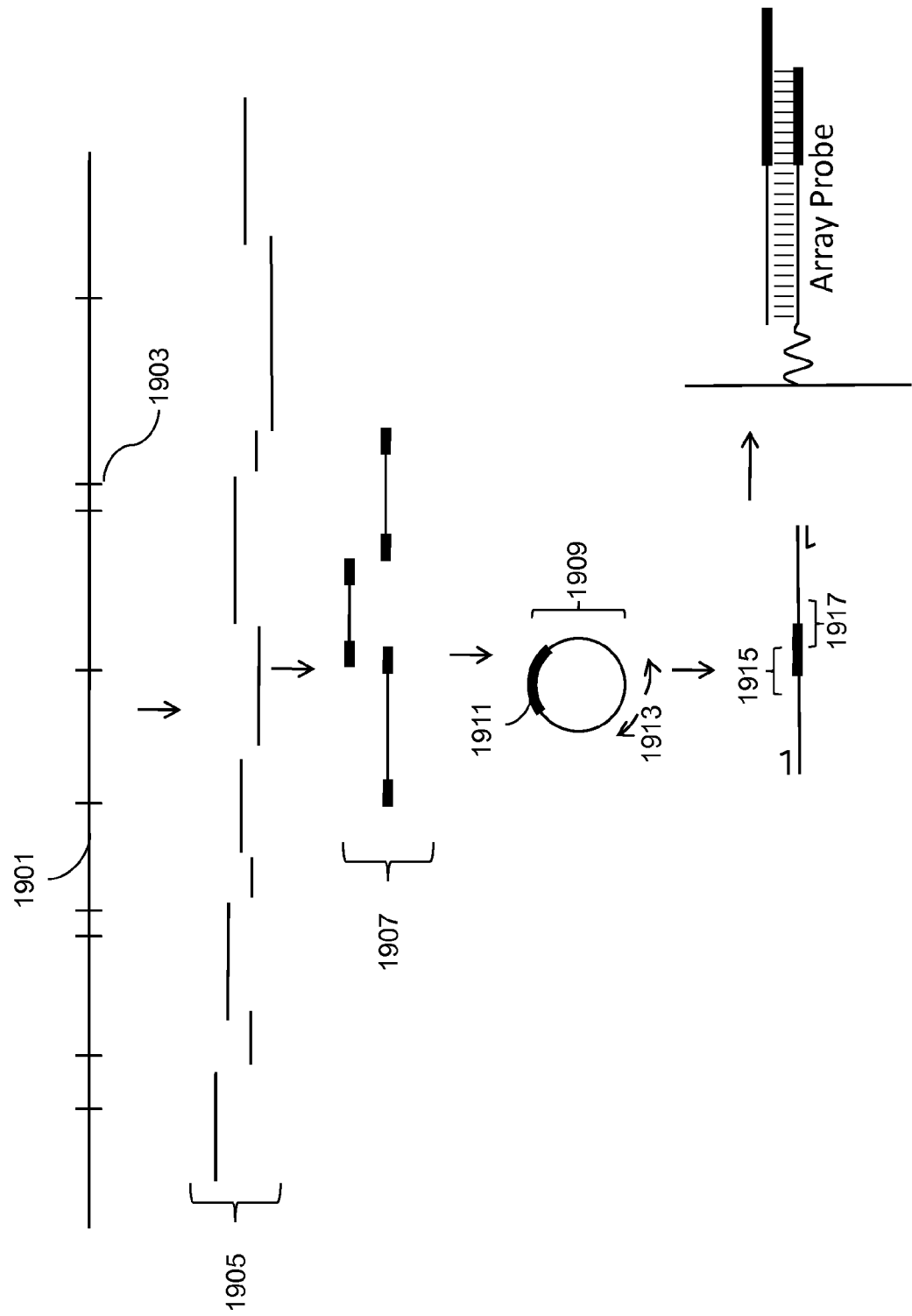
FIG. 3 shows a schematic of a method for circularizing targets and amplifying with gene specific primers.

As outlined in FIG. 3, the genomic DNA sample 1901 was first digested to completion with the BamHI restriction endo-nuclease to produce 360,679 DNA fragments 1905. A diverse set of labels consisting of 960 14-nucleotide sequences was synthesized as adaptors harboring BamHI overhangs (SEQ ID Nos. 44-1963). Genomic DNA was digested to completion with BamHI (New England BioLabs, NEB) and ligated to a pool of adaptors consisting of an equal concentration of 960 distinct labels. Each adaptor consists of a universal PCR priming site, a 14 nucleotide long counter sequence and a BamHI overhang (similar to the form of the adaptor shown in FIG. 7). The sequence of the label adaptors SEQ ID Nos. 44-1963 were selected from an all-possible $4^{14}$ nucleotide combination to be of similar melting temperature, minimal self-complementation, and maximal differences between one-another. Homopolymer runs and the sequence of the BamHI restriction site were avoided. Each pair, for example, SEQ ID Nos. 44 and 45, form an adaptor pair that has a region of complementarity starting at base 12 in SEQ ID No. 44 and base 5 in SEQ ID No. 45: SEQ ID 44 5' CGACAGACGCCT-GATCTTTTGTTAGCCGGAGT 3' 3' ACTAGAAAA-CAATCGGCCTCACTAG5' SEQ ID 45 The adaptors have a 5' overhang of 11 bases in the even numbered SEQ IDs and 4 bases (GATC) in the odd numbered SEQ IDs. Oligonucleotides were synthesized (Integrated DNA Technologies) and annealed to form double-stranded adaptors prior to pooling. For ligation, the digested DNA was diluted to the desired quantity and added to 100 pmoles (equivalent to $6 \times 10^{13}$ molecules) of pooled label-adaptors, and $2 \times 10^6$ units (equivalent to $1 \times 10^{13}$ molecules) of T4 DNA ligase (NEB) in a 30 µl reaction. The reaction was incubated at 20° C. for 3 hours until inactivation at 65° C. for 20 minutes.

Figure 21:
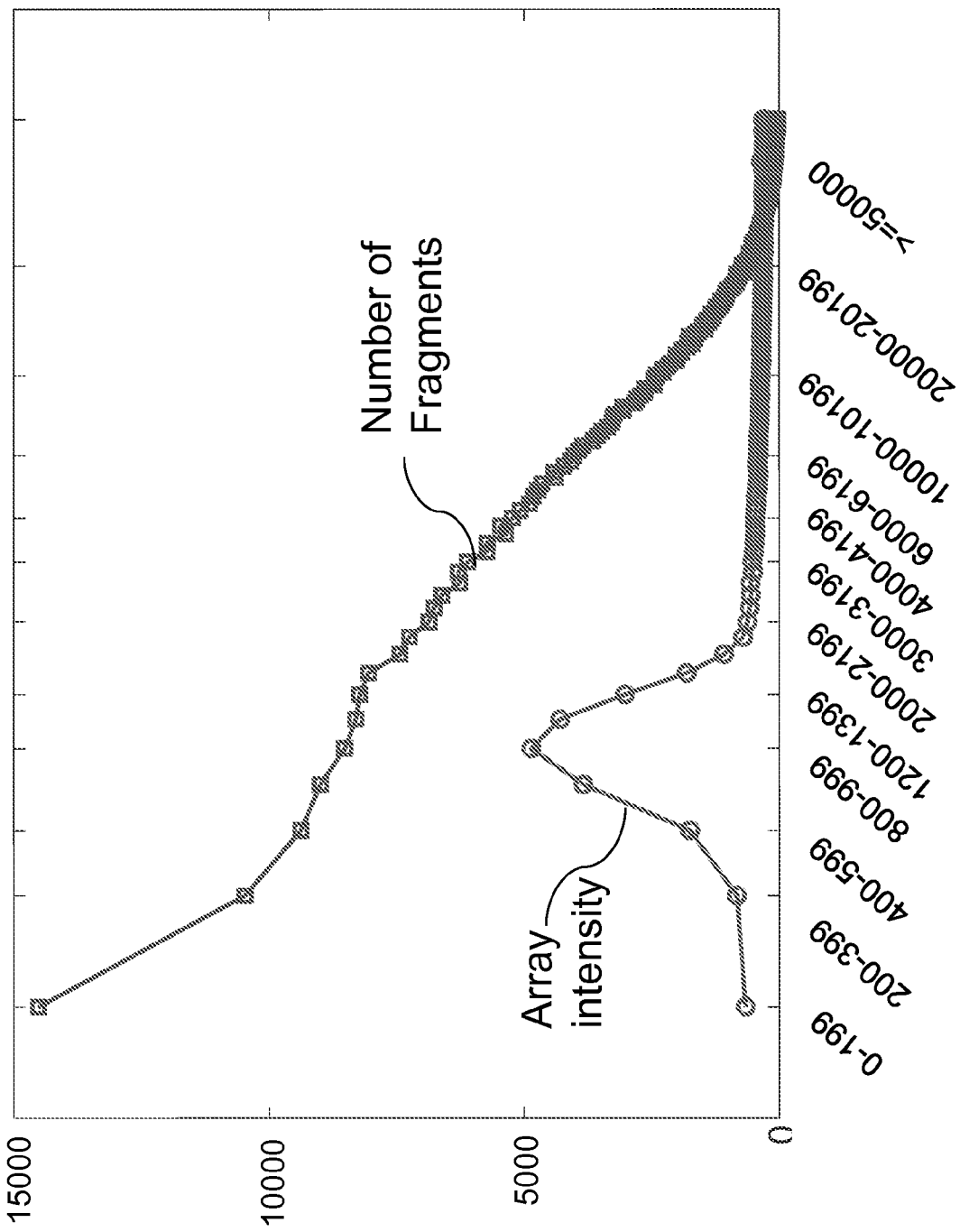
FIG. 21 is a plot of labels the array intensity observed compared to the number of fragments when fragments are binned according to size.

For the stochastic labeling reaction, each DNA fragment-end randomly attaches to a single label by means of enzymatic ligation of compatible cohesive DNA ends to generate labeled fragments 1907. High coupling efficiency is achieved through incubation with a large molar excess of labels and DNA ligase enzyme (~$10^{13}$ molecules each). At this stage, the labeling process is complete, and the samples can be amplified as desired for detection. A universal primer may be added, and the entire population of labeled DNA fragments may be PCR amplified. The PCR reaction preferentially amplifies approximately 80,000 fragments in the 150 bp-2 kb size range (FIG. 21). Adaptor-ligated fragments were amplified in a 50 µl reaction containing 1×TITANIUM Taq PCR buffer (Clontech), 1M betaine (Sigma-Aldrich), 0.3 mM dNTPs, 4 µM PCROO4StuA primer (SEQ ID No. 1974), 2.5 U Taq DNA Polymerase (USB), and 1×TITANIUM Taq DNA polymerase (Clontech). An initial PCR extension was performed with 5 minutes at 72° C.; 3 minutes at 94° C.; followed by 5 cycles of 94° C. for 30 seconds, 45° C. for 45 seconds and 68° C. for 15 seconds. This was followed by 25 cycles of 94° C. for 30 seconds, 60° C. for 45 seconds and 68° C. for 15 seconds and a final extension step of 7 minutes at 68° C. PCR products were assessed with agarose gel electrophoresis and purified using the QIAQUICK PCR purification kit (Qiagen).

The purified PCR product was denatured at 95° C. for 3 minutes prior to phosphorylation with T4 polynucleotide kinase (NEB). The phosphorylated DNA was ethanol precipitated and circularized using the CIRCLIGASE II ssDNA Ligase Kit (Epicentre). Circularization was performed at 60° C. for 2 hours followed by 80° C. inactivation for 10 minutes in a 40 µl reaction consisting of 1×CIRCLIGASE II reaction buffer, 2.5 mM $MnCl_2$, 1M betaine, and 200 U CIRCLIGASE II ssDNA ligase. Uncirculated DNAs were removed by treatment with 20 U Exonuclease I (Epicentre) at 37° C. for 30 minutes. Remaining DNA was purified with ethanol precipitation and quantified with $OD_{260}$ measurement.

Amplification of gene targets. Three assay regions were tested: One on each of chromosomes 4, 21 and X. The genomic location (fragment starting and ending positions are provided), of the selected fragments are as follows: Chr4 106415806_106416680 (SEQ ID No. 1), Chr2138298439_38299372 (SEQ ID No. 2), and ChrX 133694723_133695365 (SEQ ID No. 3). The lengths are 875, 934 and 643 bases respectively. The circularized DNA was amplified with gene specific primers (SEQ ID Nos. 4-9) in a multiplex inverse PCR reaction. PCR primers were picked using Primer3 (available from the FRODO web site hosted by MIT) to yield amplicons ranging between 121 and 168 bp. PCR was carried out with 1×TITANIUM Taq PCR buffer (Clontech), 0.3 mM dNTPs, 0.404 each primer, 1×TITANIUM Taq DNA Polymerase (Clontech), and ~200 ng of the circularized DNA. After denaturation at 94° C. for 2 minutes, reactions were cycled 30 times as follows: 94° C. for 20 seconds, 60° C. for 20 seconds, and 68° C. for 20 seconds, with a 68° C. final hold for 4 minutes. PCR products were assessed on a 4-20% gradient polyacrylamide gel (Invitrogen) and precipitated with ethanol.

The amplified DNA was fragmented with DNase I, end-labeled with Biotin, and hybridized to a whole-genome tiling array which spans the entire non-repetitive portion of the genome with uniform coverage at an average probe spacing of ~200 nt (see Matsuzaki et al., *Genome Biol* 10, R125 (2009) and Wagner et al. *Systematic Biology* 43, 250 (1994)). Probe intensity ("Array Intensity") from the whole-genome tiling array (y-axis) is grouped into 200 nt bins by the length of the BamHI fragment on which it resides. High probe intensity demonstrates the amplification of fragments in the 600 bp~1.2 kb size range (x-axis, log-scale). The computed size distribution of BamHI restricted fragments in the reference genome sequence (NCBI Build 36) is shown by the curve labeled "Number of Fragments". After circularization of the amplified products to obtain circles 1909, three test target fragments were isolated using gene-specific PCR; one on each of chromosomes X, 4, and 21, and prepared for detection.

The three labeled targets were counted using two sampling techniques: DNA microarrays and next-generation sequencing. For the array counting, a custom DNA array detector capable of distinguishing the set of labels bound to the targets was constructed by dedicating one array element for each of the 960 target-label combinations. Each array element consists of a complementary target sequence adjacent to one of the complements of the 960 label sequences (as shown in FIG. 3).

Array Design: For each gene target assayed, the array probes tiled consist of all possible combinations of the 960 counter sequences connected to the two BamHI genomic fragment ends (FIG. 8). An additional 192 counter sequences that were not included in the adaptor pool were also tiled to serve as non-specific controls. This tiling strategy enables counter detection separately at each paired end, since each target fragment is ligated to two independent counters (one on either end).

Arrays were synthesized following standard Affymetrix GENECHIP manufacturing methods utilizing lithography and phosphoramidite nucleoside monomers bearing photolabile 5'-protecting groups. Array probes were synthesized with 5' phosphate ends to allow for ligation. Fused-silica wafer substrates were prepared by standard methods with trialkoxy aminosilane as previously described in Fodor et al., Science 251:767 (1991). After the final lithographic exposure step, the wafer was de-protected in an ethanolic amine solution for a total of 8 hrs prior to dicing and packaging.

Hybridization to Arrays: PCR products were digested with Stu I (NEB), and treated with Lambda exonuclease (USB). 5 µg of the digested DNA was hybridized to a GeneChip array in 112.5 µl of hybridization solution containing 80 µg denatured Herring sperm DNA (Promega), 25% formamide, 2.5 pM biotin-labeled gridding oligo, and 70 µl hybridization buffer (4.8M TMACl, 15 mM Tris pH 8, and 0.015% Triton X-100). Hybridizations were carried out in ovens for 16 hours at 50° C. with rotation at 30 rpm. Following hybridization, arrays were washed in 0.2×SSPE containing 0.005% Trition X-100 for 30 minutes at 37° C., and with TE (10 mM Tris, 1 mM EDTA, pH 8) for 15 minutes at 37° C. A short biotin-labeled oligonucleotide (see 3119 in FIG. 8) was annealed to the hybridized DNAs, and ligated to the array probes with *E. coli* DNA ligase (USB). Excess unligated oligonucleotides were removed with TE wash for 10 minutes at 50° C. The arrays were stained with Streptavidin, R-phycoerythrin conjugate (Invitrogen) and scanned on the GCS3000 instrument (Affymetrix).

Figure 22:
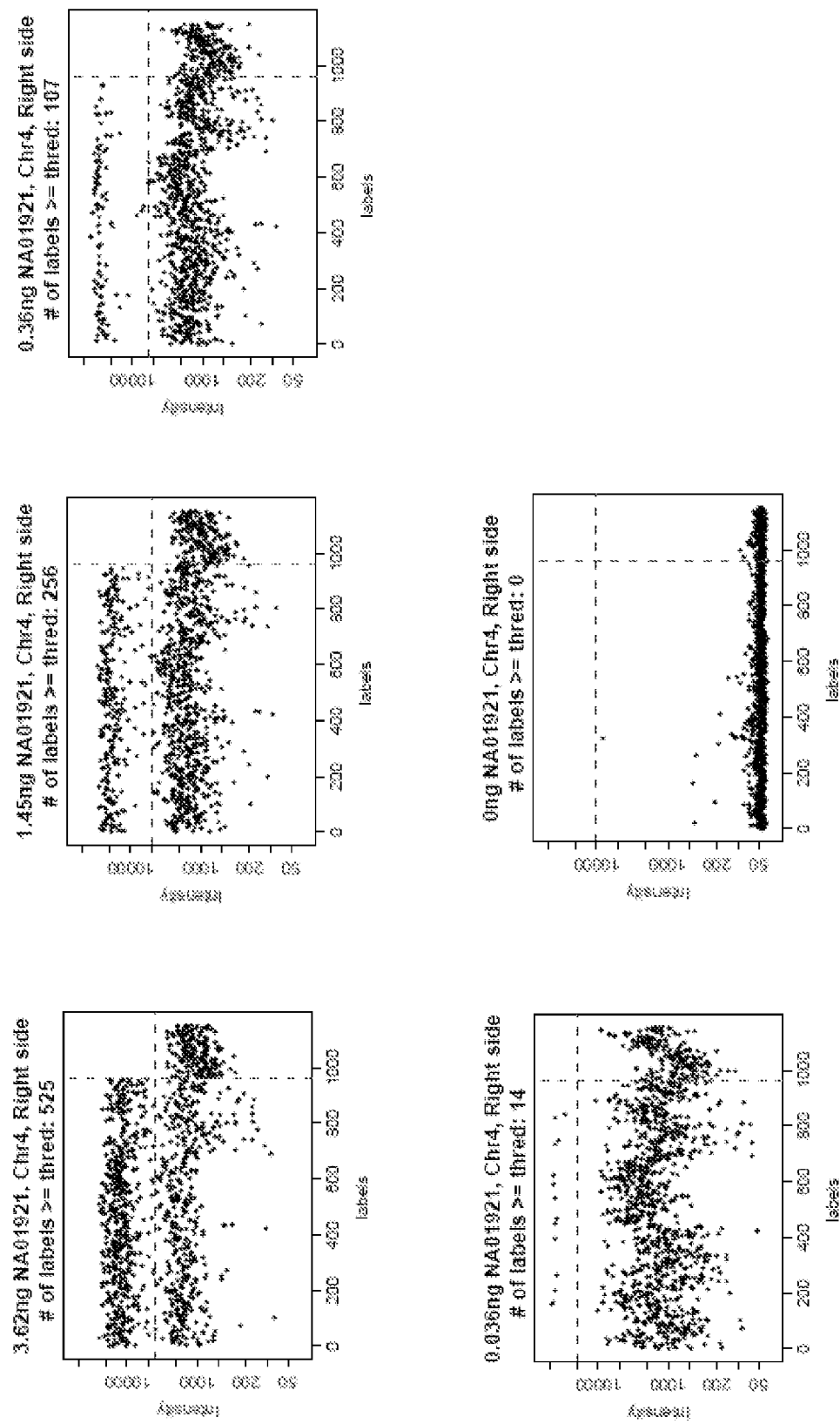
FIG. 22 shows labels observed by microarray hybridization plotted against intensity (y-axis) for each of 960 labels for the Chr 4 gene target.
Figure 23:
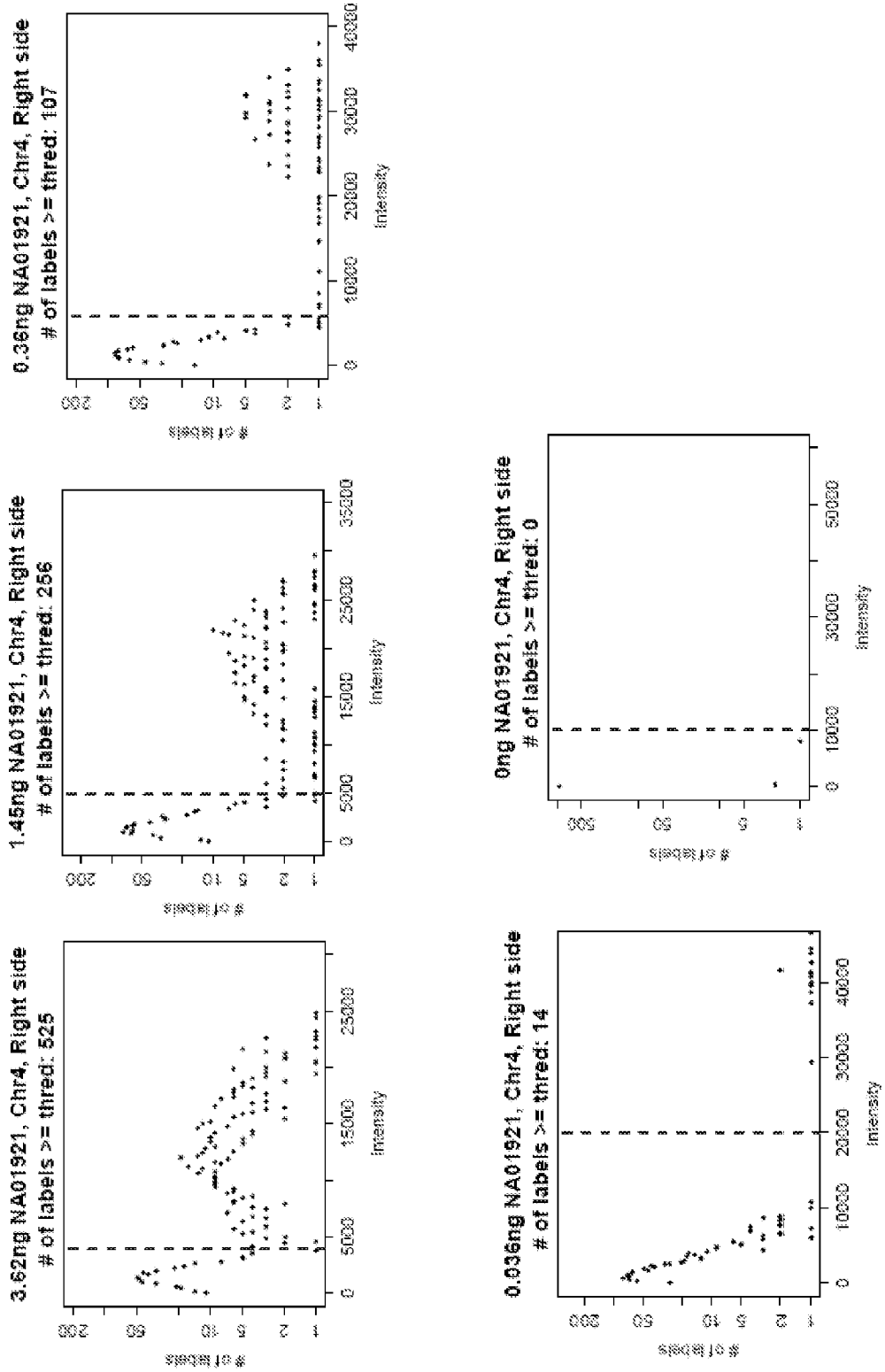
FIG. 23 shows frequency plots (y-axis, log-scale) of intensity distributions of the 960 labels in the microarray experiments with the counting threshold applied indicated by the dashed line.
Figure 29:
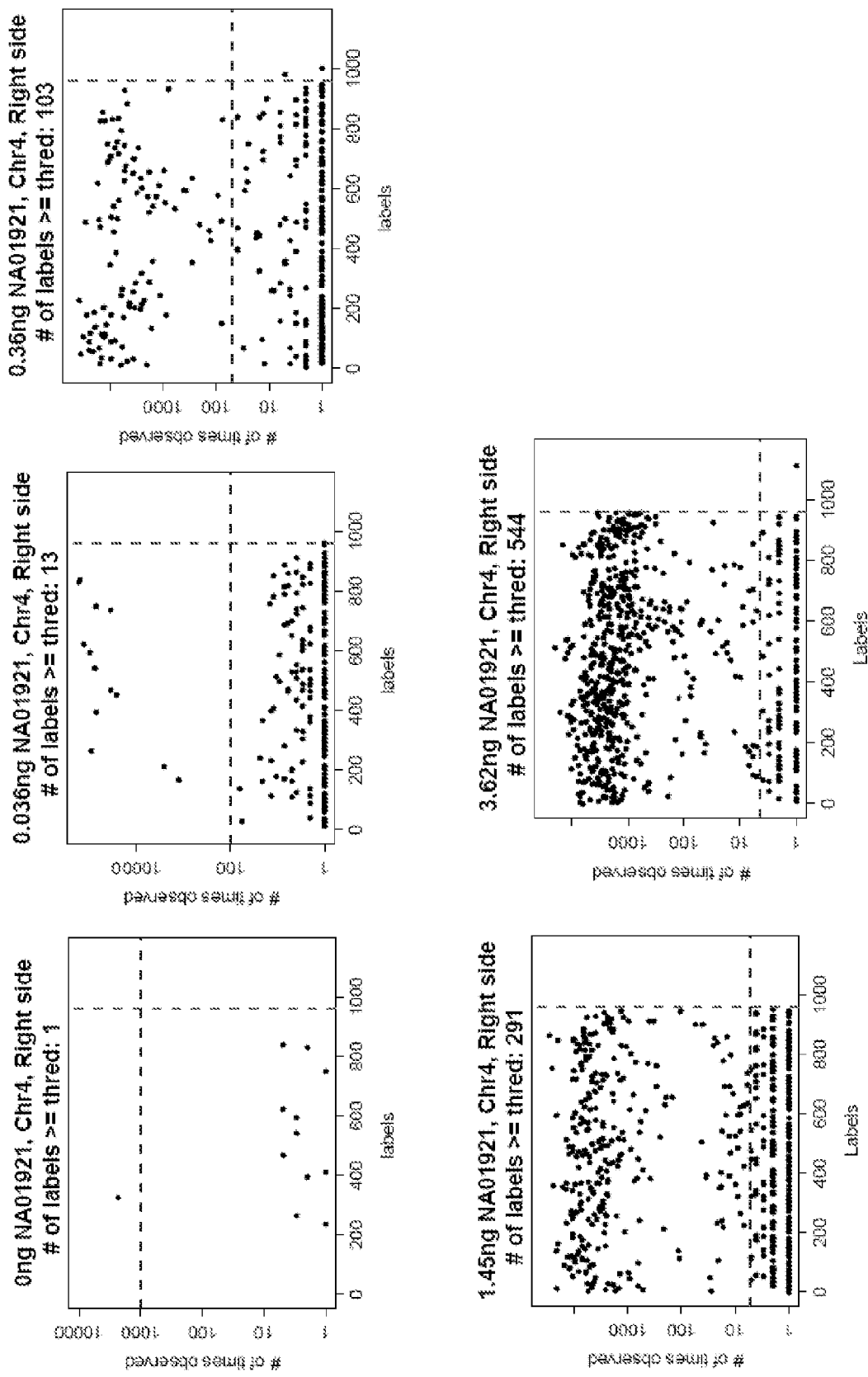
FIG. 29 shows plots of labels observed in the mapped reads from the first sequencing run for chromosome 4 with the horizontal dashed line indicating the counting threshold applied and the vertical dashed line indicating the break separating the 192 negative controls from the expected labels (controls to the right of the line).

In order to maximize the specificity of target-label hybridization and scoring, we employed a ligation labeling procedure on the captured sequences (FIG. 8). We set thresholds to best separate the intensity data from the array into two clusters, one of low intensity and one of high intensity to classify labels as either being used or not (FIGS. 22, 23 and 29). We score a label as "present" and counted if its signal intensity exceeded the threshold. To count labels we set thresholds for the array intensity, or the number of sequencing reads. Appropriate thresholds were straightforward to determine when used and un-used labels fall into two distinct clusters separated by a significant gap. In situations where a gap was not obvious, the function normalmixEM in the R package mixtools was used to classify labels. This function uses the Expectation Maximization (EM) algorithm to fit the data by mixtures of two normal distributions iteratively. The two normal distributions correspond to the two clusters to be identified. The cluster of labels with a high value is counted as "used", and the other as "not used". The average of the minimum and maximum of the two clusters, $(I_{min}+I_{max})/2$, was applied as the threshold for separating the two clusters.

Sampling error calculation. A sampling error can be introduced when preparing dilutions of the stock DNA solution. This error is a direct consequence of random fluctuations in the number of molecules in the volume of solution sampled. For example, when exactly 10 µl of a 100 µl solution containing 100 molecules is measured, the actual number of molecules in the sampled aliquot may not be exactly 10. The lower the concentration of the molecules in the entire solution, the higher the sampling error, and the more likely the actual abundance in the sampled aliquot will deviate from the expected abundance (n=10). To calculate sampling errors, we determined the number of molecules for each chromosome target in our stock DNA solution and performed numerical simulations to follow our dilution steps in preparing the test samples (3.62 ng, 1.45 ng, 0.36 ng and 0.036 ng). To illustrate, if the dilution step is sampling 1 µl of a 25 µl solution containing 250 molecules, we create 25 bins and randomly assign each of the 250 molecules into one of the bins. We randomly choose one bin and count the number of molecules assigned to that bin to simulate the process of sampling $1/25^{th}$ of the entire solution. If a serial dilution was performed, we would repeat the simulation process accordingly. For each dilution, the observed copy number ratios of Chr 4:X or 21:X for 10,000 independent trials are summarized as observed medians, along with the $10^{th}$ and $90^{th}$ percentiles and shown in FIGS. 12 and 13.

Figure 10:
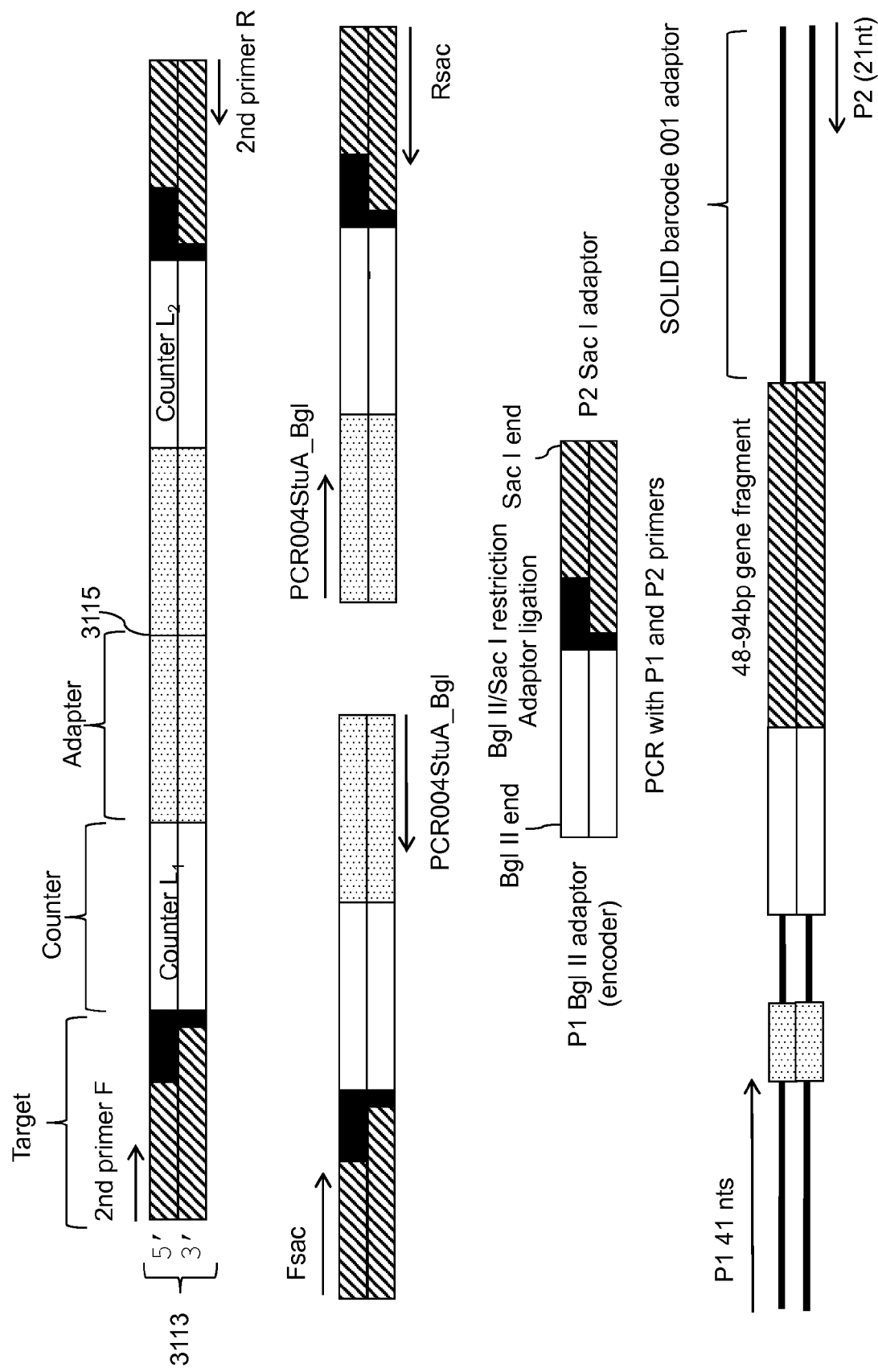
FIG. 10 shows the arrangement of the adaptors, labels and primers used to convert the labeled sample into sequencing template.

As an alternate form of detection, the samples were submitted to two independent DNA sequencing runs (FIG. 10). The arrangement and position of the adaptors and PCR primers used to convert the DNA sample hybridized to microarrays into sequencing templates are shown in the figure. The circularized junction 3115 is located between the two counter labels. PCR primers that have restriction sites are used to amplify two fragments. The fragments are digested with the restriction enzymes to generate ends compatible with ligation to sequencing adaptors. The sequencing adaptors are ligated to the ends to generate a fragment that has the label sequence and a portion of the target that is 48 to 94 base pairs in length are flanked by sequences for use with SOLID sequencing.

Validation by DNA sequencing (First SOLID run). DNA targets that were used for hybridization to arrays were converted to libraries for sequencing on the SOLID instrument (ABI). P1 and P2 SOLID amplification primers were added to the DNA ends through adaptor ligation and strand extension from gene-specific primers flanked by P1 or P2 sequences (FIG. 10). Each sample received a unique ligation adaptor harboring a 4-base encoder (SEQ ID Nos. 34-43) that unambiguously identifies the originating sample of any resulting read. Each adaptor includes two strands, SEQ ID Nos. 34 and 35, 36 and 37, 38 and 39, 40 and 41 or 42 and 43, that hybridize to form a double stranded region of 29 base pairs and a single stranded 4 base overhang (GATC). Individual libraries were prepared for each sample, and quantified with picogreen before equal amounts of each sample was combined into a single pooled library. DNA sequencing was performed on SOLID v3 by Cofactor Genomics. A total of ~46 million 50 base reads were generated. Each read is composed of three segments, corresponding to the sample encoder, label sequence and gene fragment (FIG. 10). We removed reads if: uncalled color bases were present, the average Quality Value (aQV) of the whole read <10, the aQV of the sample encoder <20, or the aQV of the label sequence <18.40% of the raw reads were removed. Filtered reads were mapped to reference sequences using the program Short Oligonucleotide Color Space (SOCS), available from ABI with a maximum tolerance of 4 color mismatches between the first 45 color bases in each read and reference sequences (the last 5 color bases on 3' end of each read were trimmed in alignment). About 64.3% reads were uniquely mapped to reference sequences, of which 89.5% (16 million) have high mapping quality, i.e., with no mismatch in the sample encoder and at most 1 mismatch in the label sequence. These high-quality reads, accounting for ~35% of the total reads generated, were used in subsequent counting analysis.

Sequencing replication (Second SOLID run). An aliquot of the exact same DNA library originally sequenced by Cofactor Genomics was subsequently re-sequenced by Beckman Coulter Genomics. Approximately 50 million 35 base reads were generated, and processed following the same rules. Approximately 61% of the raw reads passed quality filters, of which 81% uniquely mapped to a reference sequence with a maximum tolerance of 3 color mismatches (An adjusted mismatch tolerance was applied in the alignment step to account for the shorter length of these reads). Of the mapped reads, 91% (22.5 million) are of high mapping quality, i.e., with perfect match in the sample encoder and at most 1 mismatch in the label sequence. These high-quality reads (45% of the total raw reads generated) were used for counting analysis.

Between several hundred thousand to several million reads were used to score the captured labels. Table 1 shows the number of mapped reads from SOLID DNA sequencing.

TABLE 1

| DNA sample | | | 5 ng | 2 ng | 0.5 ng | 0.05 ng | 0 ng |
|---|---|---|---|---|---|---|---|
| Chr4 | Left side | $1^{st}$ SOLiD run | 709,076 | 252,211 | 237,380 | 316,629 | 1,204 |
| | | $2^{nd}$ SOLiD run | 621,372 | 73,962 | 189,937 | 237,520 | 411 |
| | Right side | $1^{st}$ SOLiD run | 1,724,955 | 1,662,958 | 1,114,246 | 2,201,078 | 3,353 |
| | | $2^{nd}$ SOLiD run | 1,422,673 | 1,359,512 | 839,775 | 980,616 | 2,386 |
| Chr21 | Left side | $1^{st}$ SOLiD run | 1,615,416 | 1,474,208 | 832,234 | 1,428,540 | 1,851 |
| | | $2^{nd}$ SOLiD run | 1,296,685 | 1,038,456 | 622,429 | 930,461 | 840 |
| | Right side | $1^{st}$ SOLiD run | 1,124,772 | 886,421 | 551,192 | 849,204 | 821 |
| | | $2^{nd}$ SOLiD run | 910,298 | 522,358 | 367,207 | 479,621 | 224 |

TABLE 1-continued

| DNA sample | | | 5 ng | 2 ng | 0.5 ng | 0.05 ng | 0 ng |
|---|---|---|---|---|---|---|---|
| ChrX | Left side | 1st SOLiD run | 444,960 | 316,975 | 254,386 | 515,213 | 744 |
| | | 2nd SOLiD run | 266,606 | 157,860 | 137,706 | 220,121 | 5 |
| | Right side | 1st SOLiD run | 1,227,047 | 921,214 | 777,033 | 1,064,531 | 64 |
| | | 2nd SOLiD run | 1,043,475 | 768,296 | 559,038 | 695,873 | 43 |

Figure 4:
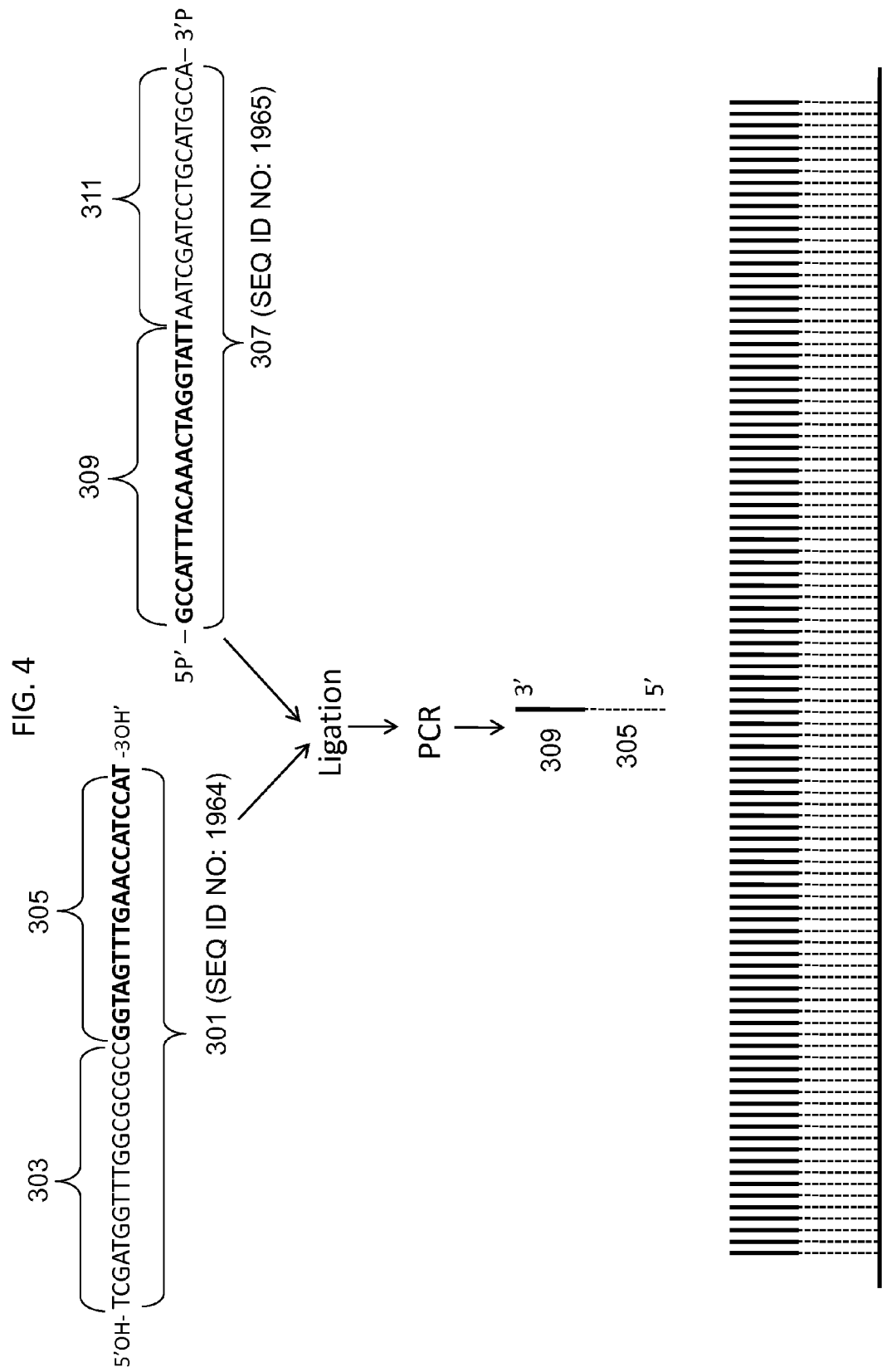
FIG. 4 shows a schematic of a method for detection of ligation products by hybridization to array probes that are complementary to the sequence resulting from the ligation.

We set thresholds for the number of sequencing reads observed for each label, and score a label as "present" and counted if the number of sequencing reads exceeded the threshold. Label usage summaries from experimental observations or from the stochastic modeling are shown in Table 2. The number of attached labels, k, detected for each target in each dilution either by microarray counting or sequence counting is presented in Table 2, and plotted in FIGS. 4 and 5.

Figure 12:
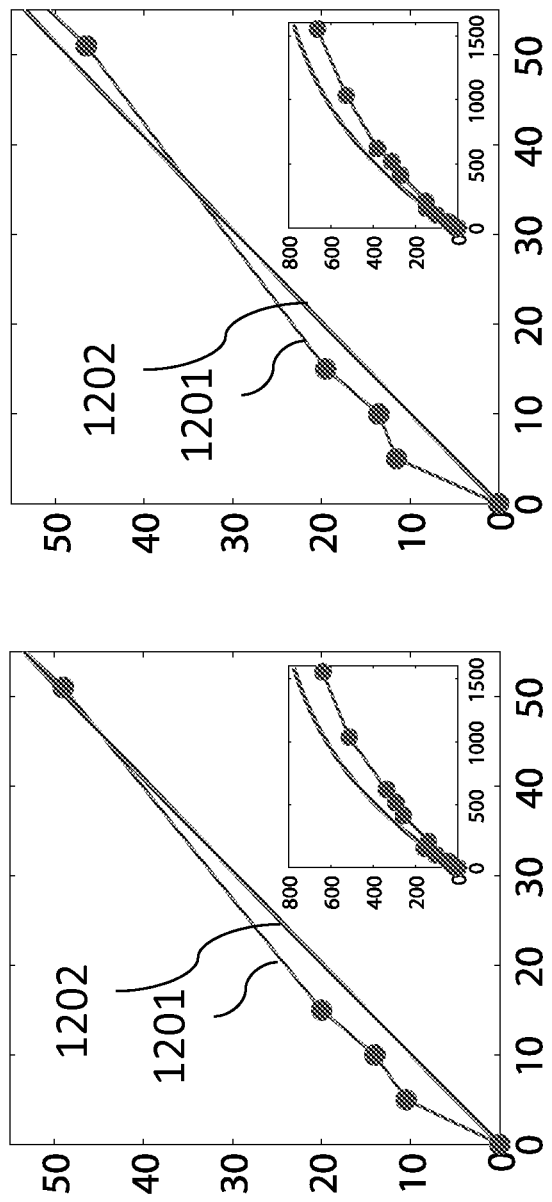
FIG. 12 is a plot of counting results for 4 different DNA copy number titrations using microarray hybridization (on left) or DNA sequencing in (on right).
Figure 13:
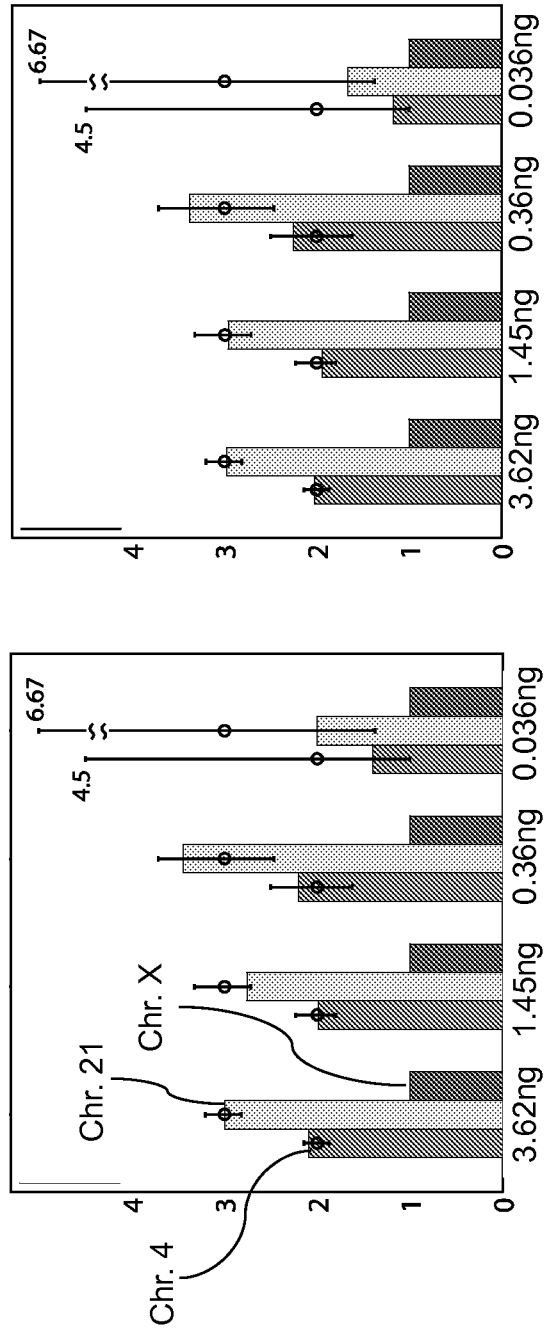
FIG. 13 shows relative copy ratios of three tested gene targets representing copy number 1, 2 or 3 at different dilutions as analyzed using the disclosed methods.

Several dilutions (3.62 ng, 1.45 ng, 0.36 ng and 0.036 ng) of DNA isolated from cultured of a Trisomy 21 male individual were processed for microarray hybridization (FIG. 12 left) and DNA sequencing (FIG. 12 right). Three gene targets were tested from chromosome X, 4 and 21, and observed numbers of detected labels are shown ("observed"). The number of target molecules for each sample was determined from the amount of DNA used, assuming a single haploid nucleus corresponds to 3.5 pg. For comparison, the calculated number of labels expected to appear using a stochastic model are also plotted ("calculated"). Numerical values are provided in Table 4. Relative copy ratios of the three gene targets (FIG. 13): ChrX (right bar), Chr4 (left bar) and Chr21 (center bar) representing one, two and three copies per cell, respectively. Different dilutions (3.62 ng, 1.45 ng, 0.36 ng and 0.036 ng) of the DNA isolated from cultured lymphoblasts of a Trisomy 21 male individual were processed for microarray hybridization and DNA sequencing. The calculated number of target molecules was determined from the number of labels detected on microarrays (Table 4, column 9) or from the SOLiD sequencing data. For each sample dilution, the copy number ratio of each gene target relative to ChrX is shown for Microarray (FIG. 13 left) and SOLiD sequencing (FIG. 13 right). For comparison, relative copy ratios obtained from in silico sampling simulations are also shown in (FIG. 13 left) and (FIG. 13 right), where circles indicate the median values from 10,000 independent trials and error bars indicate the 10th and 90th percentiles. The 90th percentile values of the relative copy ratios at the lowest concentration (0.036 ng) are explicitly labeled in the plots.

TABLE 2

| DNA sample | | 3.62 ng | 1.45 ng | 0.36 ng | 0.036 ng | 0 ng |
|---|---|---|---|---|---|---|
| Chr4 | Stochastic Model | 633 | 336 | 98 | 10 | 0 |
| | Left side Microarray | 501 | 260 | 102 | 14 | 0 |
| | 1st SOLiD run | 513 | 251 | 101 | 14 | 0 |
| | 2nd SOLiD run | 516 | 273 | 102 | 14 | 0 |
| | Right side Array | 525 | 256 | 107 | 14 | 0 |
| | 1st SOLiD run | 544 | 291 | 103 | 13 | 1 |
| | 2nd SOLiD run | 557 | 307 | 103 | 13 | 1 |
| Chr21 | Stochastic Model | 769 | 457 | 143 | 15 | 0 |
| | Left side Microarray | 651 | 335 | 160 | 20 | 0 |
| | 1st SOLiD run | 678 | 381 | 152 | 20 | 0 |
| | 2nd SOLiD run | 665 | 358 | 161 | 18 | 0 |
| | Right side Microarray | 627 | 341 | 157 | 20 | 0 |
| | 1st SOLiD run | 650 | 381 | 146 | 19 | 0 |
| | 2nd SOLiD run | 653 | 379 | 146 | 19 | 0 |
| ChrX | Stochastic Model | 400 | 186 | 50 | 5 | 0 |
| | Left Microarray | 281 | 148 | 50 | 11 | 0 |

TABLE 2-continued

| DNA sample | | 3.62 ng | 1.45 ng | 0.36 ng | 0.036 ng | 0 ng |
|---|---|---|---|---|---|---|
| | side 1st SOLiD run | 290 | 149 | 43 | 11 | 0 |
| | 2nd SOLiD run | 300 | 150 | 45 | 11 | 0 |
| | Right side Microarray | 306 | 133 | 48 | 10 | 1 |
| | 1st SOLiD run | 336 | 153 | 50 | 12 | 0 |
| | 2nd SOLiD run | 344 | 167 | 43 | 11 | 0 |

The counting results span a range of approximately 1,500 to 5 molecules, and it is useful to consider the results in two counting regimes, below and above 200 molecules. There is a striking agreement between the experimentally observed number of molecules and that expected from dilution in the first regime where the ratio of molecules to labels (n/m)<0.2 (Table 2). Below 200 molecules the data are in tight agreement, including the data from the lowest number of molecules, 5, 10 and 15 where the counting results are all within the expected sampling error for the experiment (The sampling error for 10 molecules is estimated to be 10±6.4, where 10 and 6.4 are the mean and two standard deviations from 10,000 independent simulation trials).

In the second regime above 200 molecules, there is an approximate 10-25% undercounting of molecules, increasing as the number of molecules increases. We attribute this deviation to be due to a distortion in the amplification reaction. PCR-introduced distortion occurs from small amounts of any complex template due to the differences in amplification efficiency between individual templates (2, 3). In the present case, stochastic labeling will produce only one (at low n/m ratios), and increasingly several copies (at higher n/m ratios) of each template. Modeling suggests that simple random dropout of sequences (PCR efficiencies under 100%) generate significant distortion in the final numbers of each molecule after amplification. At any labeling ratio, random dropout of sequences due to PCR efficiency will result in an undercount of the original number of molecules. At high n/m ratios, the number of labels residing on multiple targets will increase and have a statistical survival advantage through the PCR reaction causing greater distortion. In support of this argument, we observe a wide range of intensities on the microarray and a wide range in the number of occurrences of specific sequences in the sequencing experiments (FIGS. 23, 29). This effect can be reduced by carrying out the reaction at n/m ratios near or less than 0.2, increasing the number of labels m, further optimization of the amplification reaction, or by employing a linear amplification method. Other factors, such as errors from inaccurate pipetting, could also contribute.

The lymphoblast cell line used in this study provides an internal control for the relative measurement of copy number for genes residing on chromosomes X, 4 and 21. FIG. 13 presents the relative number of molecules from all three chromosomes normalized to copy number 1 for the X chromosome. As shown, the measurements above 50 molecules all yield highly precise relative copy number values. At low numbers of molecules (0.036 ng), uncertainty results because the stochastic variation of molecules captured by sampling an aliquot for dilution are significant. Numerical simulations were performed to estimate the sampling variation, and summarized medians, along with the $10^{th}$ and $90^{th}$ percentiles of the copy number ratios and are shown in FIGS. 12 and 13 as circles and range bars, respectively. At the most extreme dilutions, where ~5, 10, and 15 molecules are expected for the chromosome X, 4 and 21 genes, the copy number ratios fall within the expected sampling error.

Overall, the identity of labels detected on the microarrays and in sequencing are in good agreement, with only a small subset of labels unique to each process (Table 7). Despite a high sequencing sampling depth (Table 1), a small number of labels with high microarray intensity appear to be missing or under-represented in the sequencing results. In contrast, labels that appear in high numbers in the sequencing reaction always correlate with high microarray intensities. No trivial explanation could be found for the labels that are missing from any given sequencing experiment. While under-represented in some experiments, the same labels appear as present with high sequence counts in other experiments, suggesting that the sequences are compatible with the sequencing reactions.

PCR validation. We used PCR as an independent method to investigate isolated cases of disagreement, and demonstrated that the labels were present in the samples used for the sequencing runs.

PCR was used to detect the presence of 16 label sequences (Table 3) which were either observed as high or low hybridization intensity on microarrays, and observed with either high or low numbers of mapped reads in SOLID sequencing. The Chr4 gene target was PCR amplified with 3 dilutions (0.1 pg, 1 pg, and 10 pg) of the 3.62 ng NA01921 sample, using the DNA target that was hybridized to microarrays, or the prepared SOLID library template. PCR products were resolved on 4% agarose gels and fluorescent DNA bands were detected after ethidium bromide staining

TABLE 3

| Label ID | Label Sequence | 1st SOLiD reads | 2nd SOLiD reads | Microarray intensity | Microarray target template | SOLiD library template |
|---|---|---|---|---|---|---|
| 112 | AGATCTT GTGTCCG | 0 | 2 | 15,907 | 1 | 2 |
| 182 | ATCTTCG ACACTGG | 0 | 1 | 10,304 | 3 | 4 |
| 779 | TCGAGAT GGTGTTC | 0 | 4 | 9,411 | 5 | 6 |
| 782 | TCGGATA GAGAGCA | 0 | 0 | 6,716 | 7 | 8 |
| 783 | TCGGTAC CAACAAC | 1 | 4 | 13,132 | 9 | 10 |
| 290 | CCAAGGT TTGGTGA | 1 | 17 | 10,777 | 11 | 12 |
| 780 | TCGCAAG AGGTAAG | 1 | 1 | 8,915 | 13 | 14 |
| 570 | GGAGTTA CGGCTTT | 1 | 2 | 8,252 | 15 | 16 |
| 741 | TCAACCA GTAAGCC | 794 | 400 | 466 | 17\* | 18\* |
| 424 | CTGTAAA CAACGCC | 1,191 | 1,292 | 527 | 19\* | 20\* |
| 242 | CACGATA GTTTGCC | 905 | 781 | 1,103 | 21\* | 22 |
| 859 | TGTACTA ACACGCC | 920 | 892 | 1,107 | 23\* | 24\* |
| 83 | ACGCTAA CTCCTTG | 8,629 | 7,704 | 19,500 | 25 | 26 |
| 383 | CGTTTAC GATGTGG | 7,278 | 6,402 | 19,022 | 27 | 28 |
| 804 | TCTTAGG AAACGCC | 0 | 0 | 70 | 29\* | 30\* |
| 834 | TGCAATA GACGACC | 0 | 1 | 72 | 31\* | 32\* |

Table 3. PCR detection for the presence of label sequences in the processed DNA sample that was hybridized to microarray, or in the DNA sequencing library. Each PCR contained 0.1 pg of template, which represents approximately $1\times10^6$ DNA molecules. The number of mapped sequencing reads and the microarray intensity of each of the 16 labels for this selected gene target (Chr4, 3.62 ng) are listed. The last 2 columns show the gel lane number containing the indicated sample. Those numbers indicated by an * correspond to reactions where PCR failed to detect the label sequence in the sample.

Although we can clearly confirm their presence in the sequencing libraries, it is unclear as to why these labels are missing or under-represented in the final sequencing data.

To test the stochastic behavior of label selection, we pooled the results of multiple reactions at low target concentrations (0.36 and 0.036 ng), where the probability that a label will be chosen more than once is small.

Figure 14:
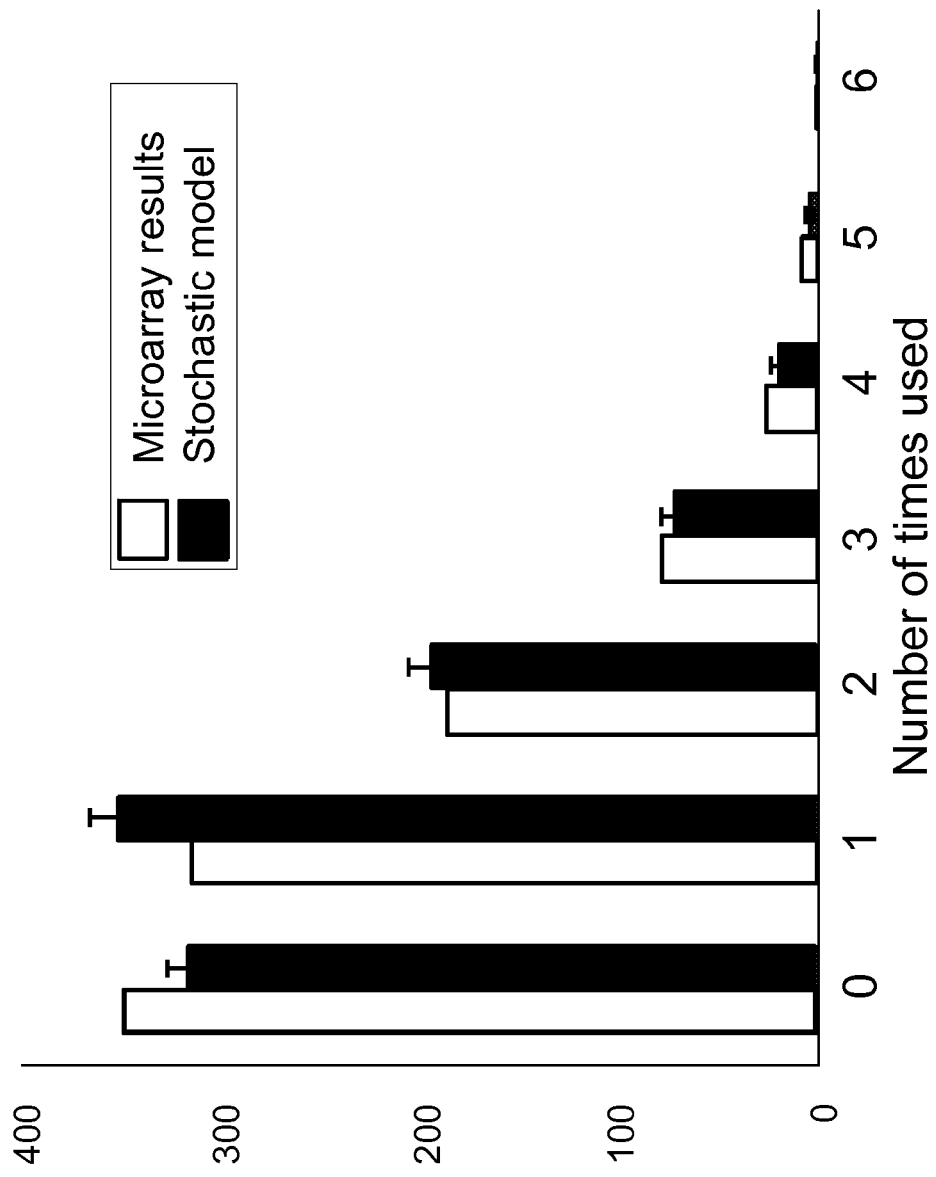
FIG. 14 shows a comparison between experimentally observed label usage with those predicted from stochastic modeling.

FIG. 14 shows that the number of times each label is used closely follows modeling for 1,064 data points obtained from microarray counting. The graph is a comparison between experimentally observed label usage rates (microarray results) with those predicted from stochastic model (stochastic model). At low target molecule numbers, the chance of multiple target ligations to the same label sequence is low. It is therefore reasonable to consider data from experiments with low target numbers (0.036 ng and 0.36 ng of DNA), from those experiments, a total of 1,064 labels were observed, with the total frequency of label usage ranging from 0 to 6. The theoretically expected label usage frequency for 1,064 target molecules was obtained by performing 5000 simulation runs, with multiple independent reactions simulated in each run. The error bars indicate one standard deviation from the corresponding means.

Furthermore, since each end of a target sequence chooses a label independently, we can compare the likely hood of the same label occurring on both ends of a target at high copy numbers. Table 4 columns 10-11 present the experimentally observed frequency of labels occurring in common across both ends of a target and their expected frequency from numerical simulations. No evidence of non-stochastic behavior was observed in this data.

TABLE 4

| Gene target | Genomic DNA amount (ng) | Estimated # of molecules at either end | Expected # of labels at either end | Expected # of labels in common across paired-ends | Microarray observed # of labels | | | # of molecules inferred from microarray observed # of labels | Expected # of labels in common across paired-ends | Microarray observed # of labels in common across paired-ends |
|---|---|---|---|---|---|---|---|---|---|---|
| | | | | | L | R | Avg | | | |
| Chr4 | 3.62 | 1034 | 633 | 417.68 ± 11.35 | 501 | 525 | 513 | 733 | 273.96 ± 10.24 | 303 |
| | 1.45 | 414 | 336 | 117.92 ± 7.83 | 260 | 256 | 258 | 300 | 69.22 ± 6.43 | 63 |
| | 0.36 | 103 | 98 | 9.93 ± 2.81 | 102 | 107 | 104 | 110 | 11.26 ± 2.99 | 20 |
| | 0.036 | 10 | 10 | 0.11 ± 0.32 | 14 | 14 | 14 | 14 | 0.20 ± 0.44 | 0 |
| | 0 | 0 | 0 | 0 | 0 | 0 | 0 | 0 | 0 | 0 |
| Chr21 | 3.62 | 1551 | 769 | 616.74 ± 11.94 | 651 | 627 | 639 | 1051 | 425.28 ± 11.37 | 453 |
| | 1.45 | 620 | 457 | 217.36 ± 9.51 | 335 | 341 | 338 | 416 | 118.79 ± 7.83 | 130 |
| | 0.36 | 155 | 143 | 21.37 ± 3.98 | 160 | 157 | 158 | 172 | 25.86 ± 4.38 | 32 |
| | 0.036 | 15 | 15 | 0.24 ± 0.48 | 20 | 20 | 20 | 20 | 0.40 ± 0.62 | 0 |
| | 0 | 0 | 0 | 0 | 0 | 0 | 0 | 0 | 0 | 0 |
| ChrX | 3.62 | 517 | 400 | 166.63 ± 8.81 | 281 | 306 | 294 | 351 | 90.14 ± 7.08 | 103 |
| | 1.45 | 207 | 186 | 36.26 ± 4.98 | 148 | 133 | 140 | 151 | 20.34 ± 3.94 | 23 |
| | 0.36 | 51 | 50 | 2.58 ± 1.52 | 50 | 48 | 49 | 50 | 2.45 ± 1.51 | 4 |
| | 0.036 | 5 | 5 | 0.03 ± 0.16 | 11 | 10 | 10 | 10 | 0.10 ± 0.31 | 2 |
| | 0 | 0 | 0 | 0 | 0 | 1 | 0 | 0 | 0 | 0 |
| 1 | 2 | 3 | 4 | 5 | 6 | 7 | 8 | 9 | 10 | 11 |

Labels detected on microarray experiments are quantified in Table 4. Indicated quantities (col. 2) of genomic DNA derived from a Trisomy 21 male sample were tested on 3 chromosome targets (col. 1). The estimated number of copies of target molecules (or haploid genome equivalents, col. 3), the number of labels expected by the stochastic model (col. 4), and the actual number of labels detected on microarrays (col. 6-8) are summarized. Because each gene target fragment paired-end consists of random, independent label ligation events at the left (L) and the right (R) termini, the number of identical labels expected (col. 5) can be predicted from computer simulations, and compared to the number actually detected (col. 11). Given the number of labels detected (col. 8), we obtain the corresponding number of copies of target molecules (col. 9) in our stochastic model, and the predicted occurrences of identical labels across paired-ends (col. 10). The numbers in col. 5 and 10 are the means from 5,000 independent simulation runs along with one standard deviation of the corresponding means, given the number of labels at either end (col. 4 and col. 9).

The detailed column information for Table 4 is as follows: column 1: name of tested gene targets; column 2: estimated number of target molecules at either left or right end, this number is determined by PICOGREEN dye measurement (Molecular Probes, Inc.), the DNA concentration is also listed in this column; column 3: number of labels expected to be observed/used at either end (predicted by theoretical models), given the estimated number of target molecules in 2nd column; column 4: number of labels expected to be observed in common across the paired-ends (predicted by theoretical models), given the estimated number of target molecules in 2nd column; column 5: empirically observed number of labels used at the left end of gene target; column 6: empirically observed number of labels used at the right end of gene target; column 7: empirically observed number of labels used in common across the paired-ends; column 8: number of target molecules predicted by theoretical models, based on the empirically observed number of labels used (i.e., number in 7th column); column 9: number of labels expected to be observed in common across the paired-ends, given the number of target molecules in 8th column; column 10: empirically observed number of labels that were used in common across the paired-ends of the gene target.

Example X

An array was designed having 48 target sequences. Each target was paired with one of 3840 labels or "counters" for a total of 48×3840 or 184,320 probes. The probes were 30 mers (30 nucleotides in length) and the assay was designed to test whether or not the 30 mer imparts sufficient discrimination. Of the 30 bases, 15 bases are from the labels and the other 15 bases are derived from the targets. The probes were assayed to determine if each label-target combination hybridizes specifically. A phage RNA ligase was used to join labels with targets. Universal priming sites of 18 bases were included on the 5' end of the labels and the 3' end of the targets, facilitating PCR amplification of the joined label-targets. The method is diagrammed in FIG. 3.

The 3840 distinct label oligos (counters) were single stranded oligos pooled from the Dde1 TACL primer panel (40 primer plates by 96 wells per plate for 3840 different oligos). An example label oligo 301 is shown (SEQ ID NO: 1964) 5'TCGATGGTTTGGCGCGCCGG-TAGTTTGAACCATCCAT-3'. The 48 different primers used as "targets" were synthesized using as target 48 different 21 nucleotide sequences from the Affymetrix TrueTag 5K_A array. An example target oligo 307 is shown (SEQ ID NO: 1965) 5'GCCATTTACAAACTAGGTATTAATC-GATCCTGCATGCC-3'.

The "label" or "counter" oligo has an 18 nt common sequence at the 5' end and a 15-28 nt "label" (or "counter") sequence at the 3' end. An example "label" 305 is shown. The universal primer 303 common to all or a group of the label oligos has sequence 5' TCGATGGTTTGGCGCGCC-3' (SEQ ID NO: 1966) at the 5' end and each target oligonucleotide has common sequence 311 5' AATCGATCCTGCAT-GCCA-3' (SEQ ID NO: 1967) at the 3' end as universal priming sequence. The target oligos vary in sequence at the 5' ends 309.

A 1:1 dilution of each of the 3840 counters was mixed with various dilutions of each of the 48 target oligos to simulate different expression levels under ligation conditions so that the 5' end of the target oligos can be ligated to the 3' end of the label oligos. In preferred aspects T4 RNA ligase may be used to join the ends of the single stranded oligos. The 5' and 3' ends of the target oligos are phosphorylated and the 5' and 3' ends of the label oligos are hydroxylated. After the ligation the products are amplified by PCR using primers to the universal priming sequences. Only those fragments that have both universal priming sequences 303 and 311 will amplify efficiently.

Each of the 48 target sequences may be tiled with each of the 3,840 counters, resulting in a total number of features on array=48×3,840=184,320. This is the number of different possible combinations of target with label. The product of the ligation and amplification reactions is hybridized to the array. For each target, the number of features that light up is determined and can be compared to the known copy number of each target in the input sample.

To test the digital counting methods, also referred to as stochastic labeling a collection of label-tag sequences was provided. Each has a common 5' universal priming sequence, preferably 15-20 bases in length to facilitate amplification, and a 3' label sequence, preferably 17-21 bases in length. Each type of primer in the collection has the same universal priming sequence but each type has a label sequence that is different from all of the other types in the collection. In one aspect there are about 4,000 to 5,000 different types of label sequences in the collection to be used. For testing the method, a set of 50 target sequences was synthesized. The target sequences each have a universal priming sequence at the 3' end (5'GCTAGGGCTAATATC-3'SEQ ID NO: 1968, was used in this experiment). Each of the 50 oligo target sequences that were generated has a different 21 base sequence from the GENFLEX array collection of sequences, for example, 5' GCCATTTACAAACTAGGTATT'3' SEQ ID NO: 1970. The collection of label-tag oligos and the collection of target oligos was mixed. Various dilutions of the different targets were used in the mixture of targets to simulate a mixed population present at different levels, for example, different expression or copy number levels. T4 RNA ligase was added to ligate the label-tag oligos to the target oligos. There are 5000 different types of label oligos and 50 different types of target oligos so the majority of the target oligos of the same type will be labeled with a type of label oligo that is different from all of the other target oligos of that type. So target oligo type 1, occurrence 1 will be labeled with a label oligo type A (11A) and target oligo type 1, occurrence 2, will be labeled with a different label oligo, label oligo type B (12B). There is a finite and calculable probability that two or more occurrences of the same target type will be labeled with the same label oligo (11A and 12A), but that probability decreases as the number of different types of label oligos increases relative to the number of occurrences of any given type of target.

The ligated target/label oligos are then amplified using primers to the universal priming sites. Labels can be incorporated during amplification. The labeled amplification product is then hybridized to an array. For each different possible combination of target (50) and label (5000) there is a different probe on the array that targets that junction of the target ligated to the label. There will therefore be 50×5000 different probes on the array or 250,000 different probes.

Scanned images of the 48×3840 array were analyzed and compared to expected results. A total of 8 of the 48 targets were ligated to a pool of 3840 labels (counters). The assay was as shown in FIG. 3. The conditions were single strand deoxyoligonucleotide ligation using a phage RNA ligase to join the labels with targets. Universal priming sites on the targets and labels were included to enable PCR amplification of the joined label-targets. The ligation conditions were essentially as described in (Tessier, D. C. et al. (1986) *Anal Biochem*. 158, 171-178, 50 mM Tris-HCl, pH 8, 10 mM MgCl2; 10 ug/mL BSA, 25% PEG, 1 mM HCC, 20 uM ATP; 5:1 acceptor (labels) to donor (the 8 targets) ratio at 25 C overnight. The products were amplified using PCR, purified, biotin labeled with TdT, hybridized to the array, washed, stained, and scanned. The expected 8 blocks show hybridization to the array in the expected patterns.

Different ligation conditions were also tested by ligating either a single target or a pool of 48 targets to the 3,840 counters. The concentrations of the targets used in the experiment were high as in the previous experiment so most counters will be ligated to targets. In ligation 1 a single target was ligated to 3,840 labels. In ligation 2, 48 targets at 1:1 copy number were ligated to 3,840 labels. Ligation 3 is a negative control for PCR so no DNA was added. PCR with the pair of universal primers was performed using the ligation products as template and the products separated on a gel. As expected a band was observed from ligations 1 and 2, but not 3. The PCR products were labeled and hybridized to the array and the scan images after array hybridization were analyzed. As expected no signal was observed for ligation 3, all of the targets were observed for ligation 2 and the single expected target was observed for ligation 1. The single target lights up in the correct region of the chip, but background signal was also observed in unexpected locations. Increased stringency of hybridization conditions can be used to minimize hybridization to unexpected probes of the array.

In another example, conditions for optimization of hybridization to decrease cross hybridization were tested. The products used were as described above and hybridization was performed with formamide and with or without non-specific competitor (herring sperm DNA). The non-specific signal is significantly decreased in the presence of formamide, with and without non specific competitor. This demonstrates that even though the targets and counters alone have 15 bases of complementarity to probes on the array, the combination of target plus counter and the resulting increase to 30 bases of complementarity to the probes, results in specific hybridization. Within the block of 3,480 probes, there is heterogeneity in the hybridization intensity. Preliminary sequence analysis shows a strong correlation of GC content with high signals. To minimize this array probes may be selected to have similar melting temps for the counters or the target-counter combination may be optimized to obtain similar hybridization stabilities. For example, if two targets are to be analyzed the portions of each target that are to be part of the probe may be selected to have similar TMs.

To test the efficiency of T4 RNA ligase in the ligation of labels to targets, DNA ligase from *E. coli* was tested. This required a slight modification of the sample prep (as depicted in FIG. 7) by creating an overhang site for duplex ligation. The target in this example has a double stranded target specific portion and a single stranded overhang. The overhang may be, for example, a run of inosine bases, for example 6 to 9, or a string of random bases, for example, N6-16. DNA ligase is used to close the gap and generate a ligated product that includes the target strand and a label/counter from the pool of 3,840 counters. The PCR is carried out in the same manner as above using common primers.

The expected targets were observed, but some non-specific bands were also detected in the amplified DNA, even in the absence of the target. This suggests that the some of the 3,840 labels are combining with each other when this method is used. Selection of an optimized pool of labels may be used to mitigate such interference.

In another example random primed PCR was tested. Instead of a ligation step, the targets have a 3' random region, that can be, for example, a degenerate region or an inosine region. The labels hybridize to the random region and the random region is used as a primer for extension through the label during the PCR step to append a copy of the label and the universal priming site at the 5' end of the label oligo to the 3' end of the target. The extended target has a copy of the label sequence and the universal priming sequence and can be amplified by PCR.

In another example, a purification method for removing excess un-ligated counters was tested. The method is shown schematically in FIG. 11. The counters 101 and the targets 2103 are ligated to form counter-target molecules as shown previously. A support bound probe that is complementary to the universal primer at the end of the target oligonucleotides 2105, is used to separate counter-targets and targets from un-ligated counters. The support 2109 may be, for example, a magnetic bead. A second separation can be used to separate counter-targets from un-ligated targets. The second separation uses a support bound probe complementary to the universal priming sequence at the end of the counters 2107. The single capture reduces background amplification. A double round of capture may also be used.

Figure 18:
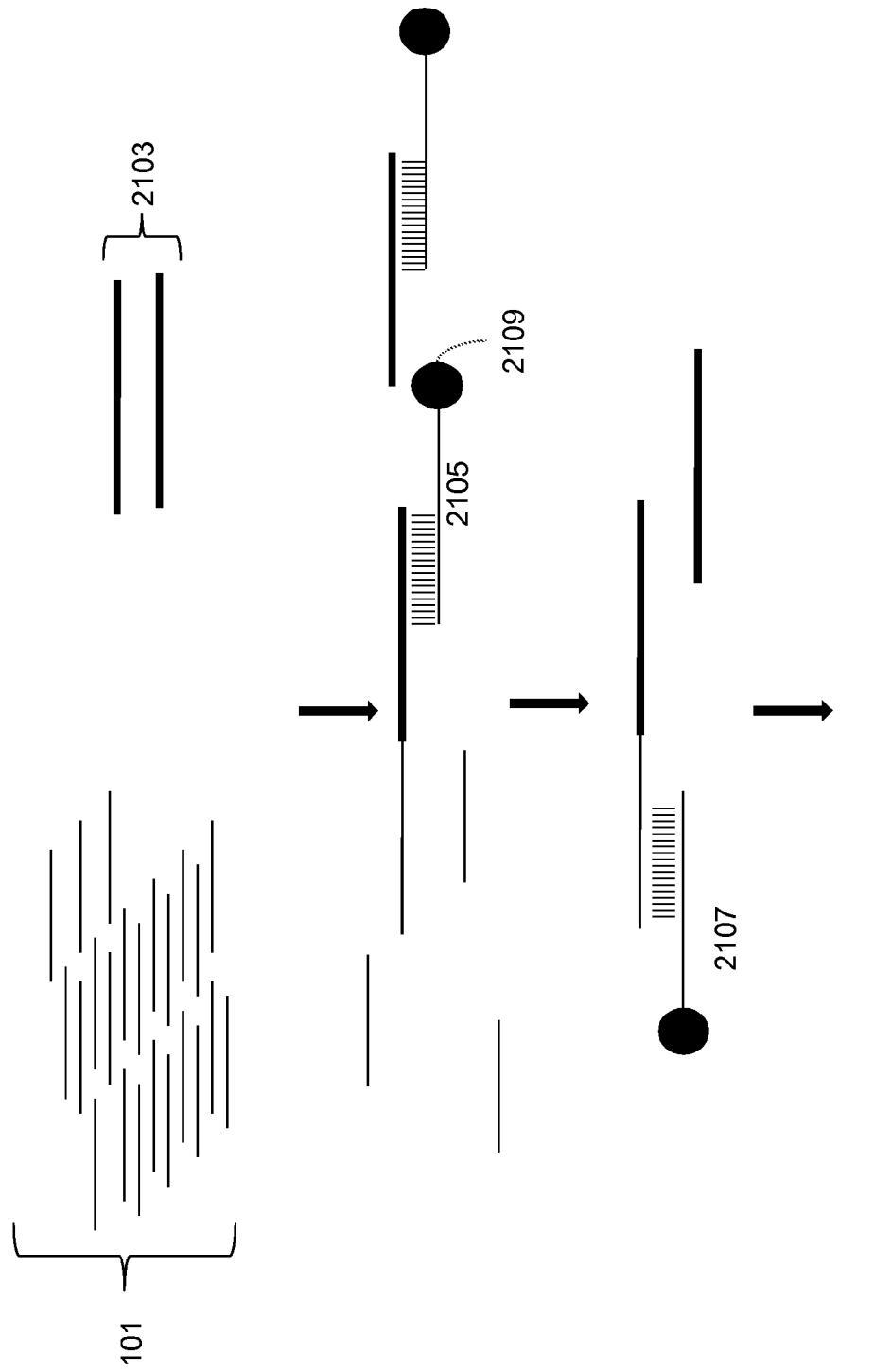
FIG. 18 shows a schematic of a method for enriching for molecules that contain labels, target or both.

In FIG. 18 a scatter plot is shown to illustrate one way of representing the combinations of different target occurrences ligated randomly to different labels in the set. The plot shows combinations for 20 different target occurrences (labeled 1 to 20) representing 20 copies of the same target. The Y-axis represents different labels identified by a number from 1 to 1000. Each of the targets can be labeled with any of the 1000 labels, for example target 1 is labeled with label 351 and has coordinates (1, 351). The labels are distinct and distinguishable while the targets are the same in this example.

Figure 19:
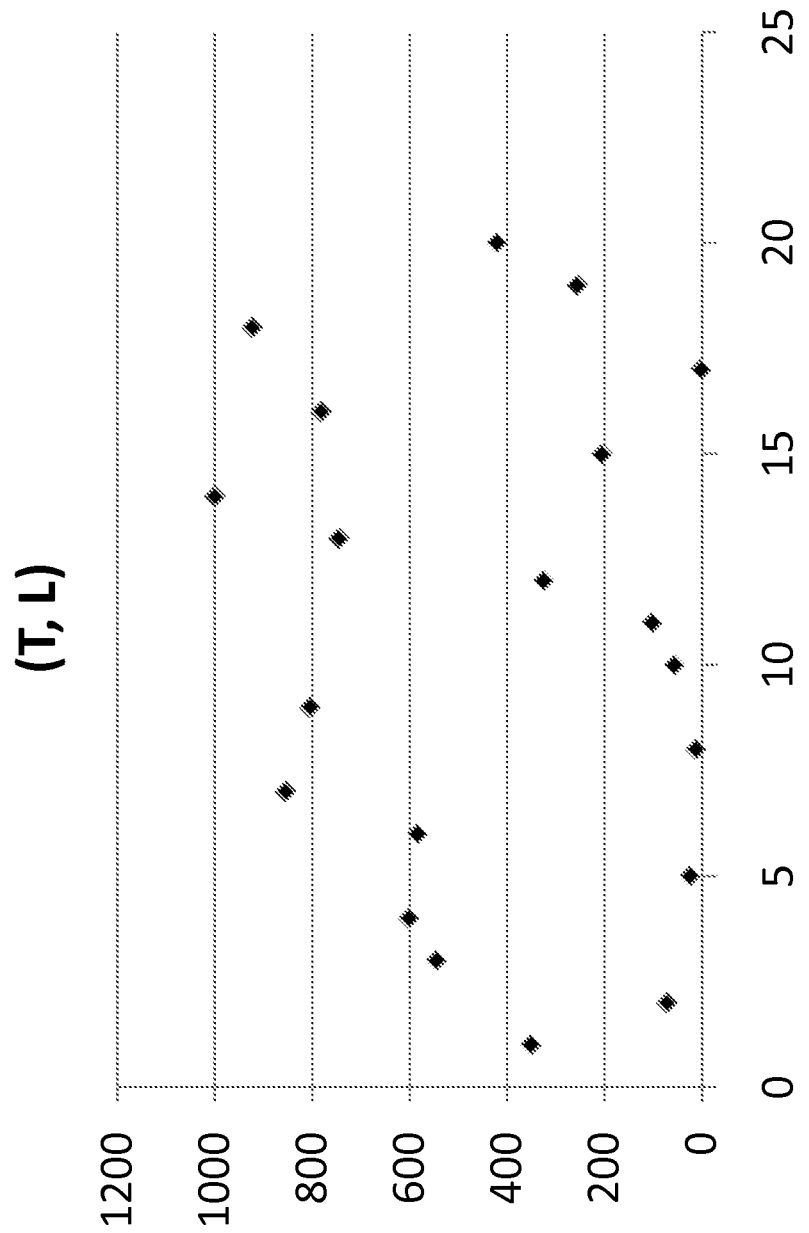
FIG. 19 shows a scatter plot of a series of different target plus label combinations.

FIG. 19 shows a schematic where genomic DNA 1901 is fragmented, for example at restriction sites 1903 to produce fragments 1905. The fragments are ligated with labels to form fragments labeled at both ends 1907. All fragments can be ligated to the labels The label-ligated fragments are circularized, for example, by ligation of the label ends to form closed circles 1909 with first and second labels forming a single label 1911. The circularized fragments can be treated with exonuclease to remove unligated fragments. The circle and label can be amplified using gene-specific PCR primers 1913. The PCR product has the label region 1911 flanked by target specific regions. The array probe is preferably complementary to the junction between the target specific region and the label. There are two such junctions 1915 and 1917 in the PCR product and each could be targeted on either strand (since the product is double stranded). The products may be fragmented, labeled and hybridized to an array of probes to the junctions. The label-target combination can be hybridized to an array for counting.

Figure 20:
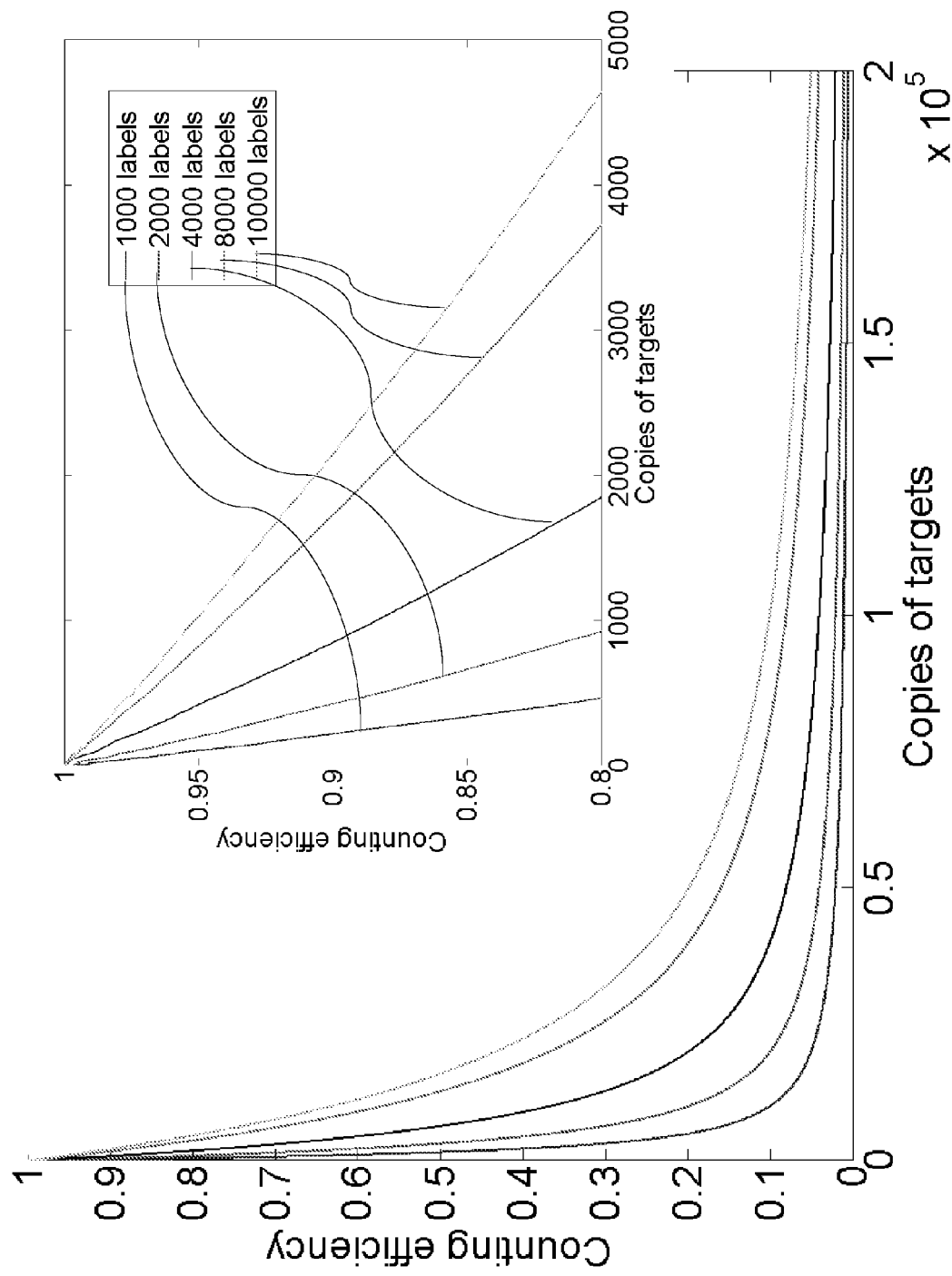
FIG. 20 shows a plot of counting efficiency versus copies of target as the number of labels varies. The inset is a magnification of the upper left portion of the graph.

FIG. 20 shows a graph of counting efficiency on Y axis and copies of target on X axis. The different lines represent different numbers of labels being used, from 1000 to 10,000. The inset graph is a blow up of the upper left hand region of the larger graph and shows how counting efficiency changes with the number of labels. Fewer labels results in a more rapid decrease in counting efficiency as the number of targets increases.

FIG. 21 is a plot of labels observed per target as the copies of targets increases and the number of label types increases.

Figure 5:
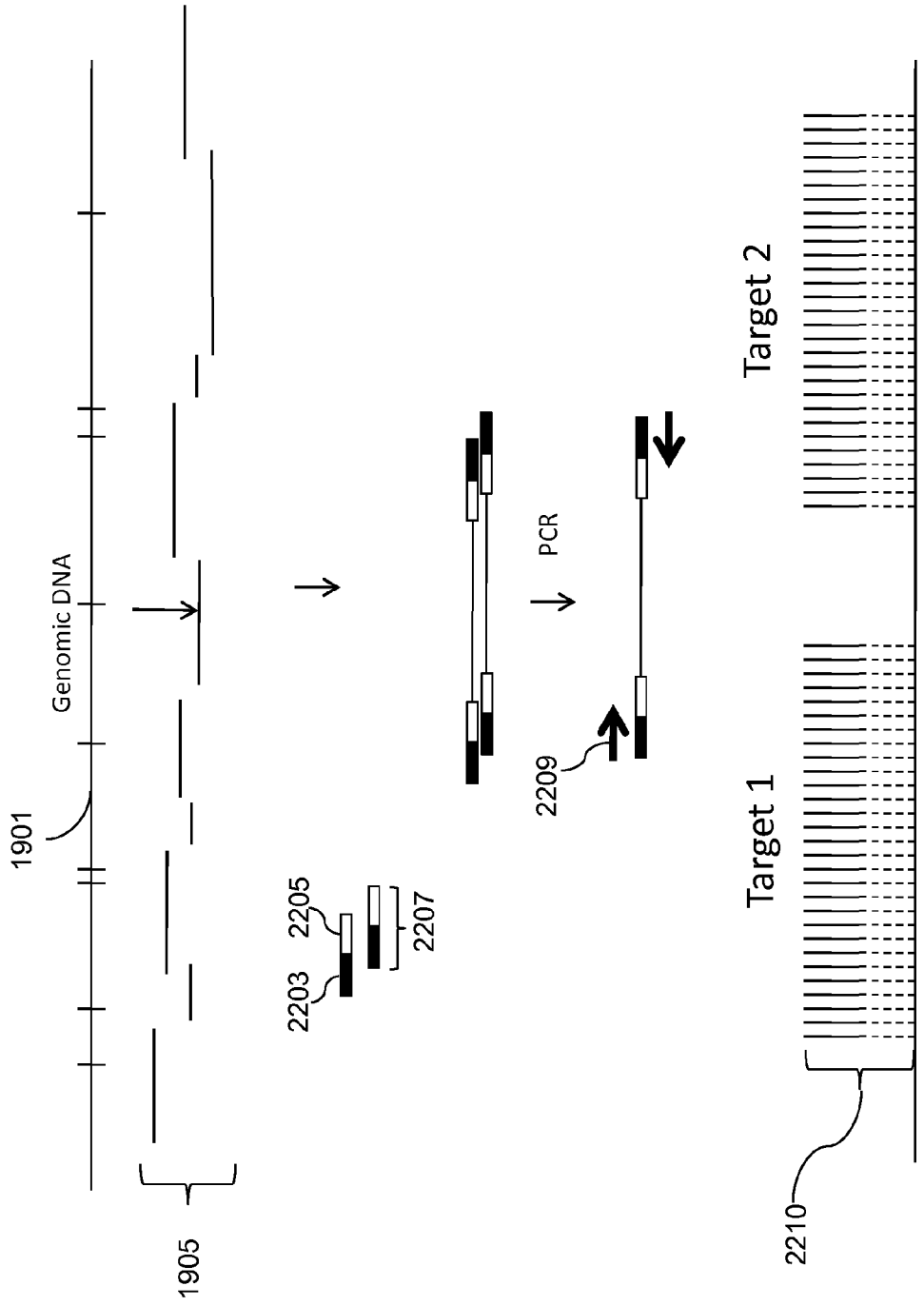
FIG. 5 shows a schematic of a method for target preparation.

In another embodiment, illustrated schematically in FIG. 5, genomic DNA 1901 is fragmented with a restriction enzyme, for example, BamHI, which generates a single stranded overhang for sticky ended ligation. The fragments 1905 are ligated to adaptors 2207 that include a label 2205 and a universal priming site 2203. Different adaptors vary in the label portion 2205 but have a common priming site 2203. The label is 3' of the universal priming site so that it is between the fragment and the universal priming site. The adaptor ligated fragments are amplified by PCR using primer 2209. The PCR product can be fragmented, labeled with a detectable label and hybridized to an array. The resulting strands are detected by hybridization to an array having target-label probes 2210 and includes different features for each target-label combination. The array has a different feature for each target-label-tag combination. The PCR amplicons may be fragmented prior to array hybridization. Preferably the fragments are labeled, for example, by TdT incorporation of a nucleotide that can be detected, such as a biotin containing nucleotide.

The probes of the array are complementary to the junction between the label and the restriction fragment. The sequences at the ends of the individual strands of the restriction fragments are predicted based on in silico digestion of the human genome. Also, fragments are targeted that are within the size range that is known to amplify efficiently by adaptor ligation PCR, for example, 200 bases to 2 kb. The adaptor 2201 had two segments, a constant priming region 2203 and a variable label region 2205. Together 2203 and 2205 form the label adaptor 2207. The primer 2209 has the same sequence 5' to 3' as the 2203. The schematic is drawn showing only one strand, but one of skill in the art would understand that in a preferred embodiment the genomic DNA is double stranded and the restriction fragments have two strands, which may be referred to as a top strand and a bottom strand. The convention is that the top strand is drawn 5' to 3' left to right and the bottom strand is the complement of the top strand and is drawn 3' to 5' left to right. Adaptors are preferably double stranded for at least a portion of the adaptor, they may have single stranded overhangs, for example to have "sticky ends" that facilitate hybridization and ligation to the overhang resulting from restriction digestion. In a preferred aspect, the same adaptor can be ligated to the two ends of a strand of a restriction fragment and may be ligated to one or both strands. The adaptor may be ligated to the ends of the top strand in opposite orientations as shown in FIG. 22, so that the label is internal to the priming site at both ends. The adaptor may have a top and a bottom strand and the top strand may be ligated to the top strand of the fragment and the bottom strand ligated to the bottom strand of the fragment. The top and bottom strands of the adaptor may be complementary over the entire length, but often have single stranded regions at one end to facilitate sticky ended ligation to an overhang created by a restriction enzyme.

To test this method several adaptors were generated. The test adaptor has PCR002 (SEQ ID No. 1969) as top or sense strand and BamAdaAS (SEQ ID No. 1970) as bottom or antisense strand.
PCR002 5' ATTATGAGCACGACAGACGCCTGATCT (1969)
BamAdaAS 3' AATACTCGTGCTGTCTGCGGACTAGAC-TAG 5'P (1970)
The single stranded region on the right is the BamHI single stranded overhang. Te adaptor also has a half Bgl II site. The "full length-label" adaptor has SEQ ID No. 1972 as top or sense strand and SEQ ID No. 1973 as bottom or antisense strand.
Sense 5' ATTATGAGCACGACAGACGCCTGATCT-NNNNNNNNNNNNNNT
AntiSense 3'AATACTCGTGCTGTCTGCGGACTA-GANNNNNNNNNNNNNNACTAG
A 5' phosphate may be added to one or both strands of the adaptor using, for example, T4 polynucleotide kinase. In some aspects a truncated adaptor may be used. An example of such an adaptor is shown in FIG. 7, the top or sense strand is SEQ ID No. 1974 and the bottom or antisense strand is SEQ ID No. 1975. The portion of the sequence that has a line through it for both SEQ ID NOs. 1974 and 1975 indicates bases missing as compared to SEQ ID NOs. 1972 and 1973 respectively. The N's in SEQ ID Nos. 1972-1975 indicate a variable sequence in the adaptor that is different for each different label. For example, if there are 1,920 different labels to be used then the $N_{14}$ represents the 1,920 different labels.

In some aspects it is preferable to use shorter oligos. The full length adaptor in includes 87 bases. The truncated adaptor has 57 bases. Since 2 different oligos must be synthesized for each different label adaptor (e.g. 1,920 labels requires 3,840 different oligos) shorter adaptors are more economical. The separate oligos are preferably annealed together prior to being combined into a pool for ligation to fragments. The primer may be, for example, SEQ ID NO. 1969 or the 5' 17 bases of SEQ ID No. 1974.

Figure 24:
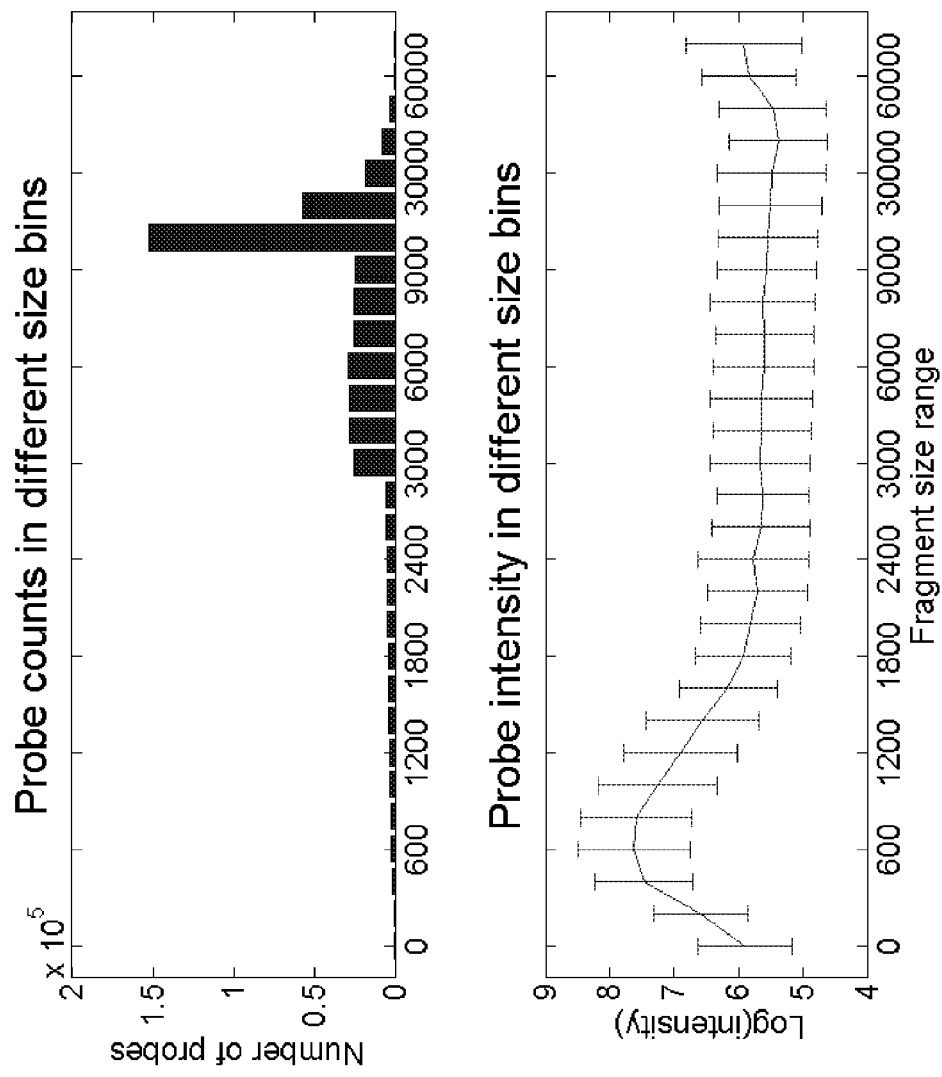
FIG. 24 shows plots showing fragment size distribution and mean raw intensity on chr22 tiling probes on the "CNV-type" array.

FIG. 24 shows the results of a control experiment where the test adaptor was ligated to fragmented genomic DNA and analyzed on an array having genomic probes. The DNA was subjected to fragmentation with a BamHI, the test adaptor was ligated to the ends and SEQ ID No. 1969 was used as a primer for PCR amplification. The PCR products were fragmented and end labeled using TdT and hybridized to a CNV-type and HG49 arrays. The upper plot is the number of probes (number of different features where each feature corresponds to a different probe sequence) complementary to restriction fragments in the different size bins shown on the X-axis. The sizes and sequences of restriction fragments from a selected genome can be predicted and binned according to size. The probes of the tiling array (probes essentially all non-redundant sequences in the genome) can be assigned to the restriction fragment to which the probe is complementary. Longer fragments will have larger numbers of probes that are complementary to that fragment, simply because the fragment is longer. Restriction fragment size is distributed based on the frequency of the occurrence of the recognition site. Note that the X axis does not increase linearly. While there are more probes that are complementary to fragments in the bins of size greater than 3000, particularly in the bins between 9000 and 30,000, but the intensity in those size bins is less than the intensity of the bins that are about 400 to about 1800. The larger fragments, greater than 9000 bases, for example, do not amplify efficiently with PCR, resulting in lower representation of those large fragments in the hybridization.

In another example, a truncated label adaptor was used (SEQ ID Nos. 1974 and 1975). The adaptor ligated fragments were extended to fill in the ends with polymerase prior to PCR. Hybridization was done in duplicate to either the CNV-type array or HG49 design C. Fragmented DNA and non-fragmented DNA were plotted. The intensity of the DNA that was not fragmented prior to hybridization is less than the intensity of the fragmented DNA. The peak of the intensity for both plots is at a fragment size of about 900 base pairs.

FIG. 11 shows a theoretical modeling of the number of counters predicted to be observed at least once 3201, exactly once 3202 or exactly twice 3203. A non-depleting reservoir of 960 diverse labels was considered. Equation (1) was used to calculate the at least once curve, equation (2) the exactly once curve and equation (3) the exactly twice curve. The error bars indicate one standard deviation from the corresponding mean value.

$$E[k] = m\left[1 - \left(1 - \frac{1}{m}\right)^n\right] \quad (1)$$

$$\mathrm{Var}[k] = m\left[1 - \left(1 - \frac{1}{m}\right)^n\right]\left(1 - \frac{1}{m}\right)^n + m(m-1)\left[\left(1 - \frac{2}{m}\right)^n - \left(1 - \frac{1}{m}\right)^{2n}\right] \quad (2)$$

FIG. 12 shows counting results for DNA copy number titrations using microarray hybridization in (A) or DNA sequencing in (B). Dilutions (3.62 ng, 1.45 ng, 0.36 ng and 0.036 ng) of a DNA sample isolated from cultured lymphoblasts of a Trisomy 21 male individual were processed for microarray hybridization (left) and DNA sequencing (right). Three chromosome targets were tested and observed numbers of counters (Y-axis) are shown (curve 1201). The number of target molecules for each sample (X-axis) was determined from the amount of DNA used, assuming a single cell corresponds to 10 pg. For comparison, the theoretical counter usage rates from the stochastic model equation are also plotted 1202. Numerical values are provided in Table 4.

BamHI cuts the human genome into an estimated 360,679 fragments with a size distribution of 6 bp to 30,020,000 bp. The median size is 5142 bp and the mean is 8320 bp. There are 79,517 fragments in the size range of 150 bp to 2 kb. For testing it may be desirable to choose fragments that meet selected criteria, for example, within a selected size range, select fragments that have more than 1 probe on the HG49m array, exclude fragments that are in known CNV regions, or exclude fragments having a SNP in the first or last 20-30 bases.

Figure 26:
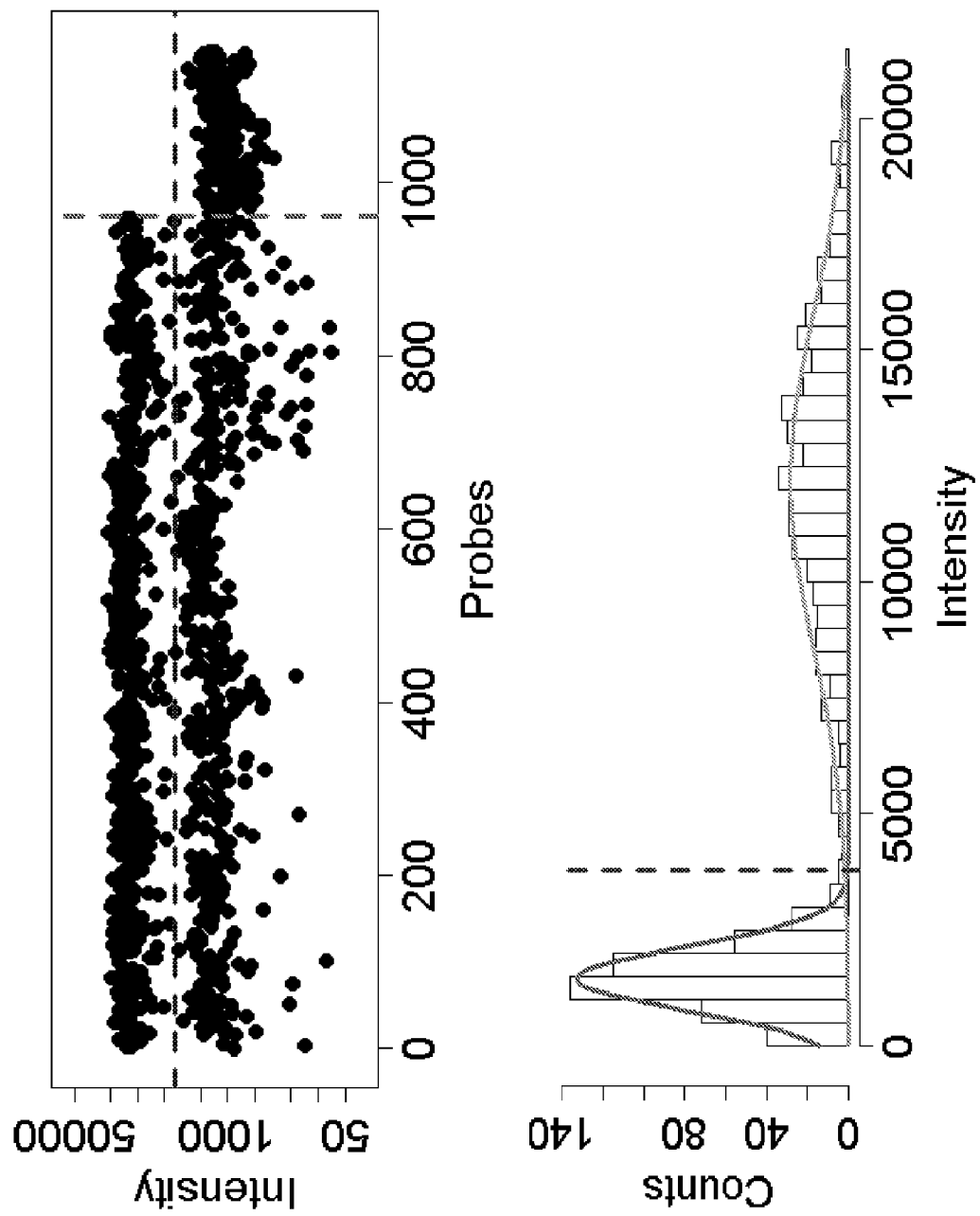
FIG. 26 shows intensities of 1,152 array probes associated with a single gene target on chromosome 4 in the upper panel and a histogram of the intensity data corresponding to 960 labels in the lower panel.

The upper panel of FIG. 26 shows the intensities of 1,152 array probes associated with one gene target on chromosome 4, chr4_01s. The data are from the array with 5 ng DNA, i.e., 1000 copies of the tested gene target. The 1,152 probes shown share the same genomic sequence portion, but have different label sequences. Each black dot represents one label sequence. The left 960 dots (on the left side of the red vertical line) correspond to specific labels (i.e., labels used in ligation reaction), and the right 192 dots correspond to non-specific labels (i.e., labels not used in ligation reaction). The probe intensities were plotted in natural log scale on the y-axis. The blue horizontal line is the threshold determined by analysis algorithm (see Materials and Methods), which has a value of 3,800.

The array design for the experiment represented in FIG. 26 is as follows. For each gene target assayed, the array probe consists of all possible combinations of the 960 label sequence and either of the two BamHI genomic fragment ends. An additional 192 label sequences that were not included in the adaptor pool were also tiled to serve as non-specific controls. This tiling strategy enables consistency check on the number of labels used at the paired ends, since each target fragment is ligated to two independent labels (one on either end), and for the same target fragment, the counts on the left and right side should be very similar.

The lower panel shows the histogram of the intensity data corresponding to 960 specific labels. Also shown in the figure are the 2 fitted normal distributions, designated by red and green curves, respectively. The fitted distributions have the mean and standard deviation of 1447±680 and 12186±3580, respectively. The blue vertical line is the threshold, which has the same value as the blue horizontal line shown in the upper panel. Based on such threshold, 501 probes (i.e., labels) were counted as "used".

Figure 27:
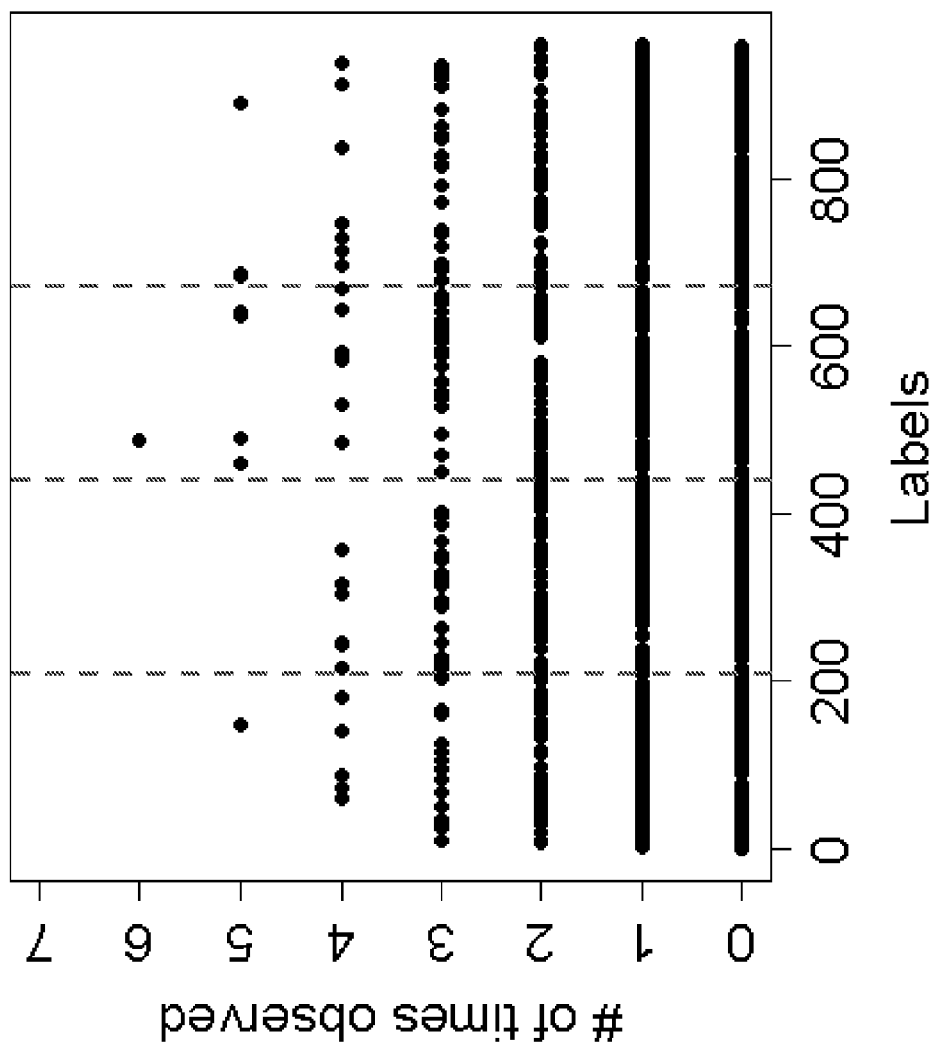
FIG. 27 shows a plot of the number of times each of the 960 labels was observed in ligations with low DNA target amounts.

FIG. 27 shows the number of times observed for each of the 960 specific labels. Empirically, we did not observe 349 labels in any of the 20 cases. By model, we would expect to observe 643.05±9.96 labels at least once, which means we expect not to observe 307~327 labels. This result shown was obtained by grouping labels used in independent ligation reactions together. To more accurately estimate the frequency of usage of labels, only data from experiments with low concentrations (0.05 ng and 0.5 ng of DNA ligation amount) were considered. Under each concentration, 5 different gene targets independently ligated to labels at both ends. Therefore, a total of 20 independent reactions (2 concentrations×5 gene targets×2 ends) were grouped together. Of these reactions, 1,064 labels were observed; some were observed more often than the others, the frequency of usage of labels ranges from 0 to 6.

Figure 28:
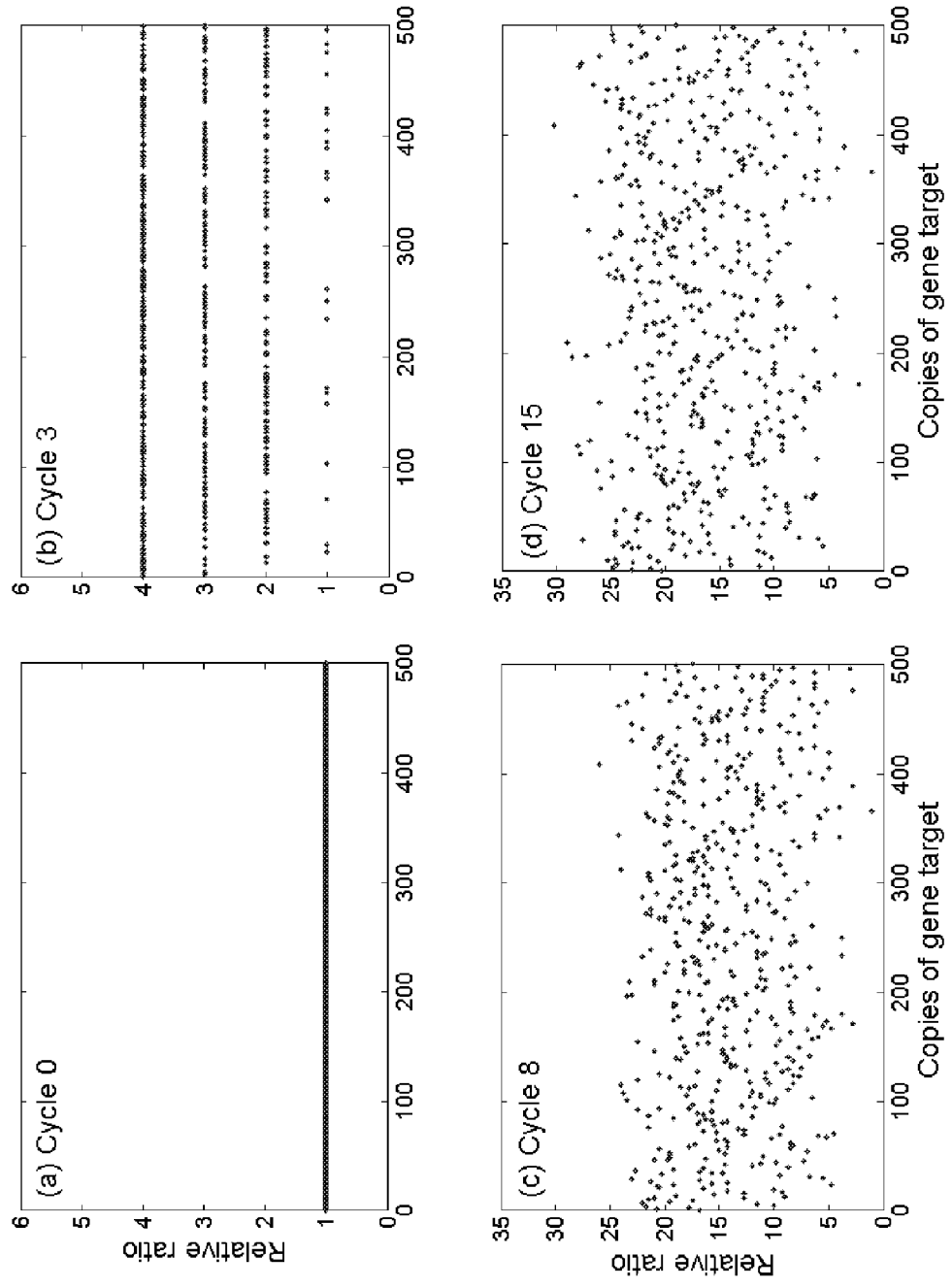
FIG. 28 shows an example of a replication process on a collection of 390 uniquely labeled target molecules resulting from 960 diverse labels independently marked with 500 copies of a target molecule.

FIG. 28 shows one example of the replication process of 500 copies of a gene target. In each subplot, copies of target molecules were plotted in the same order. The y-axis is the relative ratio of the number of amplified molecules over the minimal number of amplified molecules in each PCR cycle. Before PCR, all copies are of equal amount, i.e., each copy has one molecule at cycle 0 (subplot (a)). As the PCR process goes on, we start to see differences in the number of amplified molecules corresponding to different copies of target molecules. For example, in cycle 3 (subplot (b)), the ratio between most and least abundant of amplified molecules is 4. Such ratio becomes larger as the number of PCR cycle increases. In cycle 8 and 15, the ratio becomes 26 and 30, in cycles 8 and 15 respectively (see subplots (c) and (d)). This suggests that the differential usage of labels may be observed before PCR is started. Such difference in the amount of molecules associated with different labels will carry on as PCR process goes on.

PCR simulation. We defined n copies of a gene fragment T, each ligated to a single counter randomly selected from an infinite pool of m unique counters to generate a collection of k resulting counter-ligated gene target molecules $T^*=\{tl_i, i=1, 2, \ldots, k\}$. We assumed that each counter-ligated gene target molecule $tl_i$ replicates randomly and independently of other target molecules; and that the replication probability p (i.e., amplification efficiency) of different molecules, $tl_i$, remains constant throughout the PCR process. For each $tl_i$, we denote the number of molecules at PCR cycle c as $N_i^c$. When c=0, $N_i^0$ is the initial number of $tl_i$. The PCR process at cycle c+1 can be modeled as a series of $N_i^c$ independent trials that determine the replicability of each of the $N_i^c$ molecules with replication probability p. Let $\Delta N_i^c$ represent the number of molecules replicated at cycle c+1, then the number of molecule $tl_i$ after cycle c+1 is $$N_i^{c+1} = N_i^c + \Delta N_i^c,$$

where the probability of $\Delta N_i^c$ is $$p(\Delta N_i^c \mid N_i^c) = \binom{N_i^c}{\Delta N_i^c} p^{\Delta N_i^c} (1-p)^{N_i^c - \Delta N_i^c}. \tag{2}$$

We determined the relative abundance of different counter-ligated gene target molecules $tl_i$ upon completion of the simulated PCR run for n=500, 50, or 5, and p=0.8, 0.7 or 0.6 (Table 5). In each case, we performed 1,000 independent runs to simulate 30 cycles of adaptor PCR, followed by 30 cycles of gene-specific PCR.

TABLE 5

Shows summary statistics drawn from 100 independent simulation runs modeling PCR, ligation at each end of targets is considered.

| | Initial copy number | | | | | |
|---|---|---|---|---|---|---|
| | N = 5 | | N = 50 | | N = 500 | |
| | Side | | | | | |
| | Left | Right | Left | Right | Left | Right |
| #of labels observed | 5 | 5 | 48.61 0.99 | 48.64 1.09 | 388.91 6.85 | 389.27 7.18 |
| Max | (1.43 0.19) * 10^11 | (1.43 0.19) * 10^11 | (2.18 0.49) * 10^10 | (2.13 0.47) * 10^10 | (4.52 0.59) * 10^9 | (4.44 0.55) * 10^9 |
| Min | (5.73 2.27) * 10^10 | (5.73 2.27) * 10^10 | (2.35 1.06) * 10^9 | (2.35 1.06) * 10^9 | (1.15 0.49) * 10^8 | (1.23 0.49) * 10^8 |
| Ratio btw max & min | 3.13 2.44 | 3.13 2.44 | 14.10 11.41 | 13.87 13.42 | 43.42 25.66 | 44.92 30.04 |
| Mean | (1.00 0.16) * 10^11 | (1.00 0.16) * 10^11 | (1.03 0.06) * 10^10 | (1.03 0.06) * 10^10 | (1.27 0.03) * 10^9 | (1.27 0.03) * 10^9 |
| Standard deviation | (3.44 1.02) * 10^10 | (3.44 1.02) * 10^10 | (3.98 0.52) * 10^9 | (3.94 0.54) * 10^9 | (6.75 0.41) * 10^8 | (6.69 0.40) * 10^8 |
| Coef. of variation | 0.36 0.13 | 0.36 0.13 | 0.39 0.05 | 0.38 0.05 | 0.53 0.03 | 0.53 0.03 |

Focusing on the experiments with concentrations of 0.5 and 0.05 ng, (3$^{rd}$ and 4$^{th}$ in each group of 5), which provide the most accurate count of labels, there are 20 different opportunities for a given label to be observed (2 concentrations×5 amplicons×2 sides (left or right)). We observed 1,064 labels over the 20 opportunities.

Figure 25:
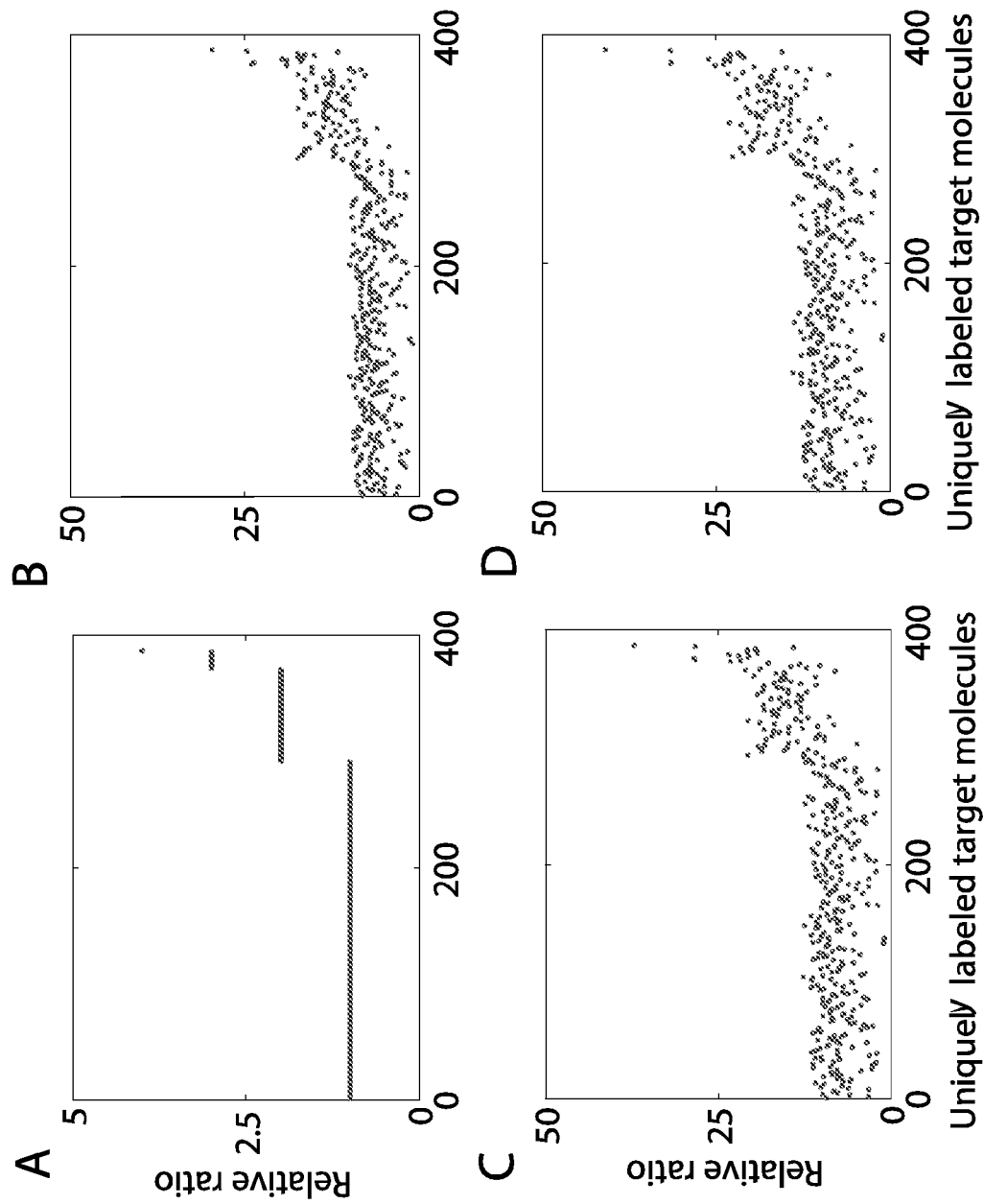
FIG. 25 shows a simulated PCR run showing the replication outcome for 500 molecules of a target fragment ligated to a library of 960 label counters.

To observe the distortion of the relative abundance of DNA molecules in the reaction resulting from the PCR process, dispersion in the quantitative distribution of PCR amplified DNA molecules was analyzed. A model of the PCR process was generated to understand the dispersion in the distribution of amplified molecules (FIG. 25, Table 6). A series of 1,000 independent simulation runs were performed to simulate the replication of uniquely labeled target molecules through PCR processes. For each run, we measured the distribution of the final amount of PCR products and quantified the dispersion of distribution using two measures: ratio of the maximal to the minimal amount, and coefficient of variation of final PCR products. This demonstrates that the degree of dispersion increases with the incidence of replicate use of identical counters, which may be in-part responsible for the deviation observed when assaying high target copy numbers. Table 6 lists the ratio and CV for distributions corresponding to different concentrations and replication probabilities (one sided ligation considered).

TABLE 6

|  | replication probability | n = 5 | n = 50 | n = 500 |
| --- | --- | --- | --- | --- |
| Ratio of max to min amount of PCR amplified product | p = 0.6 | 5.69 ± 4.95 | 26.16 ± 23.78 | 124.18 ± 88.04 |
|  | p = 0.7 | 4.59 ± 8.03 | 16.22 ± 15.53 | 71.55 ± 55.13 |
|  | p = 0.8 | 2.82 ± 1.51 | 11.54 ± 9.53 | 42.24 ± 27.49 |
| Coefficient of Variation (CV) | p = 0.6 | 0.48 ± 0.16 | 0.51 ± 0.06 | 0.62 ± 0.03 |
|  | p = 0.7 | 0.41 ± 0.14 | 0.44 ± 0.05 | 0.57 ± 0.02 |
|  | p = 0.8 | 0.34 ± 0.12 | 0.36 ± 0.05 | 0.52 ± 0.02 |

Example 1 of a method for selecting a collection of labels starting with all possible 14 mers ($4^{14}$ or ~268 million possible labels). Step 1: clustering based on the last 7 bases: all sequences with the same last 7 bases are grouped together; within each cluster, randomly pick one sequence, this gives us 11,025 sequences, denoted by set A. Step 2: clustering based on the first 7 bases: all sequences with the same first 7 bases are grouped together; within each cluster, randomly pick one sequence, this gives us 13,377 sequences, denoted by set B. Step 3: get the union set of set A and B, the combined set has 24,073 sequences. Then do clustering based on the middle 6 bases, randomly pick one sequence out of every cluster, this gives us 3,084 sequences, denoted by set C. Step 4: calculate the all-against-all alignment score of set C, which gives us a 3,084×3,084 self-similarity score matrix, denoted by S. Step 5: filter based on the score matrix. If an element of the score matrix $S(i,j)$ has a high value, that means, the corresponding sequences i and j are very similar to each other. Starting from the elements with top self-similarity score, randomly pick one and discard the other; repeat this process until the number of retained sequences <2000. Until this step, 1,927 sequences were retained.

For the retained 1,927 sequences, an all-against-all complement score was calculated for each. This gave a 1,927×1,927 cross complement score matrix. A step similar to step 5 was performed, to avoid labels with maximal cross-complement with other labels. Starting from the pairs with top cross-complement score, one was randomly pick and the other discarded. This process was repeated until the number of retained sequences was 1920. Next the 1920 labels were split into 2 sets, with one set (denoted by set A) consisting of sequences that are maximum different from one-another; and the other set (denoted by set B) consisting of the remaining sequences. The procedure used to split sequences was as follows. Starting from the original 1920 by 1920 similarity score matrix, for each sequence, (1) sum up all its similarity scores with the rest of the sequences in the pool, that is, for each sequence, calculate a total similarity score. (2) Sort the total similarity scores of all sequences and select the sequence with the lowest total score, and move it to set A. (3) Remove the row and column corresponding to the selected sequence, i.e., both the number of rows and columns in the similarity score matrix are reduced by 1. Repeat steps 1-3, until the number of rows and columns in the similarity score matrix reaches 960 or half of the original. The selected sequences belong to set A and the remaining sequences belong to set B.

In another embodiment a collection of labels is selected using the following steps. Starting with all possible 14 mers ($4^{14}$ or ~268 million possible labels) eliminate all that do not have 50% GC content. Eliminate those were each nucleotide does not occur at least twice. Eliminate those that have more than two G/C in tandem or more than three A/T in tandem. Eliminate those that contain a selected restriction site. That reduces the original set to ~33 million or 12.43% of the original set. From that set select those that have a Tm within the range of 38.5° C. to 39.5° C. This step results in a set of ~7 million or 2.73% of the original set. Remove those that have regions of self-complementarity. The resulting set in this example was now 521,291. A hierarchical clustering was performed to identify a set that has maximum sequence difference between one-another. The resulting set contained 1,927 labels. Labels were removed if the sequence had a tendency to bind to other labels in the set. This reduced the set to 1,920 labels. A final set of 960 labels was selected from the 1,920 as being maximally different for the "specific" labels and 192 additional counters to tile on the array as "non-specific" controls.

Selection of Targets and design of test array. Regions selected to assay as targets included Chr X, Chr Y, Chr 4 as a reference and Chr 21 for Trisomy. Locations on the chromosomes for assaying were selected to avoid centromeres and telomeres. Fragments were selected based on Bam HI fragments of between about 400 and 600 base pairs. Fragment intensity was checked using HG49 array hybridization. The first and the last 26 nucleotides of the fragments (from and including the Bam HI site) were tiled. Repeats were avoided and GC % was optimized.

The array format was 100/25. Feature size is 5um. There are 436×436 features or 190,096 features. Synthesis was NNPOC, 43 mer probes, 5' up, no phosphate. The chip name is STCL-test2. The gridding probe used was the same as the HG49. No QC probes were included.

Aside from reducing whole chromosomes into 360,679 smaller molecular weight DNA pieces more suitable for ligation reactions, restriction digestion also serves to reduce the overall sequence complexity of the sample, as only an estimated 79,517 fragments reside in the 150 bp-2 kb size range that is effectively amplified by PCR. To detect and quantify counters that have been selected by the target molecules, the labeled genomic target fragments may be circularized and PCR amplified to prepare for analysis, for example, using microarray hybridization or DNA sequencing. A representative BamHI target fragment was sampled for each of the three test chromosomes. Simultaneous measurements of all three chromosomes serve as an internal control independent of dilution or other systematic errors. A suitable DNA array detector capable of distinguishing the set of counters bound to copies of the target molecules was constructed using photolithography (S. P. Fodor et al., Science 251, 767 (Feb. 15, 1991).). Each array element for a target to be evaluated consists of a target complementary sequence adjacent to one of the complements to the 960 counter sequences (FIGS. 1 and 2A). For increased specificity, a ligation-readout was performed on the microarray after hybridization to avoid false positive detection of the cross-hybridization of identical targets with different counters. As a means of validation through a secondary measure, samples hybridized to microarrays were subsequently sampled by DNA sequencing (FIGS. 10 and 29).

Figure 16:
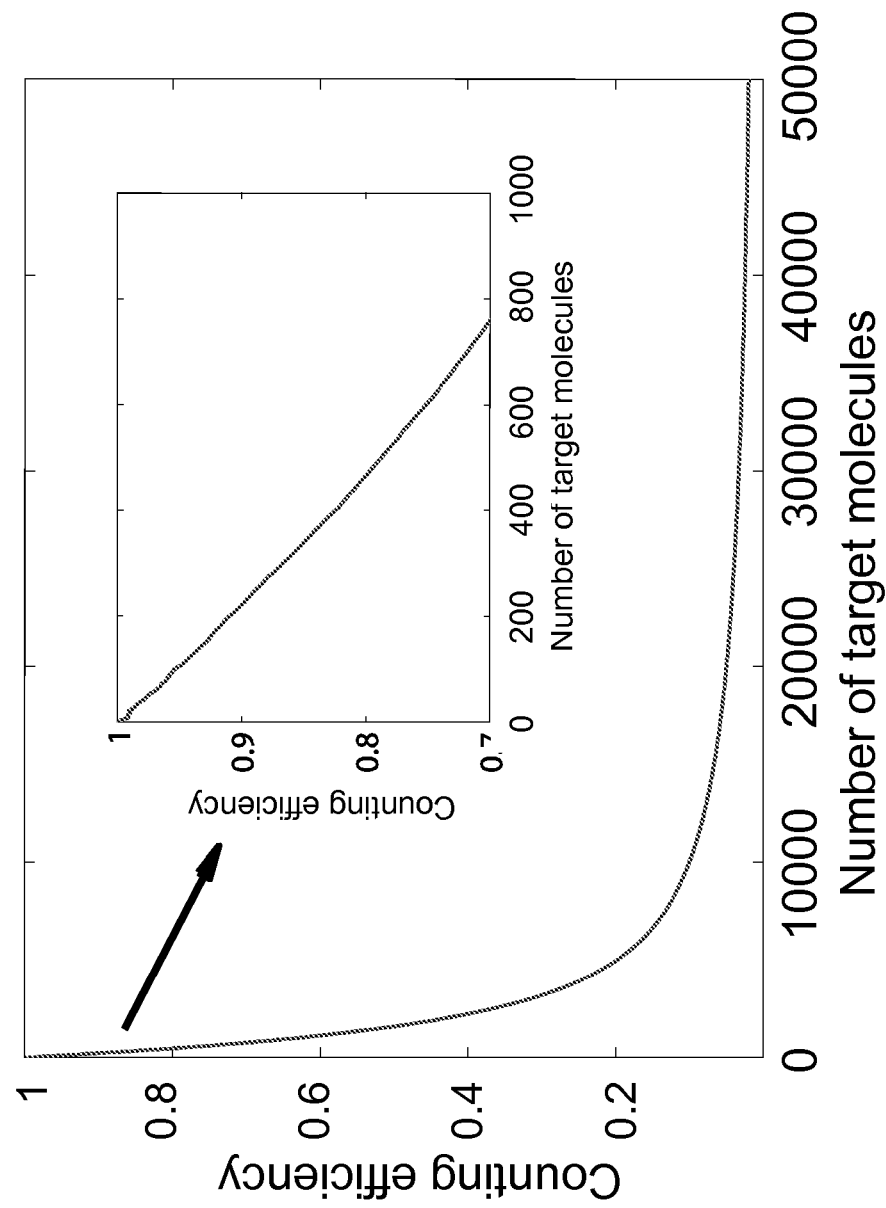
FIG. 16 shows a plot of number of target molecules (x-axis) compared to counting efficiency (y-axis).
Figure 17:
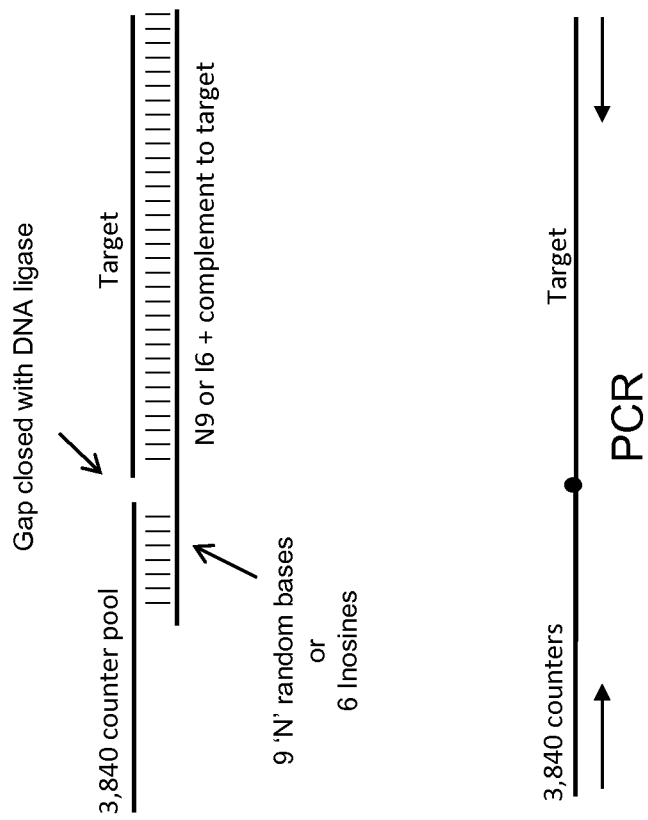
FIG. 17 shows a schematic of a method for attaching labels to targets using a splint having a variable region.

An equation to model the stochastic labeling of target molecules with a small library of 960 counters, and validate our equation model with numerical simulations is disclosed. In the model, the diversity of counters selected by, and ligated to target molecules in the reaction solution (simplified as 'used') is dictated by the number of copies of molecules present for each target fragment in the reaction (FIG. 12). Under conditions where the size of the counter library is much greater than the number of copies of a given target molecule, the counting efficiency is high, and counting the number of counters used is equivalent to counting the number of copies of the original target molecules (FIG. 16). When the number of target copies approaches and exceeds the number of different counters in the reaction, any counter in the library is more likely to be used multiple times (FIG. 15). The number of counters used at least once is an important measure because it serves as the basis for drawing yes/no conclusions in our digital readout on microarrays. Under stochastic labeling conditions, we expect that the absolute quantity of single DNA molecules can be accurately determined by proxy counts of labeling events. Indeed, microarray experiments demonstrate a high degree of correlation between the number of copies of target molecules added to the reaction and the number of counters used, as detected on microarrays (FIG. 12). In particular, counter usage precisely profiles the number of target molecules under conditions of high counting efficiency. Subtle deviations from the model may represent minor dilution errors in the preparation of the sample. However, within that sample dilution, the relative counter ratios of the three internally built-in markers are highly accurate (FIG. 13). FIG. 13 shows comparison of relative copy ratios of the three gene targets tested: ChrX, Chr4 and Chr21 representing genetic material of one, two and three copies per cell. Different dilutions (5 ng, 2 ng, 0.5 ng and 0.05 ng) of a DNA sample isolated from cultured lymphoblasts of a Trisomy 21 male individual were processed for microarray hybridization and DNA sequencing. The calculated number of target molecules (see, Table 4, column 9) was inferred from the number of counters detected on microarrays (A), and was also calculated for the SOLID sequencing data (B). For each sample dilution, the target copy number ratio of each gene target relative to ChrX is shown.

On the other hand, when target copies exceed ~100, detected labeling events appear to indicate fewer than actual molecules in solution (FIG. 12 inset in graph on left). This deviation was reproducible and consistently observed across multiple microarray experiments, and was also observed in the DNA sequencing experiments (FIG. 12 inset in graph on right). Under-counts of expected labeling events may originate from inadequate detection sensitivity of the microarray platform or from other systematic or indeterminate deficiencies in the sample preparation procedure. PCR, for example, is prone to amplification bias (T. Kanagawa, *J Biosci Bioeng* 96, 317 (2003) and M. F. Polz, C. M. Cavanaugh, *Appl Environ Microbiol* 64, 3724 (1998)), which could hinder the comprehensive detection of labeling events that may be genuinely stochastic.

To confirm the microarray results, a digital sequence counting of individual molecules in the DNA samples hybridized to microarrays was used as a means of validation, and to detect the presence of any false negatives that may have escaped microarray detection. Analysis of mapped sequence reads resulted in counts in agreement to the microarray observations. Furthermore, a second, independent sequencing run was repeated with similar findings (Table 3).

An additional feature of digital sequence counting is that unlike the microarray intensity data (FIGS. 22 and 23), which offers lower resolution into the measurement of the concentration dispersion of PCR amplified molecules, sequence counting clearly demonstrates significant variation in the representation of amplified targets (FIG. 29). This is consistent with the computed PCR model. Overall, detected counters on the microarray and sequencing experiments correlate well, but a small subset of counters appear to be unique to each process (Table 7). The observed number of labels in common between the microarray and the two sets of sequencing experiments are summarized in the table. The number of labels in each category is included. The categories are as follows: A+1+2 for labels detected in each of the 3 experiments, 1+2 for labels detected only in sequencing runs 1 and 2, 1+A for labels detected in sequencing run 1 and by array, and so on for the amounts of DNA shown in column 3.

TABLE 7

| DNA sample | | | A+1+2 | 1+2 | 1+A | 2+A | 1 | 2 | A |
|---|---|---|---|---|---|---|---|---|---|
| Chr4 | Left side | 0.036 ng | 13 | 0 | 0 | 0 | 0 | 0 | 1 |
| | | 0.36 ng | 96 | 3 | 0 | 1 | 2 | 2 | 5 |
| | | 1.45 ng | 228 | 13 | 4 | 22 | 6 | 10 | 6 |
| | | 3.62 ng | 484 | 23 | 2 | 3 | 4 | 6 | 12 |
| | Right side | 0.036 ng | 14 | 0 | 0 | 0 | 0 | 0 | 0 |
| | | 0.36 ng | 100 | 1 | 0 | 0 | 2 | 2 | 7 |
| | | 1.45 ng | 249 | 25 | 2 | 0 | 15 | 33 | 5 |
| | | 3.62 ng | 511 | 22 | 2 | 1 | 9 | 23 | 11 |
| Chr21 | Left side | 0.036 ng | 18 | 0 | 2 | 0 | 0 | 0 | 0 |
| | | 0.36 ng | 150 | 0 | 2 | 4 | 0 | 7 | 4 |
| | | 1.45 ng | 324 | 17 | 8 | 1 | 32 | 16 | 2 |
| | | 3.62 ng | 637 | 14 | 10 | 0 | 17 | 14 | 4 |
| | Right side | 0.05 ng | 18 | 0 | 1 | 1 | 0 | 0 | 0 |
| | | 0.36 ng | 144 | 0 | 2 | 2 | 0 | 0 | 9 |
| | | 1.45 ng | 330 | 34 | 2 | 3 | 15 | 12 | 6 |
| | | 3.62 ng | 615 | 29 | 1 | 7 | 5 | 2 | 4 |
| ChrX | Left side | 0.036 ng | 11 | 0 | 0 | 0 | 0 | 0 | 0 |
| | | 0.36 ng | 42 | 0 | 0 | 0 | 1 | 3 | 8 |
| | | 1.45 ng | 137 | 3 | 1 | 5 | 8 | 5 | 5 |
| | | 3.62 ng | 274 | 12 | 0 | 2 | 4 | 12 | 5 |
| | Right side | 0.036 ng | 10 | 1 | 0 | 0 | 1 | 0 | 0 |
| | | 0.36 ng | 43 | 0 | 3 | 0 | 4 | 0 | 2 |
| | | 1.45 ng | 127 | 15 | 0 | 0 | 11 | 25 | 6 |
| | | 3.62 ng | 298 | 12 | 3 | 3 | 24 | 31 | 2 |

For the reverse scenario, high numbers of mapped sequence reads were always observed to correlate with high microarray intensities in these examples. No systematic or sequence correlations, or explanations were identified for the counters that are absent from any given sequencing experiment for which the microarray readout demonstrates a strong signal. While obviously underrepresented in some experiments, the same counters are sometimes present in high sequence counts in other experiments, suggesting that they are available for sequencing. PCR was used to resolve these isolated cases of disagreement and demonstrate these were false negatives in the sequencing experiments (Table 3). Despite their presence in the sequencing library, it is unclear why the counters were not observed or were underrepresented in the original sequencing run, and also in the subsequent replicate sequencing run.

Aside from the comparative analysis of absolute and relative counts of the numbers of target molecules and counter labels, additional ways to assess the stochasticity of the labeling process were evaluated. First, if the labeling process is random, the frequency of incorporation of identical counters in independent events across the paired left and right termini of target fragments should closely resemble outcomes from numerical simulation. Observed counts on microarrays do in fact match closely with numbers obtained from computer simulations (Table 4, columns 10-11). Second, if the target molecules are labeled randomly with an equal likelihood of incorporation for any member of the 960 counters in the library, we would expect the number of repeated observations of counters to follow a stochastic nature. For this analysis, we accumulated a total of 1,064 counter observations over several microarray experiments restricted to low target copy numbers. Exclusion of data from high copy targets was necessary to avoid undercounting labeling events from multiple incidences of identical counters attaching individually to numerous target copies. As a further and final demonstration of stochastic labeling, results show that the frequency of label usage follows a pattern consistent with outcomes from numerical simulation.

CONCLUSION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby. All cited references, including patent and non-patent literature, are incorporated herein by reference in their entireties for all purposes and particularly to disclose and describe the methods or materials in connection with which the publications are cited.

We claim:

1. A composition comprising a plurality of oligonucleotide labels, wherein each oligonucleotide label of the plurality of oligonucleotide labels comprises an oligo dT sequence, a sequencing primer binding site, a common sequence that is the same for all oligonucleotide labels of the plurality of oligonucleotide labels, and a unique label tag sequence, wherein the unique label tag sequence is selected from a set of at least m different label tag sequences.

2. The composition of claim 1, further comprising a set of n target molecules hybridized to said plurality of oligonucleotide labels.

3. The composition of claim 2, wherein the target molecules are RNA molecules.

4. The composition of claim 2, wherein the target molecules are mRNA molecules.

5. The composition of claim 2, wherein n has a value ranging from 1 to 100.

6. The composition of claim 2, wherein n has a value ranging from 100 to 1,500.

7. The composition of claim 2, wherein n has a value greater than 1,500.

8. The composition of claim 2, wherein the target molecules comprise one or more different types of target molecules from a single cell.

9. The composition of claim 2, wherein m is greater than n.

10. The composition of claim 9, wherein a ratio m/n is greater than 5.

11. The composition of claim 1, wherein m is between 100 and 1,000.

12. The composition of claim 1, wherein m is between 1,000 and 10,000.

13. The composition of claim 1, wherein the plurality of oligonucleotide labels are between 48 and 76 nucleotides in length.

14. A kit comprising a plurality of oligonucleotide labels, wherein each oligonucleotide label of the plurality of oligonucleotide labels comprises an oligo dT sequence, a sequencing primer binding site, a common sequence that is the same for all oligonucleotide labels of the plurality of oligonucleotide labels, and a unique label tag sequence, wherein the unique label tag sequence is selected from a set of at least m different label tag sequences.

15. The kit of claim 14, wherein m is between 100 and 1,000.

16. The kit of claim 14, wherein m is between 1,000 and 10,000.

17. The kit of claim 14, wherein the plurality of oligonucleotide labels are between 48 and 76 nucleotides in length.

18. The kit of claim 14, further comprising PCR amplification and sequencing reagents.

* * * * *

SEQUENCE LISTING

<160> NUMBER OF SEQ ID NOS: 1979

<210> SEQ ID NO 1
<211> LENGTH: 875
<212> TYPE: DNA
<213> ORGANISM: Artificial Sequence
<220> FEATURE:
<223> OTHER INFORMATION: synthetic oligonucleotide

<400> SEQUENCE: 1

```
gatccaccaa tccatacatg agacggccca atccagttag tccttatcca aactcttcac      60
acacttcaga tatctatgga agcaccagcc ctatgaactt ctattccacc tcatctcaag     120
ctgcaggttc atatttgaat tcttctaatc ccatgaaccc ttacctggg cttttgaatc      180 agaataccca atatccatca tatcaatgca atggaaacct atcagtggac aactgctccc     240
catatctggg ttcctattct ccccagtctc agccgatgga tctgtatagg tatccaagcc     300
aagaccctct gtctaagctc agtctaccac ccatccatac actttaccag ccaaggtttg     360
gaaatagcca gagtttttaca tctaaatact taggttatgg aaaccaaaat atgcagggag     420
atggtttcag cagttgtacc attagaccaa atgtacatca tgtagggaaa ttgcctcctt     480
atcccactca tgagatggat ggccacttca tgggagccac ctctagatta ccacccaatc     540
tgagcaatcc aaacatggac tataaaaatg gtgaacatca ttcaccttct cacataatcc     600
ataactacag tgcagctccg ggcatgttca acagctctct tcatgccctg catctccaaa     660
acaaggagaa tgacatgctt tcccacacag ctaatgggtt atcaaagatg cttccagctc     720
ttaaccatga tagaactgct tgtgtccaag gaggcttaca caaattaagt gatgctaatg     780
gtcaggaaaa gcagccattg gcactagtcc agggtgtggc ttctggtgca gaggacaacg     840
atgaggtctg gtcagacagc gagcagagct ttctg                                875
```

<210> SEQ ID NO 2
<211> LENGTH: 934
<212> TYPE: DNA
<213> ORGANISM: Artificial Sequence
<220> FEATURE:
<223> OTHER INFORMATION: synthetic oligonucleotide

<400> SEQUENCE: 2

-continued

| | |
|---|---|
| gatccaggac tgttttcatg ctagtctggc tcacagaacg ctagcaggtt gtactgacct | 60 |
| tcaggacaag cgtaagtaag acctacgatg ctcgtttgat cccaacagtt atctcccctt | 120 |
| tctcagttcc tgtcttctcc cagagggtgg caggtagctg gggaagagat gactgggagt | 180 |
| ggagaggtgc cgctgaccat tatggtggca gctactcatt cagggtgctc tcctcctaat | 240 |
| tctgctggag aacactattt tgggacaatt tgtcatcttg gctggagggt cctttcctaa | 300 |
| agtctagcac tgatagaaca caaggacgta agtgctgcct tttaaccagg aaggcgaagg | 360 |
| caaactttc tttaaaggag agagttgcag gtaatccctg gtgtttttt ttttcaatag | 420 |
| ttagcaactg caggggaagg gaaaggctgt aacacccttc agctcagacg cacaatggga | 480 |
| atattaattt gagcagtttc catttcagtc ccttgtcatg ttaattttga agtctggtat | 540 |
| acgcccctca attctagttg atgataagct ctaaaagatg gcaagattgg tgaggccaaa | 600 |
| atgcagctga caaactgagc ttacttagag attttcaaac tatttgtaag actggcatct | 660 |
| ccaataacac ttttgtcatt cctgccattc aaacaggaac tgttccctgg aagacccttaa | 720 |
| aataaacctg tgctttcaac ccactcacct gccagaggtg gagcctgaaa gaactggggt | 780 |
| gtgggcttat catcccagtt gggtctcctt tatttcccac tggtgttttc tgaccatgcc | 840 |
| agggaaagca aacagtggct acattccagc ccctccacag tcaactaagt ttcattcttc | 900 |
| cctctggctg agggtctgtt ggaggtgagc ccag | 934 |

<210> SEQ ID NO 3
<211> LENGTH: 643
<212> TYPE: DNA
<213> ORGANISM: Artificial Sequence
<220> FEATURE:
<223> OTHER INFORMATION: synthetic oligonucleotide

<400> SEQUENCE: 3

| | |
|---|---|
| gatcctgtgt gccttctcct gccatggtac acacactcac acaccccctc atacacaagt | 60 |
| cctttgttga gccctgaggc aggaaatggg aaattcaaaa ggaagagcct gagaaaccat | 120 |
| tttatttcat ttcaggggc ttctcaccat cccttgaagg aggcagcccc aagtgatata | 180 |
| gaccagaacc cctctcacag agtcttagtt cacatcctag atataaaaca gagaacttcc | 240 |
| ggggcttaga agttttgtct gttgggggaa atctctgcag gctcaaaaag taacccaggg | 300 |
| ttggccttat gggtgtggtg gatttgtgtt tcagtgaagt gaacacagaa aagaggtgag | 360 |
| tatatatgta cacacagaaa tcacaggaaa aaactccaaa aactcacttg tgctaagtct | 420 |
| tgagggccag tccagcagaa agatacttgc ctttctcctt cagacttcgt tgtcagtctc | 480 |
| gttttctttg tcctgtggag tagcggggag atttggagtt catgaggatg gacgcacagg | 540 |
| cagtatgtgc cccaaagccc ttgaccaggc agtaatgggg gcctcaggaa tagctagggc | 600 |
| tgtttcctca gagaactggt catgtgaaag gacaaaggct ttg | 643 |

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4

| | |
|---|---|
| ggacaacgat gaggtctggt | 20 |

<210> SEQ ID NO 5
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 5
tagggctggt gcttccatag                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gcccctccac agtcaactaa                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
cgcttgtcct gaaggtcagt                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
ggcctcagga atagctaggg                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
tgtgtatgag ggggtgtgtg                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
tgatctagat cttgtgtccg                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
```
tgatctatct tcgacactgg                                            20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
tgatcttcga gatggtgttc                                            20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
tgatcttcgg atagagagca                                            20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
tgatcttcgg taccaacaac                                            20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
tgatctccaa ggtttggtga                                            20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
tgatcttcgc aagaggtaag                                            20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
tgatctggag ttacggcttt                                            20

<210> SEQ ID NO 18
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 18
tgatcttcaa ccagtaagcc                                               20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
tgatctctgt aaacaacgcc                                               20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
tgatctcacg atagtttgcc                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
tgatcttgta ctaacacgcc                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
tgatctacgc taactccttg                                               20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
tgatctcgtt tacgatgtgg                                               20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
tgatcttctt aggaaacgcc                                               20
```

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
tgatcttgca atagacgacc                                               20

<210> SEQ ID NO 26
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 26
ccactacgcc tccgctttcc tctctatggg cagtcggtga t                       41

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
ctgccccggg ttcctcattc                                               20

<210> SEQ ID NO 28
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 28
ggagctcgga caacgatgag gtctggt                                       27

<210> SEQ ID NO 29
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 29
ggagctctag ggctggtgct tccatag                                       27

<210> SEQ ID NO 30
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 30
ggagctcgcc cctccacagt caactaa                                       27

<210> SEQ ID NO 31
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 31
ggagctccgc ttgtcctgaa ggtcagt                                    27

<210> SEQ ID NO 32
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 32
ggagctcggc ctcaggaata gctaggg                                    27

<210> SEQ ID NO 33
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 33
ggagctctgt gtatgagggg gtgtgtg                                    27

<210> SEQ ID NO 34
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 34
ttcctctcta tgggcagtcg gtgatcgaa                                  29

<210> SEQ ID NO 35
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 35
gatcttcgat caccgactgc ccatagagag gaa                             33

<210> SEQ ID NO 36
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 36
ttcctctcta tgggcagtcg gtgatgttg                                  29

<210> SEQ ID NO 37
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 37
gatccaacat caccgactgc ccatagagag gaa                             33

<210> SEQ ID NO 38

```
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 38
ttcctctcta tgggcagtcg gtgataaga                                    29

<210> SEQ ID NO 39
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 39
gatctcttat caccgactgc ccatagagag gaa                               33

<210> SEQ ID NO 40
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 40
ttcctctcta tgggcagtcg gtgattttc                                    29

<210> SEQ ID NO 41
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 41
gatcgaaaat caccgactgc ccatagagag gaa                               33

<210> SEQ ID NO 42
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 42
ttcctctcta tgggcagtcg gtgattacc                                    29

<210> SEQ ID NO 43
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 43
gatcggtaat caccgactgc ccatagagag gaa                               33

<210> SEQ ID NO 44
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 44
```
cgacagacgc ctgatctttt gttagccgga gt                                32

<210> SEQ ID NO 45
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 45
gatcactccg gctaacaaaa gatca                                        25

<210> SEQ ID NO 46
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 46
cgacagacgc ctgatctttt ctcgaccact gt                                32

<210> SEQ ID NO 47
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 47
gatcacagtg gtcgagaaaa gatca                                        25

<210> SEQ ID NO 48
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 48
cgacagacgc ctgatctttt ctagctaccg ct                                32

<210> SEQ ID NO 49
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 49
gatcagcggt agctagaaaa gatca                                        25

<210> SEQ ID NO 50
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 50
cgacagacgc ctgatctttt cgttaggagg ct                                32

<210> SEQ ID NO 51
<211> LENGTH: 25
<212> TYPE: DNA

<213> ORGANISM: Artificial Sequence
<220> FEATURE:
<223> OTHER INFORMATION: synthetic oligonucleotide

<400> SEQUENCE: 51
gatcagcctc ctaacgaaaa gatca                                   25

<210> SEQ ID NO 52
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 52
cgacagacgc ctgatctttt cctgaacgac ct                           32

<210> SEQ ID NO 53
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 53
gatcaggtcg ttcaggaaaa gatca                                   25

<210> SEQ ID NO 54
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 54
cgacagacgc ctgatctttt ccatagcgtc ct                           32

<210> SEQ ID NO 55
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 55
gatcaggacg ctatggaaaa gatca                                   25

<210> SEQ ID NO 56
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 56
cgacagacgc ctgatctttt cactacggct ct                           32

<210> SEQ ID NO 57
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 57
gatcagagcc gtagtgaaaa gatca                                   25

<210> SEQ ID NO 58
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 58
cgacagacgc ctgatctttt caccagtcca gt                                   32

<210> SEQ ID NO 59
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 59
gatcactgga ctggtgaaaa gatca                                           25

<210> SEQ ID NO 60
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 60
cgacagacgc ctgatctttt actgcgacct ct                                   32

<210> SEQ ID NO 61
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 61
gatcagaggt cgcagtaaaa gatca                                           25

<210> SEQ ID NO 62
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 62
cgacagacgc ctgatctttt acgcctctga ct                                   32

<210> SEQ ID NO 63
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 63
gatcagtcag aggcgtaaaa gatca                                           25

<210> SEQ ID NO 64
<211> LENGTH: 32
<212> TYPE: DNA
<213> ORGANISM: Artificial Sequence
<220> FEATURE:

```
<223> OTHER INFORMATION: synthetic oligonucleotide

<400> SEQUENCE: 64
cgacagacgc ctgatctttt acctggactg ct                                    32

<210> SEQ ID NO 65
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 65
gatcagcagt ccaggtaaaa gatca                                            25

<210> SEQ ID NO 66
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 66
cgacagacgc ctgatctttt acaggagagc gt                                    32

<210> SEQ ID NO 67
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 67
gatcacgctc tcctgtaaaa gatca                                            25

<210> SEQ ID NO 68
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 68
cgacagacgc ctgatctttt aactgaggcg gt                                    32

<210> SEQ ID NO 69
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 69
gatcaccgcc tcagttaaaa gatca                                            25

<210> SEQ ID NO 70
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 70
cgacagacgc ctgatctttt aaccaggagc gt                                    32
```

<210> SEQ ID NO 71
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 71
gatcacgctc ctggttaaaa gatca                                    25

<210> SEQ ID NO 72
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 72
cgacagacgc ctgatctttg ttccacctca gt                            32

<210> SEQ ID NO 73
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 73
gatcactgag gtggaacaaa gatca                                    25

<210> SEQ ID NO 74
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 74
cgacagacgc ctgatctttg ttaggcaggt ct                            32

<210> SEQ ID NO 75
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 75
gatcagacct gcctaacaaa gatca                                    25

<210> SEQ ID NO 76
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 76
cgacagacgc ctgatctttg tgtagaccgt gt                            32

<210> SEQ ID NO 77
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 77
gatcacacgg tctacacaaa gatca                                                 25

<210> SEQ ID NO 78
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 78
cgacagacgc ctgatctttg tatcctcacg ct                                         32

<210> SEQ ID NO 79
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 79
gatcagcgtg aggatacaaa gatca                                                 25

<210> SEQ ID NO 80
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 80
cgacagacgc ctgatctttg tagacagagc gt                                         32

<210> SEQ ID NO 81
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 81
gatcacgctc tgtctacaaa gatca                                                 25

<210> SEQ ID NO 82
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 82
cgacagacgc ctgatctttg tacgtgtagg ct                                         32

<210> SEQ ID NO 83
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 83
gatcagccta cacgtacaaa gatca                                                 25

<210> SEQ ID NO 84
<211> LENGTH: 32

```
<212> TYPE: DNA
<213> ORGANISM: Artificial Sequence
<220> FEATURE:
<223> OTHER INFORMATION: synthetic oligonucleotide

<400> SEQUENCE: 84
cgacagacgc ctgatctttg gttaaggctc gt                               32

<210> SEQ ID NO 85
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 85
gatcacgagc cttaaccaaa gatca                                       25

<210> SEQ ID NO 86
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 86
cgacagacgc ctgatctttg gtctcaaggt gt                               32

<210> SEQ ID NO 87
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 87
gatcacacct tgagaccaaa gatca                                       25

<210> SEQ ID NO 88
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 88
cgacagacgc ctgatctttg gagagaacag ct                               32

<210> SEQ ID NO 89
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 89
gatcagctgt tctctccaaa gatca                                       25

<210> SEQ ID NO 90
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 90
```

```
cgacagacgc ctgatctttg gaatctgctg gt                                    32
```

<210> SEQ ID NO 91
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 91

```
gatcaccagc agattccaaa gatca                                            25
```

<210> SEQ ID NO 92
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 92

```
cgacagacgc ctgatctttg gaatcaggac gt                                    32
```

<210> SEQ ID NO 93
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 93

```
gatcacgtcc tgattccaaa gatca                                            25
```

<210> SEQ ID NO 94
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 94

```
cgacagacgc ctgatctttg gaagacgaga ct                                    32
```

<210> SEQ ID NO 95
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 95

```
gatcagtctc gtcttccaaa gatca                                            25
```

<210> SEQ ID NO 96
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 96

```
cgacagacgc ctgatctttg ctctactcac gt                                    32
```

<210> SEQ ID NO 97
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 97
gatcacgtga gtagagcaaa gatca                                              25

<210> SEQ ID NO 98
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 98
cgacagacgc ctgatctttg ctaaccagga ct                                      32

<210> SEQ ID NO 99
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 99
gatcagtcct ggttagcaaa gatca                                              25

<210> SEQ ID NO 100
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 100
cgacagacgc ctgatctttg cgtgagagat ct                                      32

<210> SEQ ID NO 101
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 101
gatcagatct ctcacgcaaa gatca                                              25

<210> SEQ ID NO 102
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 102
cgacagacgc ctgatctttg catctcacca gt                                      32

<210> SEQ ID NO 103
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 103
gatcactggt gagatgcaaa gatca                                              25
```

<210> SEQ ID NO 104
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 104
cgacagacgc ctgatctttg cagatgagga ct                                32

<210> SEQ ID NO 105
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 105
gatcagtcct catctgcaaa gatca                                        25

<210> SEQ ID NO 106
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 106
cgacagacgc ctgatctttg atgtgagcct gt                                32

<210> SEQ ID NO 107
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 107
gatcacaggc tcacatcaaa gatca                                        25

<210> SEQ ID NO 108
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 108
cgacagacgc ctgatctttg atggaacgga ct                                32

<210> SEQ ID NO 109
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 109
gatcagtccg ttccatcaaa gatca                                        25

<210> SEQ ID NO 110
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 110
cgacagacgc ctgatctttg agcacaagga gt                                32

<210> SEQ ID NO 111
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 111
gatcactcct tgtgctcaaa gatca                                        25

<210> SEQ ID NO 112
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 112
cgacagacgc ctgatctttg acgtatggag ct                                32

<210> SEQ ID NO 113
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 113
gatcagctcc atacgtcaaa gatca                                        25

<210> SEQ ID NO 114
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 114
cgacagacgc ctgatctttg acggagatga ct                                32

<210> SEQ ID NO 115
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 115
gatcagtcat ctccgtcaaa gatca                                        25

<210> SEQ ID NO 116
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 116
cgacagacgc ctgatctttg acacgaagag gt                                32

<210> SEQ ID NO 117
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 117
gatcacctct tcgtgtcaaa gatca                                           25

<210> SEQ ID NO 118
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 118
cgacagacgc ctgatctttc ttggagtagc gt                                   32

<210> SEQ ID NO 119
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 119
gatcacgcta ctccaagaaa gatca                                           25

<210> SEQ ID NO 120
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 120
cgacagacgc ctgatctttc tgagtgtgac gt                                   32

<210> SEQ ID NO 121
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 121
gatcacgtca cactcagaaa gatca                                           25

<210> SEQ ID NO 122
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 122
cgacagacgc ctgatctttc tccgacactt gt                                   32

<210> SEQ ID NO 123
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 123
```
gatcacaagt gtcggagaaa gatca                                          25

<210> SEQ ID NO 124
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 124
cgacagacgc ctgatctttc gaggttgaca gt                                  32

<210> SEQ ID NO 125
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 125
gatcactgtc aacctcgaaa gatca                                          25

<210> SEQ ID NO 126
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 126
cgacagacgc ctgatctttc gaagagaacg gt                                  32

<210> SEQ ID NO 127
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 127
gatcaccgtt ctcttcgaaa gatca                                          25

<210> SEQ ID NO 128
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 128
cgacagacgc ctgatctttc cttcaactcg gt                                  32

<210> SEQ ID NO 129
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 129
gatcaccgag ttgaaggaaa gatca                                          25

<210> SEQ ID NO 130
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 130
cgacagacgc ctgatctttc ctggagacac tt                                32

<210> SEQ ID NO 131
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 131
gatcaagtgt ctccaggaaa gatca                                        25

<210> SEQ ID NO 132
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 132
cgacagacgc ctgatctttc ctctgaaacc gt                                32

<210> SEQ ID NO 133
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 133
gatcacggtt tcagaggaaa gatca                                        25

<210> SEQ ID NO 134
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 134
cgacagacgc ctgatctttc ctattgaccg ct                                32

<210> SEQ ID NO 135
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 135
gatcagcggt caataggaaa gatca                                        25

<210> SEQ ID NO 136
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 136
cgacagacgc ctgatctttc cggtgatgat gt                                32
```

<210> SEQ ID NO 137
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 137
gatcacatca tcaccggaaa gatca                                              25

<210> SEQ ID NO 138
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 138
cgacagacgc ctgatctttc cgacaagact ct                                      32

<210> SEQ ID NO 139
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 139
gatcagagtc ttgtcggaaa gatca                                              25

<210> SEQ ID NO 140
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 140
cgacagacgc ctgatctttc catgtcgagt ct                                      32

<210> SEQ ID NO 141
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 141
gatcagactc gacatggaaa gatca                                              25

<210> SEQ ID NO 142
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 142
cgacagacgc ctgatctttc cacgttagtc ct                                      32

<210> SEQ ID NO 143
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 143
gatcaggact aacgtggaaa gatca                                          25

<210> SEQ ID NO 144
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 144
cgacagacgc ctgatctttc caagaagcca gt                                  32

<210> SEQ ID NO 145
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 145
gatcactggc ttcttggaaa gatca                                          25

<210> SEQ ID NO 146
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 146
cgacagacgc ctgatctttc atgaaggacg gt                                  32

<210> SEQ ID NO 147
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 147
gatcaccgtc cttcatgaaa gatca                                          25

<210> SEQ ID NO 148
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 148
cgacagacgc ctgatctttc ataaccgagc ct                                  32

<210> SEQ ID NO 149
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 149
gatcaggctc ggttatgaaa gatca                                          25

```
<210> SEQ ID NO 150
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 150
cgacagacgc ctgatctttc aggttggtag ct                                    32

<210> SEQ ID NO 151
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 151
gatcagctac caacctgaaa gatca                                            25

<210> SEQ ID NO 152
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 152
cgacagacgc ctgatctttc aggagccaat ct                                    32

<210> SEQ ID NO 153
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 153
gatcagattg gctcctgaaa gatca                                            25

<210> SEQ ID NO 154
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 154
cgacagacgc ctgatctttc accggatctt ct                                    32

<210> SEQ ID NO 155
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 155
gatcagaaga tccggtgaaa gatca                                            25

<210> SEQ ID NO 156
<211> LENGTH: 32
<212> TYPE: DNA
<213> ORGANISM: Artificial Sequence
<220> FEATURE:
<223> OTHER INFORMATION: synthetic oligonucleotide
```

<400> SEQUENCE: 156
cgacagacgc tgatctttc aagtggagac gt        32

<210> SEQ ID NO 157
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 157
gatcacgtct ccacttgaaa gatca        25

<210> SEQ ID NO 158
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 158
cgacagacgc tgatctttc aaacggagag gt        32

<210> SEQ ID NO 159
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 159
gatcacctct ccgtttgaaa gatca        25

<210> SEQ ID NO 160
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 160
cgacagacgc tgatcttta tgtcagaggc gt        32

<210> SEQ ID NO 161
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 161
gatcacgcct ctgacataaa gatca        25

<210> SEQ ID NO 162
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 162
cgacagacgc tgatcttta tgtacgctcg gt        32

<210> SEQ ID NO 163
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 163
gatcaccgag cgtacataaa gatca                                          25

<210> SEQ ID NO 164
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 164
cgacagacgc ctgatcttta tggcgtggat ct                                  32

<210> SEQ ID NO 165
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 165
gatcagatcc acgccataaa gatca                                          25

<210> SEQ ID NO 166
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 166
cgacagacgc ctgatcttta tgagcgacga gt                                  32

<210> SEQ ID NO 167
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 167
gatcactcgt cgctcataaa gatca                                          25

<210> SEQ ID NO 168
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 168
cgacagacgc ctgatcttta tccacgacag ct                                  32

<210> SEQ ID NO 169
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 169
```

```
gatcagctgt cgtggataaa gatca                                          25

<210> SEQ ID NO 170
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 170
cgacagacgc ctgatctttta tagtcgcgtg gt                                 32

<210> SEQ ID NO 171
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 171
gatcaccacg cgactataaa gatca                                          25

<210> SEQ ID NO 172
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 172
cgacagacgc ctgatctttta taaggccacc gt                                 32

<210> SEQ ID NO 173
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 173
gatcacggtg gccttataaa gatca                                          25

<210> SEQ ID NO 174
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 174
cgacagacgc ctgatctttta gtttcggcag gt                                 32

<210> SEQ ID NO 175
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 175
gatcacctgc cgaaactaaa gatca                                          25

<210> SEQ ID NO 176
<211> LENGTH: 32
<212> TYPE: DNA
<213> ORGANISM: Artificial Sequence
```

<220> FEATURE:
<223> OTHER INFORMATION: synthetic oligonucleotide

<400> SEQUENCE: 176
cgacagacgc ctgatcttta gtgtactggc gt                                32

<210> SEQ ID NO 177
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 177
gatcacgcca gtacactaaa gatca                                        25

<210> SEQ ID NO 178
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 178
cgacagacgc ctgatcttta gtctccaccg at                                32

<210> SEQ ID NO 179
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 179
gatcatcggt ggagactaaa gatca                                        25

<210> SEQ ID NO 180
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 180
cgacagacgc ctgatcttta gtatgctcgc ct                                32

<210> SEQ ID NO 181
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 181
gatcaggcga gcatactaaa gatca                                        25

<210> SEQ ID NO 182
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 182
cgacagacgc ctgatcttta gcctccaatc gt                                32

```
<210> SEQ ID NO 183
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 183
gatcacgatt ggaggctaaa gatca                                              25

<210> SEQ ID NO 184
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 184
cgacagacgc ctgatcttta gaactctggc gt                                      32

<210> SEQ ID NO 185
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 185
gatcacgcca gagttctaaa gatca                                              25

<210> SEQ ID NO 186
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 186
cgacagacgc ctgatcttta gaacgcgaga gt                                      32

<210> SEQ ID NO 187
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 187
gatcactctc gcgttctaaa gatca                                              25

<210> SEQ ID NO 188
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 188
cgacagacgc ctgatcttta gaaccgacac ct                                      32

<210> SEQ ID NO 189
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 189
gatcaggtgt cggttctaaa gatca                                         25

<210> SEQ ID NO 190
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 190
cgacagacgc ctgatcttta ctcagaaccg ct                                 32

<210> SEQ ID NO 191
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 191
gatcagcggt tctgagtaaa gatca                                         25

<210> SEQ ID NO 192
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 192
cgacagacgc ctgatcttta cgagaggcaa ct                                 32

<210> SEQ ID NO 193
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 193
gatcagttgc ctctcgtaaa gatca                                         25

<210> SEQ ID NO 194
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 194
cgacagacgc ctgatcttta ccttggagcc tt                                 32

<210> SEQ ID NO 195
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 195
gatcaaggct ccaaggtaaa gatca                                         25

<210> SEQ ID NO 196
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 196
cgacagacgc ctgatcttta ccagacaagc ct                              32

<210> SEQ ID NO 197
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 197
gatcaggctt gtctggtaaa gatca                                      25

<210> SEQ ID NO 198
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 198
cgacagacgc ctgatcttta aggcgagaca gt                              32

<210> SEQ ID NO 199
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 199
gatcactgtc tcgccttaaa gatca                                      25

<210> SEQ ID NO 200
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 200
cgacagacgc ctgatcttta aggacgcaag gt                              32

<210> SEQ ID NO 201
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 201
gatcaccttg cgtccttaaa gatca                                      25

<210> SEQ ID NO 202
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 202
```
cgacagacgc ctgatcttta agcggaactg gt                                    32

<210> SEQ ID NO 203
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 203
gatcaccagt tccgcttaaa gatca                                            25

<210> SEQ ID NO 204
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 204
cgacagacgc ctgatcttta agccatctcc gt                                    32

<210> SEQ ID NO 205
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 205
gatcacggag atggcttaaa gatca                                            25

<210> SEQ ID NO 206
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 206
cgacagacgc ctgatcttta acgatcctgc ct                                    32

<210> SEQ ID NO 207
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 207
gatcaggcag gatcgttaaa gatca                                            25

<210> SEQ ID NO 208
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 208
cgacagacgc ctgatcttta accggacact ct                                    32

<210> SEQ ID NO 209
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 209
gatcagagtg tccggttaaa gatca                                          25

<210> SEQ ID NO 210
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 210
cgacagacgc ctgatcttta acatcggcct ct                                  32

<210> SEQ ID NO 211
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 211
gatcagaggc cgatgttaaa gatca                                          25

<210> SEQ ID NO 212
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 212
cgacagacgc ctgatcttta acaagcggag gt                                  32

<210> SEQ ID NO 213
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 213
gatcacctcc gcttgttaaa gatca                                          25

<210> SEQ ID NO 214
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 214
cgacagacgc ctgatcttta aagcacggag gt                                  32

<210> SEQ ID NO 215
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 215
gatcacctcc gtgctttaaa gatca                                          25
```

```
<210> SEQ ID NO 216
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 216
cgacagacgc ctgatcttgt ttagcacctc ct                                32

<210> SEQ ID NO 217
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 217
gatcaggagg tgctaaacaa gatca                                        25

<210> SEQ ID NO 218
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 218
cgacagacgc ctgatcttgt tctgaaggct gt                                32

<210> SEQ ID NO 219
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 219
gatcacagcc ttcagaacaa gatca                                        25

<210> SEQ ID NO 220
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 220
cgacagacgc ctgatcttgt tatgaggacg ct                                32

<210> SEQ ID NO 221
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 221
gatcagcgtc ctcataacaa gatca                                        25

<210> SEQ ID NO 222
<211> LENGTH: 32
<212> TYPE: DNA
<213> ORGANISM: Artificial Sequence
<220> FEATURE:
```

<223> OTHER INFORMATION: synthetic oligonucleotide

<400> SEQUENCE: 222
cgacagacgc ctgatcttgt gtacaagcag gt                          32

<210> SEQ ID NO 223
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 223
gatcacctgc ttgtacacaa gatca                                  25

<210> SEQ ID NO 224
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 224
cgacagacgc ctgatcttgt ggttcatacg gt                          32

<210> SEQ ID NO 225
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 225
gatcaccgta tgaaccacaa gatca                                  25

<210> SEQ ID NO 226
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 226
cgacagacgc ctgatcttgt ggattactgg ct                          32

<210> SEQ ID NO 227
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 227
gatcagccag taatccacaa gatca                                  25

<210> SEQ ID NO 228
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 228
cgacagacgc ctgatcttgt gaagatgcct gt                          32

```
<210> SEQ ID NO 229
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 229
gatcacaggc atcttcacaa gatca                                         25

<210> SEQ ID NO 230
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 230
cgacagacgc ctgatcttgt ctgacctcca tt                                 32

<210> SEQ ID NO 231
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 231
gatcaatgga ggtcagacaa gatca                                         25

<210> SEQ ID NO 232
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 232
cgacagacgc ctgatcttgt ctacactccg at                                 32

<210> SEQ ID NO 233
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 233
gatcatcgga gtgtagacaa gatca                                         25

<210> SEQ ID NO 234
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 234
cgacagacgc ctgatcttgt cggagaacaa gt                                 32

<210> SEQ ID NO 235
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 235
gatcacttgt tctccgacaa gatca                                        25

<210> SEQ ID NO 236
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 236
cgacagacgc ctgatcttgt cataggcgtt ct                                32

<210> SEQ ID NO 237
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 237
gatcagaacg cctatgacaa gatca                                        25

<210> SEQ ID NO 238
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 238
cgacagacgc ctgatcttgt cactcttcac gt                                32

<210> SEQ ID NO 239
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 239
gatcacgtga agagtgacaa gatca                                        25

<210> SEQ ID NO 240
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 240
cgacagacgc ctgatcttgt atttccgagg ct                                32

<210> SEQ ID NO 241
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 241
gatcagcctc ggaaatacaa gatca                                        25

<210> SEQ ID NO 242
<211> LENGTH: 32
```

```
<212> TYPE: DNA
<213> ORGANISM: Artificial Sequence
<220> FEATURE:
<223> OTHER INFORMATION: synthetic oligonucleotide

<400> SEQUENCE: 242
cgacagacgc ctgatcttgt atgactgtgg ct                                 32

<210> SEQ ID NO 243
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 243
gatcagccac agtcatacaa gatca                                         25

<210> SEQ ID NO 244
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 244
cgacagacgc ctgatcttgt actgcaactg gt                                 32

<210> SEQ ID NO 245
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 245
gatcaccagt tgcagtacaa gatca                                         25

<210> SEQ ID NO 246
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 246
cgacagacgc ctgatcttgt actaacacgc ct                                 32

<210> SEQ ID NO 247
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 247
gatcaggcgt gttagtacaa gatca                                         25

<210> SEQ ID NO 248
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 248
```
cgacagacgc ctgatcttgt acctcctgca tt                                   32

<210> SEQ ID NO 249
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 249
gatcaatgca ggaggtacaa gatca                                           25

<210> SEQ ID NO 250
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 250
cgacagacgc ctgatcttgg tgtacttagc gt                                   32

<210> SEQ ID NO 251
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 251
gatcacgcta agtacaccaa gatca                                           25

<210> SEQ ID NO 252
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 252
cgacagacgc ctgatcttgg tggtcaaagt ct                                   32

<210> SEQ ID NO 253
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 253
gatcagactt tgaccaccaa gatca                                           25

<210> SEQ ID NO 254
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 254
cgacagacgc ctgatcttgg tcgaacaaga gt                                   32

<210> SEQ ID NO 255
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 255
gatcactctt gttcgaccaa gatca                                              25

<210> SEQ ID NO 256
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 256
cgacagacgc ctgatcttgg tacaatagcg gt                                      32

<210> SEQ ID NO 257
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 257
gatcaccgct attgtaccaa gatca                                              25

<210> SEQ ID NO 258
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 258
cgacagacgc ctgatcttgg cttctaatcg gt                                      32

<210> SEQ ID NO 259
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 259
gatcaccgat tagaagccaa gatca                                              25

<210> SEQ ID NO 260
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 260
cgacagacgc ctgatcttgg cttaccaact gt                                      32

<210> SEQ ID NO 261
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 261
gatcacagtt ggtaagccaa gatca                                              25

<210> SEQ ID NO 262
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 262
cgacagacgc ctgatcttgg ctattacgtg gt                                  32

<210> SEQ ID NO 263
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 263
gatcaccacg taatagccaa gatca                                          25

<210> SEQ ID NO 264
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 264
cgacagacgc ctgatcttgg caaaccacta gt                                  32

<210> SEQ ID NO 265
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 265
gatcactagt ggtttgccaa gatca                                          25

<210> SEQ ID NO 266
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 266
cgacagacgc ctgatcttgg atagccgaag at                                  32

<210> SEQ ID NO 267
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 267
gatcatcttc ggctatccaa gatca                                          25

<210> SEQ ID NO 268
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 268
cgacagacgc ctgatcttgg agatcaaacg gt                                    32

<210> SEQ ID NO 269
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 269
gatcaccgtt tgatctccaa gatca                                            25

<210> SEQ ID NO 270
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 270
cgacagacgc ctgatcttgg agagcacaat gt                                    32

<210> SEQ ID NO 271
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 271
gatcacattg tgctctccaa gatca                                            25

<210> SEQ ID NO 272
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 272
cgacagacgc ctgatcttgg agagaaccga tt                                    32

<210> SEQ ID NO 273
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 273
gatcaatcgg ttctctccaa gatca                                            25

<210> SEQ ID NO 274
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 274
cgacagacgc ctgatcttgc ttaggaatcg gt                                    32

<210> SEQ ID NO 275
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 275
gatcaccgat tcctaagcaa gatca                                              25

<210> SEQ ID NO 276
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 276
cgacagacgc ctgatcttgc ttaccactga ct                                      32

<210> SEQ ID NO 277
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 277
gatcagtcag tggtaagcaa gatca                                              25

<210> SEQ ID NO 278
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 278
cgacagacgc ctgatcttgc tcaaagctac ct                                      32

<210> SEQ ID NO 279
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 279
gatcaggtag ctttgagcaa gatca                                              25

<210> SEQ ID NO 280
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 280
cgacagacgc ctgatcttgc gatagtggtt ct                                      32

<210> SEQ ID NO 281
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 281
```
gatcagaacc actatcgcaa gatca                                      25

<210> SEQ ID NO 282
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 282
cgacagacgc ctgatcttgc gaagtagaga ct                              32

<210> SEQ ID NO 283
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 283
gatcagtctc tacttcgcaa gatca                                      25

<210> SEQ ID NO 284
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 284
cgacagacgc ctgatcttgc ctaaacgatc ct                              32

<210> SEQ ID NO 285
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 285
gatcaggatc gtttaggcaa gatca                                      25

<210> SEQ ID NO 286
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 286
cgacagacgc ctgatcttgc caacttctct gt                              32

<210> SEQ ID NO 287
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 287
gatcacagag aagttggcaa gatca                                      25

<210> SEQ ID NO 288
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 288
cgacagacgc ctgatcttgc caactatacc gt                                    32

<210> SEQ ID NO 289
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 289
gatcacggta tagttggcaa gatca                                            25

<210> SEQ ID NO 290
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 290
cgacagacgc ctgatcttgc atcttcactg gt                                    32

<210> SEQ ID NO 291
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 291
gatcaccagt gaagatgcaa gatca                                            25

<210> SEQ ID NO 292
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 292
cgacagacgc ctgatcttgc atatccttcc gt                                    32

<210> SEQ ID NO 293
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 293
gatcacggaa ggatatgcaa gatca                                            25

<210> SEQ ID NO 294
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 294
cgacagacgc ctgatcttgc aatcctacgt ct                                    32
```

<210> SEQ ID NO 295
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 295
gatcagacgt aggattgcaa gatca                                              25

<210> SEQ ID NO 296
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 296
cgacagacgc ctgatcttgc aatagacgac ct                                      32

<210> SEQ ID NO 297
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 297
gatcaggtcg tctattgcaa gatca                                              25

<210> SEQ ID NO 298
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 298
cgacagacgc ctgatcttga tttacctcgc ct                                      32

<210> SEQ ID NO 299
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 299
gatcaggcga ggtaaatcaa gatca                                              25

<210> SEQ ID NO 300
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 300
cgacagacgc ctgatcttga ttagttccgc ct                                      32

<210> SEQ ID NO 301
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 301
gatcaggcgg aactaatcaa gatca    25

<210> SEQ ID NO 302
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 302
cgacagacgc ctgatcttga ttactccgtg ct    32

<210> SEQ ID NO 303
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 303
gatcagcacg gagtaatcaa gatca    25

<210> SEQ ID NO 304
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 304
cgacagacgc ctgatcttga tggttcactg gt    32

<210> SEQ ID NO 305
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 305
gatcaccagt gaaccatcaa gatca    25

<210> SEQ ID NO 306
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 306
cgacagacgc ctgatcttga tgagaagacg ct    32

<210> SEQ ID NO 307
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 307
gatcagcgtc ttctcatcaa gatca    25

```
<210> SEQ ID NO 308
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 308
cgacagacgc ctgatcttga tccgtccaaa gt                                    32

<210> SEQ ID NO 309
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 309
gatcactttg gacggatcaa gatca                                            25

<210> SEQ ID NO 310
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 310
cgacagacgc ctgatcttga tccacaacga gt                                    32

<210> SEQ ID NO 311
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 311
gatcactcgt tgtggatcaa gatca                                            25

<210> SEQ ID NO 312
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 312
cgacagacgc ctgatcttga tcaacacctc gt                                    32

<210> SEQ ID NO 313
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 313
gatcacgagg tgttgatcaa gatca                                            25

<210> SEQ ID NO 314
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 314
cgacagacgc ctgatcttga tatcctgtgc gt                                32

<210> SEQ ID NO 315
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 315
gatcacgcac aggatatcaa gatca                                        25

<210> SEQ ID NO 316
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 316
cgacagacgc ctgatcttga tactcaacgg ct                                32

<210> SEQ ID NO 317
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 317
gatcagccgt tgagtatcaa gatca                                        25

<210> SEQ ID NO 318
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 318
cgacagacgc ctgatcttga gtccagaagg tt                                32

<210> SEQ ID NO 319
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 319
gatcaacctt ctggactcaa gatca                                        25

<210> SEQ ID NO 320
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 320
cgacagacgc ctgatcttga ggttacaagg ct                                32

<210> SEQ ID NO 321
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 321
gatcagcctt gtaacctcaa gatca                                              25

<210> SEQ ID NO 322
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 322
cgacagacgc ctgatcttga ggtcttcgga tt                                      32

<210> SEQ ID NO 323
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 323
gatcaatccg aagacctcaa gatca                                              25

<210> SEQ ID NO 324
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 324
cgacagacgc ctgatcttga gcaactgaag gt                                      32

<210> SEQ ID NO 325
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 325
gatcaccttc agttgctcaa gatca                                              25

<210> SEQ ID NO 326
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 326
cgacagacgc ctgatcttga gagttgccat gt                                      32

<210> SEQ ID NO 327
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 327
```

```
gatcacatgg caactctcaa gatca                                    25
```

<210> SEQ ID NO 328
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 328

```
cgacagacgc ctgatcttga gacaaccact gt                            32
```

<210> SEQ ID NO 329
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 329

```
gatcacagtg gttgtctcaa gatca                                    25
```

<210> SEQ ID NO 330
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 330

```
cgacagacgc ctgatcttga ctctctacgc tt                            32
```

<210> SEQ ID NO 331
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 331

```
gatcaagcgt agagagtcaa gatca                                    25
```

<210> SEQ ID NO 332
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 332

```
cgacagacgc ctgatcttga ctactcaccg tt                            32
```

<210> SEQ ID NO 333
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 333

```
gatcaacggt gagtagtcaa gatca                                    25
```

<210> SEQ ID NO 334
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 334
cgacagacgc ctgatcttga cgaaactgga gt                                 32

<210> SEQ ID NO 335
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 335
gatcactcca gtttcgtcaa gatca                                         25

<210> SEQ ID NO 336
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 336
cgacagacgc ctgatcttga ccttcaacct gt                                 32

<210> SEQ ID NO 337
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 337
gatcacaggt tgaaggtcaa gatca                                         25

<210> SEQ ID NO 338
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 338
cgacagacgc ctgatcttga caagtcacac ct                                 32

<210> SEQ ID NO 339
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 339
gatcaggtgt gacttgtcaa gatca                                         25

<210> SEQ ID NO 340
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 340
cgacagacgc ctgatcttga atctctgcca ct                                 32
```

```
<210> SEQ ID NO 341
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 341
gatcagtggc agagattcaa gatca                                           25

<210> SEQ ID NO 342
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 342
cgacagacgc ctgatcttga aggactacgg tt                                   32

<210> SEQ ID NO 343
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 343
gatcaaccgt agtccttcaa gatca                                           25

<210> SEQ ID NO 344
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 344
cgacagacgc ctgatcttga agcaacctga gt                                   32

<210> SEQ ID NO 345
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 345
gatcactcag gttgcttcaa gatca                                           25

<210> SEQ ID NO 346
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 346
cgacagacgc ctgatcttga acaccttctg gt                                   32

<210> SEQ ID NO 347
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 347
gatcaccaga aggtgttcaa gatca                                              25

<210> SEQ ID NO 348
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 348
cgacagacgc ctgatcttga aatactccgc ct                                      32

<210> SEQ ID NO 349
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 349
gatcaggcgg agtatttcaa gatca                                              25

<210> SEQ ID NO 350
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 350
cgacagacgc ctgatcttct ttgataccgc ct                                      32

<210> SEQ ID NO 351
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 351
gatcaggcgg tatcaaagaa gatca                                              25

<210> SEQ ID NO 352
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 352
cgacagacgc ctgatcttct ttccagcagt ct                                      32

<210> SEQ ID NO 353
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 353
gatcagactg ctggaaagaa gatca                                              25

<210> SEQ ID NO 354
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 354
cgacagacgc ctgatcttct ttaggatgcg gt                              32

<210> SEQ ID NO 355
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 355
gatcaccgca tcctaaagaa gatca                                      25

<210> SEQ ID NO 356
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 356
cgacagacgc ctgatcttct taggaaacgc ct                              32

<210> SEQ ID NO 357
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 357
gatcaggcgt ttcctaagaa gatca                                      25

<210> SEQ ID NO 358
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 358
cgacagacgc ctgatcttct taactcgtgc ct                              32

<210> SEQ ID NO 359
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 359
gatcaggcac gagttaagaa gatca                                      25

<210> SEQ ID NO 360
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 360
```
cgacagacgc ctgatcttct gtcctccgaa tt                                        32

<210> SEQ ID NO 361
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 361
gatcaattcg gaggacagaa gatca                                                25

<210> SEQ ID NO 362
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 362
cgacagacgc ctgatcttct ggaatgaggc tt                                        32

<210> SEQ ID NO 363
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 363
gatcaagcct cattccagaa gatca                                                25

<210> SEQ ID NO 364
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 364
cgacagacgc ctgatcttct gccaaagact ct                                        32

<210> SEQ ID NO 365
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 365
gatcagagtc tttggcagaa gatca                                                25

<210> SEQ ID NO 366
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 366
cgacagacgc ctgatcttct ctgaaactgc ct                                        32

<210> SEQ ID NO 367
<211> LENGTH: 25
<212> TYPE: DNA

<210> SEQ ID NO 367
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 367
gatcaggcag tttcagagaa gatca                                  25

<210> SEQ ID NO 368
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 368
cgacagacgc ctgatcttct cgttggaagt ct                          32

<210> SEQ ID NO 369
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 369
gatcagactt ccaacgagaa gatca                                  25

<210> SEQ ID NO 370
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 370
cgacagacgc ctgatcttct ccaggttcac at                          32

<210> SEQ ID NO 371
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 371
gatcatgtga acctggagaa gatca                                  25

<210> SEQ ID NO 372
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 372
cgacagacgc ctgatcttct ccaaggtgtc tt                          32

<210> SEQ ID NO 373
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 373
gatcaagaca ccttggagaa gatca                                  25

-continued

<210> SEQ ID NO 374
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 374
cgacagacgc ctgatcttct caaggacaac gt                                32

<210> SEQ ID NO 375
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 375
gatcacgttg tccttgagaa gatca                                        25

<210> SEQ ID NO 376
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 376
cgacagacgc ctgatcttct caacatggct ct                                32

<210> SEQ ID NO 377
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 377
gatcagagcc atgttgagaa gatca                                        25

<210> SEQ ID NO 378
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 378
cgacagacgc ctgatcttct atcacaaggc gt                                32

<210> SEQ ID NO 379
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 379
gatcacgcct tgtgatagaa gatca                                        25

<210> SEQ ID NO 380
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 380
cgacagacgc ctgatcttct aggtatgcgg tt         32

<210> SEQ ID NO 381
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 381
gatcaaccgc atacctagaa gatca         25

<210> SEQ ID NO 382
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 382
cgacagacgc ctgatcttct agcaacggaa ct         32

<210> SEQ ID NO 383
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 383
gatcagttcc gttgctagaa gatca         25

<210> SEQ ID NO 384
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 384
cgacagacgc ctgatcttct aacggtggtc tt         32

<210> SEQ ID NO 385
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 385
gatcaagacc accgttagaa gatca         25

<210> SEQ ID NO 386
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 386
cgacagacgc ctgatcttct aaagcgtcca ct         32

```
<210> SEQ ID NO 387
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 387
gatcagtgga cgctttagaa gatca                                         25

<210> SEQ ID NO 388
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 388
cgacagacgc ctgatcttct aaagaccgca ct                                 32

<210> SEQ ID NO 389
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 389
gatcagtgcg gtctttagaa gatca                                         25

<210> SEQ ID NO 390
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 390
cgacagacgc ctgatcttcg taggagaagc tt                                 32

<210> SEQ ID NO 391
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 391
gatcaagctt ctcctacgaa gatca                                         25

<210> SEQ ID NO 392
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 392
cgacagacgc ctgatcttcg tacctccaag at                                 32

<210> SEQ ID NO 393
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 393
gatcatcttg gaggtacgaa gatca                                    25

<210> SEQ ID NO 394
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 394
cgacagacgc ctgatcttcg taatacgctc ct                            32

<210> SEQ ID NO 395
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 395
gatcaggagc gtattacgaa gatca                                    25

<210> SEQ ID NO 396
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 396
cgacagacgc ctgatcttcg gttagattgg ct                            32

<210> SEQ ID NO 397
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 397
gatcagccaa tctaaccgaa gatca                                    25

<210> SEQ ID NO 398
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 398
cgacagacgc ctgatcttcg gtaccaacaa ct                            32

<210> SEQ ID NO 399
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 399
gatcagttgt tggtaccgaa gatca                                    25

<210> SEQ ID NO 400
<211> LENGTH: 32

<212> TYPE: DNA
<213> ORGANISM: Artificial Sequence
<220> FEATURE:
<223> OTHER INFORMATION: synthetic oligonucleotide

<400> SEQUENCE: 400
cgacagacgc ctgatcttcg gatagagagc at                                       32

<210> SEQ ID NO 401
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 401
gatcatgctc tctatccgaa gatca                                               25

<210> SEQ ID NO 402
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 402
cgacagacgc ctgatcttcg gaaagacgta gt                                       32

<210> SEQ ID NO 403
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 403
gatcactacg tctttccgaa gatca                                               25

<210> SEQ ID NO 404
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 404
cgacagacgc ctgatcttcg caagaggtaa gt                                       32

<210> SEQ ID NO 405
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 405
gatcacttac ctcttgcgaa gatca                                               25

<210> SEQ ID NO 406
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 406
cgacagacgc ctgatcttcg agatggtgtt ct        32

<210> SEQ ID NO 407
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 407
gatcagaaca ccatctcgaa gatca        25

<210> SEQ ID NO 408
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 408
cgacagacgc ctgatcttcg aagaagatgc ct        32

<210> SEQ ID NO 409
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 409
gatcaggcat cttcttcgaa gatca        25

<210> SEQ ID NO 410
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 410
cgacagacgc ctgatcttcg aactacacag ct        32

<210> SEQ ID NO 411
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 411
gatcagctgt gtagttcgaa gatca        25

<210> SEQ ID NO 412
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 412
cgacagacgc ctgatcttcc ttacggactc at        32

<210> SEQ ID NO 413
<211> LENGTH: 25
<212> TYPE: DNA
<213> ORGANISM: Artificial Sequence -continued

```
<220> FEATURE:
<223> OTHER INFORMATION: synthetic oligonucleotide

<400> SEQUENCE: 413
gatcatgagt ccgtaaggaa gatca                                              25

<210> SEQ ID NO 414
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 414
cgacagacgc ctgatcttcc tgttggtgaa gt                                      32

<210> SEQ ID NO 415
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 415
gatcacttca ccaacaggaa gatca                                              25

<210> SEQ ID NO 416
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 416
cgacagacgc ctgatcttcc tggatggaag tt                                      32

<210> SEQ ID NO 417
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 417
gatcaacttc catccaggaa gatca                                              25

<210> SEQ ID NO 418
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 418
cgacagacgc ctgatcttcc tcaagttcgt ct                                      32

<210> SEQ ID NO 419
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 419
gatcagacga acttgaggaa gatca                                              25
```

<210> SEQ ID NO 420
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 420
cgacagacgc ctgatcttcc taccggactt tt                                32

<210> SEQ ID NO 421
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 421
gatcaaaagt ccggtaggaa gatca                                        25

<210> SEQ ID NO 422
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 422
cgacagacgc ctgatcttcc gtgaaaggaa gt                                32

<210> SEQ ID NO 423
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 423
gatcacttcc tttcacggaa gatca                                        25

<210> SEQ ID NO 424
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 424
cgacagacgc ctgatcttcc ggatatgttg ct                                32

<210> SEQ ID NO 425
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 425
gatcagcaac atatccggaa gatca                                        25

<210> SEQ ID NO 426
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 426
cgacagacgc ctgatcttcc gctaaatgtc ct                                32

<210> SEQ ID NO 427
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 427
gatcaggaca tttagcggaa gatca                                        25

<210> SEQ ID NO 428
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 428
cgacagacgc ctgatcttcc gaaactatgc ct                                32

<210> SEQ ID NO 429
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 429
gatcaggcat agtttcggaa gatca                                        25

<210> SEQ ID NO 430
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 430
cgacagacgc ctgatcttcc actaggcaaa ct                                32

<210> SEQ ID NO 431
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 431
gatcagtttg cctagtggaa gatca                                        25

<210> SEQ ID NO 432
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 432
cgacagacgc ctgatcttcc acgaatagca ct                                32

<210> SEQ ID NO 433

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 433
gatcagtgct attcgtggaa gatca                                        25

<210> SEQ ID NO 434
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 434
cgacagacgc ctgatcttcc acgaaggaat ct                                32

<210> SEQ ID NO 435
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 435
gatcagattc cttcgtggaa gatca                                        25

<210> SEQ ID NO 436
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 436
cgacagacgc ctgatcttcc accagagaac tt                                32

<210> SEQ ID NO 437
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 437
gatcaagttc tctggtggaa gatca                                        25

<210> SEQ ID NO 438
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 438
cgacagacgc ctgatcttcc acatacaggc tt                                32

<210> SEQ ID NO 439
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 439
```

```
gatcaagcct gtatgtggaa gatca                                              25

<210> SEQ ID NO 440
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 440
cgacagacgc ctgatcttcc aagtccgttt ct                                      32

<210> SEQ ID NO 441
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 441
gatcagaaac ggacttggaa gatca                                              25

<210> SEQ ID NO 442
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 442
cgacagacgc ctgatcttca ttctggcact ct                                      32

<210> SEQ ID NO 443
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 443
gatcagagtg ccagaatgaa gatca                                              25

<210> SEQ ID NO 444
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 444
cgacagacgc ctgatcttca tgtagtgtgg ct                                      32

<210> SEQ ID NO 445
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 445
gatcagccac actacatgaa gatca                                              25

<210> SEQ ID NO 446
<211> LENGTH: 32
<212> TYPE: DNA
```

```
<213> ORGANISM: Artificial Sequence
<220> FEATURE:
<223> OTHER INFORMATION: synthetic oligonucleotide

<400> SEQUENCE: 446
cgacagacgc ctgatcttca tggttgtgga ct                                       32

<210> SEQ ID NO 447
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 447
gatcagtcca caaccatgaa gatca                                               25

<210> SEQ ID NO 448
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 448
cgacagacgc ctgatcttca tcttacacgg ct                                       32

<210> SEQ ID NO 449
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 449
gatcagccgt gtaagatgaa gatca                                               25

<210> SEQ ID NO 450
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 450
cgacagacgc ctgatcttca tacggaacac ct                                       32

<210> SEQ ID NO 451
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 451
gatcaggtgt tccgtatgaa gatca                                               25

<210> SEQ ID NO 452
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 452
cgacagacgc ctgatcttca taacactcgg ct                                       32
```

<210> SEQ ID NO 453
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 453
gatcagccga gtgttatgaa gatca                                           25

<210> SEQ ID NO 454
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 454
cgacagacgc ctgatcttca gtgaccaaac ct                                   32

<210> SEQ ID NO 455
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 455
gatcaggttt ggtcactgaa gatca                                           25

<210> SEQ ID NO 456
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 456
cgacagacgc ctgatcttca gtcattccgt ct                                   32

<210> SEQ ID NO 457
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 457
gatcagacgg aatgactgaa gatca                                           25

<210> SEQ ID NO 458
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 458
cgacagacgc ctgatcttca gcatggaaag gt                                   32

<210> SEQ ID NO 459
<211> LENGTH: 25
<212> TYPE: DNA
<213> ORGANISM: Artificial Sequence
<220> FEATURE:

```
<223> OTHER INFORMATION: synthetic oligonucleotide

<400> SEQUENCE: 459
gatcaccttt ccatgctgaa gatca                                              25

<210> SEQ ID NO 460
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 460
cgacagacgc ctgatcttca gcaaagagtc ct                                      32

<210> SEQ ID NO 461
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 461
gatcaggact ctttgctgaa gatca                                              25

<210> SEQ ID NO 462
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 462
cgacagacgc ctgatcttca gagtagagcg tt                                      32

<210> SEQ ID NO 463
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 463
gatcaacgct ctactctgaa gatca                                              25

<210> SEQ ID NO 464
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 464
cgacagacgc ctgatcttca gaaggagttg ct                                      32

<210> SEQ ID NO 465
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 465
gatcagcaac tccttctgaa gatca                                              25
```

<210> SEQ ID NO 466
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 466
cgacagacgc ctgatcttca cttagcggaa ct                                   32

<210> SEQ ID NO 467
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 467
gatcagttcc gctaagtgaa gatca                                           25

<210> SEQ ID NO 468
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 468
cgacagacgc ctgatcttca cggaggaaat gt                                   32

<210> SEQ ID NO 469
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 469
gatcacattt cctccgtgaa gatca                                           25

<210> SEQ ID NO 470
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 470
cgacagacgc ctgatcttca cacctggaaa ct                                   32

<210> SEQ ID NO 471
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 471
gatcagtttc caggtgtgaa gatca                                           25

<210> SEQ ID NO 472
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 472
cgacagacgc ctgatcttca caatctcagg ct                          32

<210> SEQ ID NO 473
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 473
gatcagcctg agattgtgaa gatca                                  25

<210> SEQ ID NO 474
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 474
cgacagacgc ctgatcttca atgagtgtcc gt                          32

<210> SEQ ID NO 475
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 475
gatcacggac actcattgaa gatca                                  25

<210> SEQ ID NO 476
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 476
cgacagacgc ctgatcttca atcacagagc ct                          32

<210> SEQ ID NO 477
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 477
gatcaggctc tgtgattgaa gatca                                  25

<210> SEQ ID NO 478
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 478
cgacagacgc ctgatcttca aggctgaaag gt                          32

<210> SEQ ID NO 479
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 479
gatcaccttt cagccttgaa gatca                                    25

<210> SEQ ID NO 480
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 480
cgacagacgc ctgatcttca agactaaccg ct                            32

<210> SEQ ID NO 481
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 481
gatcagcggt tagtcttgaa gatca                                    25

<210> SEQ ID NO 482
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 482
cgacagacgc ctgatcttca accagtaagc ct                            32

<210> SEQ ID NO 483
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 483
gatcaggctt actggttgaa gatca                                    25

<210> SEQ ID NO 484
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 484
cgacagacgc ctgatcttca aagtatccgc ct                            32

<210> SEQ ID NO 485
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 485
```

```
gatcaggcgg atactttgaa gatca                                          25

<210> SEQ ID NO 486
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 486
cgacagacgc ctgatcttat tgccgagttc ct                                  32

<210> SEQ ID NO 487
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 487
gatcaggaac tcggcaataa gatca                                          25

<210> SEQ ID NO 488
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 488
cgacagacgc ctgatcttat tgccaccaca gt                                  32

<210> SEQ ID NO 489
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 489
gatcactgtg gtggcaataa gatca                                          25

<210> SEQ ID NO 490
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 490
cgacagacgc ctgatcttat tccgaacctg ct                                  32

<210> SEQ ID NO 491
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 491
gatcagcagg ttcggaataa gatca                                          25

<210> SEQ ID NO 492
<211> LENGTH: 32
<212> TYPE: DNA
<213> ORGANISM: Artificial Sequence
```

```
<220> FEATURE:
<223> OTHER INFORMATION: synthetic oligonucleotide

<400> SEQUENCE: 492
cgacagacgc ctgatcttat tcagccgttc ct                                    32

<210> SEQ ID NO 493
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 493
gatcaggaac ggctgaataa gatca                                            25

<210> SEQ ID NO 494
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 494
cgacagacgc ctgatcttat gttgccaggt gt                                    32

<210> SEQ ID NO 495
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 495
gatcacacct ggcaacataa gatca                                            25

<210> SEQ ID NO 496
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 496
cgacagacgc ctgatcttat gcacacagac ct                                    32

<210> SEQ ID NO 497
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 497
gatcaggtct gtgtgcataa gatca                                            25

<210> SEQ ID NO 498
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 498
cgacagacgc ctgatcttat gcaaggagtc gt                                    32
```

<210> SEQ ID NO 499
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 499
gatcacgact ccttgcataa gatca                                            25

<210> SEQ ID NO 500
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 500
cgacagacgc ctgatcttat ctcgactgcc tt                                    32

<210> SEQ ID NO 501
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 501
gatcaaggca gtcgagataa gatca                                            25

<210> SEQ ID NO 502
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 502
cgacagacgc ctgatcttat cgccaagaag gt                                    32

<210> SEQ ID NO 503
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 503
gatcaccttc ttggcgataa gatca                                            25

<210> SEQ ID NO 504
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 504
cgacagacgc ctgatcttat cgcacctcaa gt                                    32

<210> SEQ ID NO 505
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 505
gatcacttga ggtgcgataa gatca                                    25

<210> SEQ ID NO 506
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 506
cgacagacgc ctgatcttat cgattggctg gt                            32

<210> SEQ ID NO 507
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 507
gatcaccagc caatcgataa gatca                                    25

<210> SEQ ID NO 508
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 508
cgacagacgc ctgatcttat cattgccgac ct                            32

<210> SEQ ID NO 509
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 509
gatcaggtcg gcaatgataa gatca                                    25

<210> SEQ ID NO 510
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 510
cgacagacgc ctgatcttat caggtgttcg ct                            32

<210> SEQ ID NO 511
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 511
gatcagcgaa cacctgataa gatca                                    25

<210> SEQ ID NO 512

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 512
cgacagacgc ctgatcttat aggcggaaac gt                              32

<210> SEQ ID NO 513
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 513
gatcacgttt ccgcctataa gatca                                      25

<210> SEQ ID NO 514
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 514
cgacagacgc ctgatcttat aggagcgagc at                              32

<210> SEQ ID NO 515
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 515
gatcatgctc gctcctataa gatca                                      25

<210> SEQ ID NO 516
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 516
cgacagacgc ctgatcttat agaacgcacg gt                              32

<210> SEQ ID NO 517
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 517
gatcaccgtg cgttctataa gatca                                      25

<210> SEQ ID NO 518
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 518
```

```
cgacagacgc ctgatcttat acggcacaag gt                                32
```

<210> SEQ ID NO 519
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 519

```
gatcaccttg tgccgtataa gatca                                        25
```

<210> SEQ ID NO 520
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 520

```
cgacagacgc ctgatcttat accttgtgcc gt                                32
```

<210> SEQ ID NO 521
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 521

```
gatcacggca caaggtataa gatca                                        25
```

<210> SEQ ID NO 522
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 522

```
cgacagacgc ctgatcttat aagccttgcc gt                                32
```

<210> SEQ ID NO 523
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 523

```
gatcacggca aggcttataa gatca                                        25
```

<210> SEQ ID NO 524
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 524

```
cgacagacgc ctgatcttag ttaacaccgc ct                                32
```

<210> SEQ ID NO 525
<211> LENGTH: 25
<212> TYPE: DNA

<210> SEQ ID NO 525
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 525
gatcaggcgg tgttaactaa gatca                                           25

<210> SEQ ID NO 526
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 526
cgacagacgc ctgatcttag tctatggcgg tt                                   32

<210> SEQ ID NO 527
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 527
gatcaaccgc catagactaa gatca                                           25

<210> SEQ ID NO 528
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 528
cgacagacgc ctgatcttag taccgctttg gt                                   32

<210> SEQ ID NO 529
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 529
gatcaccaaa gcggtactaa gatca                                           25

<210> SEQ ID NO 530
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 530
cgacagacgc ctgatcttag gtggctttac gt                                   32

<210> SEQ ID NO 531
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 531
gatcacgtaa agccacctaa gatca                                           25

<210> SEQ ID NO 532
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 532
cgacagacgc ctgatcttag gtacggcttt gt                                  32

<210> SEQ ID NO 533
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 533
gatcacaaag ccgtacctaa gatca                                          25

<210> SEQ ID NO 534
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 534
cgacagacgc ctgatcttag gcttcactgg tt                                  32

<210> SEQ ID NO 535
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 535
gatcaaccag tgaagcctaa gatca                                          25

<210> SEQ ID NO 536
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 536
cgacagacgc ctgatcttag gccatcaaca ct                                  32

<210> SEQ ID NO 537
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 537
gatcagtgtt gatggcctaa gatca                                          25

<210> SEQ ID NO 538
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 538
cgacagacgc ctgatcttag gattgaacgg ct                32

<210> SEQ ID NO 539
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 539
gatcagccgt tcaatcctaa gatca                25

<210> SEQ ID NO 540
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 540
cgacagacgc ctgatcttag ctcaaacgtc ct                32

<210> SEQ ID NO 541
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 541
gatcaggacg tttgagctaa gatca                25

<210> SEQ ID NO 542
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 542
cgacagacgc ctgatcttag cggattggtt ct                32

<210> SEQ ID NO 543
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 543
gatcagaacc aatccgctaa gatca                25

<210> SEQ ID NO 544
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 544
cgacagacgc ctgatcttag atttccacgg ct                32

```
<210> SEQ ID NO 545
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 545
gatcagccgt ggaaatctaa gatca                                              25

<210> SEQ ID NO 546
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 546
cgacagacgc ctgatcttag attgccgagt gt                                      32

<210> SEQ ID NO 547
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 547
gatcacactc ggcaatctaa gatca                                              25

<210> SEQ ID NO 548
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 548
cgacagacgc ctgatcttag aacgtggaag ct                                      32

<210> SEQ ID NO 549
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 549
gatcagcttc cacgttctaa gatca                                              25

<210> SEQ ID NO 550
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 550
cgacagacgc ctgatcttag aaactccgca ct                                      32

<210> SEQ ID NO 551
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 551
gatcagtgcg gagtttctaa gatca    25

<210> SEQ ID NO 552
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 552
cgacagacgc ctgatcttac ttcggacaac ct    32

<210> SEQ ID NO 553
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 553
gatcaggttg tccgaagtaa gatca    25

<210> SEQ ID NO 554
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 554
cgacagacgc ctgatcttac tgtatccgcc tt    32

<210> SEQ ID NO 555
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 555
gatcaaggcg gatacagtaa gatca    25

<210> SEQ ID NO 556
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 556
cgacagacgc ctgatcttac tgctgactcc tt    32

<210> SEQ ID NO 557
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 557
gatcaaggag tcagcagtaa gatca    25

<210> SEQ ID NO 558
<211> LENGTH: 32

```
<212> TYPE: DNA
<213> ORGANISM: Artificial Sequence
<220> FEATURE:
<223> OTHER INFORMATION: synthetic oligonucleotide

<400> SEQUENCE: 558
cgacagacgc ctgatcttac tcgtgaaagc ct                                32

<210> SEQ ID NO 559
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 559
gatcaggctt tcacgagtaa gatca                                        25

<210> SEQ ID NO 560
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 560
cgacagacgc ctgatcttac tcgaagccaa ct                                32

<210> SEQ ID NO 561
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 561
gatcagttgg cttcgagtaa gatca                                        25

<210> SEQ ID NO 562
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 562
cgacagacgc ctgatcttac tccagtttgc ct                                32

<210> SEQ ID NO 563
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 563
gatcaggcaa actggagtaa gatca                                        25

<210> SEQ ID NO 564
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 564
```

```
cgacagacgc ctgatcttac tattgtggcg gt                              32

<210> SEQ ID NO 565
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 565
gatcaccgcc acaatagtaa gatca                                      25

<210> SEQ ID NO 566
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 566
cgacagacgc ctgatcttac tagacacacg ct                              32

<210> SEQ ID NO 567
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 567
gatcagcgtg tgtctagtaa gatca                                      25

<210> SEQ ID NO 568
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 568
cgacagacgc ctgatcttac ggtctttcca ct                              32

<210> SEQ ID NO 569
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 569
gatcagtgga aagaccgtaa gatca                                      25

<210> SEQ ID NO 570
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 570
cgacagacgc ctgatcttac ctaacagccg at                              32

<210> SEQ ID NO 571
<211> LENGTH: 25
<212> TYPE: DNA
<213> ORGANISM: Artificial Sequence
```

<220> FEATURE:
<223> OTHER INFORMATION: synthetic oligonucleotide

<400> SEQUENCE: 571
gatcatcggc tgttaggtaa gatca         25

<210> SEQ ID NO 572
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 572
cgacagacgc ctgatcttac cggtggttag tt         32

<210> SEQ ID NO 573
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 573
gatcaactaa ccaccggtaa gatca         25

<210> SEQ ID NO 574
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 574
cgacagacgc ctgatcttac cataagtgcc gt         32

<210> SEQ ID NO 575
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 575
gatcacggca cttatggtaa gatca         25

<210> SEQ ID NO 576
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 576
cgacagacgc ctgatcttac caatgtccag ct         32

<210> SEQ ID NO 577
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 577
gatcagctgg acattggtaa gatca         25

<210> SEQ ID NO 578
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 578
cgacagacgc ctgatcttac atgttcgctc ct                                     32

<210> SEQ ID NO 579
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 579
gatcaggagc gaacatgtaa gatca                                             25

<210> SEQ ID NO 580
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 580
cgacagacgc ctgatcttac atcatccagc gt                                     32

<210> SEQ ID NO 581
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 581
gatcacgctg gatgatgtaa gatca                                             25

<210> SEQ ID NO 582
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 582
cgacagacgc ctgatcttac acaagatcgc ct                                     32

<210> SEQ ID NO 583
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 583
gatcaggcga tcttgtgtaa gatca                                             25

<210> SEQ ID NO 584
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 584
cgacagacgc ctgatcttac aaagtccgtc ct                                    32

<210> SEQ ID NO 585
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 585
gatcaggacg gactttgtaa gatca                                            25

<210> SEQ ID NO 586
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 586
cgacagacgc ctgatcttaa ttcgtccgtc ct                                    32

<210> SEQ ID NO 587
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 587
gatcaggacg gacgaattaa gatca                                            25

<210> SEQ ID NO 588
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 588
cgacagacgc ctgatcttaa tgaggagcac gt                                    32

<210> SEQ ID NO 589
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 589
gatcacgtgc tcctcattaa gatca                                            25

<210> SEQ ID NO 590
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 590
cgacagacgc ctgatcttaa gtgaagaccg ct                                    32

<210> SEQ ID NO 591
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 591
gatcagcggt cttcacttaa gatca                                    25

<210> SEQ ID NO 592
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 592
cgacagacgc ctgatcttaa gtcgtggttc gt                            32

<210> SEQ ID NO 593
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 593
gatcacgaac cacgacttaa gatca                                    25

<210> SEQ ID NO 594
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 594
cgacagacgc ctgatcttaa gctctccgtt gt                            32

<210> SEQ ID NO 595
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 595
gatcacaacg gagagcttaa gatca                                    25

<210> SEQ ID NO 596
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 596
cgacagacgc ctgatcttaa gccactccag at                            32

<210> SEQ ID NO 597
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 597
```

```
gatcatctgg agtggcttaa gatca                                            25

<210> SEQ ID NO 598
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 598
cgacagacgc ctgatcttaa gagaggtgcc at                                    32

<210> SEQ ID NO 599
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 599
gatcatggca cctctcttaa gatca                                            25

<210> SEQ ID NO 600
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 600
cgacagacgc ctgatcttaa gacctcaccg at                                    32

<210> SEQ ID NO 601
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 601
gatcatcggt gaggtcttaa gatca                                            25

<210> SEQ ID NO 602
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 602
cgacagacgc ctgatcttaa ctcaaccgga ct                                    32

<210> SEQ ID NO 603
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 603
gatcagtccg gttgagttaa gatca                                            25

<210> SEQ ID NO 604
<211> LENGTH: 32
<212> TYPE: DNA
```

```
<213> ORGANISM: Artificial Sequence
<220> FEATURE:
<223> OTHER INFORMATION: synthetic oligonucleotide

<400> SEQUENCE: 604
cgacagacgc ctgatcttaa cctctcgctt gt                              32

<210> SEQ ID NO 605
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 605
gatcacaagc gagaggttaa gatca                                      25

<210> SEQ ID NO 606
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 606
cgacagacgc ctgatcttaa ccgctttcct gt                              32

<210> SEQ ID NO 607
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 607
gatcacagga aagcggttaa gatca                                      25

<210> SEQ ID NO 608
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 608
cgacagacgc ctgatcttaa cactctggca ct                              32

<210> SEQ ID NO 609
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 609
gatcagtgcc agagtgttaa gatca                                      25

<210> SEQ ID NO 610
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 610
cgacagacgc ctgatcttaa atgcggagga ct                              32
```

<210> SEQ ID NO 611
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 611
gatcagtcct ccgcatttaa gatca 25

<210> SEQ ID NO 612
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 612
cgacagacgc ctgatcttaa ataggctggc gt 32

<210> SEQ ID NO 613
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 613
gatcacgcca gcctatttaa gatca 25

<210> SEQ ID NO 614
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 614
cgacagacgc ctgatcttaa acctcggaca ct 32

<210> SEQ ID NO 615
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 615
gatcagtgtc cgaggtttaa gatca 25

<210> SEQ ID NO 616
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 616
cgacagacgc ctgatctgtt tgaaccgagg at 32

<210> SEQ ID NO 617
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 617
gatcatcctc ggttcaaaca gatca                                    25

<210> SEQ ID NO 618
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 618
cgacagacgc ctgatctgtt tcgacttcac gt                            32

<210> SEQ ID NO 619
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 619
gatcacgtga agtcgaaaca gatca                                    25

<210> SEQ ID NO 620
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 620
cgacagacgc ctgatctgtt tcacgaccaa gt                            32

<210> SEQ ID NO 621
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 621
gatcacttgg tcgtgaaaca gatca                                    25

<210> SEQ ID NO 622
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 622
cgacagacgc ctgatctgtt tatgccactc gt                            32

<210> SEQ ID NO 623
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 623
gatcacgagt ggcataaaca gatca                                    25

```
<210> SEQ ID NO 624
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 624
cgacagacgc ctgatctgtt taatcgaccg ct                                32

<210> SEQ ID NO 625
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 625
gatcagcggt cgattaaaca gatca                                        25

<210> SEQ ID NO 626
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 626
cgacagacgc ctgatctgtt gtaatggctc gt                                32

<210> SEQ ID NO 627
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 627
gatcacgagc cattacaaca gatca                                        25

<210> SEQ ID NO 628
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 628
cgacagacgc ctgatctgtt ggttcaagtc gt                                32

<210> SEQ ID NO 629
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 629
gatcacgact tgaaccaaca gatca                                        25

<210> SEQ ID NO 630
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 630
cgacagacgc ctgatctgtt ggtaactggc tt                                    32

<210> SEQ ID NO 631
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 631
gatcaagcca gttaccaaca gatca                                            25

<210> SEQ ID NO 632
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 632
cgacagacgc ctgatctgtt ggcataacga gt                                    32

<210> SEQ ID NO 633
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 633
gatcactcgt tatgccaaca gatca                                            25

<210> SEQ ID NO 634
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 634
cgacagacgc ctgatctgtt ggaacagcaa gt                                    32

<210> SEQ ID NO 635
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 635
gatcacttgc tgttccaaca gatca                                            25

<210> SEQ ID NO 636
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 636
cgacagacgc ctgatctgtt gctctcaacc tt                                    32

<210> SEQ ID NO 637
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 637
gatcaaggtt gagagcaaca gatca                                    25

<210> SEQ ID NO 638
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 638
cgacagacgc ctgatctgtt gctcaatctc gt                            32

<210> SEQ ID NO 639
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 639
gatcacgaga ttgagcaaca gatca                                    25

<210> SEQ ID NO 640
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 640
cgacagacgc ctgatctgtt gcaggaaagt ct                            32

<210> SEQ ID NO 641
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 641
gatcagactt tcctgcaaca gatca                                    25

<210> SEQ ID NO 642
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 642
cgacagacgc ctgatctgtt gcaaacctct ct                            32

<210> SEQ ID NO 643
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 643
```
gatcagagag gtttgcaaca gatca                                            25

<210> SEQ ID NO 644
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 644
cgacagacgc ctgatctgtt gaatgccgta gt                                    32

<210> SEQ ID NO 645
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 645
gatcactacg gcattcaaca gatca                                            25

<210> SEQ ID NO 646
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 646
cgacagacgc ctgatctgtt ctggaggcat tt                                    32

<210> SEQ ID NO 647
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 647
gatcaaatgc ctccagaaca gatca                                            25

<210> SEQ ID NO 648
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 648
cgacagacgc ctgatctgtt ctgcaacctc tt                                    32

<210> SEQ ID NO 649
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 649
gatcaagagg ttgcagaaca gatca                                            25

<210> SEQ ID NO 650
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 650
cgacagacgc ctgatctgtt cgaggaagac at                          32

<210> SEQ ID NO 651
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 651
gatcatgtct tcctcgaaca gatca                                  25

<210> SEQ ID NO 652
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 652
cgacagacgc ctgatctgtt cctatcacgc tt                          32

<210> SEQ ID NO 653
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 653
gatcaagcgt gataggaaca gatca                                  25

<210> SEQ ID NO 654
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 654
cgacagacgc ctgatctgtt ccgaaagcaa gt                          32

<210> SEQ ID NO 655
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 655
gatcacttgc tttcggaaca gatca                                  25

<210> SEQ ID NO 656
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 656
cgacagacgc ctgatctgtt cagttccacc at                          32

```
<210> SEQ ID NO 657
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 657
gatcatggtg gaactgaaca gatca                                              25

<210> SEQ ID NO 658
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 658
cgacagacgc ctgatctgtt cagagatggc at                                      32

<210> SEQ ID NO 659
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 659
gatcatgcca tctctgaaca gatca                                              25

<210> SEQ ID NO 660
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 660
cgacagacgc ctgatctgtt cacagccaaa gt                                      32

<210> SEQ ID NO 661
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 661
gatcactttg gctgtgaaca gatca                                              25

<210> SEQ ID NO 662
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 662
cgacagacgc ctgatctgtt caaatgcgga gt                                      32

<210> SEQ ID NO 663
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 663
gatcactccg catttgaaca gatca                                         25

<210> SEQ ID NO 664
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 664
cgacagacgc ctgatctgtt atgaagcacc gt                                 32

<210> SEQ ID NO 665
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 665
gatcacggtg cttcataaca gatca                                         25

<210> SEQ ID NO 666
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 666
cgacagacgc ctgatctgtt agttgatgcc gt                                 32

<210> SEQ ID NO 667
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 667
gatcacggca tcaactaaca gatca                                         25

<210> SEQ ID NO 668
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 668
cgacagacgc ctgatctgtt agaaagcgca gt                                 32

<210> SEQ ID NO 669
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 669
gatcactgcg ctttctaaca gatca                                         25

<210> SEQ ID NO 670

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 670
cgacagacgc ctgatctgtt acacagctcc at                          32

<210> SEQ ID NO 671
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 671
gatcatggag ctgtgtaaca gatca                                  25

<210> SEQ ID NO 672
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 672
cgacagacgc ctgatctgtg tcattagcgg at                          32

<210> SEQ ID NO 673
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 673
gatcatccgc taatgacaca gatca                                  25

<210> SEQ ID NO 674
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 674
cgacagacgc ctgatctgtg tatgttcgca gt                          32

<210> SEQ ID NO 675
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 675
gatcactgcg aacatacaca gatca                                  25

<210> SEQ ID NO 676
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 676
```
cgacagacgc ctgatctgtg tataccgcct tt					32

<210> SEQ ID NO 677
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 677
gatcaaaggc ggtatacaca gatca					25

<210> SEQ ID NO 678
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 678
cgacagacgc ctgatctgtg taaaccgcat gt					32

<210> SEQ ID NO 679
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 679
gatcacatgc ggtttacaca gatca					25

<210> SEQ ID NO 680
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 680
cgacagacgc ctgatctgtg gtcaattcgt gt					32

<210> SEQ ID NO 681
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 681
gatcacacga attgaccaca gatca					25

<210> SEQ ID NO 682
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 682
cgacagacgc ctgatctgtg cttcaaaggt gt					32

<210> SEQ ID NO 683
<211> LENGTH: 25
<212> TYPE: DNA

<213> ORGANISM: Artificial Sequence
<220> FEATURE:
<223> OTHER INFORMATION: synthetic oligonucleotide

<400> SEQUENCE: 683
gatcacacct ttgaagcaca gatca         25

<210> SEQ ID NO 684
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 684
cgacagacgc ctgatctgtg cagaggaaac tt         32

<210> SEQ ID NO 685
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 685
gatcaagttt cctctgcaca gatca         25

<210> SEQ ID NO 686
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 686
cgacagacgc ctgatctgtg caatatcggt gt         32

<210> SEQ ID NO 687
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 687
gatcacaccg atattgcaca gatca         25

<210> SEQ ID NO 688
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 688
cgacagacgc ctgatctgtg aggttccagt tt         32

<210> SEQ ID NO 689
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 689
gatcaaactg gaacctcaca gatca         25

<210> SEQ ID NO 690
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 690
cgacagacgc ctgatctgtg aattccttgc gt                                32

<210> SEQ ID NO 691
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 691
gatcacgcaa ggaattcaca gatca                                         25

<210> SEQ ID NO 692
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 692
cgacagacgc ctgatctgtg aagtaagccg at                                32

<210> SEQ ID NO 693
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 693
gatcatcggc ttacttcaca gatca                                         25

<210> SEQ ID NO 694
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 694
cgacagacgc ctgatctgtc tttgaacgtg gt                                32

<210> SEQ ID NO 695
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 695
gatcaccacg ttcaaagaca gatca                                         25

<210> SEQ ID NO 696
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 696
cgacagacgc ctgatctgtc tgaaaccacc at                          32

<210> SEQ ID NO 697
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 697
gatcatggtg gtttcagaca gatca                                  25

<210> SEQ ID NO 698
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 698
cgacagacgc ctgatctgtc tcgaaacctg tt                          32

<210> SEQ ID NO 699
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 699
gatcaacagg tttcgagaca gatca                                  25

<210> SEQ ID NO 700
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 700
cgacagacgc ctgatctgtc gtaagaggca at                          32

<210> SEQ ID NO 701
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 701
gatcattgcc tcttacgaca gatca                                  25

<210> SEQ ID NO 702
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 702
cgacagacgc ctgatctgtc gaaacttggt gt                          32

```
<210> SEQ ID NO 703
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 703
gatcacacca agtttcgaca gatca                                         25

<210> SEQ ID NO 704
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 704
cgacagacgc ctgatctgtc ctatgttgcc at                                 32

<210> SEQ ID NO 705
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 705
gatcatggca acataggaca gatca                                         25

<210> SEQ ID NO 706
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 706
cgacagacgc ctgatctgtc cacctaaacg at                                 32

<210> SEQ ID NO 707
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 707
gatcatcgtt taggtggaca gatca                                         25

<210> SEQ ID NO 708
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 708
cgacagacgc ctgatctgtc caaatcacag ct                                 32

<210> SEQ ID NO 709
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 709
gatcagctgt gatttggaca gatca                                      25

<210> SEQ ID NO 710
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 710
cgacagacgc ctgatctgtc caaagctacc at                              32

<210> SEQ ID NO 711
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 711
gatcatggta gctttggaca gatca                                      25

<210> SEQ ID NO 712
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 712
cgacagacgc ctgatctgtc actttgcatc ct                              32

<210> SEQ ID NO 713
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 713
gatcaggatg caaagtgaca gatca                                      25

<210> SEQ ID NO 714
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 714
cgacagacgc ctgatctgtc aaacagccat ct                              32

<210> SEQ ID NO 715
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 715
gatcagatgg ctgtttgaca gatca                                      25

<210> SEQ ID NO 716
<211> LENGTH: 32

<212> TYPE: DNA
<213> ORGANISM: Artificial Sequence
<220> FEATURE:
<223> OTHER INFORMATION: synthetic oligonucleotide

<400> SEQUENCE: 716
cgacagacgc ctgatctgta tttggacacg ct                                    32

<210> SEQ ID NO 717
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 717
gatcagcgtg tccaaataca gatca                                            25

<210> SEQ ID NO 718
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 718
cgacagacgc ctgatctgta tttccgaccg tt                                    32

<210> SEQ ID NO 719
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 719
gatcaacggt cggaaataca gatca                                            25

<210> SEQ ID NO 720
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 720
cgacagacgc ctgatctgta ttgacgcttg gt                                    32

<210> SEQ ID NO 721
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 721
gatcaccaag cgtcaataca gatca                                            25

<210> SEQ ID NO 722
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 722

```
cgacagacgc ctgatctgta tacgcaaacc gt                                32
```

<210> SEQ ID NO 723
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 723

```
gatcacggtt tgcgtataca gatca                                        25
```

<210> SEQ ID NO 724
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 724

```
cgacagacgc ctgatctgta taacgccacc at                                32
```

<210> SEQ ID NO 725
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 725

```
gatcatggtg gcgttataca gatca                                        25
```

<210> SEQ ID NO 726
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 726

```
cgacagacgc ctgatctgta gtgtcaaagc gt                                32
```

<210> SEQ ID NO 727
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 727

```
gatcacgctt tgacactaca gatca                                        25
```

<210> SEQ ID NO 728
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 728

```
cgacagacgc ctgatctgta ggcggatttc tt                                32
```

<210> SEQ ID NO 729
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 729
gatcaagaaa tccgcctaca gatca                                              25

<210> SEQ ID NO 730
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 730
cgacagacgc ctgatctgta ggcaaacggt at                                      32

<210> SEQ ID NO 731
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 731
gatcataccg tttgcctaca gatca                                              25

<210> SEQ ID NO 732
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 732
cgacagacgc ctgatctgta cgtcctttcc at                                      32

<210> SEQ ID NO 733
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 733
gatcatggaa aggacgtaca gatca                                              25

<210> SEQ ID NO 734
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 734
cgacagacgc ctgatctgta ccacacgctt at                                      32

<210> SEQ ID NO 735
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 735
gatcataagc gtgtggtaca gatca                                              25
```

<210> SEQ ID NO 736
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 736
cgacagacgc ctgatctgta atgttgtccg ct                              32

<210> SEQ ID NO 737
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 737
gatcagcgga caacattaca gatca                                      25

<210> SEQ ID NO 738
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 738
cgacagacgc ctgatctgta atccgagcca tt                              32

<210> SEQ ID NO 739
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 739
gatcaatggc tcggattaca gatca                                      25

<210> SEQ ID NO 740
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 740
cgacagacgc ctgatctgta agttccgcat gt                              32

<210> SEQ ID NO 741
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 741
gatcacatgc ggaacttaca gatca                                      25

<210> SEQ ID NO 742
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 742
cgacagacgc ctgatctgta agtccgttgg tt                              32

<210> SEQ ID NO 743
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 743
gatcaaccaa cggacttaca gatca                                      25

<210> SEQ ID NO 744
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 744
cgacagacgc ctgatctgta acgtttgctg gt                              32

<210> SEQ ID NO 745
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 745
gatcaccagc aaacgttaca gatca                                      25

<210> SEQ ID NO 746
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 746
cgacagacgc ctgatctgta aattggcacg gt                              32

<210> SEQ ID NO 747
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 747
gatcaccgtg ccaatttaca gatca                                      25

<210> SEQ ID NO 748
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 748
cgacagacgc ctgatctgta aacgatggca gt                              32

<210> SEQ ID NO 749

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 749
gatcactgcc atcgtttaca gatca                                         25

<210> SEQ ID NO 750
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 750
cgacagacgc ctgatctggt ttcaatgtcg gt                                 32

<210> SEQ ID NO 751
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 751
gatcaccgac attgaaacca gatca                                         25

<210> SEQ ID NO 752
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 752
cgacagacgc ctgatctggt tgatgacctg tt                                 32

<210> SEQ ID NO 753
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 753
gatcaacagg tcatcaacca gatca                                         25

<210> SEQ ID NO 754
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 754
cgacagacgc ctgatctggt tgaccgaaag at                                 32

<210> SEQ ID NO 755
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 755
```
gatcatcttt cggtcaacca gatca                                      25

<210> SEQ ID NO 756
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 756
cgacagacgc ctgatctggt tcttccacca at                              32

<210> SEQ ID NO 757
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 757
gatcattggt ggaagaacca gatca                                      25

<210> SEQ ID NO 758
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 758
cgacagacgc ctgatctggt tcttaccacg tt                              32

<210> SEQ ID NO 759
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 759
gatcaacgtg gtaagaacca gatca                                      25

<210> SEQ ID NO 760
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 760
cgacagacgc ctgatctggt tctattgccg at                              32

<210> SEQ ID NO 761
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 761
gatcatcggc aatagaacca gatca                                      25

<210> SEQ ID NO 762
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 762
cgacagacgc ctgatctggt tccaatcacg at                          32

<210> SEQ ID NO 763
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 763
gatcatcgtg attggaacca gatca                                  25

<210> SEQ ID NO 764
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 764
cgacagacgc ctgatctggt tcaacattcg gt                          32

<210> SEQ ID NO 765
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 765
gatcaccgaa tgttgaacca gatca                                  25

<210> SEQ ID NO 766
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 766
cgacagacgc ctgatctggt taaagccgag at                          32

<210> SEQ ID NO 767
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 767
gatcatctcg gctttaacca gatca                                  25

<210> SEQ ID NO 768
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 768
cgacagacgc ctgatctggt gttaccgatg tt                          32
```

<210> SEQ ID NO 769
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 769
gatcaacatc ggtaacacca gatca                                       25

<210> SEQ ID NO 770
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 770
cgacagacgc ctgatctggt gaaccaaatg ct                               32

<210> SEQ ID NO 771
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 771
gatcagcatt tggttcacca gatca                                       25

<210> SEQ ID NO 772
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 772
cgacagacgc ctgatctggt gaaatcgcaa gt                               32

<210> SEQ ID NO 773
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 773
gatcacttgc gatttcacca gatca                                       25

<210> SEQ ID NO 774
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 774
cgacagacgc ctgatctggt ccaattctcg tt                               32

<210> SEQ ID NO 775
<211> LENGTH: 25
<212> TYPE: DNA
<213> ORGANISM: Artificial Sequence
<220> FEATURE:

```
<223> OTHER INFORMATION: synthetic oligonucleotide

<400> SEQUENCE: 775
gatcaacgag aattggacca gatca                                              25

<210> SEQ ID NO 776
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 776
cgacagacgc ctgatctggt cacaaacacc tt                                      32

<210> SEQ ID NO 777
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 777
gatcaaggtg tttgtgacca gatca                                              25

<210> SEQ ID NO 778
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 778
cgacagacgc ctgatctggt ataacgagcg at                                      32

<210> SEQ ID NO 779
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 779
gatcatcgct cgttatacca gatca                                              25

<210> SEQ ID NO 780
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 780
cgacagacgc ctgatctggt aggtttcagc at                                      32

<210> SEQ ID NO 781
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 781
gatcatgctg aaacctacca gatca                                              25
```

```
<210> SEQ ID NO 782
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 782
cgacagacgc ctgatctggt actccaaacg at                                32

<210> SEQ ID NO 783
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 783
gatcatcgtt tggagtacca gatca                                        25

<210> SEQ ID NO 784
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 784
cgacagacgc ctgatctggt acacaaatcg ct                                32

<210> SEQ ID NO 785
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 785
gatcagcgat ttgtgtacca gatca                                        25

<210> SEQ ID NO 786
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 786
cgacagacgc ctgatctggt acaaacactg ct                                32

<210> SEQ ID NO 787
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 787
gatcagcagt gtttgtacca gatca                                        25

<210> SEQ ID NO 788
<211> LENGTH: 32
<212> TYPE: DNA
<213> ORGANISM: Artificial Sequence
<220> FEATURE:
<223> OTHER INFORMATION: synthetic oligonucleotide
```

-continued

```
<400> SEQUENCE: 788
cgacagacgc ctgatctggt aagacgcaat gt                                 32

<210> SEQ ID NO 789
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 789
gatcacattg cgtcttacca gatca                                         25

<210> SEQ ID NO 790
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 790
cgacagacgc ctgatctggt aaatgcaacg gt                                 32

<210> SEQ ID NO 791
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 791
gatcaccgtt gcatttacca gatca                                         25

<210> SEQ ID NO 792
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 792
cgacagacgc ctgatctggt aaagcacatc gt                                 32

<210> SEQ ID NO 793
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 793
gatcacgatg tgctttacca gatca                                         25

<210> SEQ ID NO 794
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 794
cgacagacgc ctgatctggc ttcctaaacg tt                                 32

<210> SEQ ID NO 795
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 795
gatcaacgtt taggaagcca gatca                                        25

<210> SEQ ID NO 796
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 796
cgacagacgc ctgatctggc taaatgacgt gt                                32

<210> SEQ ID NO 797
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 797
gatcacacgt catttagcca gatca                                        25

<210> SEQ ID NO 798
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 798
cgacagacgc ctgatctggc taaacacctc at                                32

<210> SEQ ID NO 799
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 799
gatcatgagg tgtttagcca gatca                                        25

<210> SEQ ID NO 800
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 800
cgacagacgc ctgatctggc ctcaaatacc at                                32

<210> SEQ ID NO 801
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 801
```

```
gatcatggta tttgaggcca gatca                                          25

<210> SEQ ID NO 802
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 802
cgacagacgc ctgatctggc atttcaacca gt                                  32

<210> SEQ ID NO 803
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 803
gatcactggt tgaaatgcca gatca                                          25

<210> SEQ ID NO 804
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 804
cgacagacgc ctgatctggc acaagaggat tt                                  32

<210> SEQ ID NO 805
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 805
gatcaaatcc tcttgtgcca gatca                                          25

<210> SEQ ID NO 806
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 806
cgacagacgc ctgatctggc aatttgacag gt                                  32

<210> SEQ ID NO 807
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 807
gatcacctgt caaattgcca gatca                                          25

<210> SEQ ID NO 808
<211> LENGTH: 32
<212> TYPE: DNA
<213> ORGANISM: Artificial Sequence
```

```
<220> FEATURE:
<223> OTHER INFORMATION: synthetic oligonucleotide

<400> SEQUENCE: 808
cgacagacgc ctgatctggc aacttcatcc tt                          32

<210> SEQ ID NO 809
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 809
gatcaaggat gaagttgcca gatca                                  25

<210> SEQ ID NO 810
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 810
cgacagacgc ctgatctggc aacaatccat ct                          32

<210> SEQ ID NO 811
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 811
gatcagatgg attgttgcca gatca                                  25

<210> SEQ ID NO 812
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 812
cgacagacgc ctgatctgga tttcatgtgc gt                          32

<210> SEQ ID NO 813
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 813
gatcacgcac atgaaatcca gatca                                  25

<210> SEQ ID NO 814
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 814
cgacagacgc ctgatctgga ttgtttcacg gt                          32
```

<210> SEQ ID NO 815
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 815
gatcaccgtg aaacaatcca gatca                                        25

<210> SEQ ID NO 816
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 816
cgacagacgc ctgatctgga ttgtcactgg tt                                32

<210> SEQ ID NO 817
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 817
gatcaaccag tgacaatcca gatca                                        25

<210> SEQ ID NO 818
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 818
cgacagacgc ctgatctgga ttagctccgt tt                                32

<210> SEQ ID NO 819
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 819
gatcaaacgg agctaatcca gatca                                        25

<210> SEQ ID NO 820
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 820
cgacagacgc ctgatctgga tgtttacgct gt                                32

<210> SEQ ID NO 821
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 821
gatcacagcg taaacatcca gatca                                              25

<210> SEQ ID NO 822
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 822
cgacagacgc ctgatctgga tcacaacatg ct                                      32

<210> SEQ ID NO 823
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 823
gatcagcatg ttgtgatcca gatca                                              25

<210> SEQ ID NO 824
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 824
cgacagacgc ctgatctgga gttacggctt tt                                      32

<210> SEQ ID NO 825
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 825
gatcaaaagc cgtaactcca gatca                                              25

<210> SEQ ID NO 826
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 826
cgacagacgc ctgatctgga ggacttcgtt tt                                      32

<210> SEQ ID NO 827
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 827
gatcaaaacg aagtcctcca gatca                                              25

<210> SEQ ID NO 828
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 828
cgacagacgc ctgatctgga ctccacacaa tt                                      32

<210> SEQ ID NO 829
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 829
gatcaattgt gtggagtcca gatca                                              25

<210> SEQ ID NO 830
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 830
cgacagacgc ctgatctgga ctattctgcg tt                                      32

<210> SEQ ID NO 831
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 831
gatcaacgca gaatagtcca gatca                                              25

<210> SEQ ID NO 832
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 832
cgacagacgc ctgatctgga caccatttcg at                                      32

<210> SEQ ID NO 833
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 833
gatcatcgaa atggtgtcca gatca                                              25

<210> SEQ ID NO 834
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 834
```
cgacagacgc ctgatctgga caatcaccag tt        32

<210> SEQ ID NO 835
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 835
gatcaactgg tgattgtcca gatca        25

<210> SEQ ID NO 836
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 836
cgacagacgc ctgatctgga attgtgcctt gt        32

<210> SEQ ID NO 837
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 837
gatcacaagg cacaattcca gatca        25

<210> SEQ ID NO 838
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 838
cgacagacgc ctgatctgga attgtacgca gt        32

<210> SEQ ID NO 839
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 839
gatcactgcg tacaattcca gatca        25

<210> SEQ ID NO 840
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 840
cgacagacgc ctgatctgga atgcaaactg gt        32

<210> SEQ ID NO 841
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 841
gatcaccagt ttgcattcca gatca                                           25

<210> SEQ ID NO 842
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 842
cgacagacgc ctgatctgga agatgccgtt at                                   32

<210> SEQ ID NO 843
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 843
gatcataacg gcatcttcca gatca                                           25

<210> SEQ ID NO 844
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 844
cgacagacgc ctgatctgga acatcagcct tt                                   32

<210> SEQ ID NO 845
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 845
gatcaaaggc tgatgttcca gatca                                           25

<210> SEQ ID NO 846
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 846
cgacagacgc ctgatctgga acatagagcg tt                                   32

<210> SEQ ID NO 847
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 847
gatcaacgct ctatgttcca gatca                                           25
```

<210> SEQ ID NO 848
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 848
cgacagacgc ctgatctgga aactaaggcg tt                    32

<210> SEQ ID NO 849
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 849
gatcaacgcc ttagtttcca gatca                            25

<210> SEQ ID NO 850
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 850
cgacagacgc ctgatctgga aacaccttgg at                    32

<210> SEQ ID NO 851
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 851
gatcatccaa ggtgtttcca gatca                            25

<210> SEQ ID NO 852
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 852
cgacagacgc ctgatctgct ttcacacttc gt                    32

<210> SEQ ID NO 853
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 853
gatcacgaag tgtgaaagca gatca                            25

<210> SEQ ID NO 854
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 854
cgacagacgc ctgatctgct ttaatgcgag gt                32

<210> SEQ ID NO 855
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 855
gatcacctcg cattaaagca gatca                25

<210> SEQ ID NO 856
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 856
cgacagacgc ctgatctgct tgaaccatcc tt                32

<210> SEQ ID NO 857
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 857
gatcaaggat ggttcaagca gatca                25

<210> SEQ ID NO 858
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 858
cgacagacgc ctgatctgct ggaaagtgaa ct                32

<210> SEQ ID NO 859
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 859
gatcagttca ctttccagca gatca                25

<210> SEQ ID NO 860
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 860
cgacagacgc ctgatctgct gaagacaacc tt                32

```
<210> SEQ ID NO 861
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 861
gatcaaggtt gtcttcagca gatca                                          25

<210> SEQ ID NO 862
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 862
cgacagacgc ctgatctgct ccataaagcc tt                                  32

<210> SEQ ID NO 863
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 863
gatcaaggct ttatggagca gatca                                          25

<210> SEQ ID NO 864
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 864
cgacagacgc ctgatctgct catttcctcg at                                  32

<210> SEQ ID NO 865
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 865
gatcatcgag gaaatgagca gatca                                          25

<210> SEQ ID NO 866
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 866
cgacagacgc ctgatctgct caccaacaga tt                                  32

<210> SEQ ID NO 867
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 867
gatcaatctg ttggtgagca gatca                                      25

<210> SEQ ID NO 868
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 868
cgacagacgc ctgatctgct cacaaatacc gt                              32

<210> SEQ ID NO 869
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 869
gatcacggta tttgtgagca gatca                                      25

<210> SEQ ID NO 870
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 870
cgacagacgc ctgatctgct atttggcgat ct                              32

<210> SEQ ID NO 871
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 871
gatcagatcg ccaaatagca gatca                                      25

<210> SEQ ID NO 872
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 872
cgacagacgc ctgatctgct atttacgcca ct                              32

<210> SEQ ID NO 873
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 873
gatcagtggc gtaaatagca gatca                                      25

<210> SEQ ID NO 874
<211> LENGTH: 32

```
<212> TYPE: DNA
<213> ORGANISM: Artificial Sequence
<220> FEATURE:
<223> OTHER INFORMATION: synthetic oligonucleotide

<400> SEQUENCE: 874
cgacagacgc ctgatctgct attgctcctg at                                32

<210> SEQ ID NO 875
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 875
gatcatcagg agcaatagca gatca                                         25

<210> SEQ ID NO 876
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 876
cgacagacgc ctgatctgct accaaaccag tt                                32

<210> SEQ ID NO 877
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 877
gatcaactgg tttggtagca gatca                                         25

<210> SEQ ID NO 878
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 878
cgacagacgc ctgatctgct aaggcaaact gt                                32

<210> SEQ ID NO 879
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 879
gatcacagtt tgccttagca gatca                                         25

<210> SEQ ID NO 880
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 880
```

```
cgacagacgc ctgatctgct aaagagtggc at                                    32

<210> SEQ ID NO 881
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 881
gatcatgcca ctctttagca gatca                                            25

<210> SEQ ID NO 882
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 882
cgacagacgc ctgatctgcg tttactcctc at                                    32

<210> SEQ ID NO 883
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 883
gatcatgagg agtaaacgca gatca                                            25

<210> SEQ ID NO 884
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 884
cgacagacgc ctgatctgcg ttaatcctcc tt                                    32

<210> SEQ ID NO 885
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 885
gatcaaggag gattaacgca gatca                                            25

<210> SEQ ID NO 886
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 886
cgacagacgc ctgatctgcg aatctcttgt gt                                    32

<210> SEQ ID NO 887
<211> LENGTH: 25
<212> TYPE: DNA
<213> ORGANISM: Artificial Sequence
```

```
<220> FEATURE:
<223> OTHER INFORMATION: synthetic oligonucleotide

<400> SEQUENCE: 887
gatcacacaa gagattcgca gatca                                              25

<210> SEQ ID NO 888
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 888
cgacagacgc ctgatctgcg aaatacaggt gt                                      32

<210> SEQ ID NO 889
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 889
gatcacacct gtatttcgca gatca                                              25

<210> SEQ ID NO 890
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 890
cgacagacgc ctgatctgcg aaacattgag gt                                      32

<210> SEQ ID NO 891
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 891
gatcacctca atgtttcgca gatca                                              25

<210> SEQ ID NO 892
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 892
cgacagacgc ctgatctgcc ttaaactccg at                                      32

<210> SEQ ID NO 893
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 893
gatcatcgga gtttaaggca gatca                                              25
```

<210> SEQ ID NO 894
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 894
cgacagacgc ctgatctgcc tggaaattgt gt                                      32

<210> SEQ ID NO 895
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 895
gatcacacaa tttccaggca gatca                                              25

<210> SEQ ID NO 896
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 896
cgacagacgc ctgatctgcc tccttaatcg tt                                      32

<210> SEQ ID NO 897
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 897
gatcaacgat taaggaggca gatca                                              25

<210> SEQ ID NO 898
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 898
cgacagacgc ctgatctgcc ggataaaggt tt                                      32

<210> SEQ ID NO 899
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 899
gatcaaacct ttatccggca gatca                                              25

<210> SEQ ID NO 900
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 900
cgacagacgc ctgatctgcc gcaaataatc ct                                   32

<210> SEQ ID NO 901
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 901
gatcaggatt atttgcggca gatca                                           25

<210> SEQ ID NO 902
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 902
cgacagacgc ctgatctgcc attgaaacac ct                                   32

<210> SEQ ID NO 903
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 903
gatcaggtgt ttcaatggca gatca                                           25

<210> SEQ ID NO 904
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 904
cgacagacgc ctgatctgcc ataatgacac gt                                   32

<210> SEQ ID NO 905
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 905
gatcacgtgt cattatggca gatca                                           25

<210> SEQ ID NO 906
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 906
cgacagacgc ctgatctgcc aattgacctc tt                                   32

<210> SEQ ID NO 907
```

<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 907
gatcaagagg tcaattggca gatca                                    25

<210> SEQ ID NO 908
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 908
cgacagacgc ctgatctgcc aatatcctcg tt                            32

<210> SEQ ID NO 909
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 909
gatcaacgag gatattggca gatca                                    25

<210> SEQ ID NO 910
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 910
cgacagacgc ctgatctgca ttccaactac gt                            32

<210> SEQ ID NO 911
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 911
gatcacgtag ttggaatgca gatca                                    25

<210> SEQ ID NO 912
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 912
cgacagacgc ctgatctgca ttaccagacg at                            32

<210> SEQ ID NO 913
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 913
gatcatcgtc tggtaatgca gatca                                         25

<210> SEQ ID NO 914
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 914
cgacagacgc ctgatctgca tgatttggct ct                                 32

<210> SEQ ID NO 915
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 915
gatcagagcc aaatcatgca gatca                                         25

<210> SEQ ID NO 916
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 916
cgacagacgc ctgatctgca tatacgccac tt                                 32

<210> SEQ ID NO 917
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 917
gatcaagtgg cgtatatgca gatca                                         25

<210> SEQ ID NO 918
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 918
cgacagacgc ctgatctgca tataccaccg tt                                 32

<210> SEQ ID NO 919
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 919
gatcaacggt ggtatatgca gatca                                         25

<210> SEQ ID NO 920
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 920
cgacagacgc ctgatctgca tacaaggctc at                              32

<210> SEQ ID NO 921
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 921
gatcatgagc cttgtatgca gatca                                      25

<210> SEQ ID NO 922
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 922
cgacagacgc ctgatctgca taaagatgcc gt                              32

<210> SEQ ID NO 923
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 923
gatcacggca tctttatgca gatca                                      25

<210> SEQ ID NO 924
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 924
cgacagacgc ctgatctgca catatcaacc gt                              32

<210> SEQ ID NO 925
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 925
gatcacggtt gatatgtgca gatca                                      25

<210> SEQ ID NO 926
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 926
cgacagacgc ctgatctgca cactttatcc gt                              32
```

<210> SEQ ID NO 927
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 927
gatcacggat aaagtgtgca gatca                                    25

<210> SEQ ID NO 928
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 928
cgacagacgc ctgatctgca atttggtcga gt                            32

<210> SEQ ID NO 929
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 929
gatcactcga ccaaattgca gatca                                    25

<210> SEQ ID NO 930
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 930
cgacagacgc ctgatctgca atacacgtca ct                            32

<210> SEQ ID NO 931
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 931
gatcagtgac gtgtattgca gatca                                    25

<210> SEQ ID NO 932
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 932
cgacagacgc ctgatctgca agttagtcgg at                            32

<210> SEQ ID NO 933
<211> LENGTH: 25
<212> TYPE: DNA
<213> ORGANISM: Artificial Sequence
<220> FEATURE:

```
<223> OTHER INFORMATION: synthetic oligonucleotide

<400> SEQUENCE: 933
gatcatccga ctaacttgca gatca                                           25

<210> SEQ ID NO 934
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 934
cgacagacgc ctgatctgca actcctcatg tt                                   32

<210> SEQ ID NO 935
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 935
gatcaacatg aggagttgca gatca                                           25

<210> SEQ ID NO 936
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 936
cgacagacgc ctgatctgca acattcagac ct                                   32

<210> SEQ ID NO 937
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 937
gatcaggtct gaatgttgca gatca                                           25

<210> SEQ ID NO 938
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 938
cgacagacgc ctgatctgca aatgatccac ct                                   32

<210> SEQ ID NO 939
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 939
gatcaggtgg atcatttgca gatca                                           25
```

```
<210> SEQ ID NO 940
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 940
cgacagacgc ctgatctgca aagcctcact at                                32

<210> SEQ ID NO 941
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 941
gatcatagtg aggctttgca gatca                                        25

<210> SEQ ID NO 942
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 942
cgacagacgc ctgatctgca aactctcaac gt                                32

<210> SEQ ID NO 943
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 943
gatcacgttg agagtttgca gatca                                        25

<210> SEQ ID NO 944
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 944
cgacagacgc ctgatctgca aacctgtcct at                                32

<210> SEQ ID NO 945
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 945
gatcatagga caggtttgca gatca                                        25

<210> SEQ ID NO 946
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 946
cgacagacgc ctgatctgat tggtgcttac gt                                32

<210> SEQ ID NO 947
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 947
gatcacgtaa gcaccaatca gatca                                        25

<210> SEQ ID NO 948
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 948
cgacagacgc ctgatctgat tctgattggc gt                                32

<210> SEQ ID NO 949
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 949
gatcacgcca atcagaatca gatca                                        25

<210> SEQ ID NO 950
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 950
cgacagacgc ctgatctgat tcgcatctcc tt                                32

<210> SEQ ID NO 951
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 951
gatcaaggag atgcgaatca gatca                                        25

<210> SEQ ID NO 952
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 952
cgacagacgc ctgatctgat tatcgttgcc gt                                32

<210> SEQ ID NO 953
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 953
gatcacggca acgataatca gatca                                     25

<210> SEQ ID NO 954
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 954
cgacagacgc ctgatctgat gctaaaccgt gt                             32

<210> SEQ ID NO 955
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 955
gatcacacgg tttagcatca gatca                                     25

<210> SEQ ID NO 956
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 956
cgacagacgc ctgatctgat ctccatcgct tt                             32

<210> SEQ ID NO 957
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 957
gatcaaagcg atggagatca gatca                                     25

<210> SEQ ID NO 958
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 958
cgacagacgc ctgatctgat ctacgccaca at                             32

<210> SEQ ID NO 959
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 959
```
gatcattgtg gcgtagatca gatca                                        25

<210> SEQ ID NO 960
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 960
cgacagacgc ctgatctgat ccttgcacct tt                                32

<210> SEQ ID NO 961
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 961
gatcaaaggt gcaaggatca gatca                                        25

<210> SEQ ID NO 962
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 962
cgacagacgc ctgatctgat atttgctcgc ct                                32

<210> SEQ ID NO 963
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 963
gatcaggcga gcaaatatca gatca                                        25

<210> SEQ ID NO 964
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 964
cgacagacgc ctgatctgat atttgcgcct gt                                32

<210> SEQ ID NO 965
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 965
gatcacaggc gcaaatatca gatca                                        25

<210> SEQ ID NO 966
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 966
cgacagacgc ctgatctgat agtgctttgc gt                                    32

<210> SEQ ID NO 967
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 967
gatcacgcaa agcactatca gatca                                            25

<210> SEQ ID NO 968
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 968
cgacagacgc ctgatctgat aatgccgtgt gt                                    32

<210> SEQ ID NO 969
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 969
gatcacacac ggcattatca gatca                                            25

<210> SEQ ID NO 970
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 970
cgacagacgc ctgatctgat aatcaccgcc at                                    32

<210> SEQ ID NO 971
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 971
gatcatggcg gtgattatca gatca                                            25

<210> SEQ ID NO 972
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 972
cgacagacgc ctgatctgat aagtcgtggc at                                    32
```

<210> SEQ ID NO 973
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 973
gatcatgcca cgacttatca gatca                                         25

<210> SEQ ID NO 974
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 974
cgacagacgc ctgatctgat aactgtggcg at                                 32

<210> SEQ ID NO 975
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 975
gatcatcgcc acagttatca gatca                                         25

<210> SEQ ID NO 976
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 976
cgacagacgc ctgatctgag ttgaaatgcc gt                                 32

<210> SEQ ID NO 977
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 977
gatcacggca tttcaactca gatca                                         25

<210> SEQ ID NO 978
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 978
cgacagacgc ctgatctgag tcaaactccg tt                                 32

<210> SEQ ID NO 979
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 979
gatcaacgga gtttgactca gatca                                              25

<210> SEQ ID NO 980
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 980
cgacagacgc ctgatctgag taatccgcac at                                      32

<210> SEQ ID NO 981
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 981
gatcatgtgc ggattactca gatca                                              25

<210> SEQ ID NO 982
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 982
cgacagacgc ctgatctgag gtttgttcac gt                                      32

<210> SEQ ID NO 983
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 983
gatcacgtga acaaacctca gatca                                              25

<210> SEQ ID NO 984
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 984
cgacagacgc ctgatctgag gccattgttt gt                                      32

<210> SEQ ID NO 985
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 985
gatcacaaac aatggcctca gatca                                              25

<210> SEQ ID NO 986
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 986
cgacagacgc ctgatctgag gataaacggc tt                                  32

<210> SEQ ID NO 987
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 987
gatcaagccg tttatcctca gatca                                          25

<210> SEQ ID NO 988
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 988
cgacagacgc ctgatctgag cgaaatcatg gt                                  32

<210> SEQ ID NO 989
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 989
gatcaccatg atttcgctca gatca                                          25

<210> SEQ ID NO 990
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 990
cgacagacgc ctgatctgag cctccacaat tt                                  32

<210> SEQ ID NO 991
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 991
gatcaaattg tggaggctca gatca                                          25

<210> SEQ ID NO 992
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 992
```
cgacagacgc ctgatctgag atacaaccgc tt 32

<210> SEQ ID NO 993
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 993
gatcaagcgg ttgtatctca gatca 25

<210> SEQ ID NO 994
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 994
cgacagacgc ctgatctgag ataacgctcg at 32

<210> SEQ ID NO 995
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 995
gatcatcgag cgttatctca gatca 25

<210> SEQ ID NO 996
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 996
cgacagacgc ctgatctgag acttatgcgg tt 32

<210> SEQ ID NO 997
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 997
gatcaaccgc ataagtctca gatca 25

<210> SEQ ID NO 998
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 998
cgacagacgc ctgatctgag accacacact tt 32

<210> SEQ ID NO 999
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 999
gatcaaagtg tgtggtctca gatca                                              25

<210> SEQ ID NO 1000
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1000
cgacagacgc ctgatctgag aatgctacgg tt                                      32

<210> SEQ ID NO 1001
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1001
gatcaaccgt agcattctca gatca                                              25

<210> SEQ ID NO 1002
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1002
cgacagacgc ctgatctgag aaccttgagc at                                      32

<210> SEQ ID NO 1003
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1003
gatcatgctc aaggttctca gatca                                              25

<210> SEQ ID NO 1004
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1004
cgacagacgc ctgatctgac tttgacggtt gt                                      32

<210> SEQ ID NO 1005
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1005
gatcacaacc gtcaaagtca gatca                                              25
```

<210> SEQ ID NO 1006
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1006
cgacagacgc ctgatctgac ttggatggct tt        32

<210> SEQ ID NO 1007
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1007
gatcaaagcc atccaagtca gatca        25

<210> SEQ ID NO 1008
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1008
cgacagacgc ctgatctgac ttccaaaccg at        32

<210> SEQ ID NO 1009
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1009
gatcatcggt ttggaagtca gatca        25

<210> SEQ ID NO 1010
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1010
cgacagacgc ctgatctgac taactgcacc at        32

<210> SEQ ID NO 1011
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1011
gatcatggtg cagttagtca gatca        25

<210> SEQ ID NO 1012
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1012
cgacagacgc ctgatctgac gtttcctcca tt                                32

<210> SEQ ID NO 1013
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1013
gatcaatgga ggaaacgtca gatca                                        25

<210> SEQ ID NO 1014
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1014
cgacagacgc ctgatctgac cattcttccg at                                32

<210> SEQ ID NO 1015
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1015
gatcatcgga agaatggtca gatca                                        25

<210> SEQ ID NO 1016
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1016
cgacagacgc ctgatctgac caactaaccg tt                                32

<210> SEQ ID NO 1017
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1017
gatcaacggt tagttggtca gatca                                        25

<210> SEQ ID NO 1018
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1018
cgacagacgc ctgatctgac atgctttacg gt                                32

```
<210> SEQ ID NO 1019
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1019
gatcaccgta aagcatgtca gatca                                          25

<210> SEQ ID NO 1020
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1020
cgacagacgc ctgatctgac aatggagacg tt                                  32

<210> SEQ ID NO 1021
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1021
gatcaacgtc tccattgtca gatca                                          25

<210> SEQ ID NO 1022
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1022
cgacagacgc ctgatctgaa tttgtccagc gt                                  32

<210> SEQ ID NO 1023
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1023
gatcacgctg gacaaattca gatca                                          25

<210> SEQ ID NO 1024
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1024
cgacagacgc ctgatctgaa tttgagcgga ct                                  32

<210> SEQ ID NO 1025
<211> LENGTH: 25
<212> TYPE: DNA
<213> ORGANISM: Artificial Sequence
<220> FEATURE:
<223> OTHER INFORMATION: synthetic oligonucleotide
```

<400> SEQUENCE: 1025
gatcagtccg ctcaaattca gatca                                          25

<210> SEQ ID NO 1026
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1026
cgacagacgc ctgatctgaa tttcagagcg gt                                  32

<210> SEQ ID NO 1027
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1027
gatcaccgct ctgaaattca gatca                                          25

<210> SEQ ID NO 1028
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1028
cgacagacgc ctgatctgaa tgtctctcgc tt                                  32

<210> SEQ ID NO 1029
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1029
gatcaagcga gagacattca gatca                                          25

<210> SEQ ID NO 1030
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1030
cgacagacgc ctgatctgaa tggtcttggc tt                                  32

<210> SEQ ID NO 1031
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1031
gatcaagcca agaccattca gatca                                          25

<210> SEQ ID NO 1032
<211> LENGTH: 32

```
<212> TYPE: DNA
<213> ORGANISM: Artificial Sequence
<220> FEATURE:
<223> OTHER INFORMATION: synthetic oligonucleotide

<400> SEQUENCE: 1032
cgacagacgc ctgatctgaa tgcctcttcc at                           32

<210> SEQ ID NO 1033
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1033
gatcatggaa gaggcattca gatca                                   25

<210> SEQ ID NO 1034
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1034
cgacagacgc ctgatctgaa tgattgccga gt                           32

<210> SEQ ID NO 1035
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1035
gatcactcgg caatcattca gatca                                   25

<210> SEQ ID NO 1036
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1036
cgacagacgc ctgatctgaa tgaactgagc gt                           32

<210> SEQ ID NO 1037
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1037
gatcacgctc agttcattca gatca                                   25

<210> SEQ ID NO 1038
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1038
```
cgacagacgc ctgatctgaa tcgagaagcc tt                32

<210> SEQ ID NO 1039
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1039
gatcaaggct tctcgattca gatca                       25

<210> SEQ ID NO 1040
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1040
cgacagacgc ctgatctgaa tcctcaccga at                32

<210> SEQ ID NO 1041
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1041
gatcattcgg tgaggattca gatca                       25

<210> SEQ ID NO 1042
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1042
cgacagacgc ctgatctgaa tcatttggcg gt                32

<210> SEQ ID NO 1043
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1043
gatcaccgcc aaatgattca gatca                       25

<210> SEQ ID NO 1044
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1044
cgacagacgc ctgatctgaa tatgcctcgg tt                32

<210> SEQ ID NO 1045
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 1045
gatcaaccga ggcatattca gatca                                              25

<210> SEQ ID NO 1046
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1046
cgacagacgc ctgatctgaa gttgttgacc gt                                      32

<210> SEQ ID NO 1047
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1047
gatcacggtc aacaacttca gatca                                              25

<210> SEQ ID NO 1048
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1048
cgacagacgc ctgatctgaa gttcgcaaga gt                                      32

<210> SEQ ID NO 1049
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1049
gatcactctt gcgaacttca gatca                                              25

<210> SEQ ID NO 1050
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1050
cgacagacgc ctgatctgaa gttatggcac gt                                      32

<210> SEQ ID NO 1051
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1051
gatcacgtgc cataacttca gatca                                              25
```

<210> SEQ ID NO 1052
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1052
cgacagacgc ctgatctgaa ggcaattcga gt    32

<210> SEQ ID NO 1053
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1053
gatcactcga attgccttca gatca    25

<210> SEQ ID NO 1054
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1054
cgacagacgc ctgatctgaa gactcgttgg at    32

<210> SEQ ID NO 1055
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1055
gatcatccaa cgagtcttca gatca    25

<210> SEQ ID NO 1056
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1056
cgacagacgc ctgatctgaa gacacttccg at    32

<210> SEQ ID NO 1057
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1057
gatcatcgga agtgtcttca gatca    25

<210> SEQ ID NO 1058
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 1058
cgacagacgc ctgatctgaa ctctttcacg ct                                32

<210> SEQ ID NO 1059
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1059
gatcagcgtg aaagagttca gatca                                        25

<210> SEQ ID NO 1060
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1060
cgacagacgc ctgatctgaa cgtactcacc at                                32

<210> SEQ ID NO 1061
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1061
gatcatggtg agtacgttca gatca                                        25

<210> SEQ ID NO 1062
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1062
cgacagacgc ctgatctgaa ccttgcttcc tt                                32

<210> SEQ ID NO 1063
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1063
gatcaaggaa gcaaggttca gatca                                        25

<210> SEQ ID NO 1064
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1064
cgacagacgc ctgatctgaa attcgtgctg gt                                32

<210> SEQ ID NO 1065
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1065
gatcaccagc acgaatttca gatca                                          25

<210> SEQ ID NO 1066
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1066
cgacagacgc ctgatctgaa attcctcgcc tt                                  32

<210> SEQ ID NO 1067
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1067
gatcaaggcg aggaatttca gatca                                          25

<210> SEQ ID NO 1068
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1068
cgacagacgc ctgatctgaa atgcttggac gt                                  32

<210> SEQ ID NO 1069
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1069
gatcacgtcc aagcatttca gatca                                          25

<210> SEQ ID NO 1070
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1070
cgacagacgc ctgatctgaa agtccaccga tt                                  32

<210> SEQ ID NO 1071
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1071
```
gatcaatcgg tggactttca gatca        25

<210> SEQ ID NO 1072
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1072
cgacagacgc ctgatctgaa actctgcaac ct        32

<210> SEQ ID NO 1073
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1073
gatcaggttg cagagtttca gatca        25

<210> SEQ ID NO 1074
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1074
cgacagacgc ctgatctgaa acggatggct at        32

<210> SEQ ID NO 1075
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1075
gatcatagcc atccgtttca gatca        25

<210> SEQ ID NO 1076
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1076
cgacagacgc ctgatctgaa accattccac gt        32

<210> SEQ ID NO 1077
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1077
gatcacgtgg aatggtttca gatca        25

<210> SEQ ID NO 1078
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 1078
cgacagacgc ctgatctctt tgacggagtg tt                              32

<210> SEQ ID NO 1079
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1079
gatcaacact ccgtcaaaga gatca                                      25

<210> SEQ ID NO 1080
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1080
cgacagacgc ctgatctctt tgaaggcagg at                              32

<210> SEQ ID NO 1081
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1081
gatcatcctg ccttcaaaga gatca                                      25

<210> SEQ ID NO 1082
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1082
cgacagacgc ctgatctctt tcctaagccg tt                              32

<210> SEQ ID NO 1083
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1083
gatcaacggc ttaggaaaga gatca                                      25

<210> SEQ ID NO 1084
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1084
cgacagacgc ctgatctctt gtgaggcgta tt                              32
```

<210> SEQ ID NO 1085
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1085
gatcaatacg cctcacaaga gatca                              25

<210> SEQ ID NO 1086
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1086
cgacagacgc ctgatctctt gccaacagaa ct                      32

<210> SEQ ID NO 1087
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1087
gatcagttct gttggcaaga gatca                              25

<210> SEQ ID NO 1088
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1088
cgacagacgc ctgatctctt gatatggcgg tt                      32

<210> SEQ ID NO 1089
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1089
gatcaaccgc catatcaaga gatca                              25

<210> SEQ ID NO 1090
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1090
cgacagacgc ctgatctctt gaggttagcg at                      32

<210> SEQ ID NO 1091
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 1091
gatcatcgct aacctcaaga gatca                                    25

<210> SEQ ID NO 1092
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1092
cgacagacgc ctgatctctt gaacacagca ct                            32

<210> SEQ ID NO 1093
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1093
gatcagtgct gtgttcaaga gatca                                    25

<210> SEQ ID NO 1094
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1094
cgacagacgc ctgatctctt cttgaatcgc ct                            32

<210> SEQ ID NO 1095
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1095
gatcaggcga ttcaagaaga gatca                                    25

<210> SEQ ID NO 1096
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1096
cgacagacgc ctgatctctt cgcaatgaac ct                            32

<210> SEQ ID NO 1097
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1097
gatcaggttc attgcgaaga gatca                                    25

```
<210> SEQ ID NO 1098
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1098
cgacagacgc ctgatctctt ccaagaatcg ct                           32

<210> SEQ ID NO 1099
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1099
gatcagcgat tcttggaaga gatca                                   25

<210> SEQ ID NO 1100
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1100
cgacagacgc ctgatctctt caacaagacg ct                           32

<210> SEQ ID NO 1101
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1101
gatcagcgtc ttgttgaaga gatca                                   25

<210> SEQ ID NO 1102
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1102
cgacagacgc ctgatctctt agaggcgaac at                           32

<210> SEQ ID NO 1103
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1103
gatcatgttc gcctctaaga gatca                                   25

<210> SEQ ID NO 1104
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 1104
cgacagacgc ctgatctctt acatgaggcg tt                              32

<210> SEQ ID NO 1105
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1105
gatcaacgcc tcatgtaaga gatca                                      25

<210> SEQ ID NO 1106
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1106
cgacagacgc ctgatctctt acagcaaagg ct                              32

<210> SEQ ID NO 1107
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1107
gatcagcctt tgctgtaaga gatca                                      25

<210> SEQ ID NO 1108
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1108
cgacagacgc ctgatctctt aaggtggctg tt                              32

<210> SEQ ID NO 1109
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1109
gatcaacagc caccttaaga gatca                                      25

<210> SEQ ID NO 1110
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1110
cgacagacgc ctgatctctt aaagcggatg ct                              32

<210> SEQ ID NO 1111
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 1111
gatcagcatc cgctttaaga gatca                                               25

<210> SEQ ID NO 1112
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1112
cgacagacgc ctgatctctg tttaagtggc gt                                       32

<210> SEQ ID NO 1113
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1113
gatcacgcca cttaaacaga gatca                                               25

<210> SEQ ID NO 1114
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1114
cgacagacgc ctgatctctg ttgtgaagtg ct                                       32

<210> SEQ ID NO 1115
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1115
gatcagcact tcacaacaga gatca                                               25

<210> SEQ ID NO 1116
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1116
cgacagacgc ctgatctctg taaacaacgc ct                                       32

<210> SEQ ID NO 1117
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1117
```
gatcaggcgt tgtttacaga gatca                                         25

<210> SEQ ID NO 1118
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1118
cgacagacgc ctgatctctg gtaaagtggc tt                                 32

<210> SEQ ID NO 1119
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1119
gatcaagcca ctttaccaga gatca                                         25

<210> SEQ ID NO 1120
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1120
cgacagacgc ctgatctctg gatcaaacgg tt                                 32

<210> SEQ ID NO 1121
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1121
gatcaaccgt ttgatccaga gatca                                         25

<210> SEQ ID NO 1122
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1122
cgacagacgc ctgatctctg ctaagaaccg tt                                 32

<210> SEQ ID NO 1123
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1123
gatcaacggt tcttagcaga gatca                                         25

<210> SEQ ID NO 1124
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 1124
cgacagacgc ctgatctctg cataacgagg tt                              32

<210> SEQ ID NO 1125
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1125
gatcaacctc gttatgcaga gatca                                      25

<210> SEQ ID NO 1126
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1126
cgacagacgc ctgatctctg cagaaaggag tt                              32

<210> SEQ ID NO 1127
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1127
gatcaactcc tttctgcaga gatca                                      25

<210> SEQ ID NO 1128
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1128
cgacagacgc ctgatctctg acaggtggaa at                              32

<210> SEQ ID NO 1129
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1129
gatcatttcc acctgtcaga gatca                                      25

<210> SEQ ID NO 1130
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1130
cgacagacgc ctgatctctg aataaggcgg at                              32
```

<210> SEQ ID NO 1131
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1131
gatcatccgc cttattcaga gatca    25

<210> SEQ ID NO 1132
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1132
cgacagacgc ctgatctctg aacttggtgg tt    32

<210> SEQ ID NO 1133
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1133
gatcaaccac caagttcaga gatca    25

<210> SEQ ID NO 1134
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1134
cgacagacgc ctgatctctg aaccgcctaa at    32

<210> SEQ ID NO 1135
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1135
gatcatttag gcggttcaga gatca    25

<210> SEQ ID NO 1136
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1136
cgacagacgc ctgatctctg aaataccgcc tt    32

<210> SEQ ID NO 1137
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1137
gatcaaggcg gtatttcaga gatca                                    25

<210> SEQ ID NO 1138
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1138
cgacagacgc ctgatctctc tccgaaactg tt                            32

<210> SEQ ID NO 1139
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1139
gatcaacagt ttcggagaga gatca                                    25

<210> SEQ ID NO 1140
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1140
cgacagacgc ctgatctctc gttgtaatgc ct                            32

<210> SEQ ID NO 1141
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1141
gatcaggcat tacaacgaga gatca                                    25

<210> SEQ ID NO 1142
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1142
cgacagacgc ctgatctctc gacaaagagg tt                            32

<210> SEQ ID NO 1143
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1143
gatcaacctc tttgtcgaga gatca                                    25

<210> SEQ ID NO 1144

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1144
cgacagacgc ctgatctctc gaatcaagcc tt                              32

<210> SEQ ID NO 1145
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1145
gatcaaggct tgattcgaga gatca                                      25

<210> SEQ ID NO 1146
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1146
cgacagacgc ctgatctctc cggaaacact tt                              32

<210> SEQ ID NO 1147
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1147
gatcaaagtg tttccggaga gatca                                      25

<210> SEQ ID NO 1148
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1148
cgacagacgc ctgatctctc caaacgagct at                              32

<210> SEQ ID NO 1149
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1149
gatcatagct cgtttggaga gatca                                      25

<210> SEQ ID NO 1150
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1150
```

-continued cgacagacgc ctgatctctc atttgtacgg ct                                             32

<210> SEQ ID NO 1151
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1151
gatcagccgt acaaatgaga gatca                                                     25

<210> SEQ ID NO 1152
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1152
cgacagacgc ctgatctctc atcatttcgg ct                                             32

<210> SEQ ID NO 1153
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1153
gatcagccga aatgatgaga gatca                                                     25

<210> SEQ ID NO 1154
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1154
cgacagacgc ctgatctctc agaatgccac at                                             32

<210> SEQ ID NO 1155
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1155
gatcatgtgg cattctgaga gatca                                                     25

<210> SEQ ID NO 1156
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1156
cgacagacgc ctgatctctc aatcaggcac at                                             32

<210> SEQ ID NO 1157
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 1157
gatcatgtgc ctgattgaga gatca                                          25

<210> SEQ ID NO 1158
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1158
cgacagacgc ctgatctctc aacggtcttc tt                                  32

<210> SEQ ID NO 1159
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1159
gatcaagaag accgttgaga gatca                                          25

<210> SEQ ID NO 1160
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1160
cgacagacgc ctgatctcta ttgccacgac tt                                  32

<210> SEQ ID NO 1161
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1161
gatcaagtcg tggcaataga gatca                                          25

<210> SEQ ID NO 1162
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1162
cgacagacgc ctgatctcta tgtttcacgg ct                                  32

<210> SEQ ID NO 1163
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1163
gatcagccgt gaaacataga gatca                                          25
```

<210> SEQ ID NO 1164
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1164
cgacagacgc ctgatctcta tcttggtgcg at        32

<210> SEQ ID NO 1165
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1165
gatcatcgca ccaagataga gatca        25

<210> SEQ ID NO 1166
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1166
cgacagacgc ctgatctcta gttggtgcag tt        32

<210> SEQ ID NO 1167
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1167
gatcaactgc accaactaga gatca        25

<210> SEQ ID NO 1168
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1168
cgacagacgc ctgatctcta gtggcaaggt tt        32

<210> SEQ ID NO 1169
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1169
gatcaaacct tgccactaga gatca        25

<210> SEQ ID NO 1170
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1170
cgacagacgc ctgatctcta ggtaaacggc at                       32

<210> SEQ ID NO 1171
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1171
gatcatgccg tttacctaga gatca                               25

<210> SEQ ID NO 1172
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1172
cgacagacgc ctgatctcta gagtgtgcgt tt                       32

<210> SEQ ID NO 1173
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1173
gatcaaacgc acactctaga gatca                               25

<210> SEQ ID NO 1174
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1174
cgacagacgc ctgatctcta ctgcgaaaca ct                       32

<210> SEQ ID NO 1175
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1175
gatcagtgtt tcgcagtaga gatca                               25

<210> SEQ ID NO 1176
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1176
cgacagacgc ctgatctcta atcacggcaa ct                       32

```
<210> SEQ ID NO 1177
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1177
gatcagttgc cgtgattaga gatca                                              25

<210> SEQ ID NO 1178
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1178
cgacagacgc ctgatctcta agttgcgagg at                                      32

<210> SEQ ID NO 1179
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1179
gatcatcctc gcaacttaga gatca                                              25

<210> SEQ ID NO 1180
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1180
cgacagacgc ctgatctcta agtgctggtg tt                                      32

<210> SEQ ID NO 1181
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1181
gatcaacacc agcacttaga gatca                                              25

<210> SEQ ID NO 1182
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1182
cgacagacgc ctgatctcta aggaactgcg at                                      32

<210> SEQ ID NO 1183
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 1183
gatcatcgca gttccttaga gatca                                              25

<210> SEQ ID NO 1184
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1184
cgacagacgc ctgatctcta aatgtccacg ct                                      32

<210> SEQ ID NO 1185
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1185
gatcagcgtg gacatttaga gatca                                              25

<210> SEQ ID NO 1186
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1186
cgacagacgc ctgatctcta aatcgccaac gt                                      32

<210> SEQ ID NO 1187
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1187
gatcacgttg gcgatttaga gatca                                              25

<210> SEQ ID NO 1188
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1188
cgacagacgc ctgatctcta aatacgtgcg gt                                      32

<210> SEQ ID NO 1189
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1189
gatcaccgca cgtatttaga gatca                                              25

<210> SEQ ID NO 1190
<211> LENGTH: 32
```

<212> TYPE: DNA
<213> ORGANISM: Artificial Sequence
<220> FEATURE:
<223> OTHER INFORMATION: synthetic oligonucleotide

<400> SEQUENCE: 1190
cgacagacgc ctgatctcta aaggcgatgg tt                          32

<210> SEQ ID NO 1191
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1191
gatcaaccat cgcctttaga gatca                                  25

<210> SEQ ID NO 1192
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1192
cgacagacgc ctgatctcgt ttggaatggt ct                          32

<210> SEQ ID NO 1193
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1193
gatcagacca ttccaaacga gatca                                  25

<210> SEQ ID NO 1194
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1194
cgacagacgc ctgatctcgt ttctcacagg tt                          32

<210> SEQ ID NO 1195
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1195
gatcaacctg tgagaaacga gatca                                  25

<210> SEQ ID NO 1196
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1196
cgacagacgc ctgatctcgt ttcgaggtag tt                                    32

<210> SEQ ID NO 1197
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1197
gatcaactac ctcgaaacga gatca                                            25

<210> SEQ ID NO 1198
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1198
cgacagacgc ctgatctcgt ttacgatgtg gt                                    32

<210> SEQ ID NO 1199
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1199
gatcaccaca tcgtaaacga gatca                                            25

<210> SEQ ID NO 1200
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1200
cgacagacgc ctgatctcgt tgtgtgaagt ct                                    32

<210> SEQ ID NO 1201
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1201
gatcagactt cacacaacga gatca                                            25

<210> SEQ ID NO 1202
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1202
cgacagacgc ctgatctcgt tggtaattcg gt                                    32

<210> SEQ ID NO 1203
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 1203
gatcaccgaa ttaccaacga gatca                                          25

<210> SEQ ID NO 1204
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1204
cgacagacgc ctgatctcgt tggaatctgg tt                                  32

<210> SEQ ID NO 1205
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1205
gatcaaccag attccaacga gatca                                          25

<210> SEQ ID NO 1206
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1206
cgacagacgc ctgatctcgt tggaagacag at                                  32

<210> SEQ ID NO 1207
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1207
gatcatctgt cttccaacga gatca                                          25

<210> SEQ ID NO 1208
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1208
cgacagacgc ctgatctcgt tcgttaggtg at                                  32

<210> SEQ ID NO 1209
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1209
gatcatcacc taacgaacga gatca                                          25
```

```
<210> SEQ ID NO 1210
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1210
cgacagacgc ctgatctcgt tcctcaacag at                              32

<210> SEQ ID NO 1211
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1211
gatcatctgt tgaggaacga gatca                                      25

<210> SEQ ID NO 1212
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1212
cgacagacgc ctgatctcgt tcatttccga gt                              32

<210> SEQ ID NO 1213
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1213
gatcactcgg aaatgaacga gatca                                      25

<210> SEQ ID NO 1214
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1214
cgacagacgc ctgatctcgt tcaactactg ct                              32

<210> SEQ ID NO 1215
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1215
gatcagcagt agttgaacga gatca                                      25

<210> SEQ ID NO 1216
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 1216
cgacagacgc ctgatctcgt tatggatgtg ct                                    32

<210> SEQ ID NO 1217
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1217
gatcagcaca tccataacga gatca                                            25

<210> SEQ ID NO 1218
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1218
cgacagacgc ctgatctcgt taagtctcgg tt                                    32

<210> SEQ ID NO 1219
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1219
gatcaaccga gacttaacga gatca                                            25

<210> SEQ ID NO 1220
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1220
cgacagacgc ctgatctcgt gtttaggtcg at                                    32

<210> SEQ ID NO 1221
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1221
gatcatcgac ctaaacacga gatca                                            25

<210> SEQ ID NO 1222
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1222
cgacagacgc ctgatctcgt ggcaataaag gt                                    32

<210> SEQ ID NO 1223
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1223
gatcaccttt attgccacga gatca                                    25

<210> SEQ ID NO 1224
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1224
cgacagacgc ctgatctcgt ggaaacagga tt                            32

<210> SEQ ID NO 1225
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1225
gatcaatcct gtttccacga gatca                                    25

<210> SEQ ID NO 1226
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1226
cgacagacgc ctgatctcgt gacatttggt gt                            32

<210> SEQ ID NO 1227
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1227
gatcacacca aatgtcacga gatca                                    25

<210> SEQ ID NO 1228
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1228
cgacagacgc ctgatctcgt atatcgcacc tt                            32

<210> SEQ ID NO 1229
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1229
```

-continued gatcaaggtg cgatatacga gatca 25

<210> SEQ ID NO 1230
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1230
cgacagacgc ctgatctcgt ataaggtcgc at 32

<210> SEQ ID NO 1231
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1231
gatcatgcga ccttatacga gatca 25

<210> SEQ ID NO 1232
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1232
cgacagacgc ctgatctcgt agtaaagcgg at 32

<210> SEQ ID NO 1233
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1233
gatcatccgc tttactacga gatca 25

<210> SEQ ID NO 1234
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1234
cgacagacgc ctgatctcgt aatgacgaag ct 32

<210> SEQ ID NO 1235
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1235
gatcagcttc gtcattacga gatca 25

<210> SEQ ID NO 1236
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 1236
cgacagacgc ctgatctcgt aacataacgg ct                                    32

<210> SEQ ID NO 1237
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1237
gatcagccgt tatgttacga gatca                                            25

<210> SEQ ID NO 1238
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1238
cgacagacgc ctgatctcgt aacaagcact ct                                    32

<210> SEQ ID NO 1239
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1239
gatcagagtg cttgttacga gatca                                            25

<210> SEQ ID NO 1240
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1240
cgacagacgc ctgatctcgt aaatgcggaa gt                                    32

<210> SEQ ID NO 1241
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1241
gatcacttcc gcatttacga gatca                                            25

<210> SEQ ID NO 1242
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1242
cgacagacgc ctgatctcgt aaagtcggag at                                    32
```

<210> SEQ ID NO 1243
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1243
gatcatctcc gactttacga gatca                                              25

<210> SEQ ID NO 1244
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1244
cgacagacgc ctgatctcgt aaacaggagc tt                                      32

<210> SEQ ID NO 1245
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1245
gatcaagctc ctgtttacga gatca                                              25

<210> SEQ ID NO 1246
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1246
cgacagacgc ctgatctcgg ttgtattcgg at                                      32

<210> SEQ ID NO 1247
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1247
gatcatccga atacaaccga gatca                                              25

<210> SEQ ID NO 1248
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1248
cgacagacgc ctgatctcgg ttatttcgag ct                                      32

<210> SEQ ID NO 1249
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 1249
gatcagctcg aaataaccga gatca       25

<210> SEQ ID NO 1250
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1250
cgacagacgc ctgatctcgg tgttaatgtg ct       32

<210> SEQ ID NO 1251
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1251
gatcagcaca ttaacaccga gatca       25

<210> SEQ ID NO 1252
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1252
cgacagacgc ctgatctcgg tatacaaggc at       32

<210> SEQ ID NO 1253
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1253
gatcatgcct tgtataccga gatca       25

<210> SEQ ID NO 1254
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1254
cgacagacgc ctgatctcgg taagtttgtg ct       32

<210> SEQ ID NO 1255
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1255
gatcagcaca aacttaccga gatca       25

-continued

```
<210> SEQ ID NO 1256
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1256
cgacagacgc ctgatctcgg taacaacctg at                                   32

<210> SEQ ID NO 1257
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1257
gatcatcagg ttgttaccga gatca                                           25

<210> SEQ ID NO 1258
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1258
cgacagacgc ctgatctcgg cgaatttatg gt                                   32

<210> SEQ ID NO 1259
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1259
gatcaccata aattcgccga gatca                                           25

<210> SEQ ID NO 1260
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1260
cgacagacgc ctgatctcgg atcacctttg tt                                   32

<210> SEQ ID NO 1261
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1261
gatcaacaaa ggtgatccga gatca                                           25

<210> SEQ ID NO 1262
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 1262
cgacagacgc ctgatctcgg aacacaccta tt                            32

<210> SEQ ID NO 1263
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1263
gatcaatagg tgtgttccga gatca                                    25

<210> SEQ ID NO 1264
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1264
cgacagacgc ctgatctcgc ttatctgtgg at                            32

<210> SEQ ID NO 1265
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1265
gatcatccac agataagcga gatca                                    25

<210> SEQ ID NO 1266
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1266
cgacagacgc ctgatctcgc gatgtttaag gt                            32

<210> SEQ ID NO 1267
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1267 gatcaccttaa aacatcgcga gatca                                   25

<210> SEQ ID NO 1268
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1268
cgacagacgc ctgatctcgc ctttaacctt gt                            32

<210> SEQ ID NO 1269
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 1269
gatcacaagg ttaaaggcga gatca                                               25

<210> SEQ ID NO 1270
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1270
cgacagacgc ctgatctcgc caaagaggta tt                                       32

<210> SEQ ID NO 1271
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1271
gatcaatacc tctttggcga gatca                                               25

<210> SEQ ID NO 1272
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1272
cgacagacgc ctgatctcga tttggttacg gt                                       32

<210> SEQ ID NO 1273
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1273
gatcaccgta accaaatcga gatca                                               25

<210> SEQ ID NO 1274
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1274
cgacagacgc ctgatctcga tctggtttgg at                                       32

<210> SEQ ID NO 1275
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1275
```
gatcatccaa accagatcga gatca                                          25

<210> SEQ ID NO 1276
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1276
cgacagacgc ctgatctcga ggcaaatagg tt                                  32

<210> SEQ ID NO 1277
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1277
gatcaaccta tttgcctcga gatca                                          25

<210> SEQ ID NO 1278
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1278
cgacagacgc ctgatctcga atgtgtgact gt                                  32

<210> SEQ ID NO 1279
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1279
gatcacagtc acacattcga gatca                                          25

<210> SEQ ID NO 1280
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1280
cgacagacgc ctgatctcga acttctggtg at                                  32

<210> SEQ ID NO 1281
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1281
gatcatcacc agaagttcga gatca                                          25

<210> SEQ ID NO 1282
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 1282
cgacagacgc ctgatctcga aatctaggcg at                              32

<210> SEQ ID NO 1283
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1283
gatcatcgcc tagatttcga gatca                                      25

<210> SEQ ID NO 1284
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1284
cgacagacgc ctgatctcga aacagtggag tt                              32

<210> SEQ ID NO 1285
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1285
gatcaactcc actgtttcga gatca                                      25

<210> SEQ ID NO 1286
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1286
cgacagacgc ctgatctcct ttcagtgtcc at                              32

<210> SEQ ID NO 1287
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1287
gatcatggac actgaaagga gatca                                      25

<210> SEQ ID NO 1288
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1288
cgacagacgc ctgatctcct ttaaggagcg at                              32
```

<210> SEQ ID NO 1289
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1289
gatcatcgct ccttaaagga gatca					25

<210> SEQ ID NO 1290
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1290
cgacagacgc ctgatctcct tctattcggc at				32

<210> SEQ ID NO 1291
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1291
gatcatgccg aatagaagga gatca					25

<210> SEQ ID NO 1292
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1292
cgacagacgc ctgatctcct tattccagcg tt				32

<210> SEQ ID NO 1293
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1293
gatcaacgct ggaataagga gatca					25

<210> SEQ ID NO 1294
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1294
cgacagacgc ctgatctcct taactttgcc gt				32

<210> SEQ ID NO 1295
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 1295
gatcacggca aagttaagga gatca                                                25

<210> SEQ ID NO 1296
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1296
cgacagacgc ctgatctcct taaagcggac at                                        32

<210> SEQ ID NO 1297
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1297
gatcatgtcc gctttaagga gatca                                                25

<210> SEQ ID NO 1298
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1298
cgacagacgc ctgatctcct gatttggacg at                                        32

<210> SEQ ID NO 1299
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1299
gatcatcgtc caaatcagga gatca                                                25

<210> SEQ ID NO 1300
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1300
cgacagacgc ctgatctcct gaattgctcc tt                                        32

<210> SEQ ID NO 1301
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1301
gatcaaggag caattcagga gatca                                                25

<210> SEQ ID NO 1302
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1302
cgacagacgc ctgatctcct gaagaatggc at                               32

<210> SEQ ID NO 1303
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1303
gatcatgcca ttcttcagga gatca                                       25

<210> SEQ ID NO 1304
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1304
cgacagacgc ctgatctcct ctttgaagcc tt                               32

<210> SEQ ID NO 1305
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1305
gatcaaggct tcaaagagga gatca                                       25

<210> SEQ ID NO 1306
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1306
cgacagacgc ctgatctcct cgcaaaggtt at                               32

<210> SEQ ID NO 1307
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1307
gatcataacc tttgcgagga gatca                                       25

<210> SEQ ID NO 1308
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1308
```
cgacagacgc ctgatctcct atggaagcga at          32

<210> SEQ ID NO 1309
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1309
gatcattcgc ttccatagga gatca          25

<210> SEQ ID NO 1310
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1310
cgacagacgc ctgatctcct atcaaagcgg tt          32

<210> SEQ ID NO 1311
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1311
gatcaaccgc tttgatagga gatca          25

<210> SEQ ID NO 1312
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1312
cgacagacgc ctgatctcct aattgtcgtg ct          32

<210> SEQ ID NO 1313
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1313
gatcagcacg acaattagga gatca          25

<210> SEQ ID NO 1314
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1314
cgacagacgc ctgatctcct aattcgtgcc tt          32

<210> SEQ ID NO 1315
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 1315
gatcaaggca cgaattagga gatca                                              25

<210> SEQ ID NO 1316
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1316
cgacagacgc ctgatctcct aagattcgcc at                                      32

<210> SEQ ID NO 1317
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1317
gatcatggcg aatcttagga gatca                                              25

<210> SEQ ID NO 1318
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1318
cgacagacgc ctgatctcct aacgaaagcc tt                                      32

<210> SEQ ID NO 1319
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1319
gatcaaggct ttcgttagga gatca                                              25

<210> SEQ ID NO 1320
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1320
cgacagacgc ctgatctccg tgtggaattt gt                                      32

<210> SEQ ID NO 1321
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1321
gatcacaaat tccacacgga gatca                                              25
```

<210> SEQ ID NO 1322
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1322
cgacagacgc ctgatctccg tatttcagcc tt                          32

<210> SEQ ID NO 1323
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1323
gatcaaggct gaaatacgga gatca                                  25

<210> SEQ ID NO 1324
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1324
cgacagacgc ctgatctccg gtaatgtgtg tt                          32

<210> SEQ ID NO 1325
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1325
gatcaacaca cattaccgga gatca                                  25

<210> SEQ ID NO 1326
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1326
cgacagacgc ctgatctccg gcttaaacaa ct                          32

<210> SEQ ID NO 1327
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1327
gatcagttgt ttaagccgga gatca                                  25

<210> SEQ ID NO 1328
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1328
cgacagacgc ctgatctccg gaggaattga at                                    32

<210> SEQ ID NO 1329
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1329
gatcattcaa ttcctccgga gatca                                            25

<210> SEQ ID NO 1330
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1330
cgacagacgc ctgatctccg gaatttggaa ct                                    32

<210> SEQ ID NO 1331
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1331
gatcagttcc aaattccgga gatca                                            25

<210> SEQ ID NO 1332
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1332
cgacagacgc ctgatctccg gaaattgatg ct                                    32

<210> SEQ ID NO 1333
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1333
gatcagcatc aatttccgga gatca                                            25

<210> SEQ ID NO 1334
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1334
cgacagacgc ctgatctccg cggaattaaa gt                                    32

```
<210> SEQ ID NO 1335
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1335 gatcactttta attccgcgga gatca                                          25

<210> SEQ ID NO 1336
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1336
cgacagacgc ctgatctccg atttgtgatg ct                                   32

<210> SEQ ID NO 1337
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1337
gatcagcatc acaaatcgga gatca                                           25

<210> SEQ ID NO 1338
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1338
cgacagacgc ctgatctccg atttaccgtc tt                                   32

<210> SEQ ID NO 1339
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1339
gatcaagacg gtaaatcgga gatca                                           25

<210> SEQ ID NO 1340
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1340
cgacagacgc ctgatctccg attgtgtagg tt                                   32

<210> SEQ ID NO 1341
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 1341
gatcaaccta cacaatcgga gatca                                          25

<210> SEQ ID NO 1342
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1342
cgacagacgc ctgatctcca tttcacggtc tt                                  32

<210> SEQ ID NO 1343
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1343
gatcaagacc gtgaaatgga gatca                                          25

<210> SEQ ID NO 1344
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1344
cgacagacgc ctgatctcca tttaggcagg tt                                  32

<210> SEQ ID NO 1345
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1345
gatcaacctg cctaaatgga gatca                                          25

<210> SEQ ID NO 1346
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1346
cgacagacgc ctgatctcca ttgttagcgt ct                                  32

<210> SEQ ID NO 1347
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1347
gatcagacgc taacaatgga gatca                                          25

<210> SEQ ID NO 1348
<211> LENGTH: 32
```

```
<212> TYPE: DNA
<213> ORGANISM: Artificial Sequence
<220> FEATURE:
<223> OTHER INFORMATION: synthetic oligonucleotide

<400> SEQUENCE: 1348
cgacagacgc ctgatctcca ttgaacgaac ct                                    32

<210> SEQ ID NO 1349
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1349
gatcaggttc gttcaatgga gatca                                            25

<210> SEQ ID NO 1350
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1350
cgacagacgc ctgatctcca ttaggcgaga at                                    32

<210> SEQ ID NO 1351
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1351
gatcattctc gcctaatgga gatca                                            25

<210> SEQ ID NO 1352
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1352
cgacagacgc ctgatctcca tgatgtgaac gt                                    32

<210> SEQ ID NO 1353
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1353
gatcacgttc acatcatgga gatca                                            25

<210> SEQ ID NO 1354
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1354
```
cgacagacgc ctgatctcca tagaatccgc at                                32

<210> SEQ ID NO 1355
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1355
gatcatgcgg attctatgga gatca                                        25

<210> SEQ ID NO 1356
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1356
cgacagacgc ctgatctcca tacttgtcgc tt                                32

<210> SEQ ID NO 1357
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1357
gatcaagcga caagtatgga gatca                                        25

<210> SEQ ID NO 1358
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1358
cgacagacgc ctgatctcca taacgtgtcc at                                32

<210> SEQ ID NO 1359
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1359
gatcatggac acgttatgga gatca                                        25

<210> SEQ ID NO 1360
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1360
cgacagacgc ctgatctcca gttgttcctc at                                32

<210> SEQ ID NO 1361
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 1361
gatcatgagg aacaactgga gatca                                              25

<210> SEQ ID NO 1362
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1362
cgacagacgc ctgatctcca gttatgttcg ct                                      32

<210> SEQ ID NO 1363
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1363
gatcagcgaa cataactgga gatca                                              25

<210> SEQ ID NO 1364
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1364
cgacagacgc ctgatctcca gtgttgagtg tt                                      32

<210> SEQ ID NO 1365
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1365
gatcaacact caacactgga gatca                                              25

<210> SEQ ID NO 1366
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1366
cgacagacgc ctgatctcca ggtgaaagtg at                                      32

<210> SEQ ID NO 1367
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1367
gatcatcact ttcacctgga gatca                                              25
```

<210> SEQ ID NO 1368
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1368
cgacagacgc ctgatctcca gaaggttgtc at                           32

<210> SEQ ID NO 1369
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1369
gatcatgaca accttctgga gatca                                   25

<210> SEQ ID NO 1370
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1370
cgacagacgc ctgatctcca ctggtggaaa tt                           32

<210> SEQ ID NO 1371
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1371
gatcaatttc caccagtgga gatca                                   25

<210> SEQ ID NO 1372
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1372
cgacagacgc ctgatctcca cgttgagaag at                           32

<210> SEQ ID NO 1373
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1373
gatcatcttc tcaacgtgga gatca                                   25

<210> SEQ ID NO 1374
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 1374
cgacagacgc ctgatctcca cattagcgtt ct                                    32

<210> SEQ ID NO 1375
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1375
gatcagaacg ctaatgtgga gatca                                            25

<210> SEQ ID NO 1376
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1376
cgacagacgc ctgatctcca caagttccga tt                                    32

<210> SEQ ID NO 1377
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1377
gatcaatcgg aacttgtgga gatca                                            25

<210> SEQ ID NO 1378
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1378
cgacagacgc ctgatctcca atttagccac gt                                    32

<210> SEQ ID NO 1379
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1379
gatcacgtgg ctaaattgga gatca                                            25

<210> SEQ ID NO 1380
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1380
cgacagacgc ctgatctcca attgcgtctt ct                                    32

<210> SEQ ID NO 1381
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1381
gatcagaaga cgcaattgga gatca                                              25

<210> SEQ ID NO 1382
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1382
cgacagacgc ctgatctcca attacagacg ct                                      32

<210> SEQ ID NO 1383
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1383
gatcagcgtc tgtaattgga gatca                                              25

<210> SEQ ID NO 1384
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1384
cgacagacgc ctgatctcca aggtttggtg at                                      32

<210> SEQ ID NO 1385
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1385
gatcatcacc aaaccttgga gatca                                              25

<210> SEQ ID NO 1386
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1386
cgacagacgc ctgatctcca agagtggtca at                                      32

<210> SEQ ID NO 1387
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1387
```
gatcattgac cactcttgga gatca                                          25

<210> SEQ ID NO 1388
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1388
cgacagacgc ctgatctcca agaatacggc tt                                  32

<210> SEQ ID NO 1389
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1389
gatcaagccg tattcttgga gatca                                          25

<210> SEQ ID NO 1390
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1390
cgacagacgc ctgatctcca acactggaac tt                                  32

<210> SEQ ID NO 1391
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1391
gatcaagttc cagtgttgga gatca                                          25

<210> SEQ ID NO 1392
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1392
cgacagacgc ctgatctcca aactgctgaa ct                                  32

<210> SEQ ID NO 1393
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1393
gatcagttca gcagtttgga gatca                                          25

<210> SEQ ID NO 1394
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 1394
cgacagacgc ctgatctcca aacattagcc gt                              32

<210> SEQ ID NO 1395
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1395
gatcacggct aatgtttgga gatca                                      25

<210> SEQ ID NO 1396
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1396
cgacagacgc ctgatctcat ttgtgcggta gt                              32

<210> SEQ ID NO 1397
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1397
gatcactacc gcacaaatga gatca                                      25

<210> SEQ ID NO 1398
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1398
cgacagacgc ctgatctcat ttgcgacctt ct                              32

<210> SEQ ID NO 1399
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1399
gatcagaagg tcgcaaatga gatca                                      25

<210> SEQ ID NO 1400
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1400
cgacagacgc ctgatctcat ttgatcgtgg ct                              32
```

<210> SEQ ID NO 1401
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1401
gatcagccac gatcaaatga gatca    25

<210> SEQ ID NO 1402
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1402
cgacagacgc ctgatctcat ttcatgcggt ct    32

<210> SEQ ID NO 1403
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1403
gatcagaccg catgaaatga gatca    25

<210> SEQ ID NO 1404
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1404
cgacagacgc ctgatctcat ttactggtgc gt    32

<210> SEQ ID NO 1405
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1405
gatcacgcac cagtaaatga gatca    25

<210> SEQ ID NO 1406
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1406
cgacagacgc ctgatctcat tgttctaccg ct    32

<210> SEQ ID NO 1407
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 1407
gatcagcggt agaacaatga gatca     25

<210> SEQ ID NO 1408
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1408
cgacagacgc ctgatctcat tgtggatgct gt     32

<210> SEQ ID NO 1409
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1409
gatcacagca tccacaatga gatca     25

<210> SEQ ID NO 1410
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1410
cgacagacgc ctgatctcat tggaacggac tt     32

<210> SEQ ID NO 1411
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1411
gatcaagtcc gttccaatga gatca     25

<210> SEQ ID NO 1412
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1412
cgacagacgc ctgatctcat tgaactctcg ct     32

<210> SEQ ID NO 1413
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1413
gatcagcgag agttcaatga gatca     25

```
<210> SEQ ID NO 1414
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1414
cgacagacgc ctgatctcat tctaaggcgg tt                                     32

<210> SEQ ID NO 1415
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1415
gatcaaccgc cttagaatga gatca                                             25

<210> SEQ ID NO 1416
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1416
cgacagacgc ctgatctcat tcgtagttgg ct                                     32

<210> SEQ ID NO 1417
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1417
gatcagccaa ctacgaatga gatca                                             25

<210> SEQ ID NO 1418
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1418
cgacagacgc ctgatctcat tccaatgtcg ct                                     32

<210> SEQ ID NO 1419
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1419
gatcagcgac attggaatga gatca                                             25

<210> SEQ ID NO 1420
<211> LENGTH: 32
<212> TYPE: DNA
<213> ORGANISM: Artificial Sequence
<220> FEATURE:
<223> OTHER INFORMATION: synthetic oligonucleotide
```

<400> SEQUENCE: 1420
cgacagacgc ctgatctcat tatgtcacgc ct                    32

<210> SEQ ID NO 1421
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1421
gatcaggcgt gacataatga gatca                            25

<210> SEQ ID NO 1422
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1422
cgacagacgc ctgatctcat tatggtgcgt ct                    32

<210> SEQ ID NO 1423
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1423
gatcagacgc accataatga gatca                            25

<210> SEQ ID NO 1424
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1424
cgacagacgc ctgatctcat taaccgtccg at                    32

<210> SEQ ID NO 1425
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1425
gatcatcgga cggttaatga gatca                            25

<210> SEQ ID NO 1426
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1426
cgacagacgc ctgatctcat ggtgattgtc gt                    32

<210> SEQ ID NO 1427
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 1427
gatcacgaca atcaccatga gatca                                          25

<210> SEQ ID NO 1428
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1428
cgacagacgc ctgatctcat ggccaaactt ct                                  32

<210> SEQ ID NO 1429
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1429
gatcagaagt ttggccatga gatca                                          25

<210> SEQ ID NO 1430
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1430
cgacagacgc ctgatctcat gacaggtggt tt                                  32

<210> SEQ ID NO 1431
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1431
gatcaaacca cctgtcatga gatca                                          25

<210> SEQ ID NO 1432
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1432
cgacagacgc ctgatctcat ctcaagtccg tt                                  32

<210> SEQ ID NO 1433
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1433
```
gatcaacgga cttgagatga gatca                                               25

<210> SEQ ID NO 1434
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1434
cgacagacgc ctgatctcat cgagaaatgg ct                                       32

<210> SEQ ID NO 1435
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1435
gatcagccat ttctcgatga gatca                                               25

<210> SEQ ID NO 1436
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1436
cgacagacgc ctgatctcat cgaagacacc tt                                       32

<210> SEQ ID NO 1437
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1437
gatcaaggtg tcttcgatga gatca                                               25

<210> SEQ ID NO 1438
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1438
cgacagacgc ctgatctcat agttaccgcc at                                       32

<210> SEQ ID NO 1439
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1439
gatcatggcg gtaactatga gatca                                               25

<210> SEQ ID NO 1440
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 1440
cgacagacgc ctgatctcat agtcgtttgg ct                              32

<210> SEQ ID NO 1441
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1441
gatcagccaa acgactatga gatca                                      25

<210> SEQ ID NO 1442
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1442
cgacagacgc ctgatctcat acttgagcgg at                              32

<210> SEQ ID NO 1443
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1443
gatcatccgc tcaagtatga gatca                                      25

<210> SEQ ID NO 1444
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1444
cgacagacgc ctgatctcat aattcgcgtg gt                              32

<210> SEQ ID NO 1445
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1445
gatcaccacg cgaattatga gatca                                      25

<210> SEQ ID NO 1446
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1446
cgacagacgc ctgatctcag ttgtagttgc gt                              32
```

<210> SEQ ID NO 1447
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1447
gatcacgcaa ctacaactga gatca                                               25

<210> SEQ ID NO 1448
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1448
cgacagacgc ctgatctcag gttcacttcc at                                       32

<210> SEQ ID NO 1449
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1449
gatcatggaa gtgaacctga gatca                                               25

<210> SEQ ID NO 1450
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1450
cgacagacgc ctgatctcag gcgaggttta tt                                       32

<210> SEQ ID NO 1451
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1451
gatcaataaa cctcgcctga gatca                                               25

<210> SEQ ID NO 1452
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1452
cgacagacgc ctgatctcag gaataagcgg tt                                       32

<210> SEQ ID NO 1453
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 1453
gatcaaccgc ttattcctga gatca                                                25

<210> SEQ ID NO 1454
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1454
cgacagacgc ctgatctcag attctttccg ct                                        32

<210> SEQ ID NO 1455
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1455
gatcagcgga aagaatctga gatca                                                25

<210> SEQ ID NO 1456
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1456
cgacagacgc ctgatctcag atcctttgcc at                                        32

<210> SEQ ID NO 1457
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1457
gatcatggca aaggatctga gatca                                                25

<210> SEQ ID NO 1458
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1458
cgacagacgc ctgatctcac tttccgttga ct                                        32

<210> SEQ ID NO 1459
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1459
gatcagtcaa cggaaagtga gatca                                                25

<210> SEQ ID NO 1460
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1460
cgacagacgc ctgatctcac tttaagcacc gt                              32

<210> SEQ ID NO 1461
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1461
gatcacggtg cttaaagtga gatca                                      25

<210> SEQ ID NO 1462
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1462
cgacagacgc ctgatctcac tgttattcgc ct                              32

<210> SEQ ID NO 1463
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1463
gatcaggcga ataacagtga gatca                                      25

<210> SEQ ID NO 1464
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1464
cgacagacgc ctgatctcac tcttgtaacg ct                              32

<210> SEQ ID NO 1465
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1465
gatcagcgtt acaagagtga gatca                                      25

<210> SEQ ID NO 1466
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1466
```
cgacagacgc ctgatctcac tccaaggtca at                32

<210> SEQ ID NO 1467
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1467
gatcattgac cttggagtga gatca                25

<210> SEQ ID NO 1468
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1468
cgacagacgc ctgatctcac tagtttgcgt ct                32

<210> SEQ ID NO 1469
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1469
gatcagacgc aaactagtga gatca                25

<210> SEQ ID NO 1470
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1470
cgacagacgc ctgatctcac taatgaacgg ct                32

<210> SEQ ID NO 1471
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1471
gatcagccgt tcattagtga gatca                25

<210> SEQ ID NO 1472
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1472
cgacagacgc ctgatctcac gttatcttgg ct                32

<210> SEQ ID NO 1473
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 1473
gatcagccaa gataacgtga gatca                                            25

<210> SEQ ID NO 1474
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1474
cgacagacgc ctgatctcac ggagatggtt tt                                    32

<210> SEQ ID NO 1475
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1475
gatcaaaacc atctccgtga gatca                                            25

<210> SEQ ID NO 1476
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1476
cgacagacgc ctgatctcac ggaagagatg tt                                    32

<210> SEQ ID NO 1477
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1477
gatcaacatc tcttccgtga gatca                                            25

<210> SEQ ID NO 1478
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1478
cgacagacgc ctgatctcac gatttagcac ct                                    32

<210> SEQ ID NO 1479
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1479
gatcaggtgc taaatcgtga gatca                                            25
```

<210> SEQ ID NO 1480
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1480
cgacagacgc ctgatctcac gatagtttgc ct                                     32

<210> SEQ ID NO 1481
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1481
gatcaggcaa actatcgtga gatca                                             25

<210> SEQ ID NO 1482
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1482
cgacagacgc ctgatctcac cttattgcac gt                                     32

<210> SEQ ID NO 1483
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1483
gatcacgtgc aataaggtga gatca                                             25

<210> SEQ ID NO 1484
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1484
cgacagacgc ctgatctcac ctccggttaa at                                     32

<210> SEQ ID NO 1485
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1485
gatcatttaa ccggaggtga gatca                                             25

<210> SEQ ID NO 1486
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1486
cgacagacgc ctgatctcac ctatgcgaaa ct                          32

<210> SEQ ID NO 1487
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1487
gatcagtttc gcataggtga gatca                                  25

<210> SEQ ID NO 1488
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1488
cgacagacgc ctgatctcac attggcagaa ct                          32

<210> SEQ ID NO 1489
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1489
gatcagttct gccaatgtga gatca                                  25

<210> SEQ ID NO 1490
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1490
cgacagacgc ctgatctcac ataggagcgt tt                          32

<210> SEQ ID NO 1491
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1491
gatcaaacgc tcctatgtga gatca                                  25

<210> SEQ ID NO 1492
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1492
cgacagacgc ctgatctcac aatgttgcct ct                          32

```
<210> SEQ ID NO 1493
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1493
gatcagaggc aacattgtga gatca                                          25

<210> SEQ ID NO 1494
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1494
cgacagacgc ctgatctcac aatatgtccg ct                                  32

<210> SEQ ID NO 1495
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1495
gatcagcgga catattgtga gatca                                          25

<210> SEQ ID NO 1496
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1496
cgacagacgc ctgatctcaa ttcgagcaac ct                                  32

<210> SEQ ID NO 1497
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1497
gatcaggttg ctcgaattga gatca                                          25

<210> SEQ ID NO 1498
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1498
cgacagacgc ctgatctcaa tgttgctgag gt                                  32

<210> SEQ ID NO 1499
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 1499
gatcacctca gcaacattga gatca                                          25

<210> SEQ ID NO 1500
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1500
cgacagacgc ctgatctcaa tggatgacgg at                                  32

<210> SEQ ID NO 1501
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1501
gatcatccgt catccattga gatca                                          25

<210> SEQ ID NO 1502
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1502
cgacagacgc ctgatctcaa tcttcgttgg ct                                  32

<210> SEQ ID NO 1503
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1503
gatcagccaa cgaagattga gatca                                          25

<210> SEQ ID NO 1504
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1504
cgacagacgc ctgatctcaa tcctttctgc gt                                  32

<210> SEQ ID NO 1505
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1505
gatcacgcag aaaggattga gatca                                          25

<210> SEQ ID NO 1506
<211> LENGTH: 32
```

```
<212> TYPE: DNA
<213> ORGANISM: Artificial Sequence
<220> FEATURE:
<223> OTHER INFORMATION: synthetic oligonucleotide

<400> SEQUENCE: 1506
cgacagacgc ctgatctcaa gtttgagtgg ct                               32

<210> SEQ ID NO 1507
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1507
gatcagccac tcaaacttga gatca                                       25

<210> SEQ ID NO 1508
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1508
cgacagacgc ctgatctcaa gtagtcggtg tt                               32

<210> SEQ ID NO 1509
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1509
gatcaacacc gactacttga gatca                                       25

<210> SEQ ID NO 1510
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1510
cgacagacgc ctgatctcaa gccttggaaa ct                               32

<210> SEQ ID NO 1511
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1511
gatcagtttc caaggcttga gatca                                       25

<210> SEQ ID NO 1512
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1512
```

```
cgacagacgc ctgatctcaa gcatgtgagg at                              32

<210> SEQ ID NO 1513
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1513
gatcatcctc acatgcttga gatca                                     25

<210> SEQ ID NO 1514
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1514
cgacagacgc ctgatctcaa gattccgtcc at                              32

<210> SEQ ID NO 1515
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1515
gatcatggac ggaatcttga gatca                                     25

<210> SEQ ID NO 1516
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1516
cgacagacgc ctgatctcaa gaattggagc gt                              32

<210> SEQ ID NO 1517
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1517
gatcacgctc caattcttga gatca                                     25

<210> SEQ ID NO 1518
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1518
cgacagacgc ctgatctcaa gaagtgtgtg ct                              32

<210> SEQ ID NO 1519
<211> LENGTH: 25
<212> TYPE: DNA
<213> ORGANISM: Artificial Sequence
```

<220> FEATURE:
<223> OTHER INFORMATION: synthetic oligonucleotide

<400> SEQUENCE: 1519
gatcagcaca cacttcttga gatca                                              25

<210> SEQ ID NO 1520
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1520
cgacagacgc ctgatctcaa gaactggtgg at                                      32

<210> SEQ ID NO 1521
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1521
gatcatccac cagttcttga gatca                                              25

<210> SEQ ID NO 1522
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1522
cgacagacgc ctgatctcaa ctttgatccg ct                                      32

<210> SEQ ID NO 1523
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1523
gatcagcgga tcaaagttga gatca                                              25

<210> SEQ ID NO 1524
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1524
cgacagacgc ctgatctcaa cgtggtttct gt                                      32

<210> SEQ ID NO 1525
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1525
gatcacagaa accacgttga gatca                                              25

<210> SEQ ID NO 1526
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1526
cgacagacgc ctgatctcaa cacctcttgg at         32

<210> SEQ ID NO 1527
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1527
gatcatccaa gaggtgttga gatca         25

<210> SEQ ID NO 1528
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1528
cgacagacgc ctgatctcaa attgcctcgt ct         32

<210> SEQ ID NO 1529
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1529
gatcagacga ggcaatttga gatca         25

<210> SEQ ID NO 1530
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1530
cgacagacgc ctgatctcaa atgatgcgga gt         32

<210> SEQ ID NO 1531
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1531
gatcactccg catcatttga gatca         25

<210> SEQ ID NO 1532
<211> LENGTH: 32
<212> TYPE: DNA
<213> ORGANISM: Artificial Sequence
<220> FEATURE:
<223> OTHER INFORMATION: synthetic oligonucleotide

```
-continued

<400> SEQUENCE: 1532
cgacagacgc ctgatctcaa atccttcgct gt                                    32

<210> SEQ ID NO 1533
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1533
gatcacagcg aaggatttga gatca                                            25

<210> SEQ ID NO 1534
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1534
cgacagacgc ctgatctcaa atcatcggct ct                                    32

<210> SEQ ID NO 1535
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1535
gatcagagcc gatgatttga gatca                                            25

<210> SEQ ID NO 1536
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1536
cgacagacgc ctgatctcaa atacaggtcg ct                                    32

<210> SEQ ID NO 1537
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1537
gatcagcgac ctgtatttga gatca                                            25

<210> SEQ ID NO 1538
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1538
cgacagacgc ctgatctcaa ataagcggtg gt                                    32

<210> SEQ ID NO 1539
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1539
gatcaccacc gcttatttga gatca                                    25

<210> SEQ ID NO 1540
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1540
cgacagacgc ctgatctcaa agaggtttgg ct                            32

<210> SEQ ID NO 1541
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1541
gatcagccaa acctctttga gatca                                    25

<210> SEQ ID NO 1542
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1542
cgacagacgc ctgatctcaa acgtgttcct ct                            32

<210> SEQ ID NO 1543
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1543
gatcagagga acacgtttga gatca                                    25

<210> SEQ ID NO 1544
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1544
cgacagacgc ctgatctatt tggcagaggt ct                            32

<210> SEQ ID NO 1545
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1545
```

```
gatcagacct ctgccaaata gatca                                           25
```

<210> SEQ ID NO 1546
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1546

```
cgacagacgc ctgatctatt tgaggacacg gt                                   32
```

<210> SEQ ID NO 1547
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1547

```
gatcaccgtg tcctcaaata gatca                                           25
```

<210> SEQ ID NO 1548
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1548

```
cgacagacgc ctgatctatt tccggttgag gt                                   32
```

<210> SEQ ID NO 1549
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1549

```
gatcacctca accggaaata gatca                                           25
```

<210> SEQ ID NO 1550
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1550

```
cgacagacgc ctgatctatt tatcggagcg gt                                   32
```

<210> SEQ ID NO 1551
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1551

```
gatcaccgct ccgataaata gatca                                           25
```

<210> SEQ ID NO 1552
<211> LENGTH: 32
<212> TYPE: DNA

```
<213> ORGANISM: Artificial Sequence
<220> FEATURE:
<223> OTHER INFORMATION: synthetic oligonucleotide

<400> SEQUENCE: 1552
cgacagacgc ctgatctatt ggcaaggaga ct                                  32

<210> SEQ ID NO 1553
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1553
gatcagtctc cttgccaata gatca                                          25

<210> SEQ ID NO 1554
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1554
cgacagacgc ctgatctatt gccaagtcct ct                                  32

<210> SEQ ID NO 1555
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1555
gatcagagga cttggcaata gatca                                          25

<210> SEQ ID NO 1556
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1556
cgacagacgc ctgatctatt ctatggtccg ct                                  32

<210> SEQ ID NO 1557
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1557
gatcagcgga ccatagaata gatca                                          25

<210> SEQ ID NO 1558
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1558
cgacagacgc ctgatctatt ccaacgacca gt                                  32
```

<210> SEQ ID NO 1559
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1559
gatcactggt cgttggaata gatca                                         25

<210> SEQ ID NO 1560
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1560
cgacagacgc ctgatctatt atgcgagagg ct                                 32

<210> SEQ ID NO 1561
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1561
gatcagcctc tcgcataata gatca                                         25

<210> SEQ ID NO 1562
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1562
cgacagacgc ctgatctatt aggacacacg gt                                 32

<210> SEQ ID NO 1563
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1563
gatcaccgtg tgtcctaata gatca                                         25

<210> SEQ ID NO 1564
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1564
cgacagacgc ctgatctatt acgtaccagc ct                                 32

<210> SEQ ID NO 1565
<211> LENGTH: 25
<212> TYPE: DNA
<213> ORGANISM: Artificial Sequence
<220> FEATURE:

<223> OTHER INFORMATION: synthetic oligonucleotide

<400> SEQUENCE: 1565
gatcaggctg gtacgtaata gatca                                    25

<210> SEQ ID NO 1566
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1566
cgacagacgc ctgatctatt acctcagtcg ct                            32

<210> SEQ ID NO 1567
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1567
gatcagcgac tgaggtaata gatca                                    25

<210> SEQ ID NO 1568
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1568
cgacagacgc ctgatctatt acaaggcgag gt                            32

<210> SEQ ID NO 1569
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1569
gatcacctcg ccttgtaata gatca                                    25

<210> SEQ ID NO 1570
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1570
cgacagacgc ctgatctatt aaggcaccac ct                            32

<210> SEQ ID NO 1571
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1571
gatcaggtgg tgccttaata gatca                                    25

<210> SEQ ID NO 1572
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1572
cgacagacgc ctgatctatt aactgcctcc gt                                    32

<210> SEQ ID NO 1573
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1573
gatcacggag gcagttaata gatca                                            25

<210> SEQ ID NO 1574
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1574
cgacagacgc ctgatctatg tttcaggtcg gt                                    32

<210> SEQ ID NO 1575
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1575
gatcaccgac ctgaaacata gatca                                            25

<210> SEQ ID NO 1576
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1576
cgacagacgc ctgatctatg ttagacgcag gt                                    32

<210> SEQ ID NO 1577
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1577
gatcacctgc gtctaacata gatca                                            25

<210> SEQ ID NO 1578
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 1578
cgacagacgc ctgatctatg tgtatcaggc gt                                32

<210> SEQ ID NO 1579
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1579
gatcacgcct gatacacata gatca                                        25

<210> SEQ ID NO 1580
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1580
cgacagacgc ctgatctatg gttactgctc gt                                32

<210> SEQ ID NO 1581
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1581
gatcacgagc agtaaccata gatca                                        25

<210> SEQ ID NO 1582
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1582
cgacagacgc ctgatctatg gaggctttgt ct                                32

<210> SEQ ID NO 1583
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1583
gatcagacaa agcctccata gatca                                        25

<210> SEQ ID NO 1584
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1584
cgacagacgc ctgatctatg cttgtggact ct                                32

<210> SEQ ID NO 1585
<211> LENGTH: 25
```

```
<212> TYPE: DNA
<213> ORGANISM: Artificial Sequence
<220> FEATURE:
<223> OTHER INFORMATION: synthetic oligonucleotide

<400> SEQUENCE: 1585
gatcagagtc cacaagcata gatca                                      25

<210> SEQ ID NO 1586
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1586
cgacagacgc ctgatctatg ctaaaggtcg gt                              32

<210> SEQ ID NO 1587
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1587
gatcaccgac ctttagcata gatca                                      25

<210> SEQ ID NO 1588
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1588
cgacagacgc ctgatctatg cctttacctc gt                              32

<210> SEQ ID NO 1589
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1589
gatcacgagg taaaggcata gatca                                      25

<210> SEQ ID NO 1590
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1590
cgacagacgc ctgatctatg atgtctgtgc ct                              32

<210> SEQ ID NO 1591
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1591
```
gatcaggcac agacatcata gatca                    25

<210> SEQ ID NO 1592
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1592
cgacagacgc ctgatctatg agaagccagt gt             32

<210> SEQ ID NO 1593
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1593
gatcacactg gcttctcata gatca                     25

<210> SEQ ID NO 1594
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1594
cgacagacgc ctgatctatg acctgttgtg gt             32

<210> SEQ ID NO 1595
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1595
gatcaccaca acaggtcata gatca                     25

<210> SEQ ID NO 1596
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1596
cgacagacgc ctgatctatg aagtcacgag gt             32

<210> SEQ ID NO 1597
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1597
gatcacctcg tgacttcata gatca                     25

<210> SEQ ID NO 1598
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 1598
cgacagacgc ctgatctatc ttgaggtgtg ct                              32

<210> SEQ ID NO 1599
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1599
gatcagcaca cctcaagata gatca                                      25

<210> SEQ ID NO 1600
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1600
cgacagacgc ctgatctatc ttcgacactg gt                              32

<210> SEQ ID NO 1601
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1601
gatcaccagt gtcgaagata gatca                                      25

<210> SEQ ID NO 1602
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1602
cgacagacgc ctgatctatc tccaagcaca gt                              32

<210> SEQ ID NO 1603
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1603
gatcactgtg cttggagata gatca                                      25

<210> SEQ ID NO 1604
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1604
cgacagacgc ctgatctatc taccgaacac gt                              32
```

<210> SEQ ID NO 1605
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1605
gatcacgtgt tcggtagata gatca                                         25

<210> SEQ ID NO 1606
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1606
cgacagacgc ctgatctatc gaatgagcag gt                                 32

<210> SEQ ID NO 1607
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1607
gatcacctgc tcattcgata gatca                                         25

<210> SEQ ID NO 1608
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1608
cgacagacgc ctgatctatc cgtattgagc ct                                 32

<210> SEQ ID NO 1609
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1609
gatcaggctc aatacggata gatca                                         25

<210> SEQ ID NO 1610
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1610
cgacagacgc ctgatctatc catgagcaac ct                                 32

<210> SEQ ID NO 1611
<211> LENGTH: 25
<212> TYPE: DNA
<213> ORGANISM: Artificial Sequence
<220> FEATURE:
<223> OTHER INFORMATION: synthetic oligonucleotide -continued

```
<400> SEQUENCE: 1611
gatcaggttg ctcatggata gatca                                                25

<210> SEQ ID NO 1612
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1612
cgacagacgc ctgatctatc atgcctaacc gt                                        32

<210> SEQ ID NO 1613
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1613
gatcacggtt aggcatgata gatca                                                25

<210> SEQ ID NO 1614
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1614
cgacagacgc ctgatctatc aggtgaatgg ct                                        32

<210> SEQ ID NO 1615
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1615
gatcagccat tcacctgata gatca                                                25

<210> SEQ ID NO 1616
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1616
cgacagacgc ctgatctatc accatgttcc gt                                        32

<210> SEQ ID NO 1617
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1617
gatcacggaa catggtgata gatca                                                25

<210> SEQ ID NO 1618
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1618
cgacagacgc ctgatctatc aacagtccag ct                                    32

<210> SEQ ID NO 1619
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1619
gatcagctgg actgttgata gatca                                            25

<210> SEQ ID NO 1620
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1620
cgacagacgc ctgatctata ttaccgcgac ct                                    32

<210> SEQ ID NO 1621
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1621
gatcaggtcg cggtaatata gatca                                            25

<210> SEQ ID NO 1622
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1622
cgacagacgc ctgatctata tggacgaacg gt                                    32

<210> SEQ ID NO 1623
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1623
gatcaccgtt cgtccatata gatca                                            25

<210> SEQ ID NO 1624
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1624
```

```
cgacagacgc ctgatctata tgcggtgtct gt                                    32
```

<210> SEQ ID NO 1625
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1625

```
gatcacagac accgcatata gatca                                            25
```

<210> SEQ ID NO 1626
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1626

```
cgacagacgc ctgatctata tctcgtgtgc ct                                    32
```

<210> SEQ ID NO 1627
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1627

```
gatcaggcac acgagatata gatca                                            25
```

<210> SEQ ID NO 1628
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1628

```
cgacagacgc ctgatctata tccaaccagc gt                                    32
```

<210> SEQ ID NO 1629
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1629

```
gatcacgctg gttggatata gatca                                            25
```

<210> SEQ ID NO 1630
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1630

```
cgacagacgc ctgatctata taaggcaggc gt                                    32
```

<210> SEQ ID NO 1631
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 1631
gatcacgcct gccttatata gatca                                       25

<210> SEQ ID NO 1632
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1632
cgacagacgc ctgatctata gtgcaagtcg gt                               32

<210> SEQ ID NO 1633
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1633
gatcaccgac ttgcactata gatca                                       25

<210> SEQ ID NO 1634
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1634
cgacagacgc ctgatctata gtgagaacgg ct                               32

<210> SEQ ID NO 1635
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1635
gatcagccgt tctcactata gatca                                       25

<210> SEQ ID NO 1636
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1636
cgacagacgc ctgatctata ggcaggtttc gt                               32

<210> SEQ ID NO 1637
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1637
gatcacgaaa cctgcctata gatca                                       25
```

<210> SEQ ID NO 1638
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1638
cgacagacgc ctgatctata gatcgatggc gt                            32

<210> SEQ ID NO 1639
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1639
gatcacgcca tcgatctata gatca                                    25

<210> SEQ ID NO 1640
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1640
cgacagacgc ctgatctata ctctgttccg ct                            32

<210> SEQ ID NO 1641
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1641
gatcagcgga acagagtata gatca                                    25

<210> SEQ ID NO 1642
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1642
cgacagacgc ctgatctata ctaacggacg ct                            32

<210> SEQ ID NO 1643
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1643
gatcagcgtc cgttagtata gatca                                    25

<210> SEQ ID NO 1644
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1644
cgacagacgc ctgatctata cgttctgctc ct                          32

<210> SEQ ID NO 1645
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1645
gatcaggagc agaacgtata gatca                                  25

<210> SEQ ID NO 1646
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1646
cgacagacgc ctgatctata atctcgaccg ct                          32

<210> SEQ ID NO 1647
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1647
gatcagcggt cgagattata gatca                                  25

<210> SEQ ID NO 1648
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1648
cgacagacgc ctgatctata agcggagtgt ct                          32

<210> SEQ ID NO 1649
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1649
gatcagacac tccgcttata gatca                                  25

<210> SEQ ID NO 1650
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1650
cgacagacgc ctgatctata agcctggaac gt                          32

<210> SEQ ID NO 1651
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1651
gatcacgttc caggcttata gatca                                          25

<210> SEQ ID NO 1652
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1652
cgacagacgc ctgatctata agacggtgag ct                                  32

<210> SEQ ID NO 1653
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1653
gatcagctca ccgtcttata gatca                                          25

<210> SEQ ID NO 1654
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1654
cgacagacgc ctgatctata agaacctccg ct                                  32

<210> SEQ ID NO 1655
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1655
gatcagcgga ggttcttata gatca                                          25

<210> SEQ ID NO 1656
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1656
cgacagacgc ctgatctata aatggccgga gt                                  32

<210> SEQ ID NO 1657
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1657
gatcactccg gccatttata gatca					25

<210> SEQ ID NO 1658
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1658
cgacagacgc ctgatctagt tggcctgaaa gt					32

<210> SEQ ID NO 1659
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1659
gatcactttc aggccaacta gatca					25

<210> SEQ ID NO 1660
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1660
cgacagacgc ctgatctagt tgcatctctg gt					32

<210> SEQ ID NO 1661
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1661
gatcaccaga gatgcaacta gatca					25

<210> SEQ ID NO 1662
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1662
cgacagacgc ctgatctagt tctccgactt gt					32

<210> SEQ ID NO 1663
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1663
gatcacaagt cggagaacta gatca					25

<210> SEQ ID NO 1664
<211> LENGTH: 32

```
<212> TYPE: DNA
<213> ORGANISM: Artificial Sequence
<220> FEATURE:
<223> OTHER INFORMATION: synthetic oligonucleotide

<400> SEQUENCE: 1664
cgacagacgc ctgatctagt tctcaaccag ct                            32

<210> SEQ ID NO 1665
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1665
gatcagctgg ttgagaacta gatca                                    25

<210> SEQ ID NO 1666
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1666
cgacagacgc ctgatctagt tatggaagcc gt                            32

<210> SEQ ID NO 1667
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1667
gatcacggct tccataacta gatca                                    25

<210> SEQ ID NO 1668
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1668
cgacagacgc ctgatctagt gtctaatgcg gt                            32

<210> SEQ ID NO 1669
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1669
gatcaccgca ttagacacta gatca                                    25

<210> SEQ ID NO 1670
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1670
```

```
cgacagacgc ctgatctagt ggtttcgtca gt                                  32
```

<210> SEQ ID NO 1671
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1671

```
gatcactgac gaaaccacta gatca                                          25
```

<210> SEQ ID NO 1672
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1672

```
cgacagacgc ctgatctagt cggaaccttt gt                                  32
```

<210> SEQ ID NO 1673
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1673

```
gatcacaaag gttccgacta gatca                                          25
```

<210> SEQ ID NO 1674
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1674

```
cgacagacgc ctgatctagt caacgacatc ct                                  32
```

<210> SEQ ID NO 1675
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1675

```
gatcaggatg tcgttgacta gatca                                          25
```

<210> SEQ ID NO 1676
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1676

```
cgacagacgc ctgatctagt caacaccagt ct                                  32
```

<210> SEQ ID NO 1677
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 1677
gatcagactg gtgttgacta gatca                                            25

<210> SEQ ID NO 1678
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1678
cgacagacgc ctgatctagt atagccaccg at                                    32

<210> SEQ ID NO 1679
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1679
gatcatcggt ggctatacta gatca                                            25

<210> SEQ ID NO 1680
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1680
cgacagacgc ctgatctagt agtacgaggc at                                    32

<210> SEQ ID NO 1681
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1681
gatcatgcct cgtactacta gatca                                            25

<210> SEQ ID NO 1682
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1682
cgacagacgc ctgatctagt agaacatgcg gt                                    32

<210> SEQ ID NO 1683
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1683
gatcaccgca tgttctacta gatca                                            25
```

<210> SEQ ID NO 1684
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1684
cgacagacgc ctgatctagt actgtgcttg gt       32

<210> SEQ ID NO 1685
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1685
gatcaccaag cacagtacta gatca       25

<210> SEQ ID NO 1686
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1686
cgacagacgc ctgatctagt acacatcacc gt       32

<210> SEQ ID NO 1687
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1687
gatcacggtg atgtgtacta gatca       25

<210> SEQ ID NO 1688
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1688
cgacagacgc ctgatctagg tttacgcctt ct       32

<210> SEQ ID NO 1689
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1689
gatcagaagg cgtaaaccta gatca       25

<210> SEQ ID NO 1690
<211> LENGTH: 32
<212> TYPE: DNA
<213> ORGANISM: Artificial Sequence
<220> FEATURE:
<223> OTHER INFORMATION: synthetic oligonucleotide

```
<400> SEQUENCE: 1690
cgacagacgc ctgatctagg ttcttagcgt gt                    32

<210> SEQ ID NO 1691
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1691
gatcacacgc taagaaccta gatca                            25

<210> SEQ ID NO 1692
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1692
cgacagacgc ctgatctagg ctttatccgt gt                    32

<210> SEQ ID NO 1693
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1693
gatcacacgg ataaagccta gatca                            25

<210> SEQ ID NO 1694
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1694
cgacagacgc ctgatctagg cttcttcaca ct                    32

<210> SEQ ID NO 1695
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1695
gatcagtgtg aagaagccta gatca                            25

<210> SEQ ID NO 1696
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1696
cgacagacgc ctgatctagg caaagttcag gt                    32

<210> SEQ ID NO 1697
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1697
gatcacctga actttgccta gatca                                    25

<210> SEQ ID NO 1698
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1698
cgacagacgc ctgatctagg accttaccac at                            32

<210> SEQ ID NO 1699
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1699
gatcatgtgg taaggtccta gatca                                    25

<210> SEQ ID NO 1700
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1700
cgacagacgc ctgatctagg aatgtatcgg ct                            32

<210> SEQ ID NO 1701
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1701
gatcagccga tacattccta gatca                                    25

<210> SEQ ID NO 1702
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1702
cgacagacgc ctgatctagg aatcatcagc gt                            32

<210> SEQ ID NO 1703
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1703
```

```
gatcacgctg atgattccta gatca                                          25

<210> SEQ ID NO 1704
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1704
cgacagacgc ctgatctagc tccatttacc gt                                  32

<210> SEQ ID NO 1705
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1705
gatcacggta aatggagcta gatca                                          25

<210> SEQ ID NO 1706
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1706
cgacagacgc ctgatctagc taaagcaggt ct                                  32

<210> SEQ ID NO 1707
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1707
gatcagacct gctttagcta gatca                                          25

<210> SEQ ID NO 1708
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1708
cgacagacgc ctgatctagc gtttactgag gt                                  32

<210> SEQ ID NO 1709
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1709
gatcacctca gtaaacgcta gatca                                          25

<210> SEQ ID NO 1710
<211> LENGTH: 32
<212> TYPE: DNA
```

```
<213> ORGANISM: Artificial Sequence
<220> FEATURE:
<223> OTHER INFORMATION: synthetic oligonucleotide

<400> SEQUENCE: 1710
cgacagacgc ctgatctagc ctttgtcact ct                            32

<210> SEQ ID NO 1711
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1711
gatcagagtg acaaaggcta gatca                                    25

<210> SEQ ID NO 1712
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1712
cgacagacgc ctgatctagc cttcattcct gt                            32

<210> SEQ ID NO 1713
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1713
gatcacagga atgaaggcta gatca                                    25

<210> SEQ ID NO 1714
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1714
cgacagacgc ctgatctagc ctattgttcc gt                            32

<210> SEQ ID NO 1715
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1715
gatcacggaa caataggcta gatca                                    25

<210> SEQ ID NO 1716
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1716
cgacagacgc ctgatctagc ctatacaccg at                            32
```

<210> SEQ ID NO 1717
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1717
gatcatcggt gtataggcta gatca                                          25

<210> SEQ ID NO 1718
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1718
cgacagacgc ctgatctagc ctaaaccact gt                                  32

<210> SEQ ID NO 1719
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1719
gatcacagtg gtttaggcta gatca                                          25

<210> SEQ ID NO 1720
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1720
cgacagacgc ctgatctagc caaagtatcc gt                                  32

<210> SEQ ID NO 1721
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1721
gatcacggat actttggcta gatca                                          25

<210> SEQ ID NO 1722
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1722
cgacagacgc ctgatctagc attgtctcac ct                                  32

<210> SEQ ID NO 1723
<211> LENGTH: 25
<212> TYPE: DNA
<213> ORGANISM: Artificial Sequence
<220> FEATURE:

```
<223> OTHER INFORMATION: synthetic oligonucleotide

<400> SEQUENCE: 1723
gatcaggtga gacaatgcta gatca                                               25

<210> SEQ ID NO 1724
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1724
cgacagacgc ctgatctagc atagtgaacc gt                                       32

<210> SEQ ID NO 1725
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1725
gatcacggtt cactatgcta gatca                                               25

<210> SEQ ID NO 1726
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1726
cgacagacgc ctgatctagc aactaccatc gt                                       32

<210> SEQ ID NO 1727
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1727
gatcacgatg gtagttgcta gatca                                               25

<210> SEQ ID NO 1728
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1728
cgacagacgc ctgatctagc aacatctacg gt                                       32

<210> SEQ ID NO 1729
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1729
gatcaccgta gatgttgcta gatca                                               25
```

```
<210> SEQ ID NO 1730
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1730
cgacagacgc ctgatctagc aaagtggagt ct                                    32

<210> SEQ ID NO 1731
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1731
gatcagactc cactttgcta gatca                                            25

<210> SEQ ID NO 1732
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1732
cgacagacgc ctgatctaga tgtggtgttc ct                                    32

<210> SEQ ID NO 1733
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1733
gatcaggaac accacatcta gatca                                            25

<210> SEQ ID NO 1734
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1734
cgacagacgc ctgatctaga tgtaagtgcc gt                                    32

<210> SEQ ID NO 1735
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1735
gatcacggca cttacatcta gatca                                            25

<210> SEQ ID NO 1736
<211> LENGTH: 32
<212> TYPE: DNA
<213> ORGANISM: Artificial Sequence
<220> FEATURE:
<223> OTHER INFORMATION: synthetic oligonucleotide
```

<400> SEQUENCE: 1736
cgacagacgc ctgatctaga tgccttcctt gt					32

<210> SEQ ID NO 1737
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1737
gatcacaagg aaggcatcta gatca					25

<210> SEQ ID NO 1738
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1738
cgacagacgc ctgatctaga tgattccggt gt					32

<210> SEQ ID NO 1739
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1739
gatcacaccg gaatcatcta gatca					25

<210> SEQ ID NO 1740
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1740
cgacagacgc ctgatctaga tcttgtgtcc gt					32

<210> SEQ ID NO 1741
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1741
gatcacggac acaagatcta gatca					25

<210> SEQ ID NO 1742
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1742
cgacagacgc ctgatctaga tcctcattcg ct					32

<210> SEQ ID NO 1743
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 1743
gatcagcgaa tgaggatcta gatca                                         25

<210> SEQ ID NO 1744
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1744
cgacagacgc ctgatctaga tagtgttcgg ct                                 32

<210> SEQ ID NO 1745
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1745
gatcagccga acactatcta gatca                                         25

<210> SEQ ID NO 1746
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1746
cgacagacgc ctgatctaga ggttgttgtc ct                                 32

<210> SEQ ID NO 1747
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1747
gatcaggaca acaacctcta gatca                                         25

<210> SEQ ID NO 1748
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1748
cgacagacgc ctgatctaga ggaacttgac gt                                 32

<210> SEQ ID NO 1749
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1749
```

```
gatcacgtca agttcctcta gatca                                              25

<210> SEQ ID NO 1750
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1750
cgacagacgc ctgatctaga ctacaatccg ct                                      32

<210> SEQ ID NO 1751
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1751
gatcagcgga ttgtagtcta gatca                                              25

<210> SEQ ID NO 1752
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1752
cgacagacgc ctgatctaga ccacttacac gt                                      32

<210> SEQ ID NO 1753
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1753
gatcacgtgt aagtggtcta gatca                                              25

<210> SEQ ID NO 1754
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1754
cgacagacgc ctgatctaga cagccacctt at                                      32

<210> SEQ ID NO 1755
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1755
gatcataagg tggctgtcta gatca                                              25

<210> SEQ ID NO 1756
<211> LENGTH: 32
<212> TYPE: DNA
<213> ORGANISM: Artificial Sequence
```

```
<220> FEATURE:
<223> OTHER INFORMATION: synthetic oligonucleotide

<400> SEQUENCE: 1756
cgacagacgc ctgatctaga caacctctgg at                              32

<210> SEQ ID NO 1757
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1757
gatcatccag aggttgtcta gatca                                      25

<210> SEQ ID NO 1758
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1758
cgacagacgc ctgatctaga caaaccttcc gt                              32

<210> SEQ ID NO 1759
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1759
gatcacggaa ggtttgtcta gatca                                      25

<210> SEQ ID NO 1760
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1760
cgacagacgc ctgatctaga atcactacgc ct                              32

<210> SEQ ID NO 1761
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1761
gatcaggcgt agtgattcta gatca                                      25

<210> SEQ ID NO 1762
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1762
cgacagacgc ctgatctact ttgtggagag ct                              32
```

<210> SEQ ID NO 1763
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1763
gatcagctct ccacaaagta gatca                                              25

<210> SEQ ID NO 1764
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1764
cgacagacgc ctgatctact tggtaagagc gt                                      32

<210> SEQ ID NO 1765
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1765
gatcacgctc ttaccaagta gatca                                              25

<210> SEQ ID NO 1766
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1766
cgacagacgc ctgatctact tgagcagaac ct                                      32

<210> SEQ ID NO 1767
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1767
gatcaggttc tgctcaagta gatca                                              25

<210> SEQ ID NO 1768
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1768
cgacagacgc ctgatctact tcgttgagtc ct                                      32

<210> SEQ ID NO 1769
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 1769
gatcaggact caacgaagta gatca                                         25

<210> SEQ ID NO 1770
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1770
cgacagacgc ctgatctact tcgagttgtc ct                                 32

<210> SEQ ID NO 1771
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1771
gatcaggaca actcgaagta gatca                                         25

<210> SEQ ID NO 1772
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1772
cgacagacgc ctgatctact tagaagcgac ct                                 32

<210> SEQ ID NO 1773
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1773
gatcaggtcg cttctaagta gatca                                         25

<210> SEQ ID NO 1774
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1774
cgacagacgc ctgatctact tagaacaggc gt                                 32

<210> SEQ ID NO 1775
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1775
gatcacgcct gttctaagta gatca                                         25

<210> SEQ ID NO 1776
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1776
cgacagacgc ctgatctact taagcgagga ct                                  32

<210> SEQ ID NO 1777
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1777
gatcagtcct cgcttaagta gatca                                          25

<210> SEQ ID NO 1778
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1778
cgacagacgc ctgatctact ggtgtttgga ct                                  32

<210> SEQ ID NO 1779
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1779
gatcagtcca aacaccagta gatca                                          25

<210> SEQ ID NO 1780
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1780
cgacagacgc ctgatctact gatgagttgg ct                                  32

<210> SEQ ID NO 1781
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1781
gatcagccaa ctcatcagta gatca                                          25

<210> SEQ ID NO 1782
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1782
```
cgacagacgc ctgatctact cggaacattg gt         32

<210> SEQ ID NO 1783
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1783
gatcaccaat gttccgagta gatca         25

<210> SEQ ID NO 1784
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1784
cgacagacgc ctgatctact caatagaccg ct         32

<210> SEQ ID NO 1785
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1785
gatcagcggt ctattgagta gatca         25

<210> SEQ ID NO 1786
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1786
cgacagacgc ctgatctact acactgaacc gt         32

<210> SEQ ID NO 1787
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1787
gatcacggtt cagtgtag         18

<210> SEQ ID NO 1788
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1788
cgacagacgc ctgatctact acaagtccac gt         32

<210> SEQ ID NO 1789
<211> LENGTH: 18
<212> TYPE: DNA

```
<213> ORGANISM: Artificial Sequence
<220> FEATURE:
<223> OTHER INFORMATION: synthetic oligonucleotide

<400> SEQUENCE: 1789
gatcacgtgg acttgtag                                                 18

<210> SEQ ID NO 1790
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1790
cgacagacgc ctgatctact aagagttgcc gt                                 32

<210> SEQ ID NO 1791
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1791
gatcacggca actcttagta gatca                                         25

<210> SEQ ID NO 1792
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1792
cgacagacgc ctgatctacg ttctccttag ct                                 32

<210> SEQ ID NO 1793
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1793
gatcagctaa ggagaacgta gatca                                         25

<210> SEQ ID NO 1794
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1794
cgacagacgc ctgatctacg tgtaggtgtt ct                                 32

<210> SEQ ID NO 1795
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1795
gatcagaaca cctacacgta gatca                                         25
```

<210> SEQ ID NO 1796
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1796
cgacagacgc ctgatctacg tagttggtct gt                     32

<210> SEQ ID NO 1797
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1797
gatcacagac caactacgta gatca                             25

<210> SEQ ID NO 1798
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1798
cgacagacgc ctgatctacg ctaactcctt gt                     32

<210> SEQ ID NO 1799
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1799
gatcacaagg agttagcgta gatca                             25

<210> SEQ ID NO 1800
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1800
cgacagacgc ctgatctacg ccaaatccta gt                     32

<210> SEQ ID NO 1801
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1801
gatcactagg atttggcgta gatca                             25

<210> SEQ ID NO 1802
<211> LENGTH: 32
<212> TYPE: DNA
<213> ORGANISM: Artificial Sequence
<220> FEATURE:

<223> OTHER INFORMATION: synthetic oligonucleotide

<400> SEQUENCE: 1802
cgacagacgc ctgatctacg attctgtgag gt                        32

<210> SEQ ID NO 1803
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1803
gatcacctca cagaatcgta gatca                                25

<210> SEQ ID NO 1804
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1804
cgacagacgc ctgatctacg attccaccaa gt                        32

<210> SEQ ID NO 1805
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1805
gatcacttgg tggaatcgta gatca                                25

<210> SEQ ID NO 1806
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1806
cgacagacgc ctgatctacg atattgcctc ct                        32

<210> SEQ ID NO 1807
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1807
gatcaggagg caatatcgta gatca                                25

<210> SEQ ID NO 1808
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1808
cgacagacgc ctgatctacg atagaggttg ct                        32

```
<210> SEQ ID NO 1809
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1809
gatcagcaac ctctatcgta gatca                                          25

<210> SEQ ID NO 1810
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1810
cgacagacgc ctgatctacg aatgactgga gt                                  32

<210> SEQ ID NO 1811
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1811
gatcactcca gtcattcgta gatca                                          25

<210> SEQ ID NO 1812
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1812
cgacagacgc ctgatctacg aaatcctagc ct                                  32

<210> SEQ ID NO 1813
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1813
gatcaggcta ggatttcgta gatca                                          25

<210> SEQ ID NO 1814
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1814
cgacagacgc ctgatctacc ttagtagccg at                                  32

<210> SEQ ID NO 1815
<211> LENGTH: 25
<212> TYPE: DNA
<213> ORGANISM: Artificial Sequence
<220> FEATURE:
<223> OTHER INFORMATION: synthetic oligonucleotide
```

```
<400> SEQUENCE: 1815
gatcatcggc tactaaggta gatca                                              25

<210> SEQ ID NO 1816
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1816
cgacagacgc ctgatctacc tggtgtttac gt                                      32

<210> SEQ ID NO 1817
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1817
gatcacgtaa acaccaggta gatca                                              25

<210> SEQ ID NO 1818
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1818
cgacagacgc ctgatctacc tggcctcttt at                                      32

<210> SEQ ID NO 1819
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1819
gatcataaag aggccaggta gatca                                              25

<210> SEQ ID NO 1820
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1820
cgacagacgc ctgatctacc tggaaaggac tt                                      32

<210> SEQ ID NO 1821
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1821
gatcaagtcc tttccaggta gatca                                              25

<210> SEQ ID NO 1822
<211> LENGTH: 32
```

```
<212> TYPE: DNA
<213> ORGANISM: Artificial Sequence
<220> FEATURE:
<223> OTHER INFORMATION: synthetic oligonucleotide

<400> SEQUENCE: 1822
cgacagacgc ctgatctacc tgaggtgttt gt                              32

<210> SEQ ID NO 1823
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1823
gatcacaaac acctcaggta gatca                                      25

<210> SEQ ID NO 1824
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1824
cgacagacgc ctgatctacc tattctgtgc gt                              32

<210> SEQ ID NO 1825
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1825
gatcacgcac agaataggta gatca                                      25

<210> SEQ ID NO 1826
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1826
cgacagacgc ctgatctacc gttgttagtc ct                              32

<210> SEQ ID NO 1827
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1827
gatcaggact aacaacggta gatca                                      25

<210> SEQ ID NO 1828
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1828
```
cgacagacgc ctgatctacc gtgtatggtt gt                                32

<210> SEQ ID NO 1829
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1829
gatcacaacc atacacggta gatca                                        25

<210> SEQ ID NO 1830
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1830
cgacagacgc ctgatctacc ggtgtaagag at                                32

<210> SEQ ID NO 1831
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1831
gatcatctct tacaccggta gatca                                        25

<210> SEQ ID NO 1832
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1832
cgacagacgc ctgatctacc ggaaatggat gt                                32

<210> SEQ ID NO 1833
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1833
gatcacatcc atttccggta gatca                                        25

<210> SEQ ID NO 1834
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1834
cgacagacgc ctgatctacc gattgaggag at                                32

<210> SEQ ID NO 1835
<211> LENGTH: 25
<212> TYPE: DNA
<213> ORGANISM: Artificial Sequence

```
<220> FEATURE:
<223> OTHER INFORMATION: synthetic oligonucleotide

<400> SEQUENCE: 1835
gatcatctcc tcaatcggta gatca                                              25

<210> SEQ ID NO 1836
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1836
cgacagacgc ctgatctacc atctgtcttc gt                                      32

<210> SEQ ID NO 1837
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1837
gatcacgaag acagatggta gatca                                              25

<210> SEQ ID NO 1838
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1838
cgacagacgc ctgatctacc agttgacttc ct                                      32

<210> SEQ ID NO 1839
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1839
gatcaggaag tcaactggta gatca                                              25

<210> SEQ ID NO 1840
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1840
cgacagacgc ctgatctacc actttcggat ct                                      32

<210> SEQ ID NO 1841
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1841
gatcagatcc gaaagtggta gatca                                              25
```

```
<210> SEQ ID NO 1842
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1842
cgacagacgc ctgatctacc aatagcggat ct                                    32

<210> SEQ ID NO 1843
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1843
gatcagatcc gctattggta gatca                                            25

<210> SEQ ID NO 1844
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1844
cgacagacgc ctgatctacc aaggtatgca gt                                    32

<210> SEQ ID NO 1845
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1845
gatcactgca taccttggta gatca                                            25

<210> SEQ ID NO 1846
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1846
cgacagacgc ctgatctacc aaatagctcc gt                                    32

<210> SEQ ID NO 1847
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1847
gatcacggag ctatttggta gatca                                            25

<210> SEQ ID NO 1848
<211> LENGTH: 32
<212> TYPE: DNA
<213> ORGANISM: Artificial Sequence
<220> FEATURE:
<223> OTHER INFORMATION: synthetic oligonucleotide
```

```
<400> SEQUENCE: 1848
cgacagacgc ctgatctaca tttgacctcc gt                                    32

<210> SEQ ID NO 1849
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1849
gatcacggag gtcaaatgta gatca                                            25

<210> SEQ ID NO 1850
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1850
cgacagacgc ctgatctaca tgttcctctc gt                                    32

<210> SEQ ID NO 1851
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1851
gatcacgaga ggaacatgta gatca                                            25

<210> SEQ ID NO 1852
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1852
cgacagacgc ctgatctaca tgtgtggagt ct                                    32

<210> SEQ ID NO 1853
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1853
gatcagactc cacacatgta gatca                                            25

<210> SEQ ID NO 1854
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1854
cgacagacgc ctgatctaca tacctagccg at                                    32

<210> SEQ ID NO 1855
```

```
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1855
gatcatcggc taggtatgta gatca                                          25

<210> SEQ ID NO 1856
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1856
cgacagacgc ctgatctaca gttcgttgag gt                                  32

<210> SEQ ID NO 1857
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1857
gatcacctca acgaactgta gatca                                          25

<210> SEQ ID NO 1858
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1858
cgacagacgc ctgatctaca ggaattgagg ct                                  32

<210> SEQ ID NO 1859
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1859
gatcagcctc aattcctgta gatca                                          25

<210> SEQ ID NO 1860
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1860
cgacagacgc ctgatctaca gaagttgagc ct                                  32

<210> SEQ ID NO 1861
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1861
```

```
gatcaggctc aacttctgta gatca                                              25

<210> SEQ ID NO 1862
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1862
cgacagacgc ctgatctaca cctaatgacc gt                                      32

<210> SEQ ID NO 1863
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1863
gatcacggtc attaggtgta gatca                                              25

<210> SEQ ID NO 1864
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1864
cgacagacgc ctgatctaca ataggtgctc gt                                      32

<210> SEQ ID NO 1865
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1865
gatcacgagc acctattgta gatca                                              25

<210> SEQ ID NO 1866
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1866
cgacagacgc ctgatctaca acgataggct ct                                      32

<210> SEQ ID NO 1867
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1867
gatcagagcc tatcgttgta gatca                                              25

<210> SEQ ID NO 1868
<211> LENGTH: 32
<212> TYPE: DNA
```

```
<213> ORGANISM: Artificial Sequence
<220> FEATURE:
<223> OTHER INFORMATION: synthetic oligonucleotide

<400> SEQUENCE: 1868
cgacagacgc ctgatctaca acaggtcttc ct                                       32

<210> SEQ ID NO 1869
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1869
gatcaggaag acctgttgta gatca                                               25

<210> SEQ ID NO 1870
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1870
cgacagacgc ctgatctaat tggtctcgtg gt                                       32

<210> SEQ ID NO 1871
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1871
gatcaccacg agaccaatta gatca                                               25

<210> SEQ ID NO 1872
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1872
cgacagacgc ctgatctaat tctgctctcg gt                                       32

<210> SEQ ID NO 1873
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1873
gatcaccgag agcagaatta gatca                                               25

<210> SEQ ID NO 1874
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1874
cgacagacgc ctgatctaat tcgaccacca gt                                       32
```

<210> SEQ ID NO 1875
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1875
gatcactggt ggtcgaatta gatca                                              25

<210> SEQ ID NO 1876
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1876
cgacagacgc ctgatctaat tcacctctgg ct                                      32

<210> SEQ ID NO 1877
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1877
gatcagccag aggtgaatta gatca                                              25

<210> SEQ ID NO 1878
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1878
cgacagacgc ctgatctaat tagctggacg gt                                      32

<210> SEQ ID NO 1879
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1879
gatcaccgtc cagctaatta gatca                                              25

<210> SEQ ID NO 1880
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1880
cgacagacgc ctgatctaat gtcctggttg gt                                      32

<210> SEQ ID NO 1881
<211> LENGTH: 25
<212> TYPE: DNA
<213> ORGANISM: Artificial Sequence
<220> FEATURE:

```
<223> OTHER INFORMATION: synthetic oligonucleotide

<400> SEQUENCE: 1881
gatcaccaac caggacatta gatca                                              25

<210> SEQ ID NO 1882
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1882
cgacagacgc ctgatctaat ggagtcaagg ct                                      32

<210> SEQ ID NO 1883
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1883
gatcagcctt gactccatta gatca                                              25

<210> SEQ ID NO 1884
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1884
cgacagacgc ctgatctaat gatacggcag gt                                      32

<210> SEQ ID NO 1885
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1885
gatcacctgc cgtatcatta gatca                                              25

<210> SEQ ID NO 1886
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1886
cgacagacgc ctgatctaat ctatccacgg ct                                      32

<210> SEQ ID NO 1887
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1887
gatcagccgt ggatagatta gatca                                              25
```

```
<210> SEQ ID NO 1888
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1888
cgacagacgc ctgatctaat ctaccttgcc gt                                       32

<210> SEQ ID NO 1889
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1889
gatcacggca aggtagatta gatca                                               25

<210> SEQ ID NO 1890
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1890
cgacagacgc ctgatctaat cgaaggtagg ct                                       32

<210> SEQ ID NO 1891
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1891
gatcagccta ccttcgatta gatca                                               25

<210> SEQ ID NO 1892
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1892
cgacagacgc ctgatctaat ccttgcctct gt                                       32

<210> SEQ ID NO 1893
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1893
gatcacagag gcaaggatta gatca                                               25

<210> SEQ ID NO 1894
<211> LENGTH: 32
<212> TYPE: DNA
<213> ORGANISM: Artificial Sequence
<220> FEATURE:
<223> OTHER INFORMATION: synthetic oligonucleotide
```

<400> SEQUENCE: 1894
cgacagacgc ctgatctaat ccgtcttgtc ct    32

<210> SEQ ID NO 1895
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1895
gatcaggaca agacggatta gatca    25

<210> SEQ ID NO 1896
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1896
cgacagacgc ctgatctaat cactgtctcc gt    32

<210> SEQ ID NO 1897
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1897
gatcacggag acagtgatta gatca    25

<210> SEQ ID NO 1898
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1898
cgacagacgc ctgatctaat attcggaggc gt    32

<210> SEQ ID NO 1899
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1899
gatcacgcct ccgaatatta gatca    25

<210> SEQ ID NO 1900
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1900
cgacagacgc ctgatctaat attcgcctcc gt    32

<210> SEQ ID NO 1901
<211> LENGTH: 25

```
<212> TYPE: DNA
<213> ORGANISM: Artificial Sequence
<220> FEATURE:
<223> OTHER INFORMATION: synthetic oligonucleotide

<400> SEQUENCE: 1901
gatcacggag gcgaatatta gatca                                        25

<210> SEQ ID NO 1902
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1902
cgacagacgc ctgatctaat atgccgaggt gt                                32

<210> SEQ ID NO 1903
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1903
gatcacacct cggcatatta gatca                                        25

<210> SEQ ID NO 1904
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1904
cgacagacgc ctgatctaat agttggctcg gt                                32

<210> SEQ ID NO 1905
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1905
gatcaccgag ccaactatta gatca                                        25

<210> SEQ ID NO 1906
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1906
cgacagacgc ctgatctaat accacctgac gt                                32

<210> SEQ ID NO 1907
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1907
```

```
gatcacgtca ggtggtatta gatca                                              25
```

<210> SEQ ID NO 1908
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1908

```
cgacagacgc ctgatctaag ttggtgtcct gt                                      32
```

<210> SEQ ID NO 1909
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1909

```
gatcacagga caccaactta gatca                                              25
```

<210> SEQ ID NO 1910
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1910

```
cgacagacgc ctgatctaag ttgctcctgt ct                                      32
```

<210> SEQ ID NO 1911
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1911

```
gatcagacag gagcaactta gatca                                              25
```

<210> SEQ ID NO 1912
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1912

```
cgacagacgc ctgatctaag ttcggttagg ct                                      32
```

<210> SEQ ID NO 1913
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1913

```
gatcagccta accgaactta gatca                                              25
```

<210> SEQ ID NO 1914
<211> LENGTH: 32
<212> TYPE: DNA
<213> ORGANISM: Artificial Sequence

```
<220> FEATURE:
<223> OTHER INFORMATION: synthetic oligonucleotide

<400> SEQUENCE: 1914
cgacagacgc ctgatctaag ttcctcggtt gt                                    32

<210> SEQ ID NO 1915
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1915
gatcacaacc gaggaactta gatca                                            25

<210> SEQ ID NO 1916
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1916
cgacagacgc ctgatctaag tgtagaagcc gt                                    32

<210> SEQ ID NO 1917
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1917
gatcacggct tctacactta gatca                                            25

<210> SEQ ID NO 1918
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1918
cgacagacgc ctgatctaag tacatcaggc gt                                    32

<210> SEQ ID NO 1919
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1919
gatcacgcct gatgtactta gatca                                            25

<210> SEQ ID NO 1920
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1920
cgacagacgc ctgatctaag gttgcttctg gt                                    32
```

<210> SEQ ID NO 1921
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1921
gatcaccaga agcaacctta gatca                                       25

<210> SEQ ID NO 1922
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1922
cgacagacgc ctgatctaag gttctctcac gt                               32

<210> SEQ ID NO 1923
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1923
gatcacgtga gagaacctta gatca                                       25

<210> SEQ ID NO 1924
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1924
cgacagacgc ctgatctaag gcctttacca ct                               32

<210> SEQ ID NO 1925
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1925
gatcagtggt aaaggcctta gatca                                       25

<210> SEQ ID NO 1926
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1926
cgacagacgc ctgatctaag gatctttcgg ct                               32

<210> SEQ ID NO 1927
<211> LENGTH: 25
<212> TYPE: DNA
<213> ORGANISM: Artificial Sequence
<220> FEATURE:
<223> OTHER INFORMATION: synthetic oligonucleotide

```
<400> SEQUENCE: 1927
gatcagccga aagatcctta gatca                                             25

<210> SEQ ID NO 1928
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1928
cgacagacgc ctgatctaag gataactcgg ct                                     32

<210> SEQ ID NO 1929
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1929
gatcagccga gttatcctta gatca                                             25

<210> SEQ ID NO 1930
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1930
cgacagacgc ctgatctaag gaatactggc gt                                     32

<210> SEQ ID NO 1931
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1931
gatcacgcca gtattcctta gatca                                             25

<210> SEQ ID NO 1932
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1932
cgacagacgc ctgatctaac tttccggtct ct                                     32

<210> SEQ ID NO 1933
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1933
gatcagagac cggaaagtta gatca                                             25

<210> SEQ ID NO 1934
```

```
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1934
cgacagacgc ctgatctaac ttagagtggc gt                              32

<210> SEQ ID NO 1935
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1935
gatcacgcca ctctaagtta gatca                                      25

<210> SEQ ID NO 1936
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1936
cgacagacgc ctgatctaac gtcttctcag gt                              32

<210> SEQ ID NO 1937
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1937
gatcacctga gaagacgtta gatca                                      25

<210> SEQ ID NO 1938
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1938
cgacagacgc ctgatctaac gtatggagag ct                              32

<210> SEQ ID NO 1939
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1939
gatcagctct ccatacgtta gatca                                      25

<210> SEQ ID NO 1940
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1940
```
cgacagacgc ctgatctaac gaactcacct gt            32

<210> SEQ ID NO 1941
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1941
gatcacaggt gagttcgtta gatca                    25

<210> SEQ ID NO 1942
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1942
cgacagacgc ctgatctaac cggttcttct ct            32

<210> SEQ ID NO 1943
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1943
gatcagagaa gaaccggtta gatca                    25

<210> SEQ ID NO 1944
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1944
cgacagacgc ctgatctaaa ttggctcctc ct            32

<210> SEQ ID NO 1945
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1945
gatcaggagg agccaattta gatca                    25

<210> SEQ ID NO 1946
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1946
cgacagacgc ctgatctaaa ttcggagagg ct            32

<210> SEQ ID NO 1947
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 1947
gatcagcctc tccgaattta gatca                                              25

<210> SEQ ID NO 1948
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1948
cgacagacgc ctgatctaaa tgacctccac gt                                      32

<210> SEQ ID NO 1949
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1949
gatcacgtgg aggtcattta gatca                                              25

<210> SEQ ID NO 1950
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1950
cgacagacgc ctgatctaaa tcaggctcca ct                                      32

<210> SEQ ID NO 1951
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1951
gatcagtgga gcctgattta gatca                                              25

<210> SEQ ID NO 1952
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1952
cgacagacgc ctgatctaaa gttccagctc ct                                      32

<210> SEQ ID NO 1953
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1953
gatcaggagc tggaacttta gatca                                              25
```

<210> SEQ ID NO 1954
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1954
cgacagacgc ctgatctaaa gtaacctcgc ct                                    32

<210> SEQ ID NO 1955
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1955
gatcaggcga ggttacttta gatca                                            25

<210> SEQ ID NO 1956
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1956
cgacagacgc ctgatctaaa ggtgtctggt ct                                    32

<210> SEQ ID NO 1957
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1957
gatcagacca gacacctttta gatca                                           25

<210> SEQ ID NO 1958
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1958
cgacagacgc ctgatctaaa gctgttcctc ct                                    32

<210> SEQ ID NO 1959
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1959
gatcaggagg aacagcttta gatca                                            25

<210> SEQ ID NO 1960
<211> LENGTH: 32
<212> TYPE: DNA
<213> ORGANISM: Artificial Sequence
<220> FEATURE:

```
<223> OTHER INFORMATION: synthetic oligonucleotide

<400> SEQUENCE: 1960
cgacagacgc ctgatctaaa ctggacacct ct                                    32

<210> SEQ ID NO 1961
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1961
gatcagaggt gtccagttta gatca                                            25

<210> SEQ ID NO 1962
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1962
cgacagacgc ctgatctaaa cctatccgag ct                                    32

<210> SEQ ID NO 1963
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1963
gatcagctcg gataggttta gatca                                            25

<210> SEQ ID NO 1964
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 1964
tcgatggttt ggcgcgccgg tagtttgaac catccat                               37

<210> SEQ ID NO 1965
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 1965
gccatttaca aactaggtat taatcgatcc tgcatgcc                              38

<210> SEQ ID NO 1966
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1966
tcgatggttt ggcgcgcc                                                    18
```

```
<210> SEQ ID NO 1967
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1967
aatcgatcct gcatgcca                                                  18

<210> SEQ ID NO 1968
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 1968
gctagggcta atatc                                                     15

<210> SEQ ID NO 1969
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 1969
attatgagca cgacagacgc ctgatct                                        27

<210> SEQ ID NO 1970
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 1970
gatcagatca ggcgtctgtc gtcgtgctca taa                                 33

<210> SEQ ID NO 1971
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 1971
gccatttaca aactaggtat t                                              21

<210> SEQ ID NO 1972
<211> LENGTH: 42
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (28)..(41)
<223> OTHER INFORMATION: n is a, c, g, or t

<400> SEQUENCE: 1972
attatgagca cgacagacgc ctgatctnnn nnnnnnnnn nt                        42

<210> SEQ ID NO 1973
<211> LENGTH: 46
<212> TYPE: DNA
```

<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(19)
<223> OTHER INFORMATION: n is a, c, g, or t

<400> SEQUENCE: 1973
gatcannnnn nnnnnnnna gatcaggcgt ctgtcgtgct cagtaa                46

<210> SEQ ID NO 1974
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (18)..(31)
<223> OTHER INFORMATION: n is a, c, g, or t

<400> SEQUENCE: 1974
cgacagacgc ctgatctnnn nnnnnnnnn nt                               32

<210> SEQ ID NO 1975
<211> LENGTH: 25
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(19)
<223> OTHER INFORMATION: n is a, c, g, or t

<400> SEQUENCE: 1975
gatcannnnn nnnnnnnna gatca                                       25

<210> SEQ ID NO 1976
<211> LENGTH: 103
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (7)..(20)
<223> OTHER INFORMATION: n is a, c, g, or t
<220> FEATURE:
<221> NAME/KEY: misc_feature
<222> LOCATION: (27)..(77)
<223> OTHER INFORMATION: n is a, c, g, or t
<220> FEATURE:
<221> NAME/KEY: misc_feature
<222> LOCATION: (84)..(97)
<223> OTHER INFORMATION: n is a, c, g, or t

<400> SEQUENCE: 1976
tgatctnnnn nnnnnnnnn tgatccnnnn nnnnnnnnn nnnnnnnnn nnnnnnnnn    60 nnnnnnnnnn nnnnnnngga tcannnnnnn nnnnnnnaga tca                 103

<210> SEQ ID NO 1977
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1977

```
aaggccttca cgacagacgc ctgat                                              25

<210> SEQ ID NO 1978
<211> LENGTH: 32
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (18)..(31)
<223> OTHER INFORMATION: n is a, c, g, or t

<400> SEQUENCE: 1978
cgacagacgc ctgatctnnn nnnnnnnnnn nt                                      32

<210> SEQ ID NO 1979
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(19)
<223> OTHER INFORMATION: n is a, c, g, or t

<400> SEQUENCE: 1979
ctagannnnn nnnnnnnnna ctag                                               24
```